(12) United States Patent
Ling et al.

(10) Patent No.: US 8,067,616 B2
(45) Date of Patent: Nov. 29, 2011

(54) TOTAL SYNTHESIS OF SALINOSPORAMIDE A AND ANALOGS THEREOF

(75) Inventors: Taotao Ling, La Jolla, CA (US); Venkata Rami Reddy Macherla, San Diego, CA (US); Barbara Christine Potts, Escondido, CA (US); Rama Rao Manam, San Diego, CA (US); Katherine A. McArthur, La Mesa, CA (US)

(73) Assignee: Nereus Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 12/913,624

(22) Filed: Oct. 27, 2010

(65) Prior Publication Data

US 2011/0105762 A1 May 5, 2011

Related U.S. Application Data

(62) Division of application No. 11/697,689, filed on Apr. 6, 2007, now Pat. No. 7,842,814.

(60) Provisional application No. 60/790,168, filed on Apr. 6, 2006, provisional application No. 60/816,968, filed on Jun. 27, 2006, provisional application No. 60/836,155, filed on Aug. 7, 2006, provisional application No. 60/844,132, filed on Sep. 12, 2006, provisional application No. 60/885,379, filed on Jan. 17, 2007.

(51) Int. Cl.
*C07D 487/02* (2006.01)
(52) U.S. Cl. ........................ 548/428; 548/453
(58) Field of Classification Search .................. 548/453, 548/428
See application file for complete search history.

(56) References Cited

U.S. PATENT DOCUMENTS

| | | | |
|---|---|---|---|
| 7,144,723 | B2 | 12/2006 | Fenical et al. |
| 7,176,232 | B2 | 2/2007 | Fenical et al. |
| 7,176,233 | B2 | 2/2007 | Fenical et al. |
| 7,179,834 | B2 | 2/2007 | Fenical et al. |
| 7,183,417 | B2 | 2/2007 | Corey |
| 7,276,530 | B2 | 10/2007 | Potts et al. |
| 7,371,875 | B2 | 5/2008 | Xiao et al. |
| 7,465,720 | B2 | 12/2008 | Corey et al. |
| 7,511,156 | B2 | 3/2009 | Corey |
| 7,544,814 | B2 | 6/2009 | Potts et al. |
| 7,579,371 | B2 | 8/2009 | Palladino et al. |
| 7,635,712 | B2 | 12/2009 | Fenical et al. |
| 7,691,896 | B2 | 4/2010 | Myers et al. |
| 7,842,814 | B2 | 11/2010 | Ling et al. |
| 2005/0049294 | A1 | 3/2005 | Palladino et al. |
| 2005/0228186 | A1 | 10/2005 | Corey |
| 2006/0264495 | A1 | 11/2006 | Palladino et al. |
| 2006/0287520 | A1 | 12/2006 | Danishefsky et al. |
| 2007/0004676 | A1 | 1/2007 | Palladino et al. |
| 2008/0070273 | A1 | 3/2008 | Fenical et al. |
| 2009/0035390 | A1 | 2/2009 | Anderson et al. |
| 2009/0069401 | A1 | 3/2009 | Fenical et al. |
| 2009/0182027 | A1 | 7/2009 | Palladino et al. |
| 2009/0197937 | A1 | 8/2009 | Fenical et al. |
| 2009/0234137 | A1 | 9/2009 | Ling et al. |
| 2009/0298906 | A1 | 12/2009 | Macherla et al. |
| 2010/0144826 | A1 | 6/2010 | Fenical et al. |

FOREIGN PATENT DOCUMENTS

| | | |
|---|---|---|
| WO | WO 96/32105 | 10/1996 |
| WO | WO 99/09006 | 2/1999 |
| WO | WO 99/15183 | 4/1999 |
| WO | WO 2004/071382 | 8/2004 |
| WO | WO 2005/002572 | 1/2005 |
| WO | WO 2005/099687 | 10/2005 |
| WO | WO 2005/113558 | 12/2005 |
| WO | WO 2006/005551 | 1/2006 |
| WO | WO 2006/028525 | 3/2006 |
| WO | WO 2006/060676 | 6/2006 |
| WO | WO 2006/060809 | 6/2006 |
| WO | WO 2006/118973 | 11/2006 |
| WO | WO 2007/021897 | 2/2007 |
| WO | WO 2007/033039 | 3/2007 |
| WO | WO 2007/117591 | 10/2007 |
| WO | WO 2009/140287 | 11/2009 |

OTHER PUBLICATIONS

Definition of "aminal," IUPAC Compendium of Chemical Terminology 2nd Edition (1997).*
Caubert et al. (Tetrahedron Letters, vol. 47, Issue 26, Jun. 26, 2006, pp. 4473-4475).*
Fukuda et al. "Total Synthesis of Salinsporamide A" (2008) 10(19):4239-42.
Ling et al., "Concise Formal Synthesis of (−)-Salinosporamide A (Marizomib) Using a Regio- and Stereoselective Epoxidation and Reductive Oxirane Ring-Opening Strategy" J. Org. Chem. (2010) 75(11):3882-5.

(Continued)

*Primary Examiner* — Robert Havlin
(74) *Attorney, Agent, or Firm* — Knobbe Martens Olson & Bear LLP

(57) ABSTRACT

The present invention relates to certain compounds and to methods for the preparation of certain compounds that can be used in the fields of chemistry and medicine. Specifically, described herein are methods for the preparation of various compounds and intermediates, and the compounds and intermediates themselves. More specifically, described herein are methods for synthesizing Salinosporamide A and its analogs from a compound of formula (V).

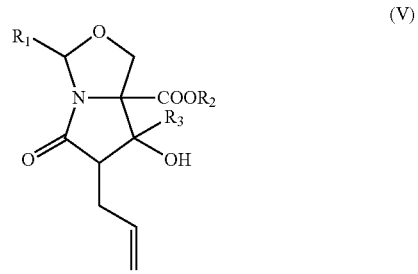

31 Claims, 64 Drawing Sheets

OTHER PUBLICATIONS

Margalef, et al, "Formal Synthesis of Salinosporamide A Using a Nickel-catalyzed Reductive Aldol Cyclization-lactonization as a Key Step,", Tetrahedron, (2008) 64(34):7896-7901.

Momose et al. "Formal Synthesis of Salinosporamide A Starting from D-Glucose" (2009) Synthesis, 17:2983-2991.

Mosey et al, "New Synthetic Route to Access (±) Salinosporamide A via an Oxazolone-Mediated Ene-Type Reaction" Tetrahedron Letters (2009) 50:295-7.

Struble et al., "Formal Synthesis of Salinosporamide Aj via NHC-Catalyzed Intramolecular Lactonization" Tetrahedron (2009) 65:4957-67.

Takahashi, et al., "Entry of Heterocycles Based on Indium Catalyzed Conia-Ene Reactions: Asymmetric Synthesis of (−)-Salinosporamide A" Angew. Chemie. Int. Ed., (2008) 47:1-4.

International Search Report and Written Opinion dated Sep. 28, 2010 for PCT Application No. PCT/US2009/036376, Filed Mar. 6, 2009.

International Preliminary Report on Patenability dated Oct. 5, 2010 for PCT Application No. PCT/US2009/036376, Filed Mar. 6, 2009.

EFS of U.S. Appl. No. 11/697,689, filed Apr. 6, 2007.

EFS of U.S. Appl. No. 12/399,382, filed Mar. 6, 2009 as of Jan. 25, 2011.

EFS of U.S. Appl. No. 10/821,621, filed Apr. 9, 2004.

EFS of U.S. Appl. No. 11/539,648, filed Oct. 9, 2006.

EFS of U.S. Appl. No. 12/028,024, filed Feb. 8, 2008.

EFS of U.S. Appl. No. 11/224,589, filed Sep. 12, 2005.

Andrews, et al., "Highly Functionalised Pyroglutamates by Intramolecular Aldol Reactions: Towards the Pyroglutamate Skeleton of Oxazolomycin", Synlett: Letters (1996) 612-614.

Andrews, et al., "Regioselective dieckmann cyclisations leading to enantiopure highly functionalised tetramic acid derivatives", J. Chem. Soc., Perkin Trans. (1998) 1:223-235.

Caubert et al., "Stereoselective formal synthesis of the potent proteasome inhibitor: salinosporamide A" Tetrahedron Lett. (2007) 48 :381-4.

Caubert et al., "Studies toward the synthesis of salinosporamide A, a potent proteasome inhibitor" Tetrahedron Lett (2006) 47:4473-5.

Corey, et al., "An efficient tool synthesis of a new and highly active analog of lactacystin", Tetrahedron Letters (1998) 39:7475-7478.

Endo, et al., "Total synthesis of salinosporamide A", J. Am. Chem. Soc. (2005) 127:8298-8299 and S1-S23.

Hogan, et al., "Proteasome inhibition by a totally synthetic β-lactam related to salinosporamide A and omuralide", J. Am. Chem. Soc. (2005) 127:15386-15387.

Kramer et al., "Organoboranes: XIX *. The Preparation and Some Unusual Chemistry of B-allyl Derivatives of 9-Borabicyclo[3.3.1]nonane" J. Organomet. Chem (1977) 132 :9-27.

Ling et al., "Enantioselective Total Synthesis of (−)-Salinosporamide A (NPI-0052)" Org. Lett (2007) 9:2289-92 & Supporting Information, pp. S1-S34.

Ma, et al., Concise total synthesis of (±)-salinosporamide A, (±)-cinnabaramide A, and derivatives via a bis-cyclization process: implications for a biosynthetic pathway?, Org. Lett., (2007) 9(11):2143-2146.

Manam et al. "Enantioselective enzymatic conversion of keto-salinosporamide to (−)-Salinosporamide A (NPI-0052)" Tetrahedron Lett (2007) 48 :2537-40.

Mulholland, et al., "A concise total synthesis of salinosporamide A", Org. Biomol. Chem. (2006) 4:2845-2846.

Potts et al. "Generating a Generation of Proteasome Inhibitors: From Microbial Fermentation to Total Synthesis of Salinosporamide A (Marizomib) and Other Salinosporamides" Marine Drugs (2010) 8(4):835-80.

Reddy, et al., "A simple stereocontrolled synthesis of salinosporamide A", J. Am. Chem. Soc. (2004) 126:6230-6231.

Reddy, et al., "An efficient, stereocontrolled synthesis of a potent omuralide-salinosporin hybrid for selective proteasome inhibition", J. Am. Chem. Soc. (2005) 127:8974-8976.

Reddy, et al., "New synthetic route for the enantioselective total synthesis of salinosporamide A and biologically active analogues", Org. Lett. (2005) 7(13): 2699-2701.

Seebach et al., "73. Structure and Reactivity of Five- and Siz-Ring N,N-, N,O-, and O,O-Acetals: A Lesson in Allylic 1,3-Strain (A1,3 Strain)" Hely Chim Acta (1992) 75:913-34.

Seebach et al., "Self-Regeneration of Stereocenters (SRS)-Applications, Limitations, and Abandonment of a Synthetic Principle" Angew Chem Int. Ed (1996) 35:2708-48.

Seebach, et al., "α-Alkylation of serine with self-reproduction of the center of chirality", Tetrahedron Letters (1984) 25(24):2545-2548.

International Preliminary Report on Patenability dated Oct. 8, 2008 for PCT Application No. PCT/US2007/008562, Filed Apr. 6, 2007.

International Search Report and Written Opinion dated Mar. 26, 2008, for PCT/US2007/008562, filed Apr. 6, 2007.

* cited by examiner

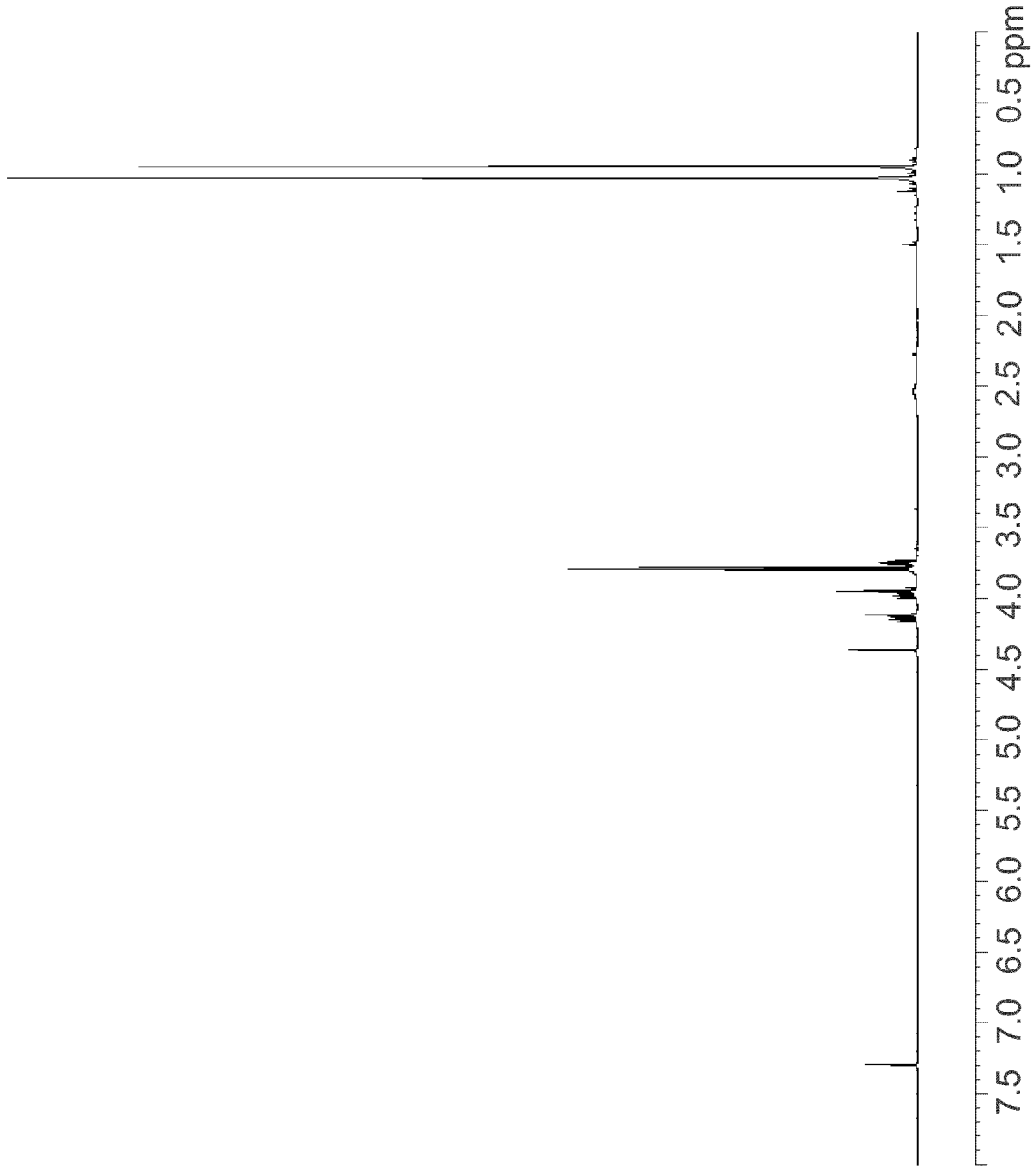

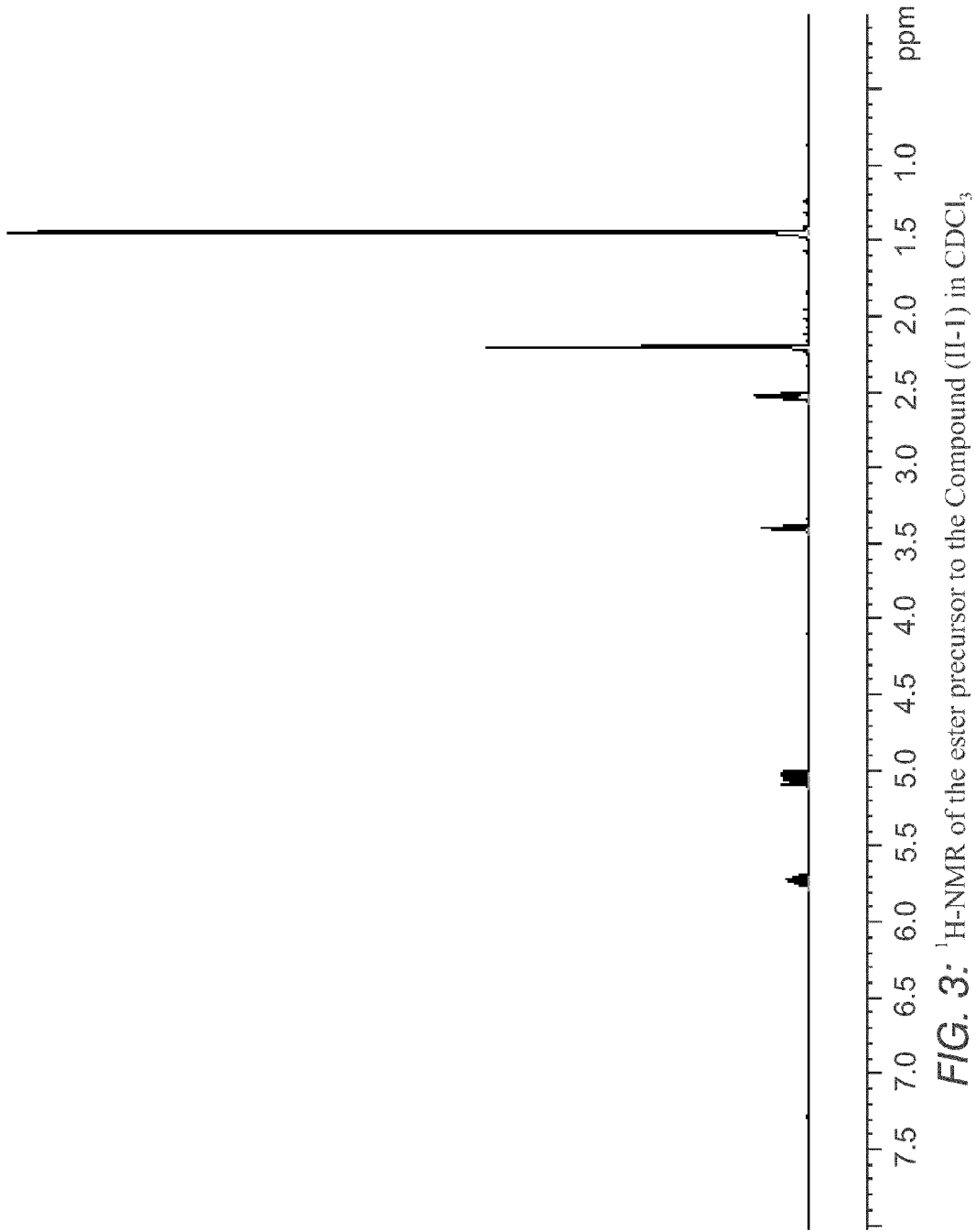
FIG. 3: $^1$H-NMR of the ester precursor to the Compound (II-1) in CDCl$_3$

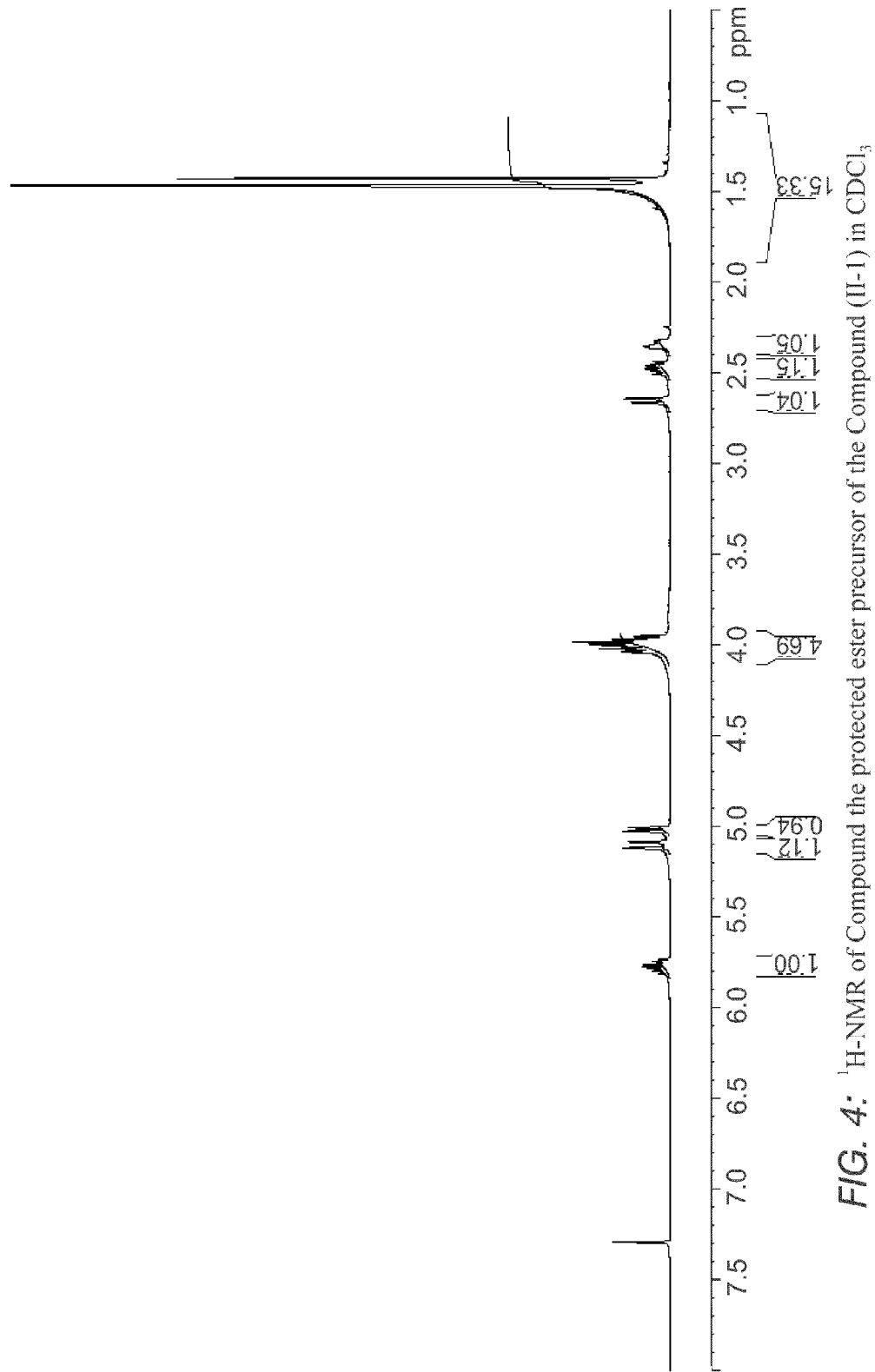
FIG. 4: ¹H-NMR of Compound the protected ester precursor of the Compound (II-1) in CDCl₃

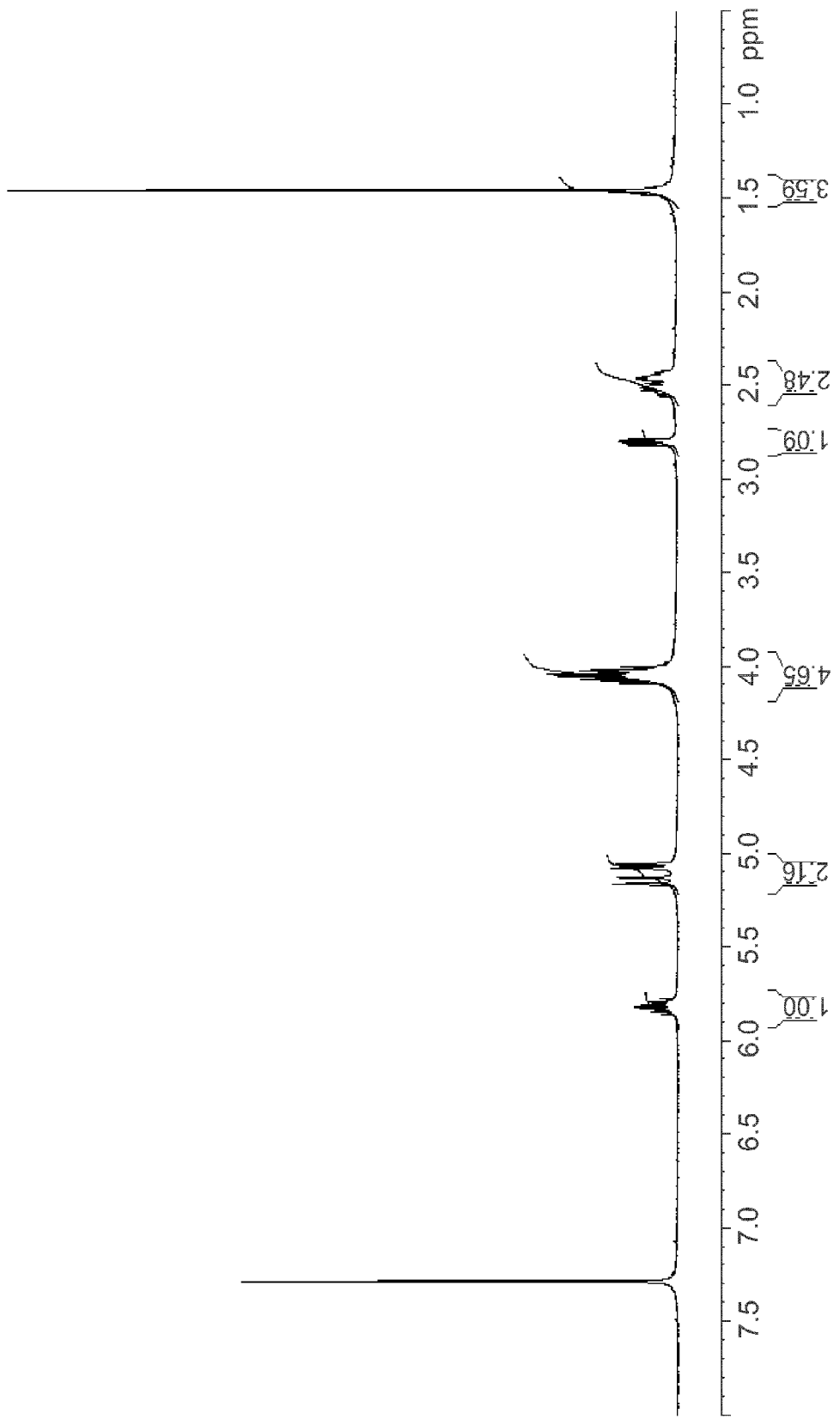
FIG. 5: ¹H-NMR of the Compound (II-1) in CDCl₃

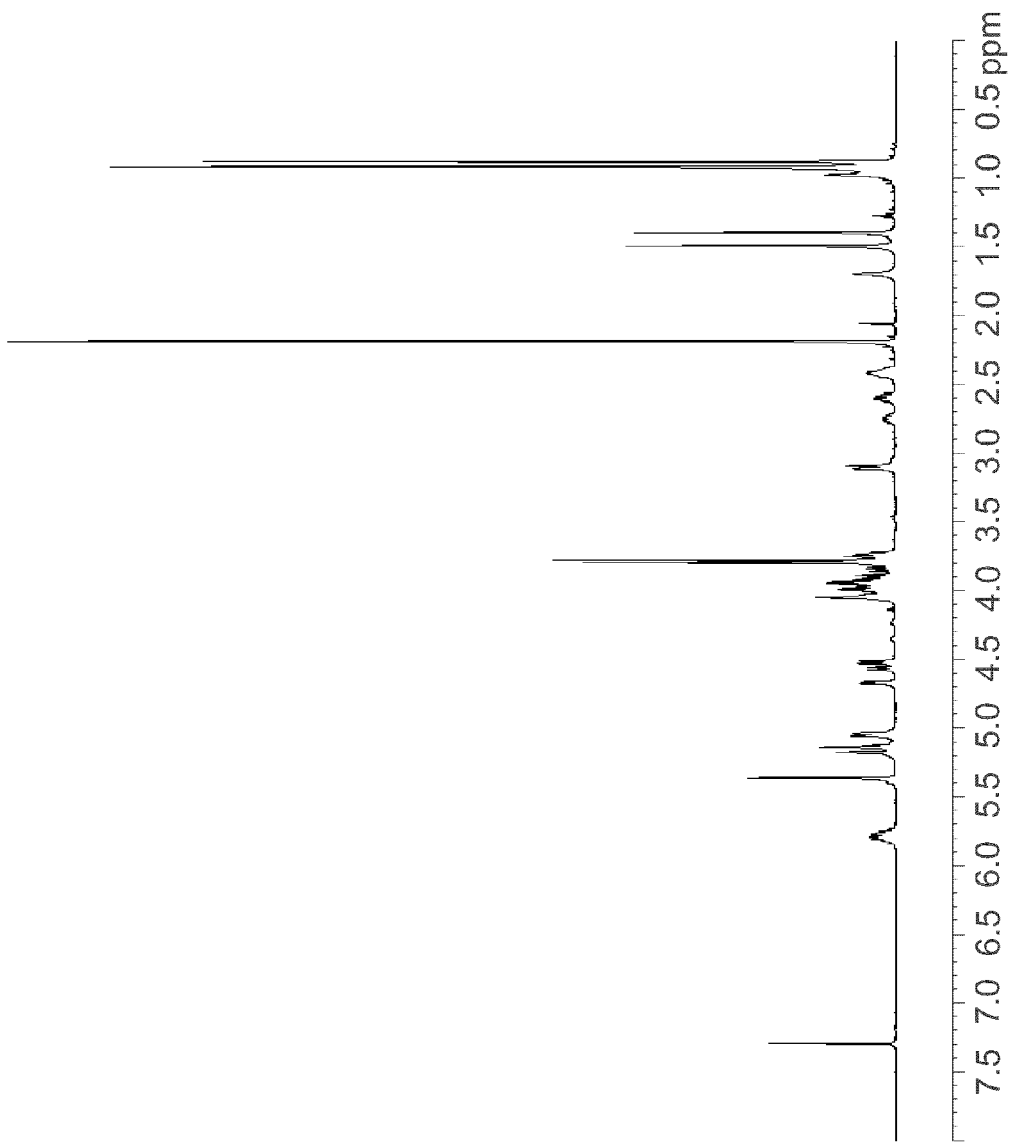
FIG. 6a: ¹H-NMR of Compound (III-1) in CDCl₃

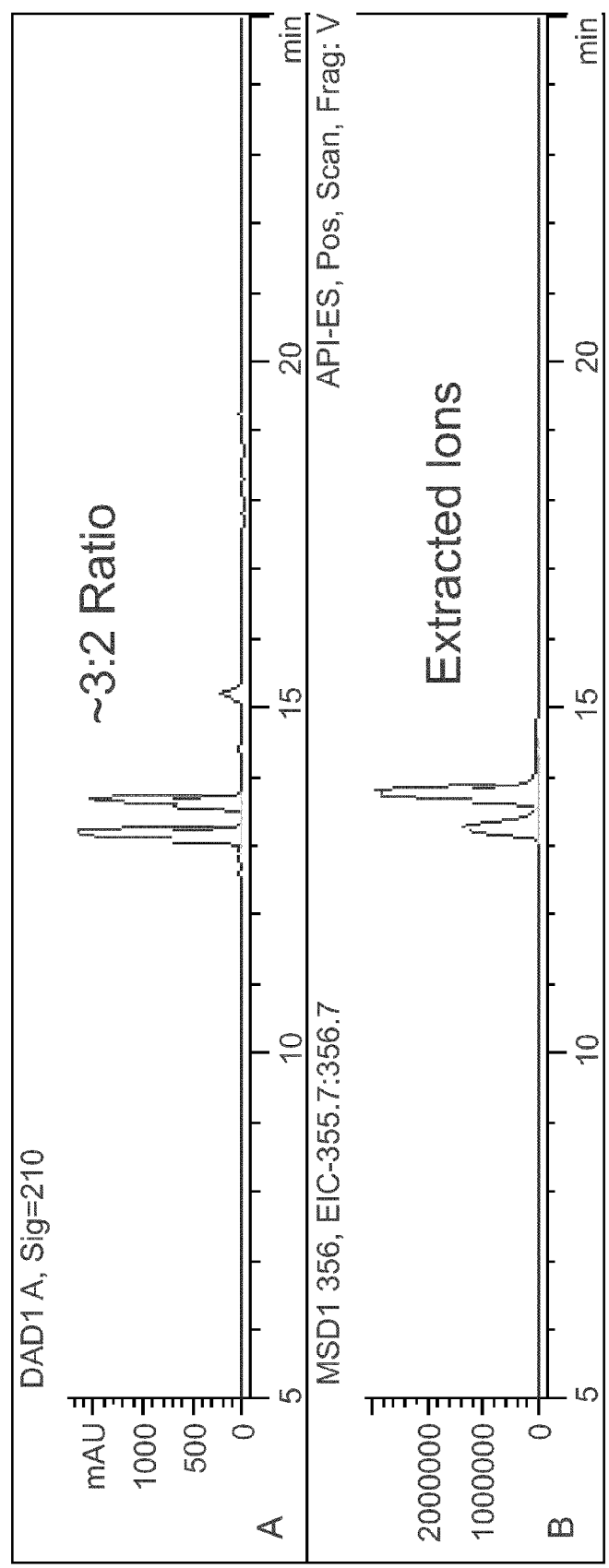
FIG. 6b: LC-MS of Compound (III-1)

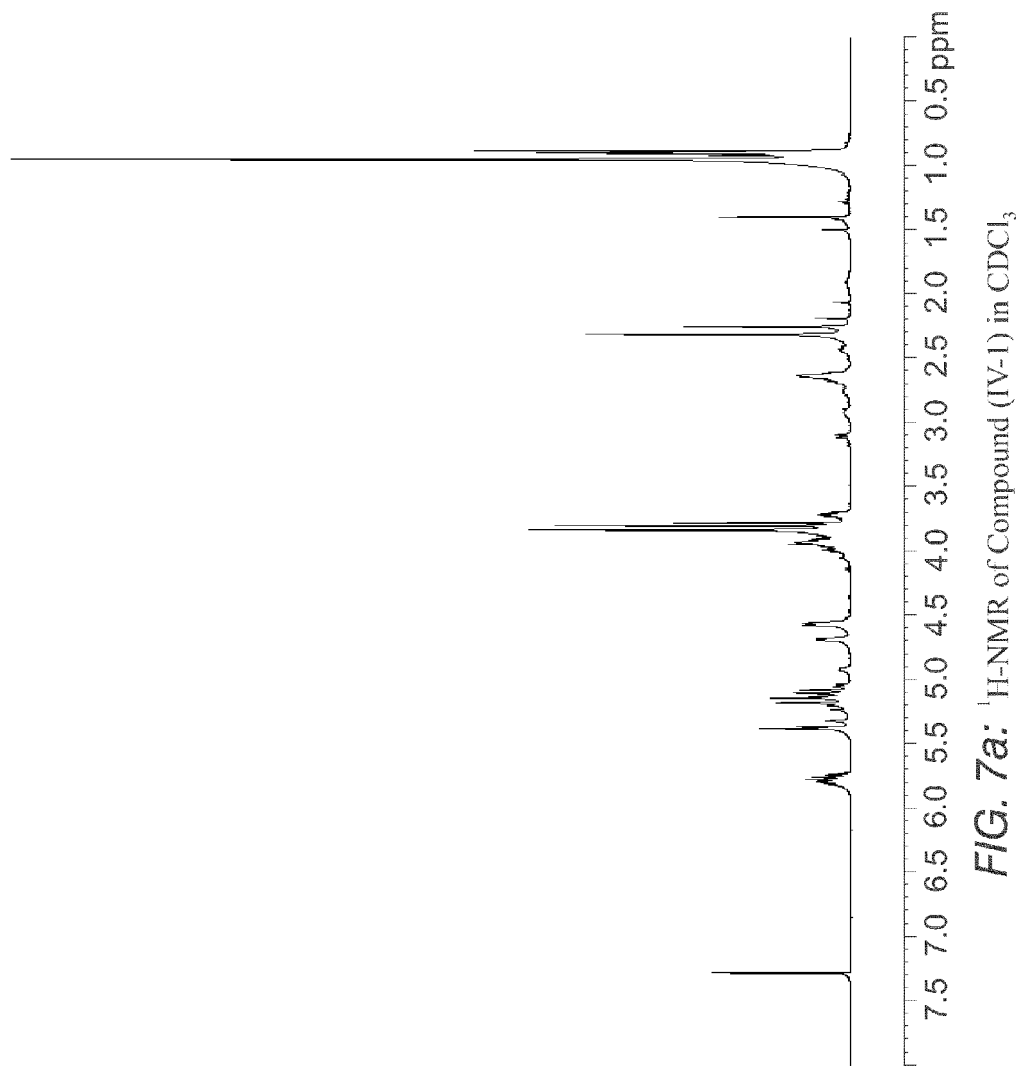

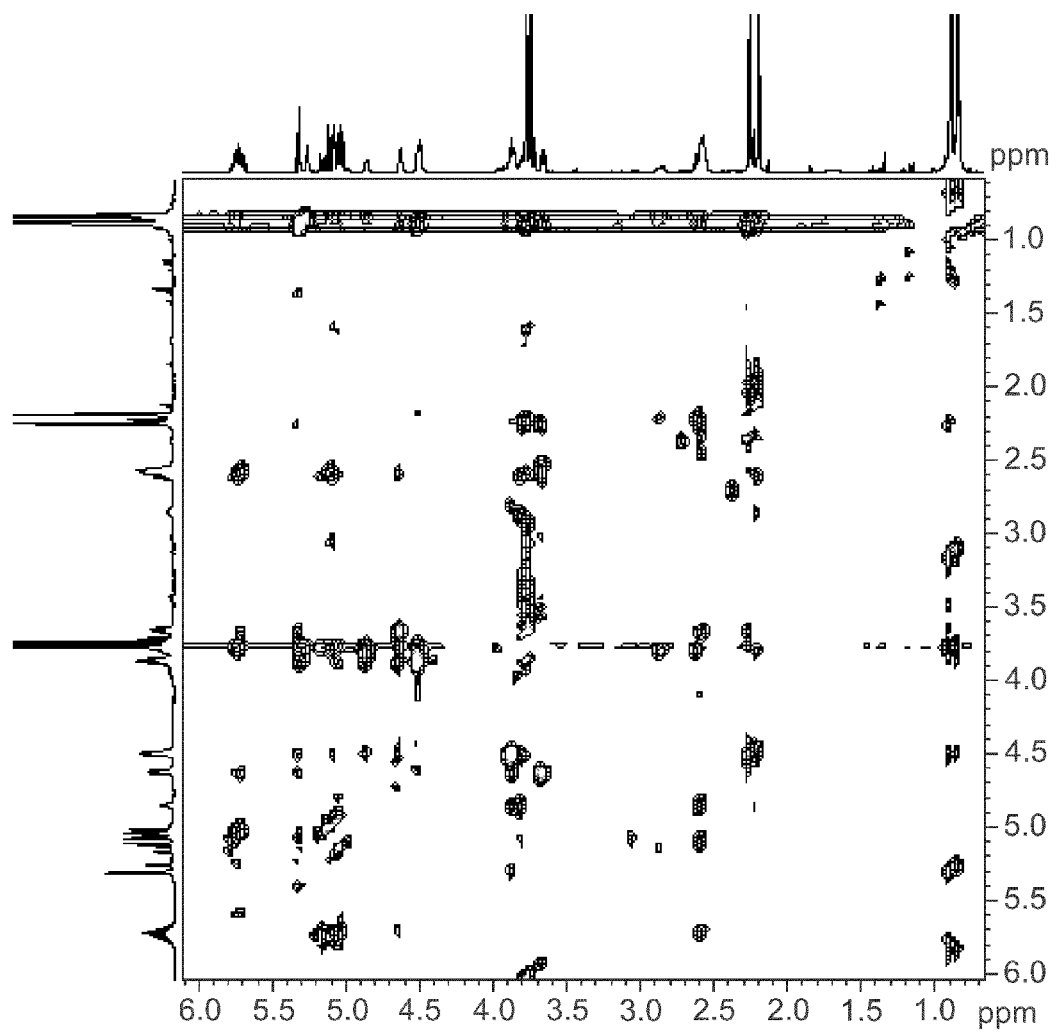
FIG. 7b: NOESY of Compound (IV-1)

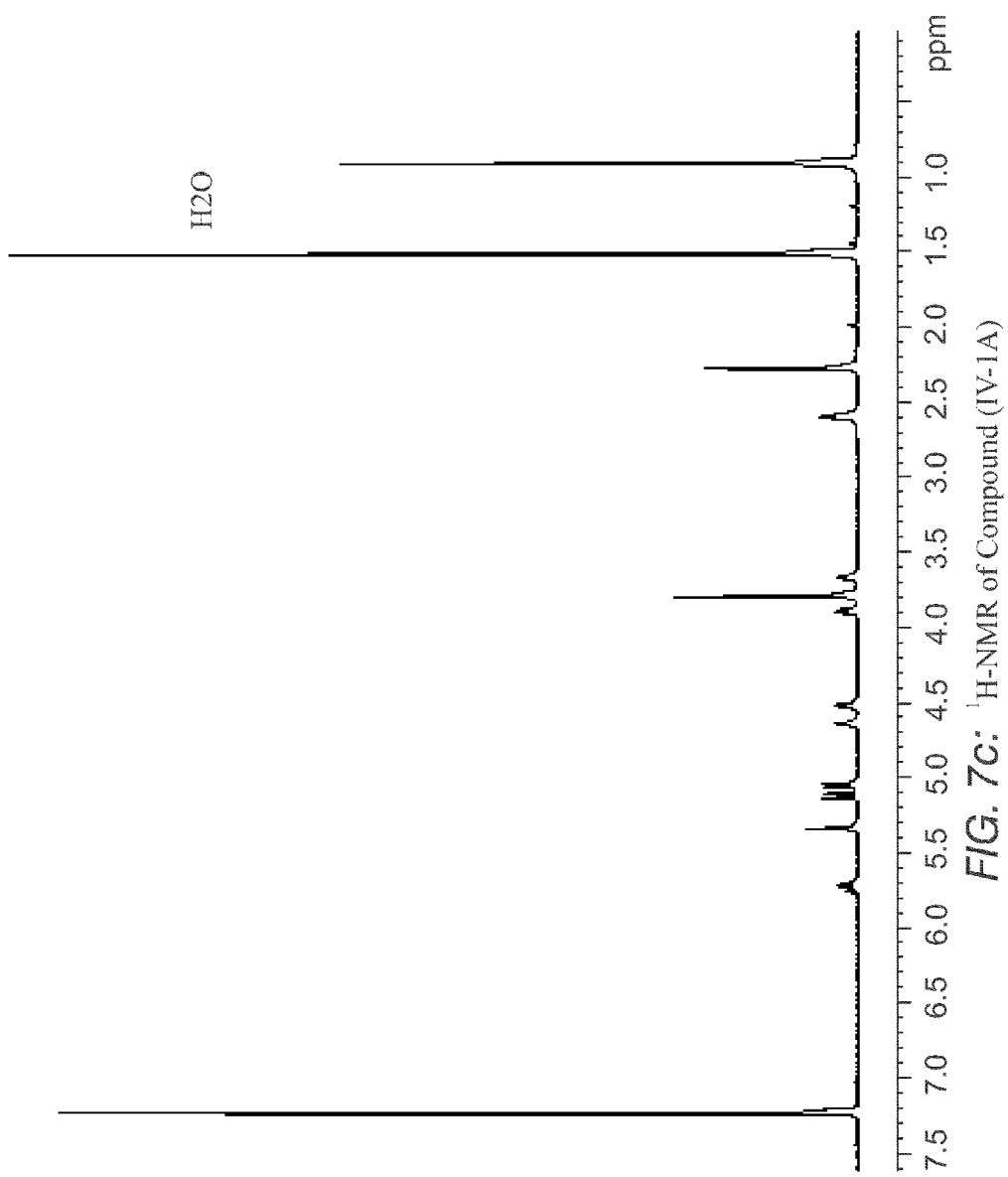

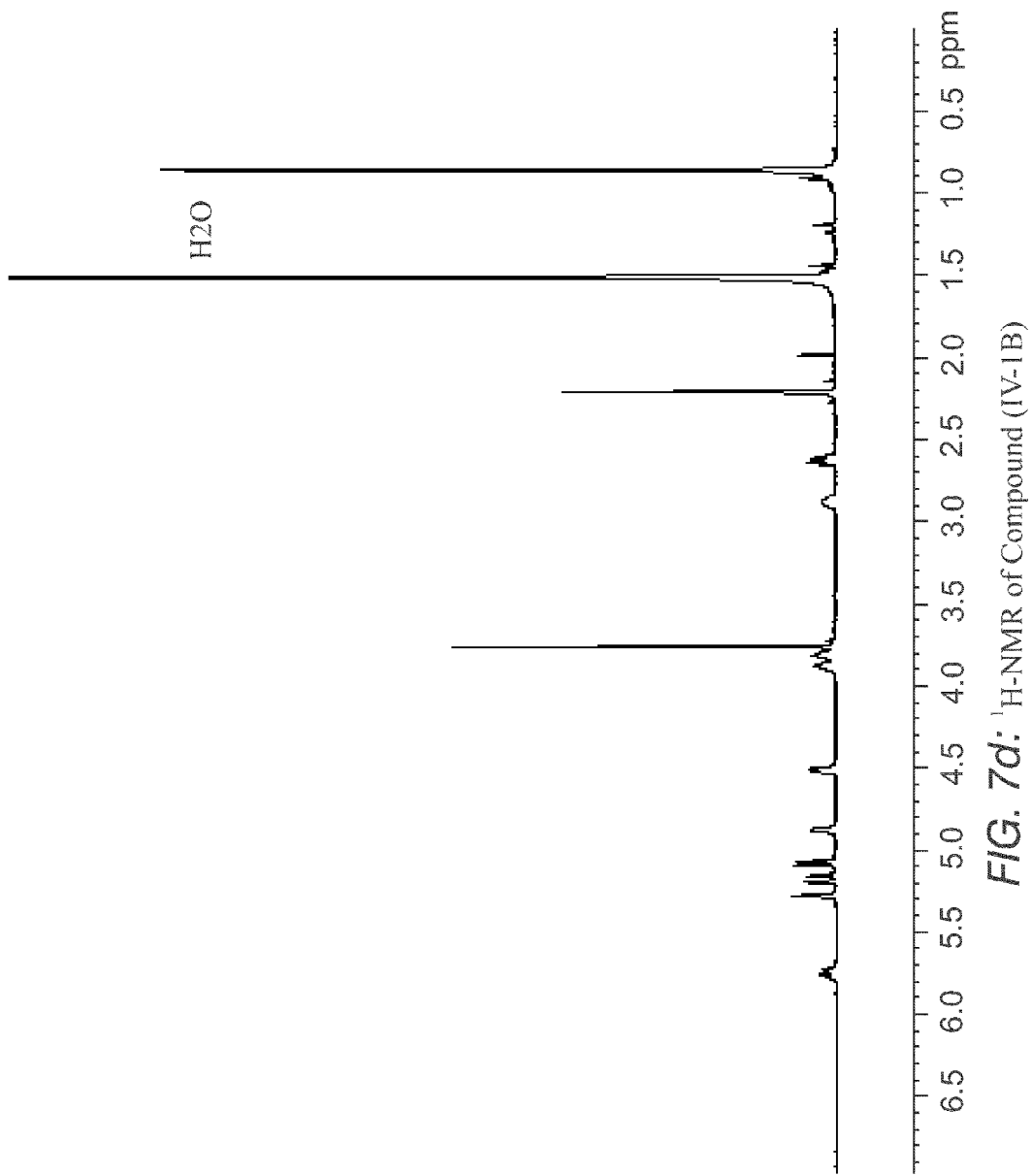
FIG. 7d: ¹H-NMR of Compound (IV-1B)

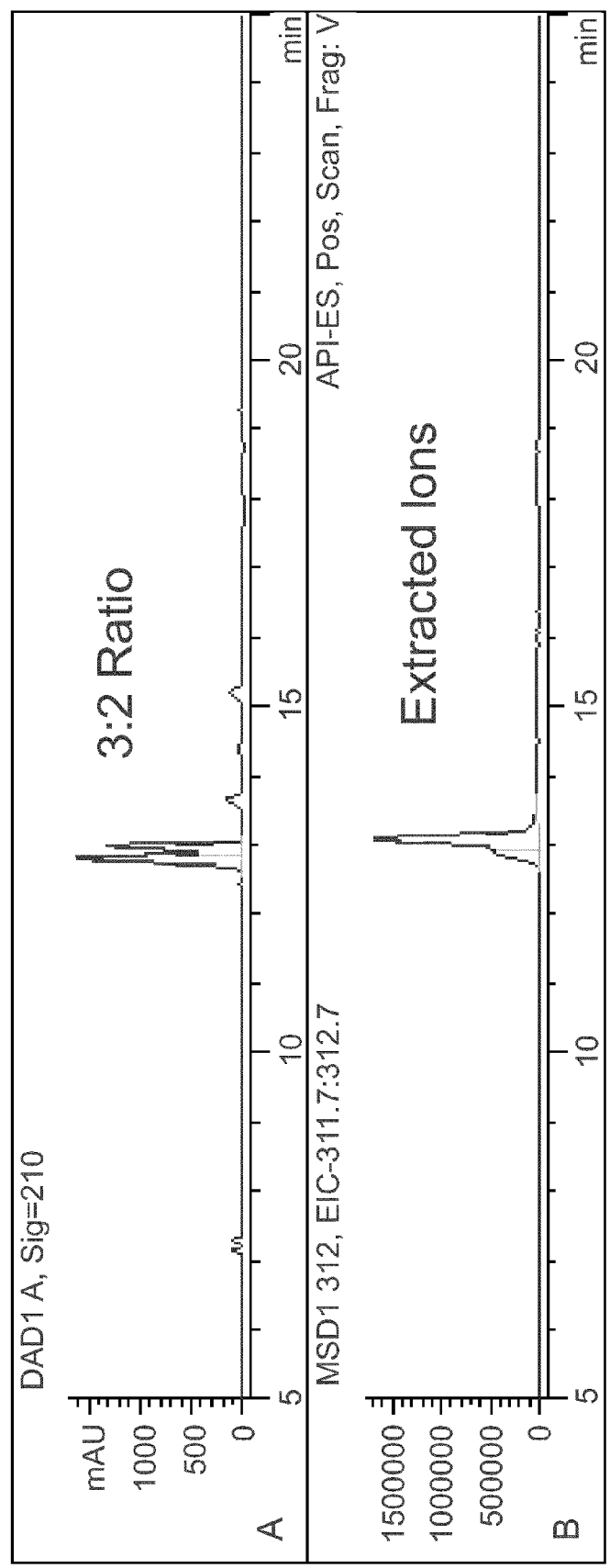
FIG. 7e: LC-MS of Compound (IV-1)

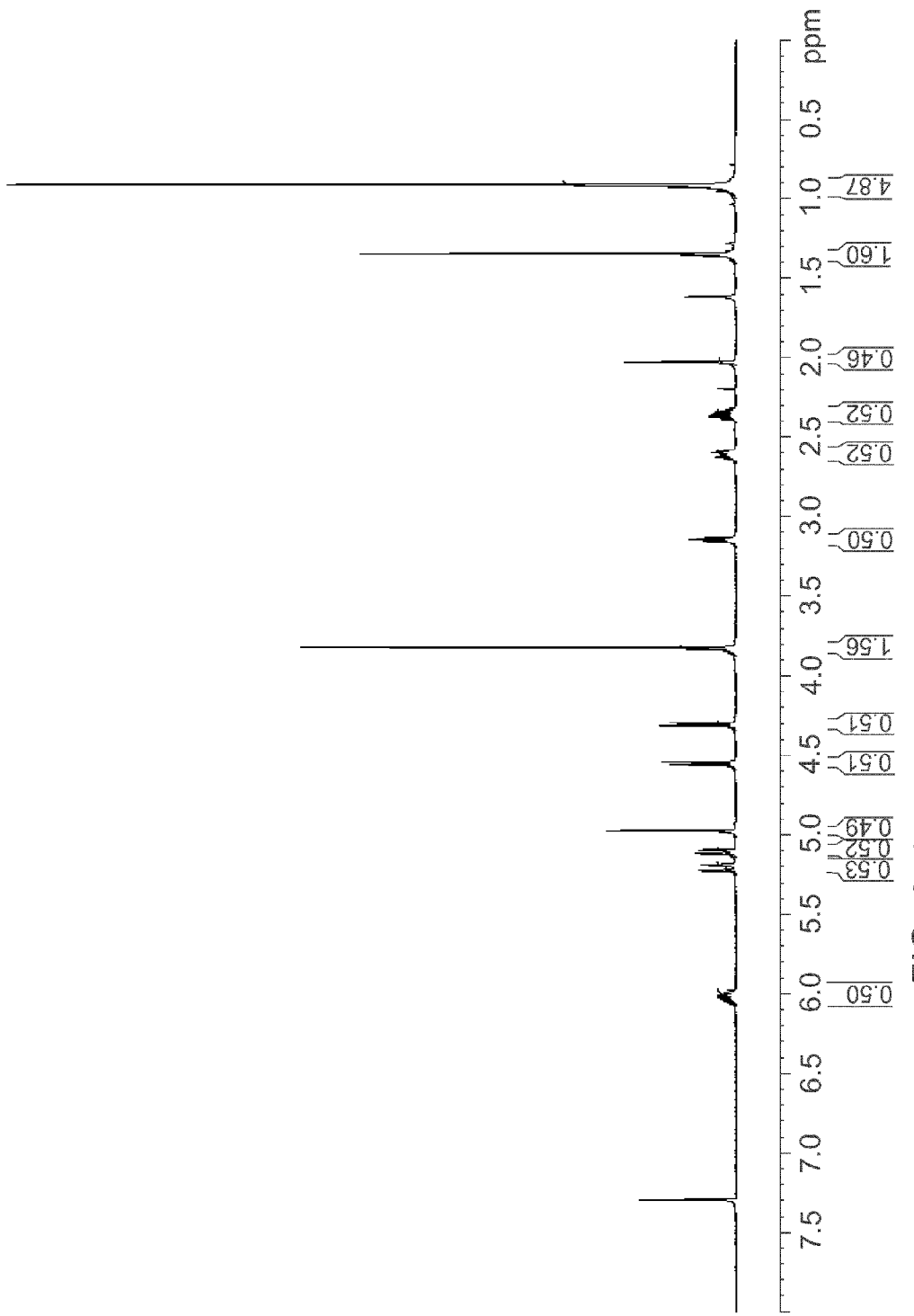
FIG. 8: $^1$H-NMR of Compound (VI-A) in CDCl$_3$

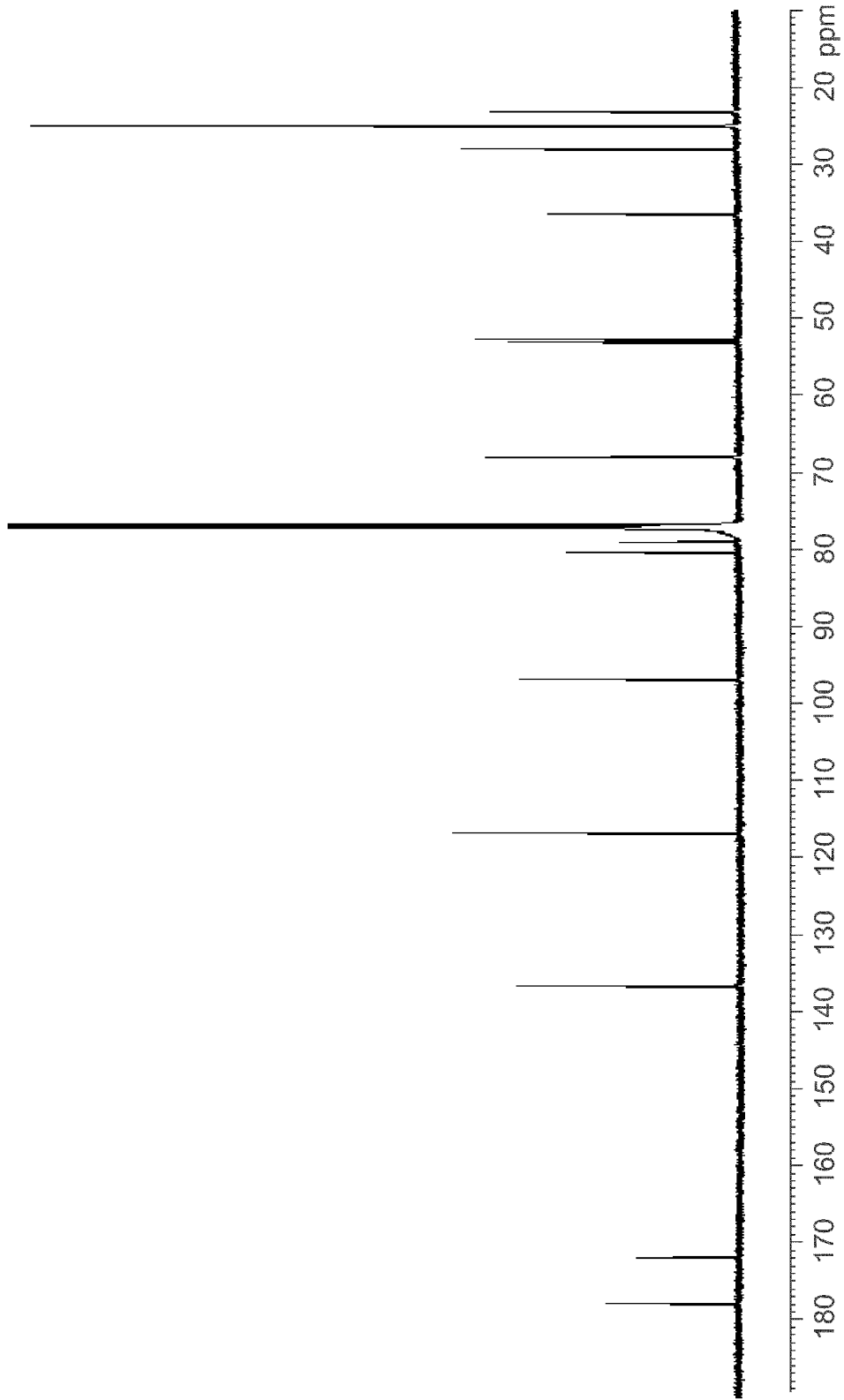
FIG. 9: $^{13}$C-NMR of Compound (V-1A) in CDCl$_3$

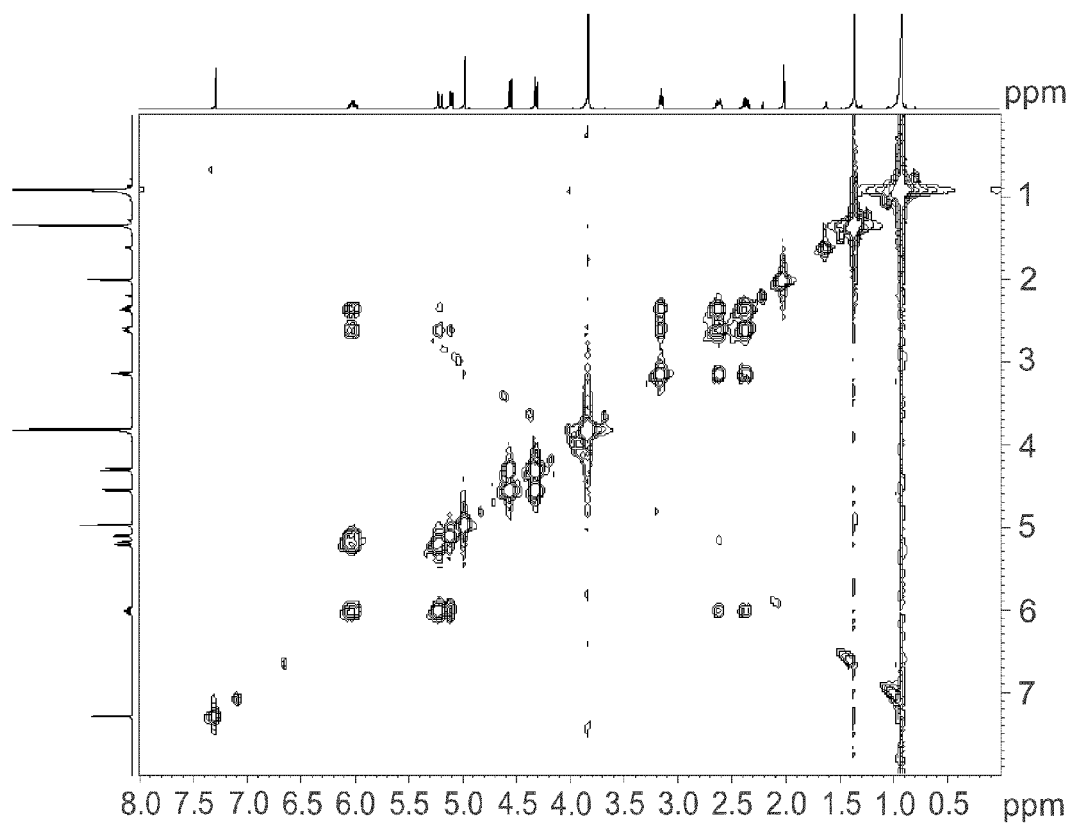
FIG. 10: $^1$H-$^1$H COSY of Compound (V-1A) in CDCl$_3$

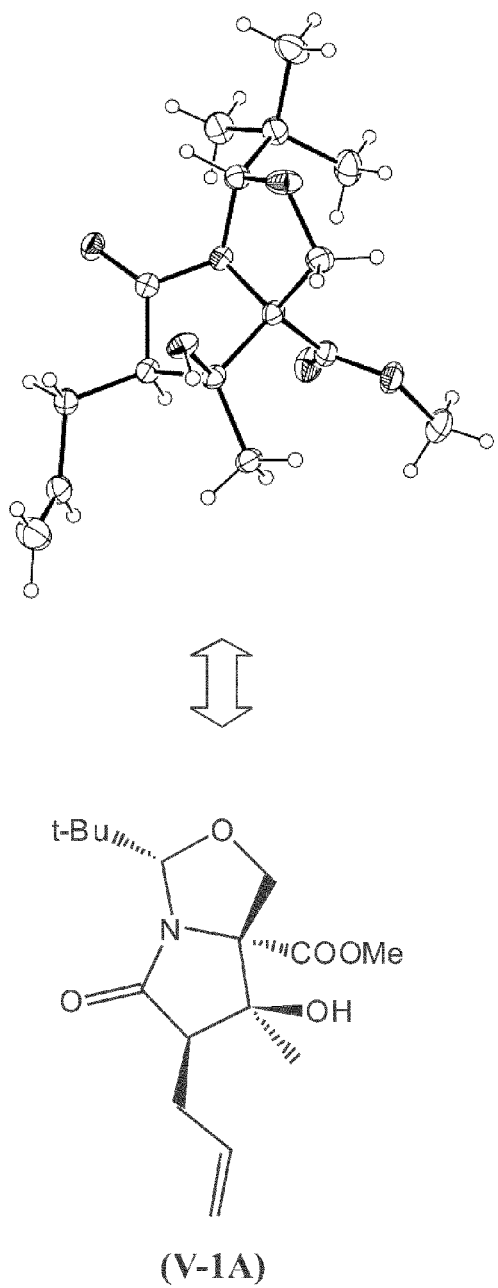
FIG. 11: ORTEP Plot of the X-ray Crystal Structure of Compound (V-1A)

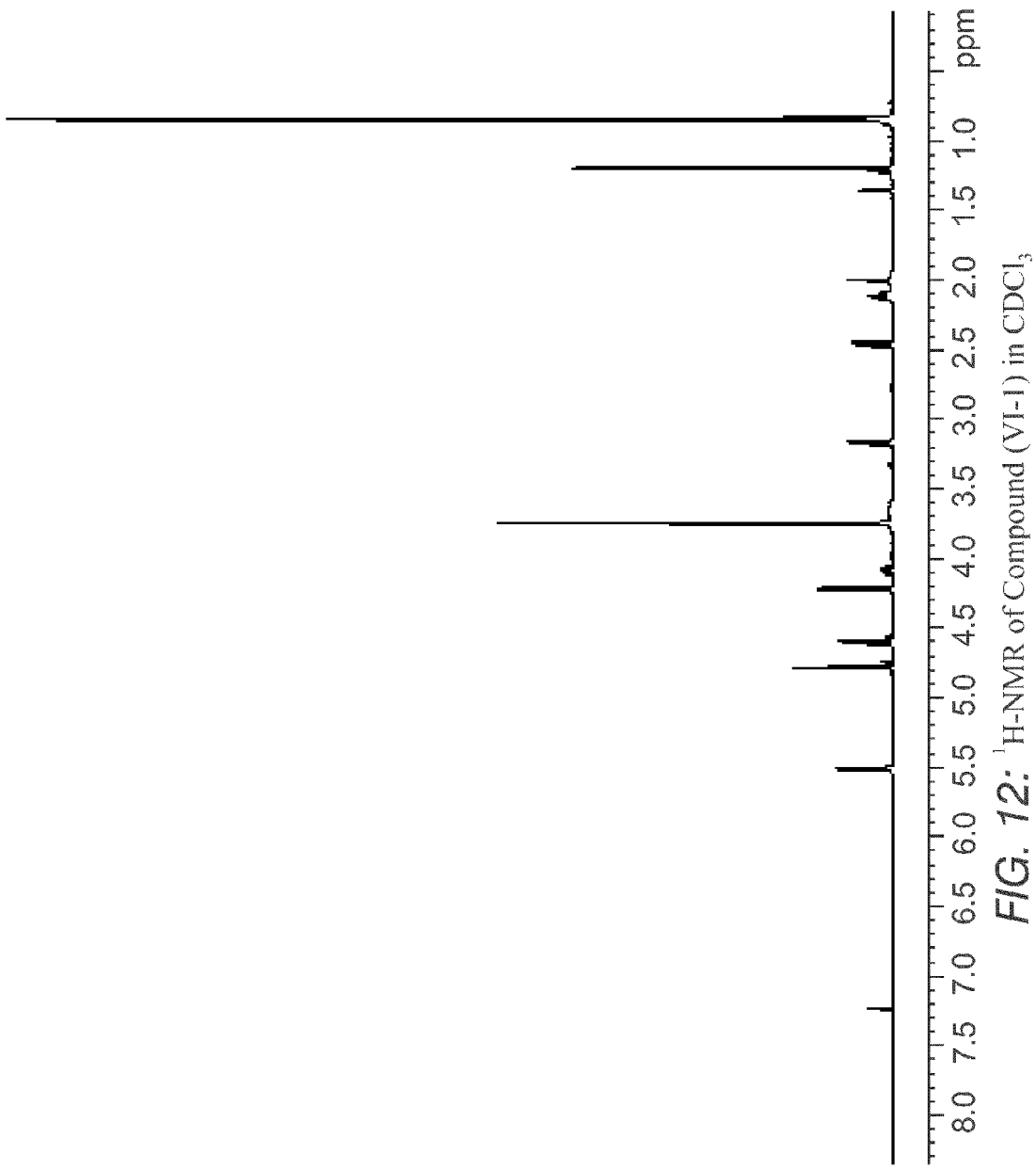
FIG. 12: ¹H-NMR of Compound (VI-1) in CDCl₃

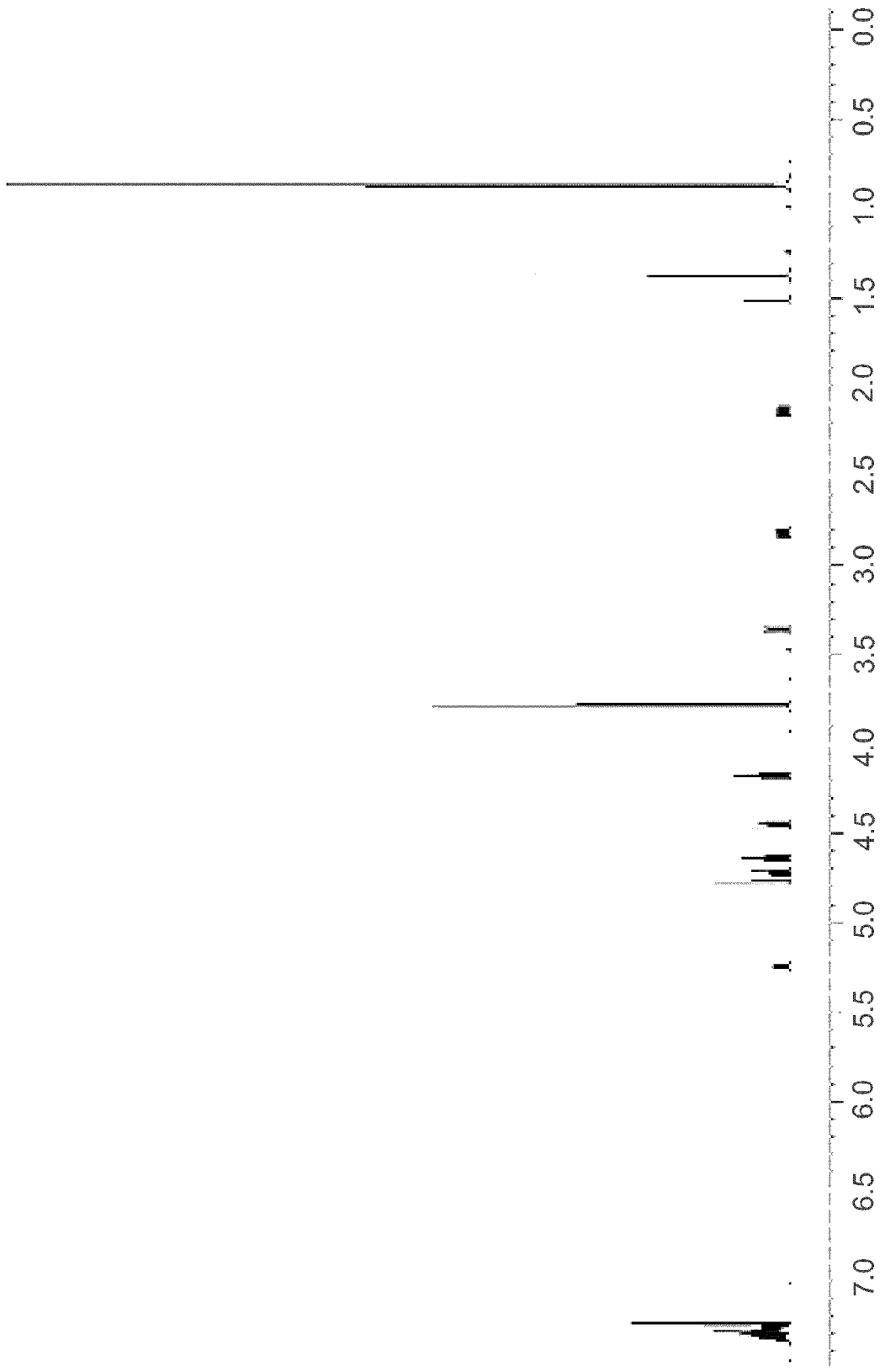
FIG. 13: $^1$H-NMR of Compound (VII-1$_a$) in CDCl$_3$

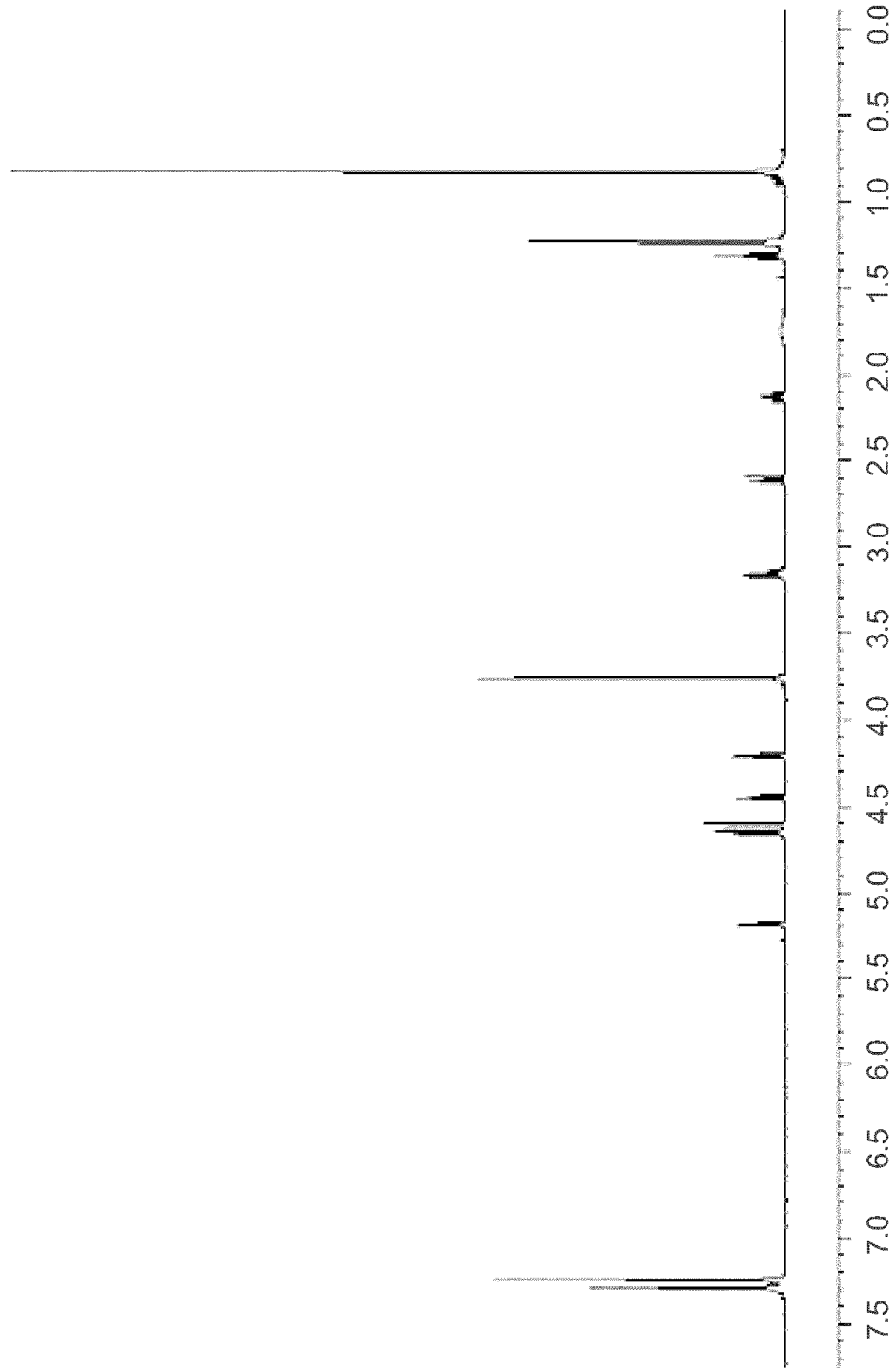

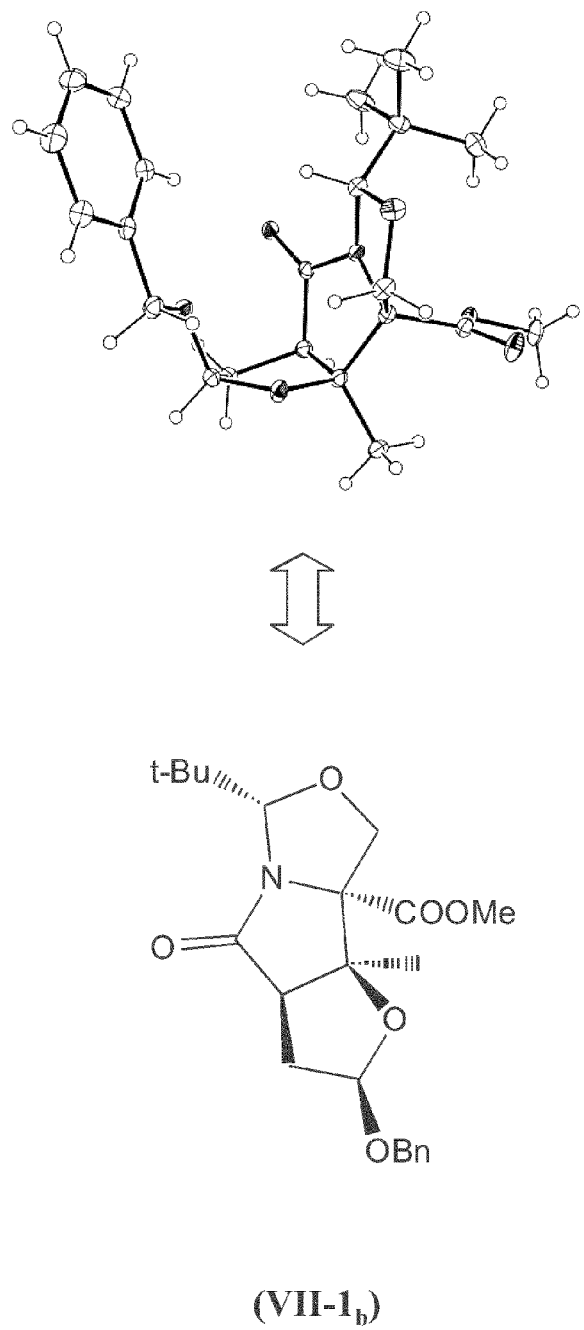
(VII-1_b)
FIG. 15: ORTEP Plot of the X-ray Crystal Structure of Compound (VII-1_b)

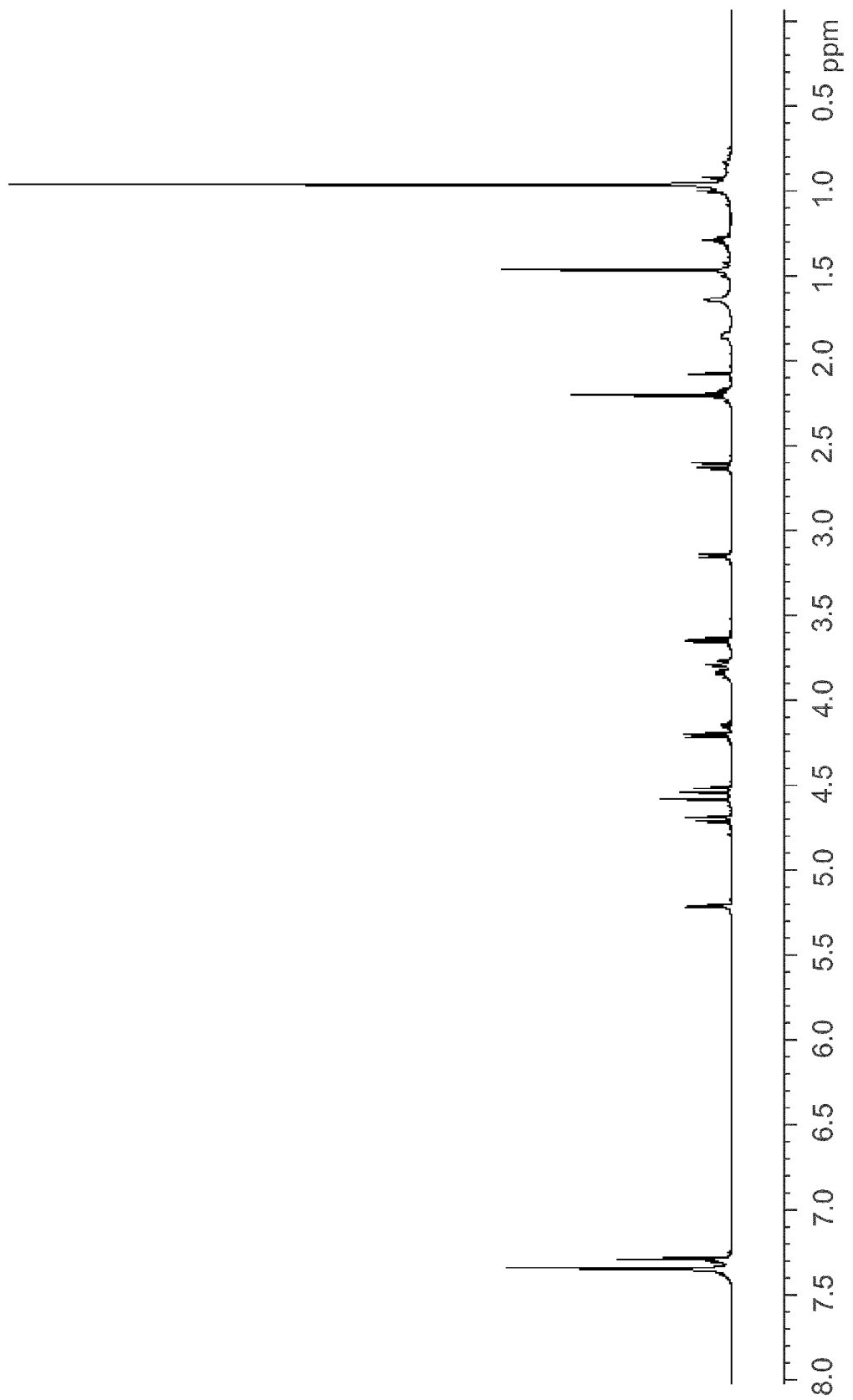
FIG. 16: $^1$H-NMR of Compound (VIII-1$_b$) in CDCl$_3$

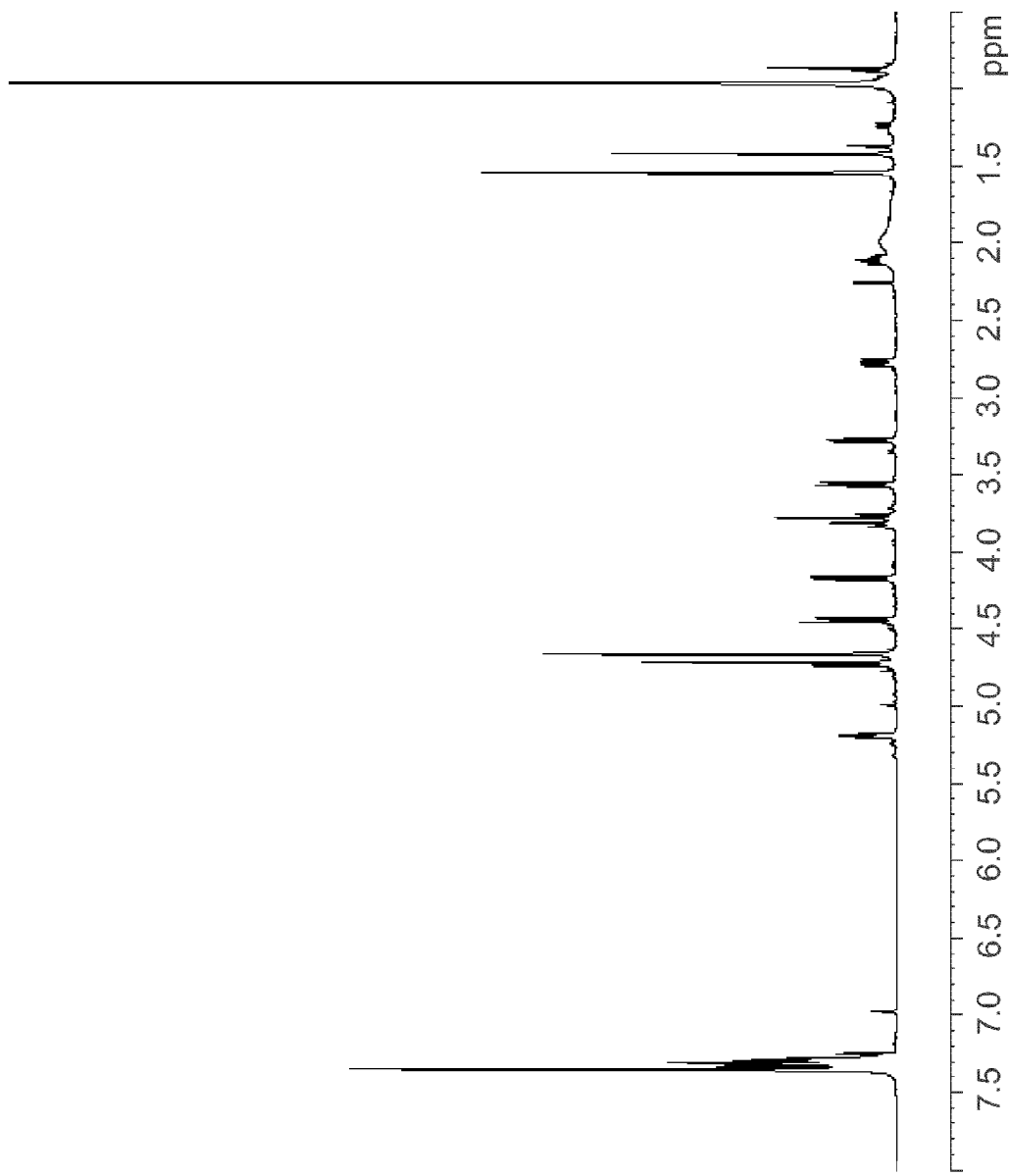

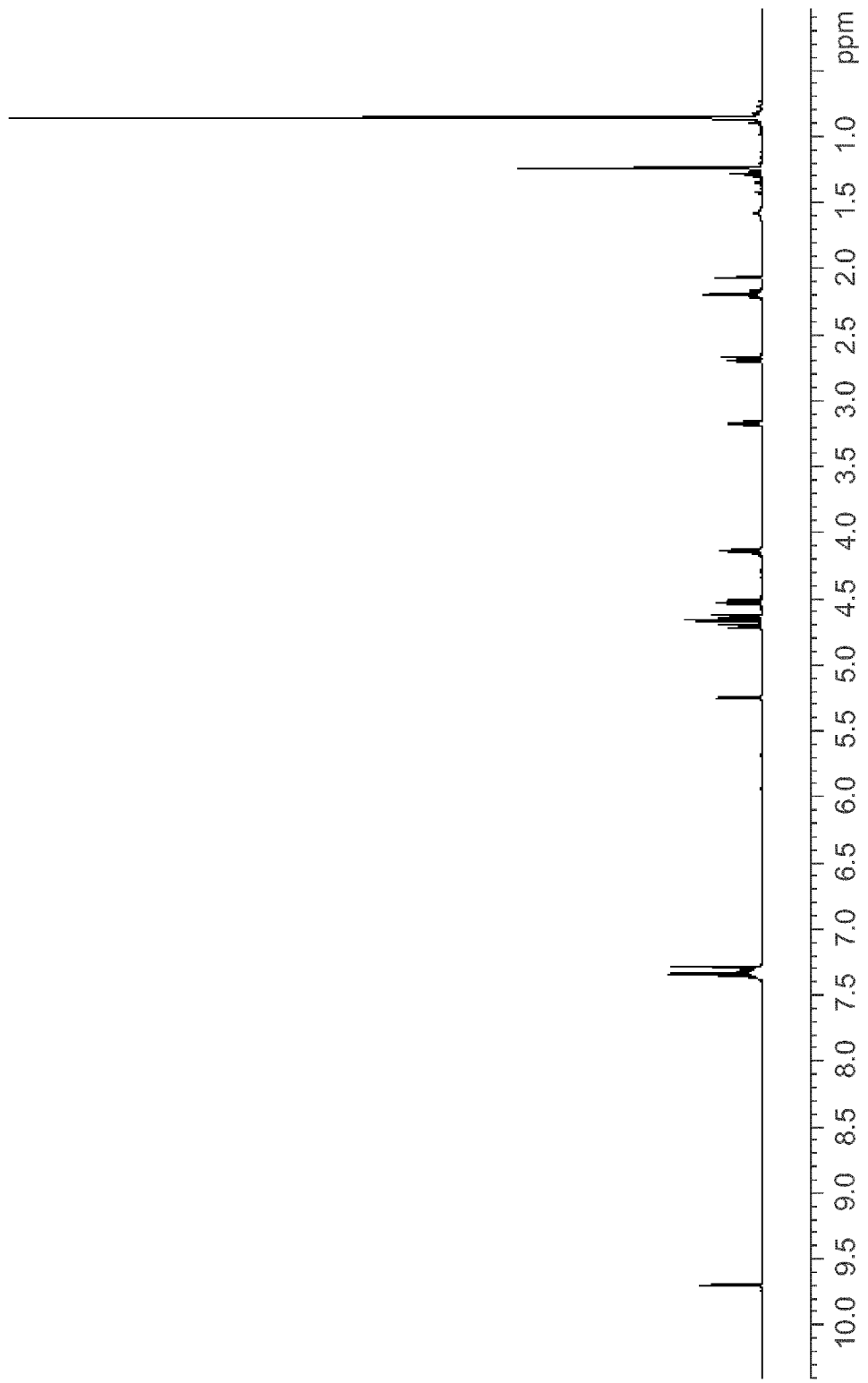
FIG. 18: $^1$H-NMR of Compound (IX-1$_b$) in CDCl$_3$

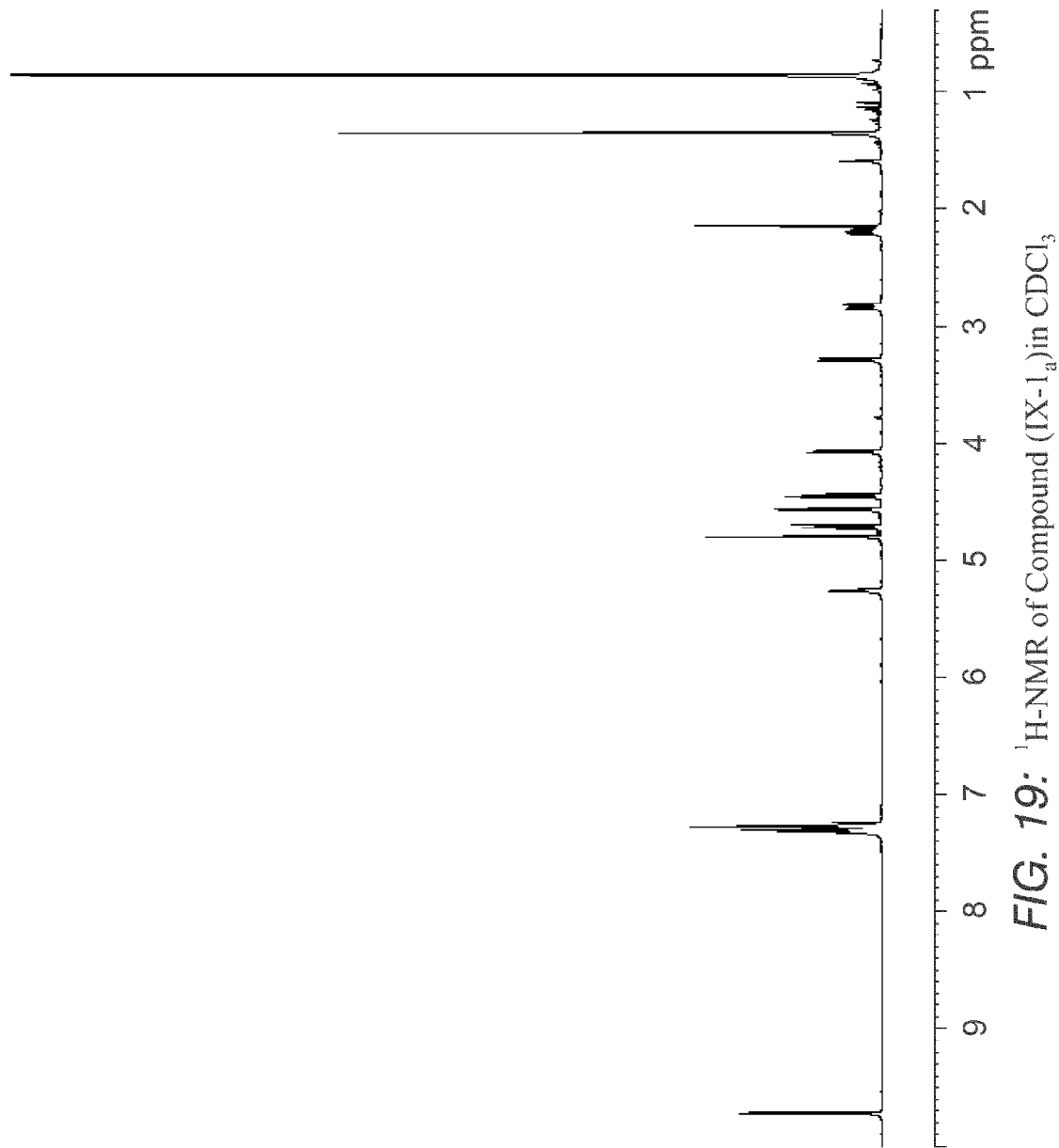
FIG. 19: ¹H-NMR of Compound (IX-1$_a$) in CDCl$_3$

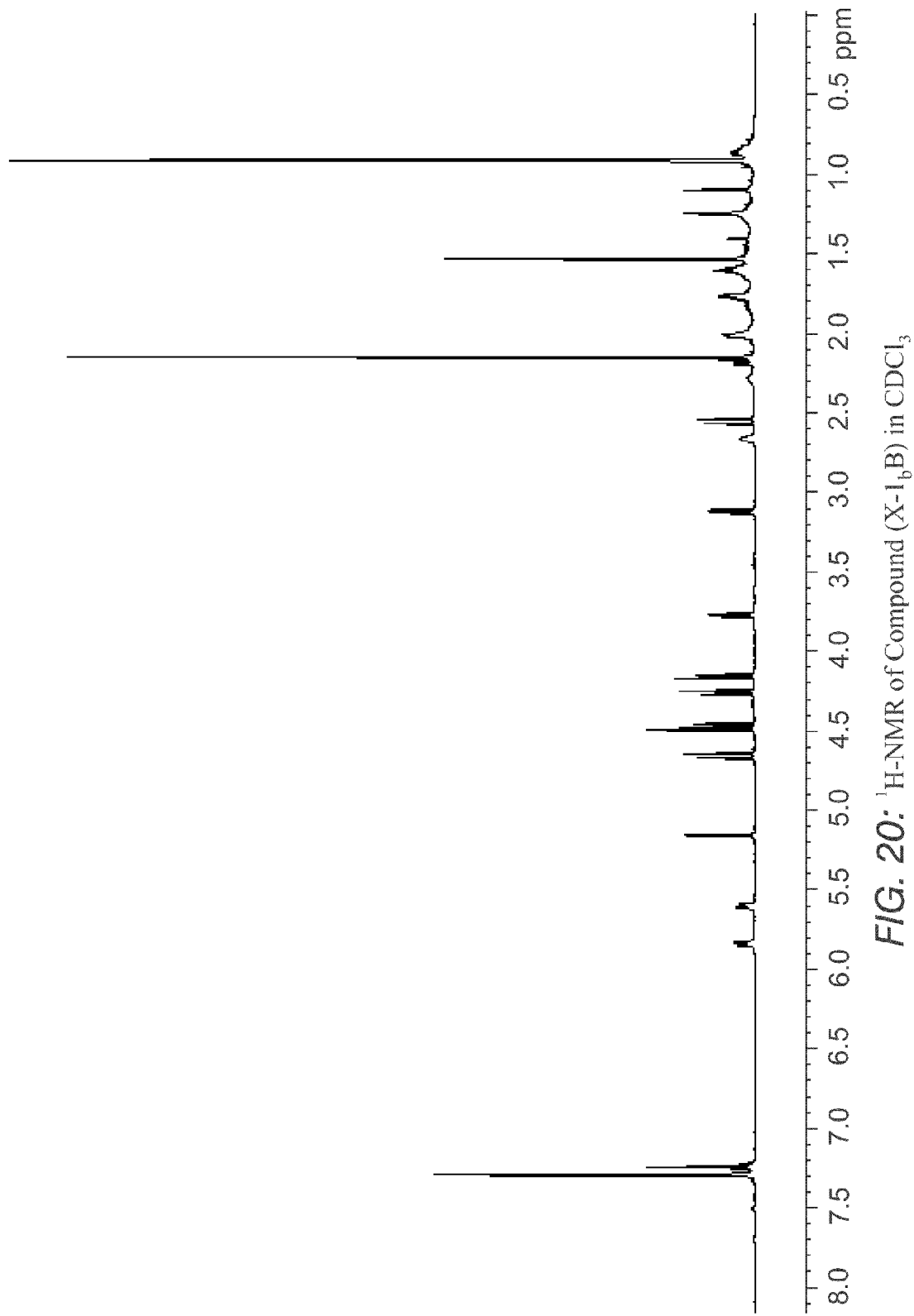
FIG. 20: $^1$H-NMR of Compound (X-1$_b$B) in CDCl$_3$

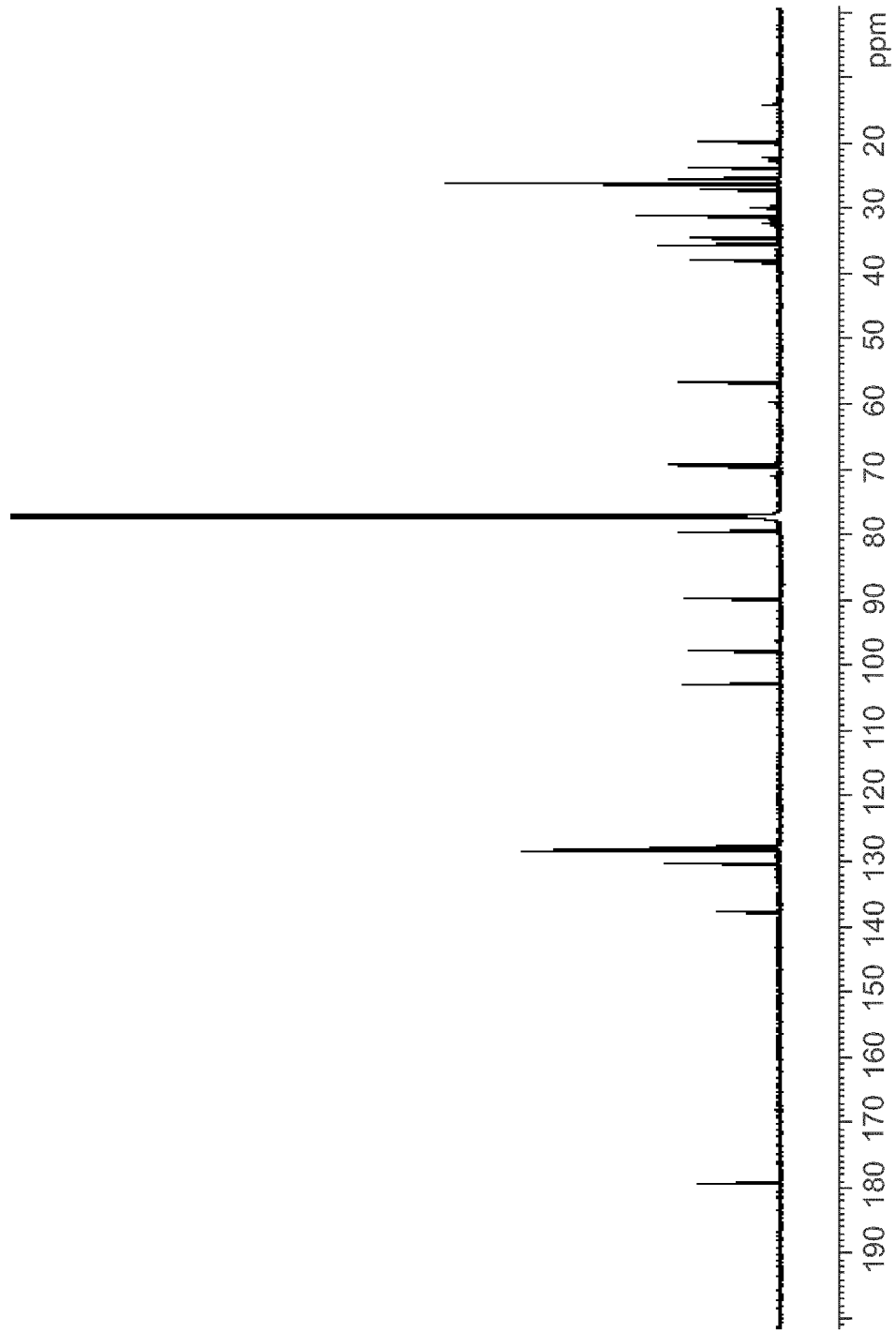
FIG. 21: $^{13}$C NMR of Compound (X-1$_b$B) in CDCl$_3$

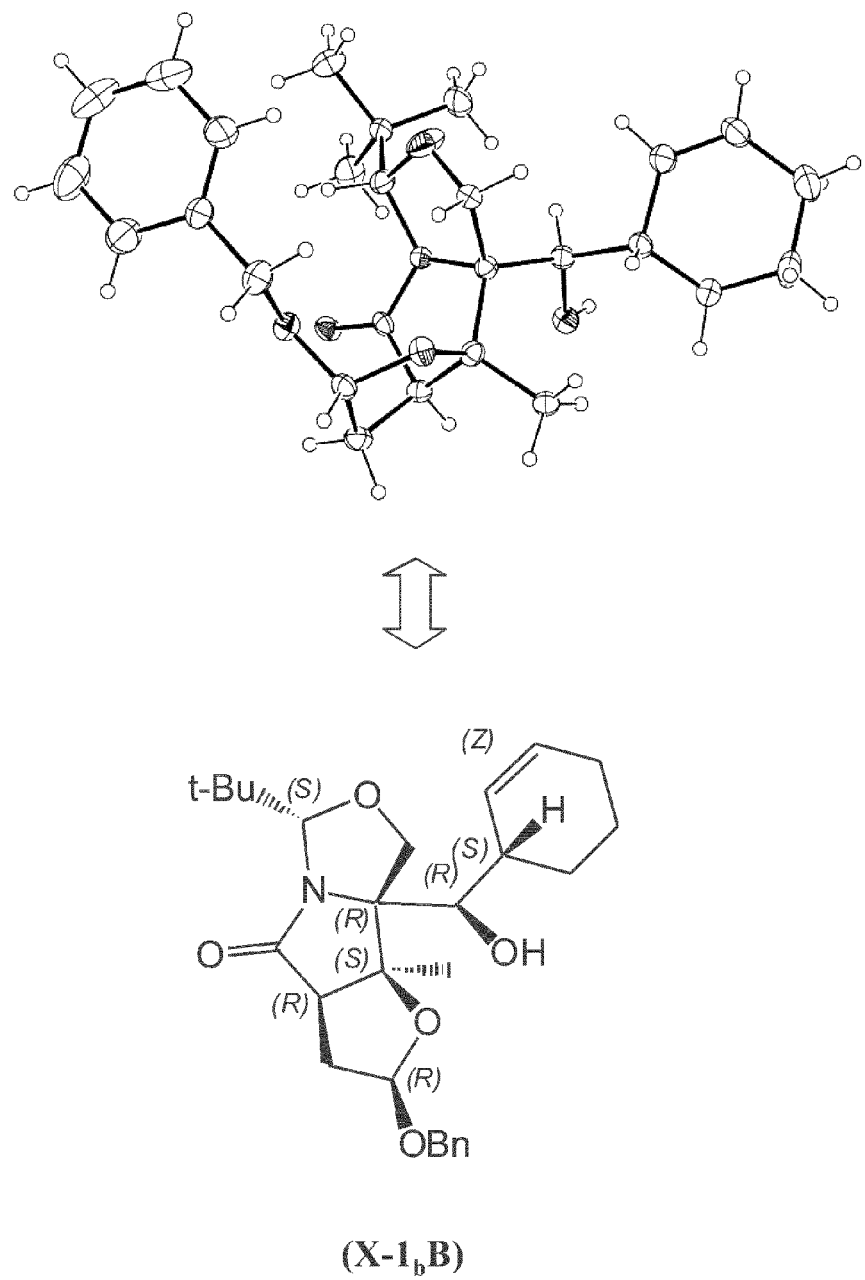
FIG. 22: ORTEP Plot of the X-ray Crystal Structure of Compound (X-1ᵦB)

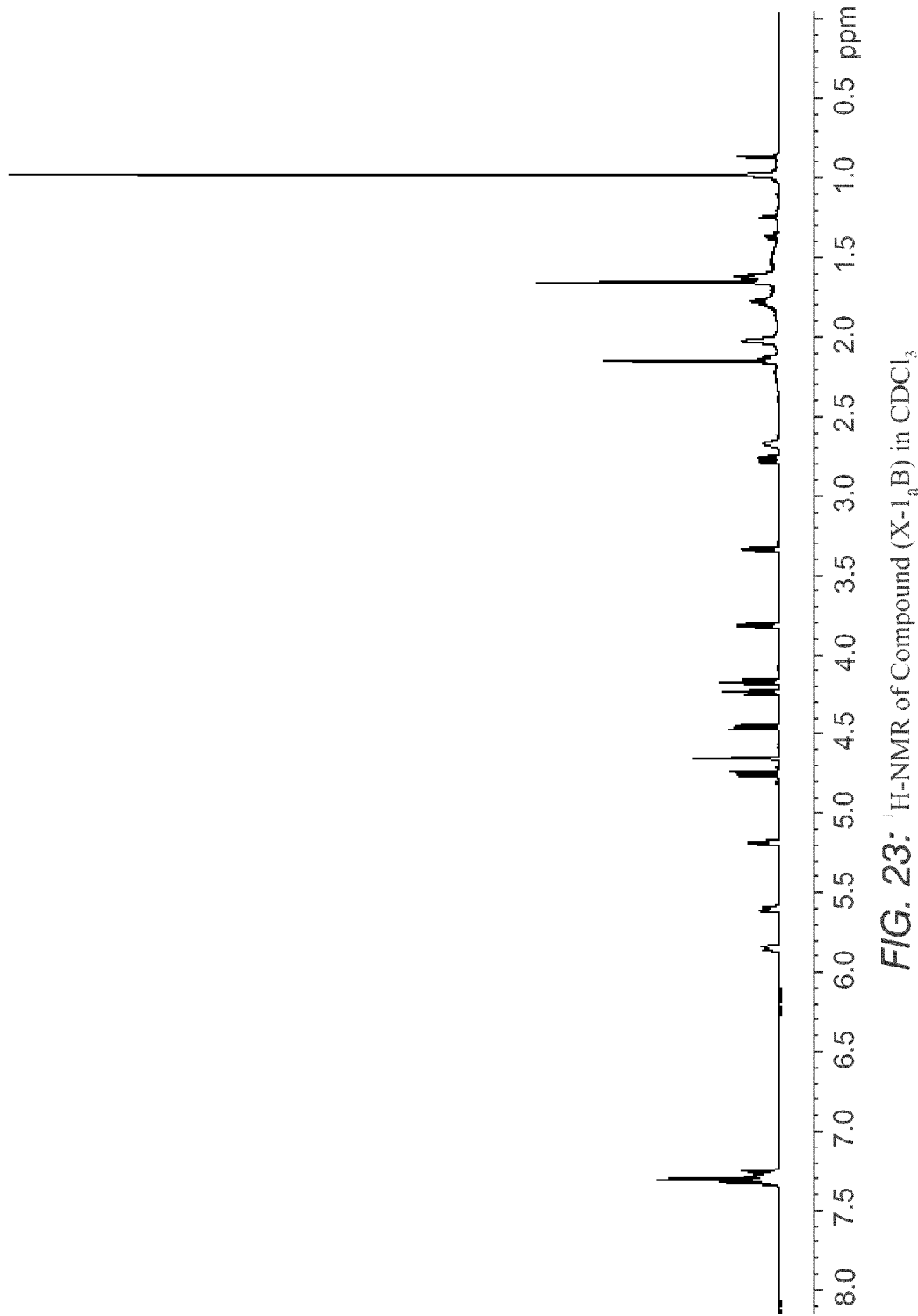
FIG. 23: $^1$H-NMR of Compound (X-1$_a$B) in CDCl$_3$

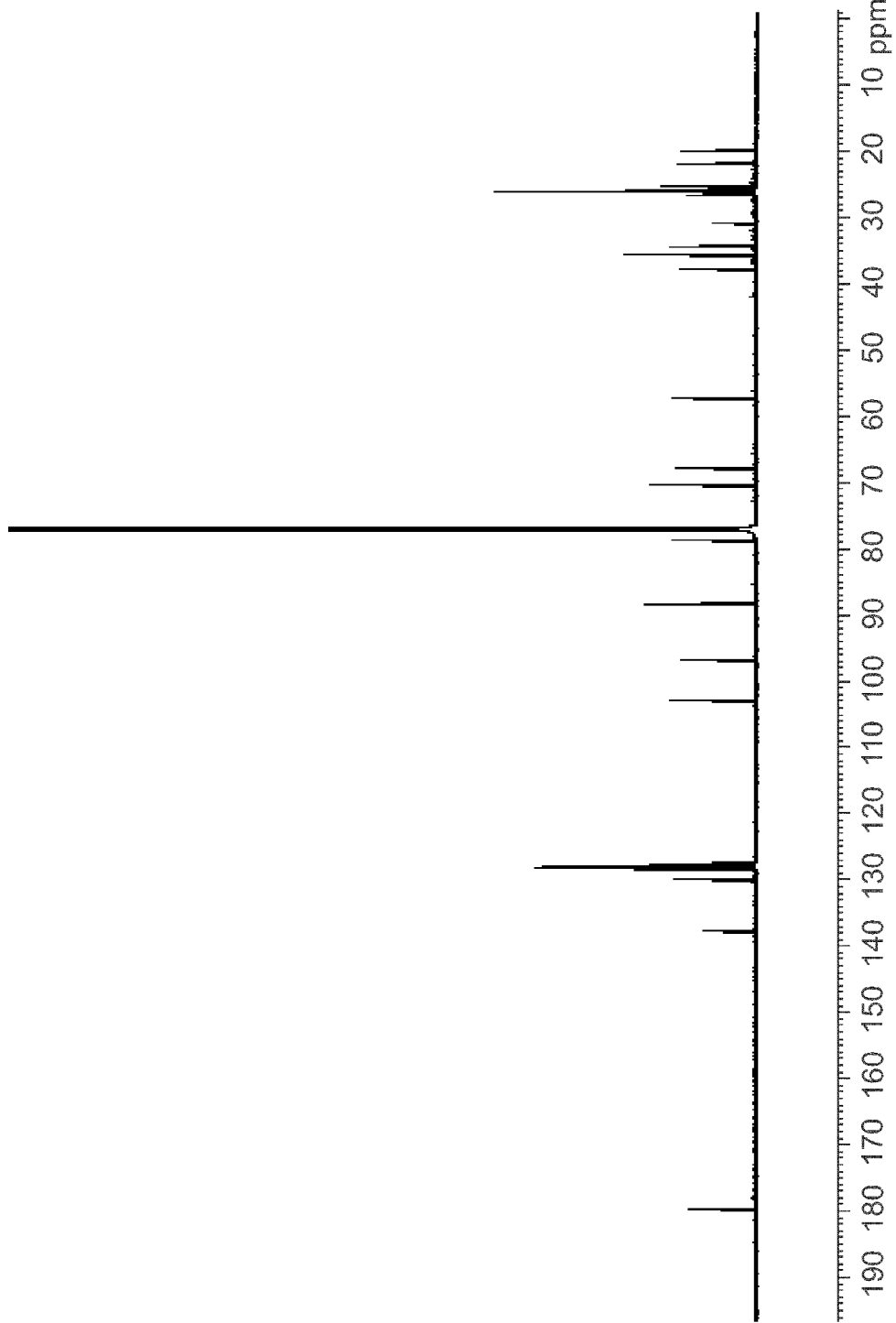
FIG. 24: $^{13}$C NMR of Compound (X-1$_a$B) in CDCl$_3$

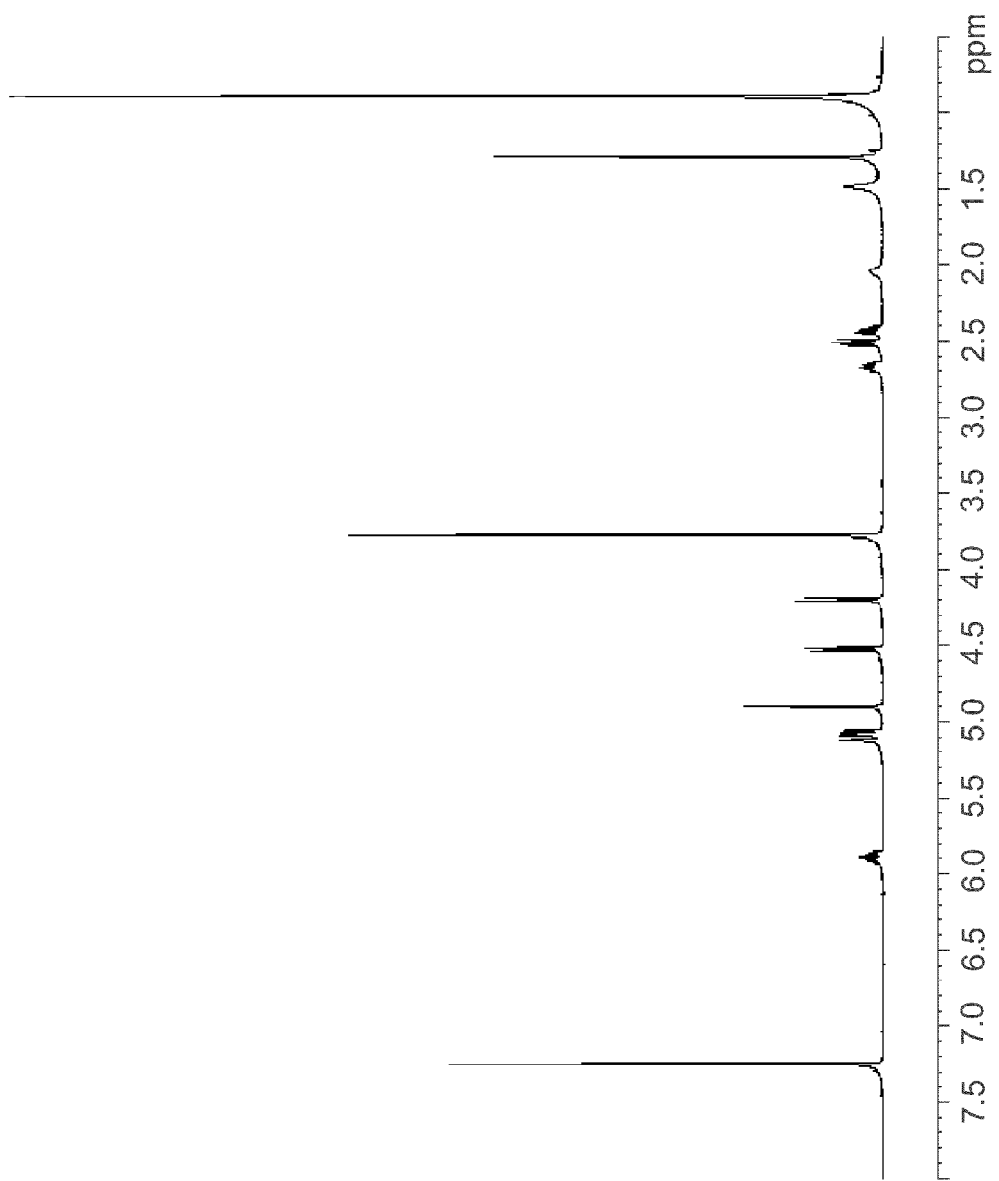

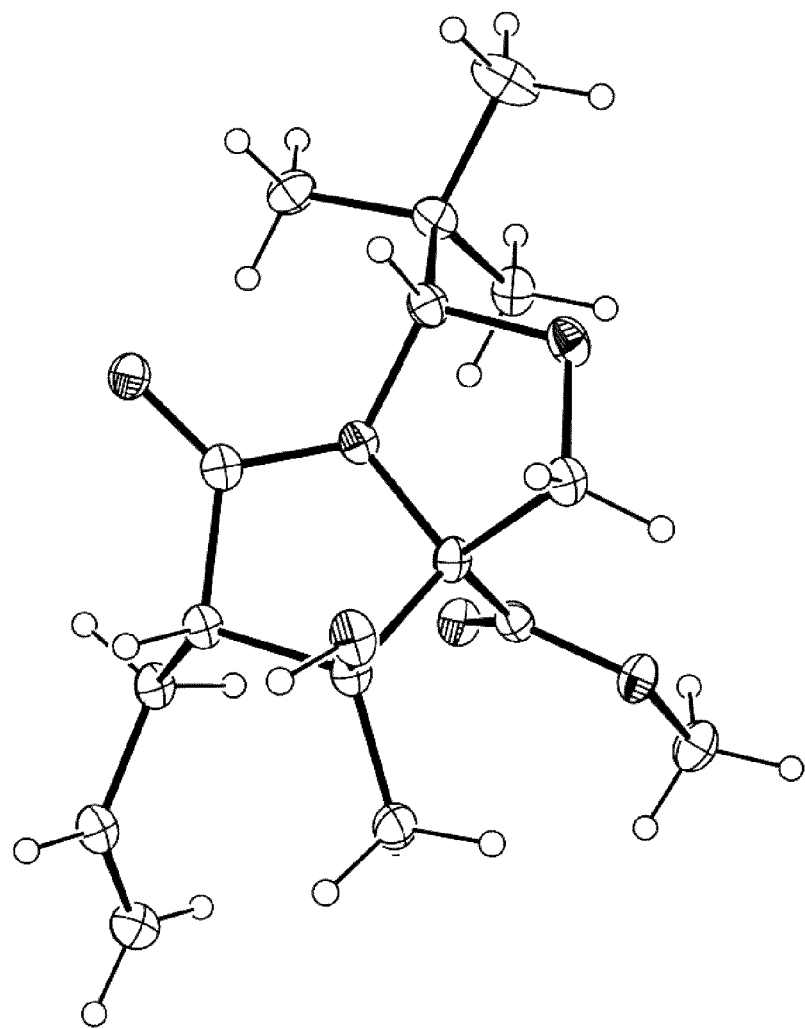
FIG. 26: ORTEP Plot of the X-ray Crystal Structure of Compound (V-1B)

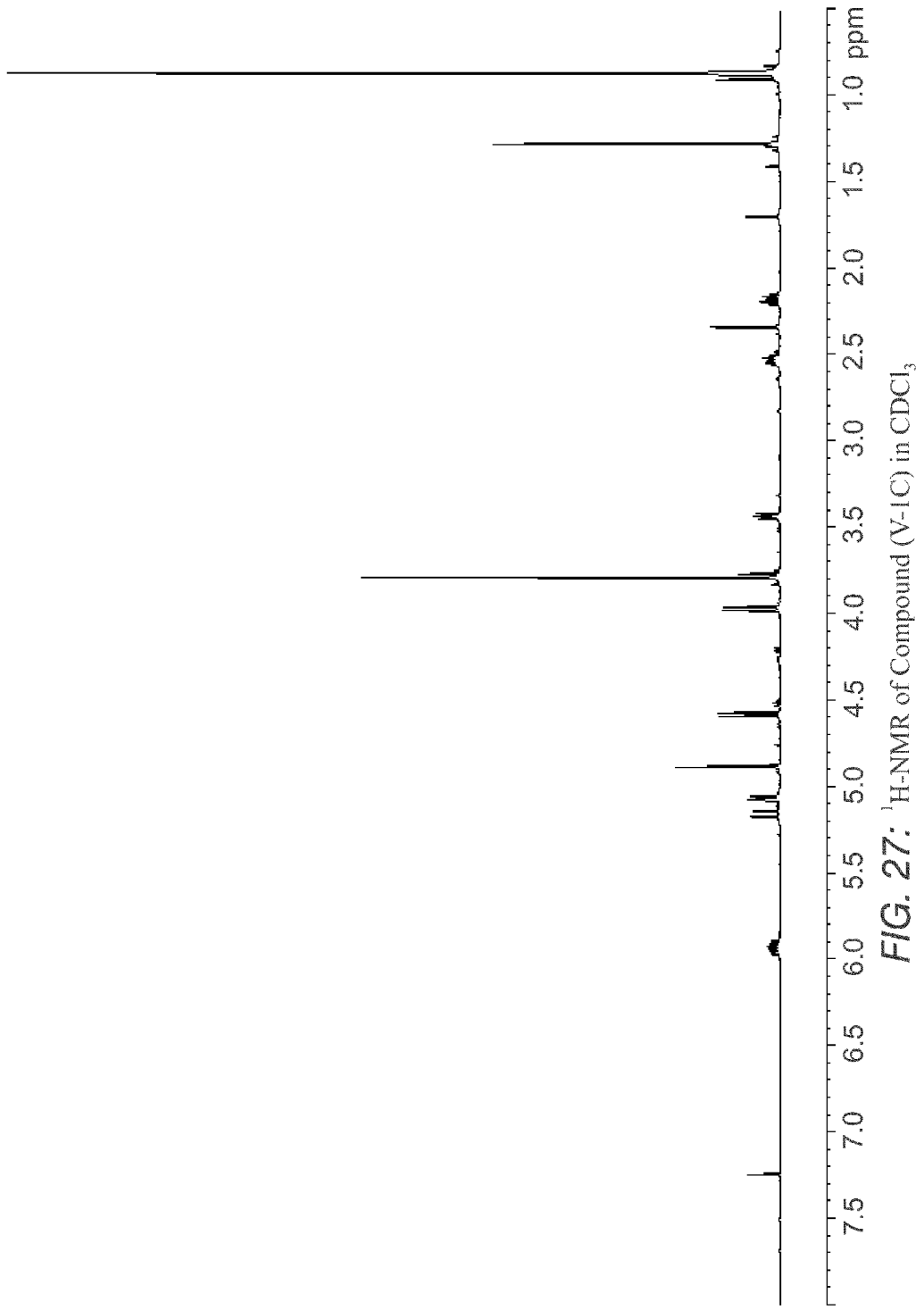
FIG. 27: ¹H-NMR of Compound (V-1C) in CDCl₃

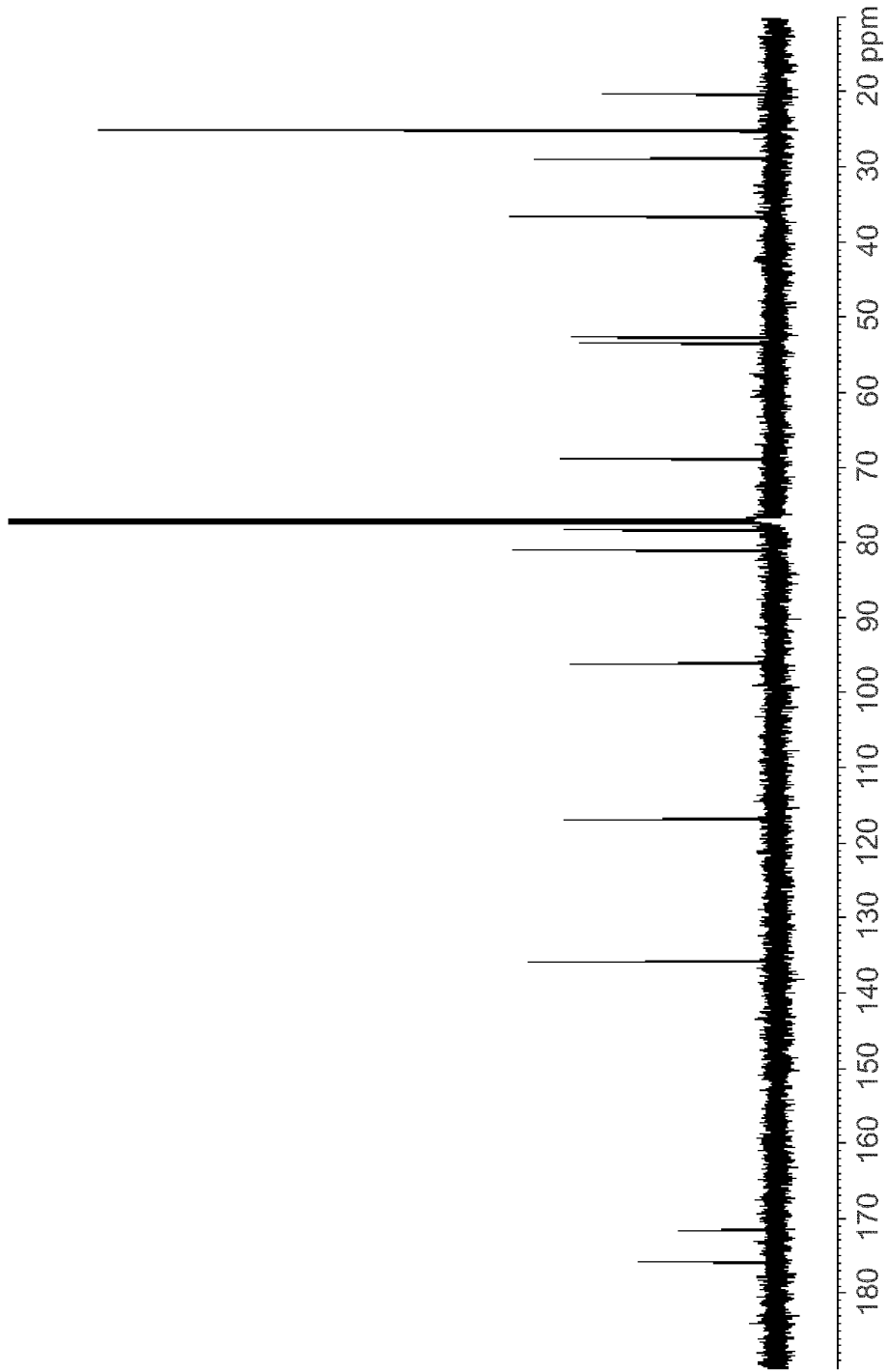
FIG. 28: $^{13}$C NMR of Compound (V-1C) in CDCl$_3$

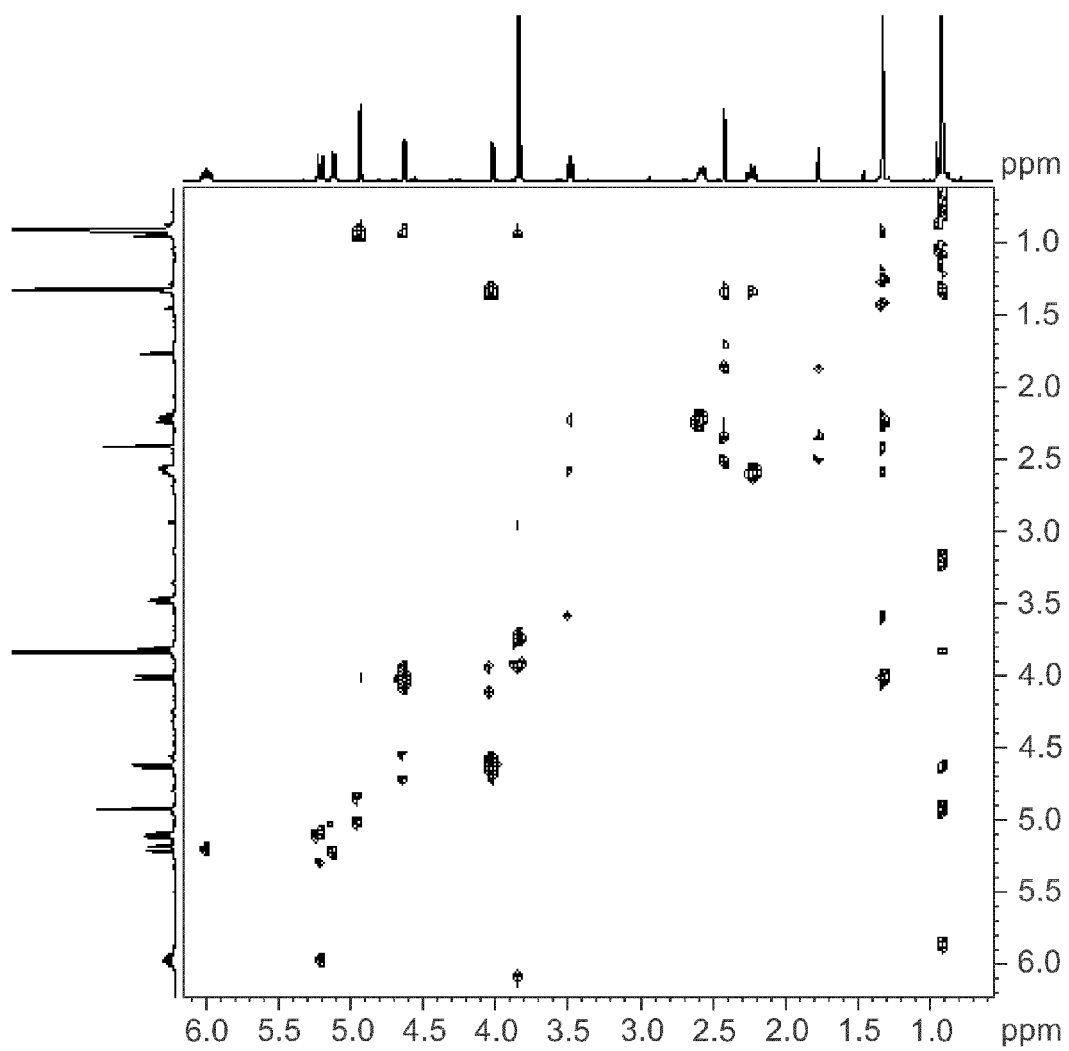
FIG. 29: NOESY of Compound (V-C1) in CDCl$_3$

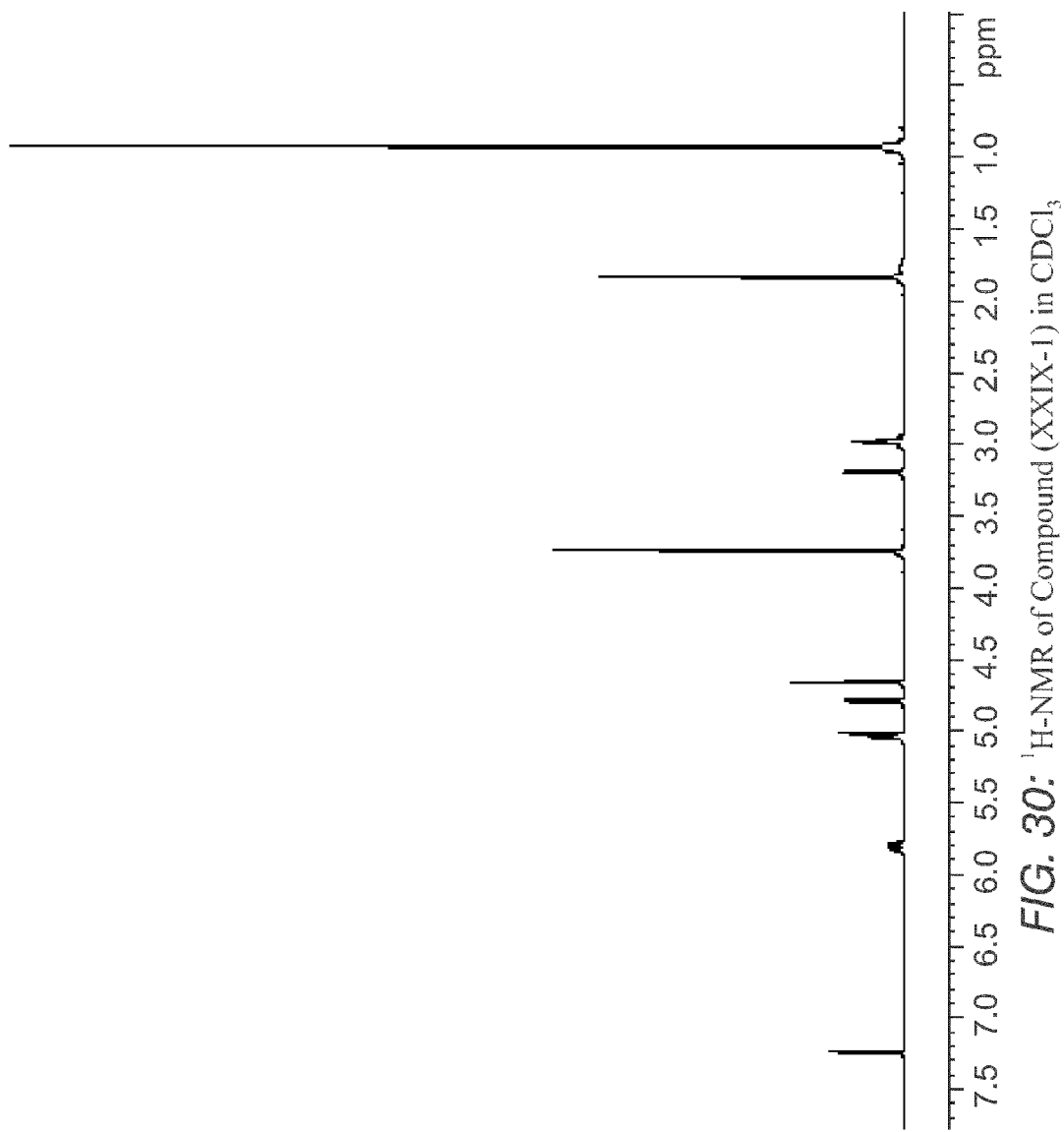

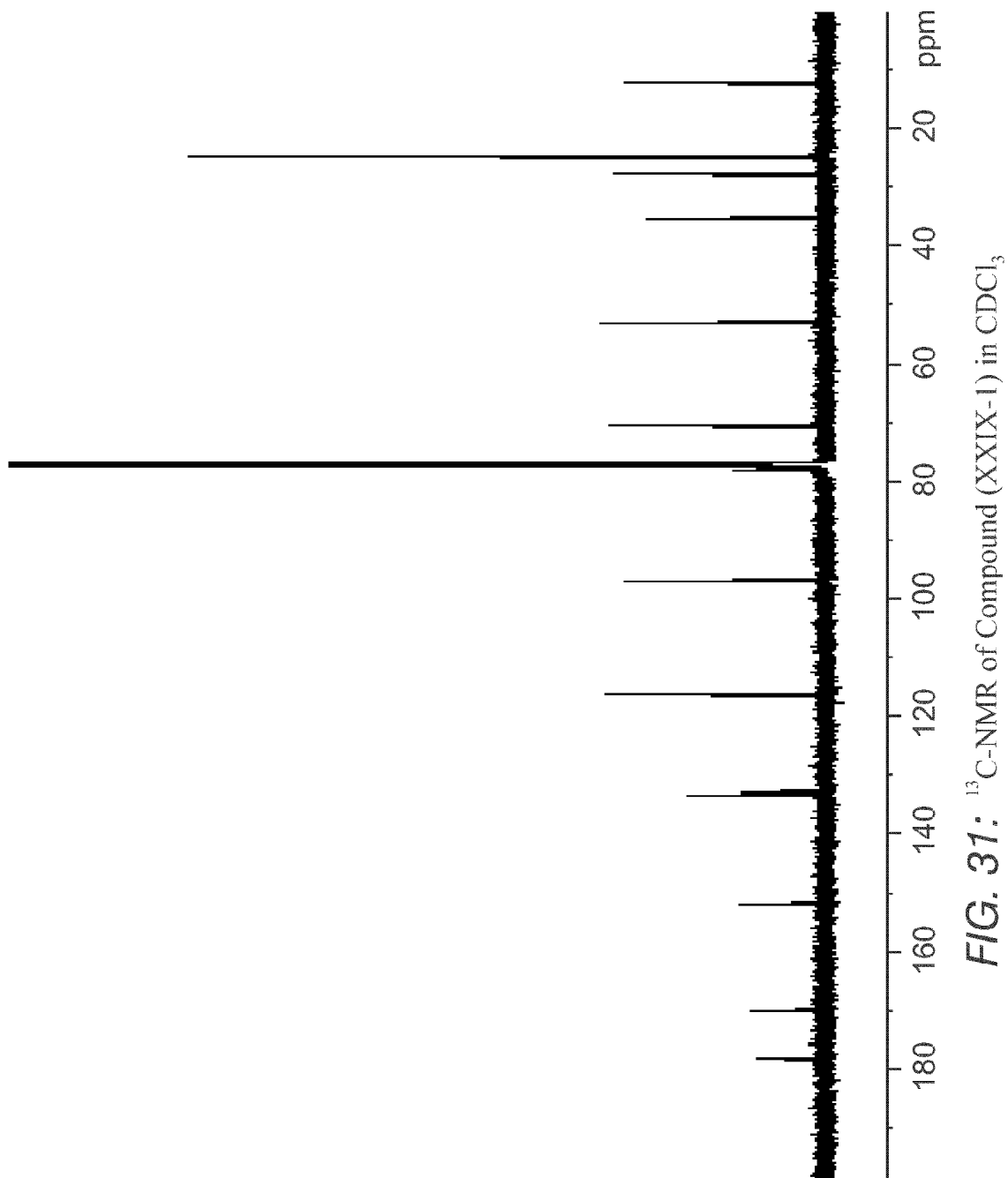
FIG. 31: ¹³C-NMR of Compound (XXIX-1) in CDCl₃

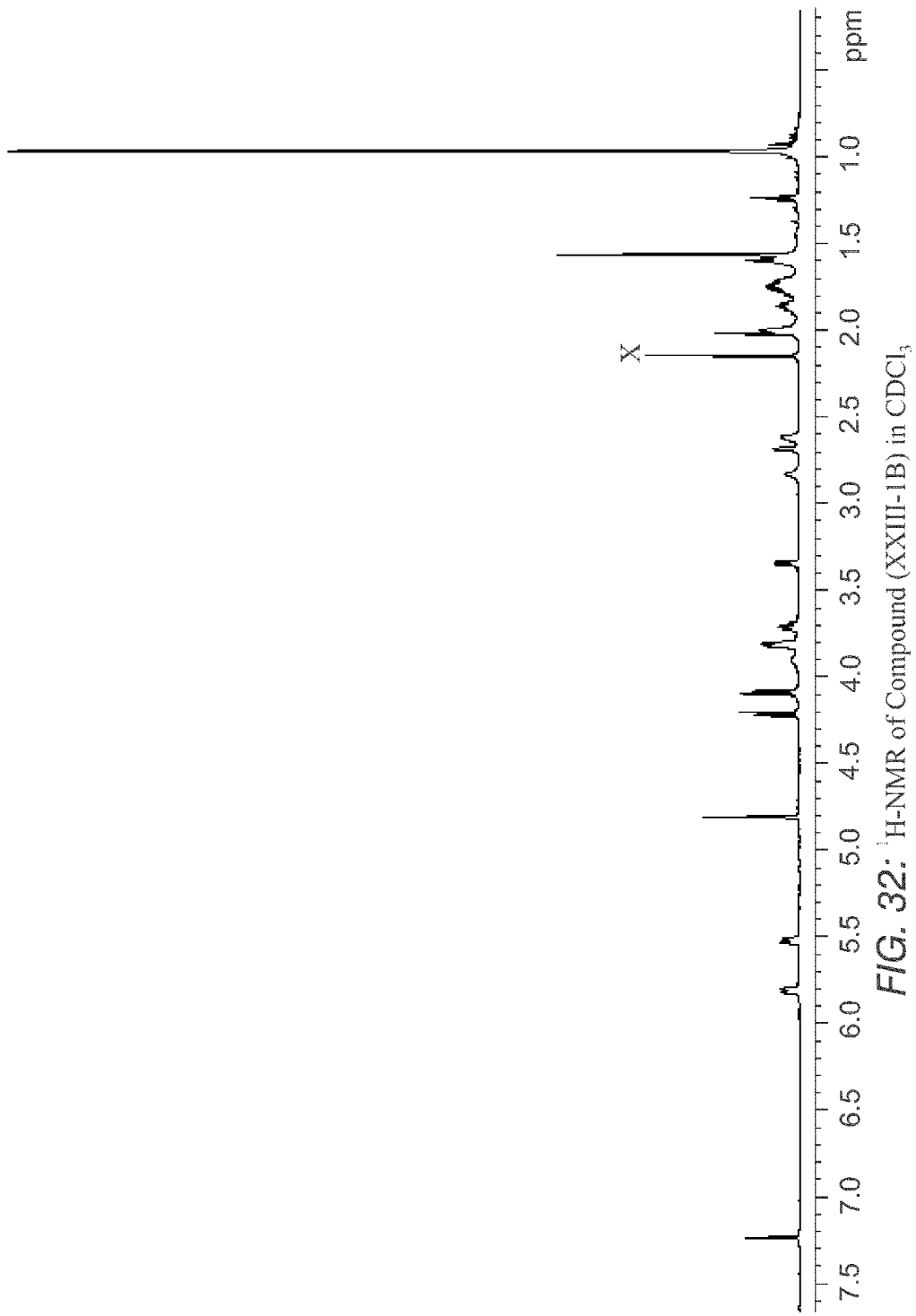

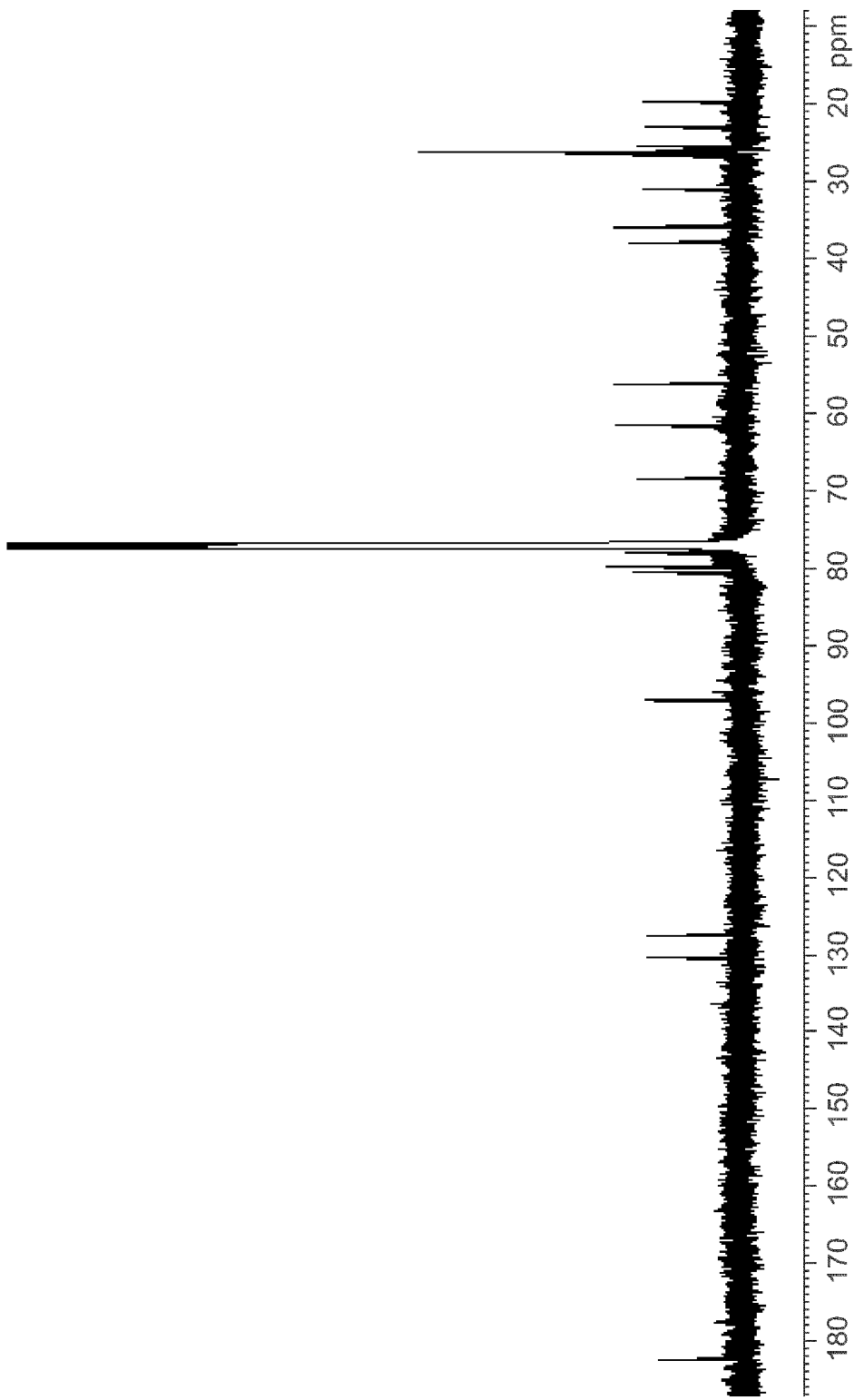
FIG. 33: $^{13}$C-NMR of Compound (XXIII-1B) in CDCl$_3$

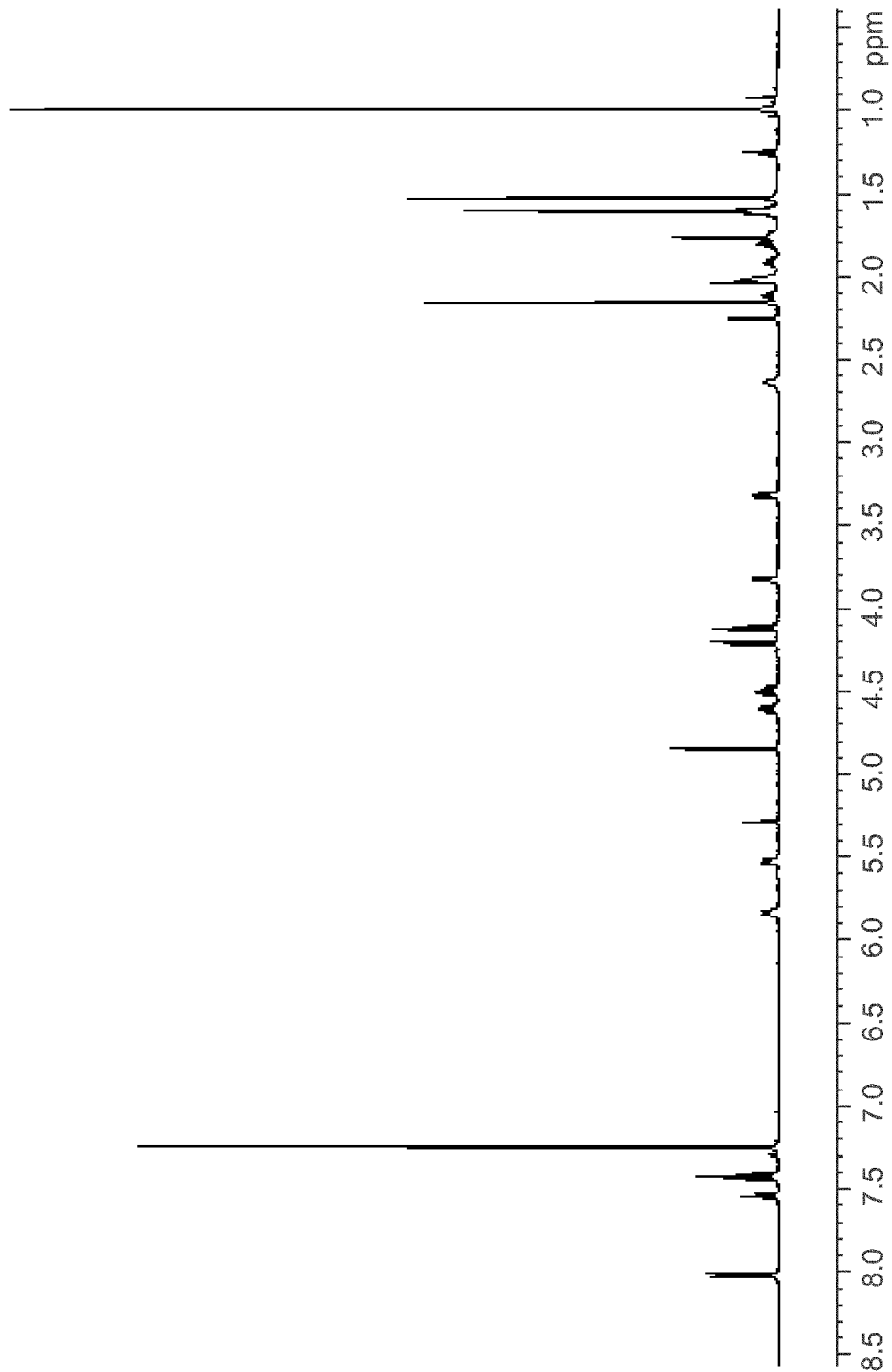
FIG. 34: $^1$H-NMR of spectrum of the compound of formula (XXIV-1B-Bz) in CDCl$_3$

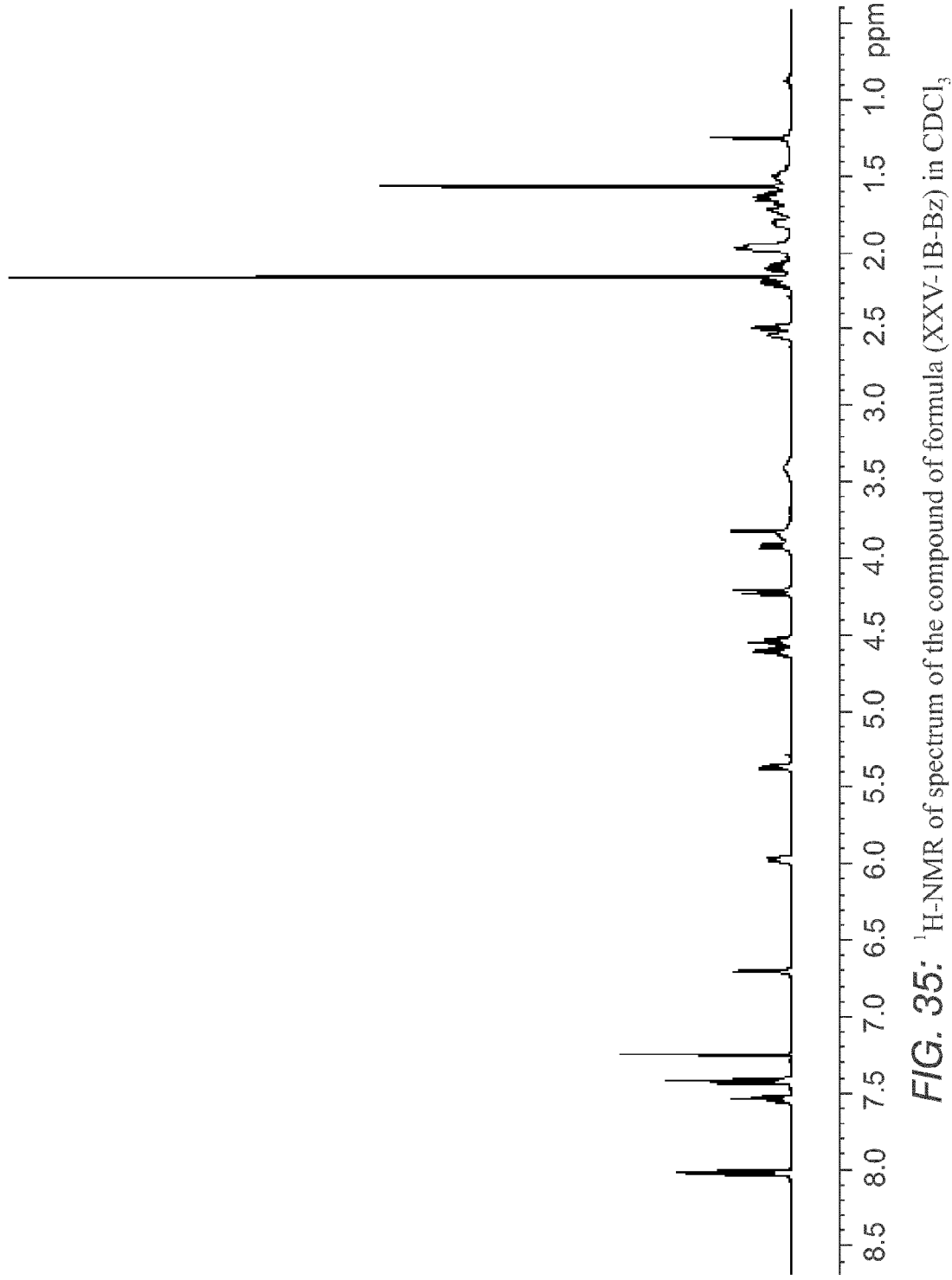
FIG. 35: ¹H-NMR of spectrum of the compound of formula (XXV-1B-Bz) in CDCl₃

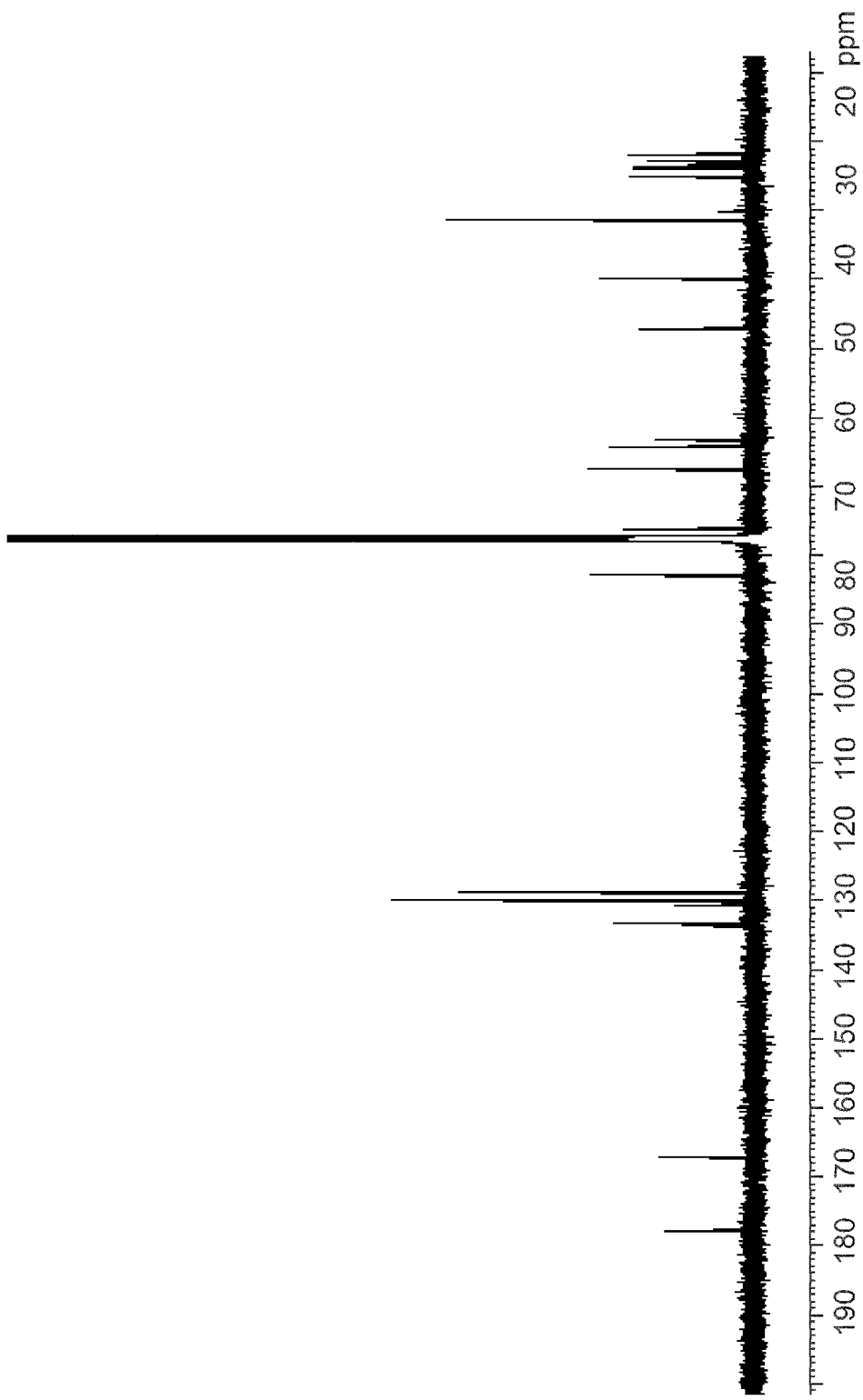
FIG. 36: $^{13}$C-NMR spectrum of the compound of formula (XXV-1B-Bz) in CDCl$_3$

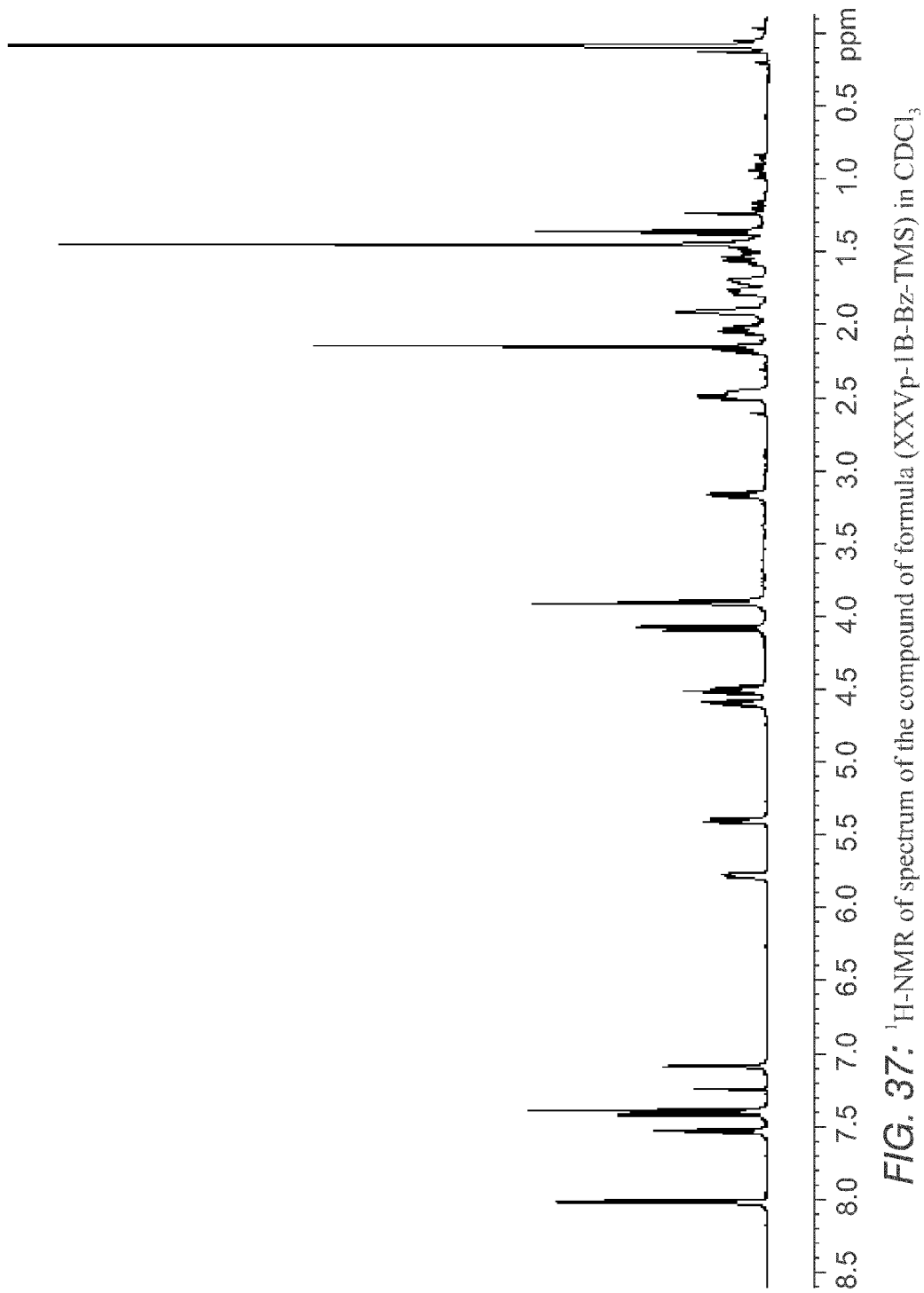
FIG. 37: ¹H-NMR of spectrum of the compound of formula (XXVp-1B-Bz-TMS) in CDCl₃

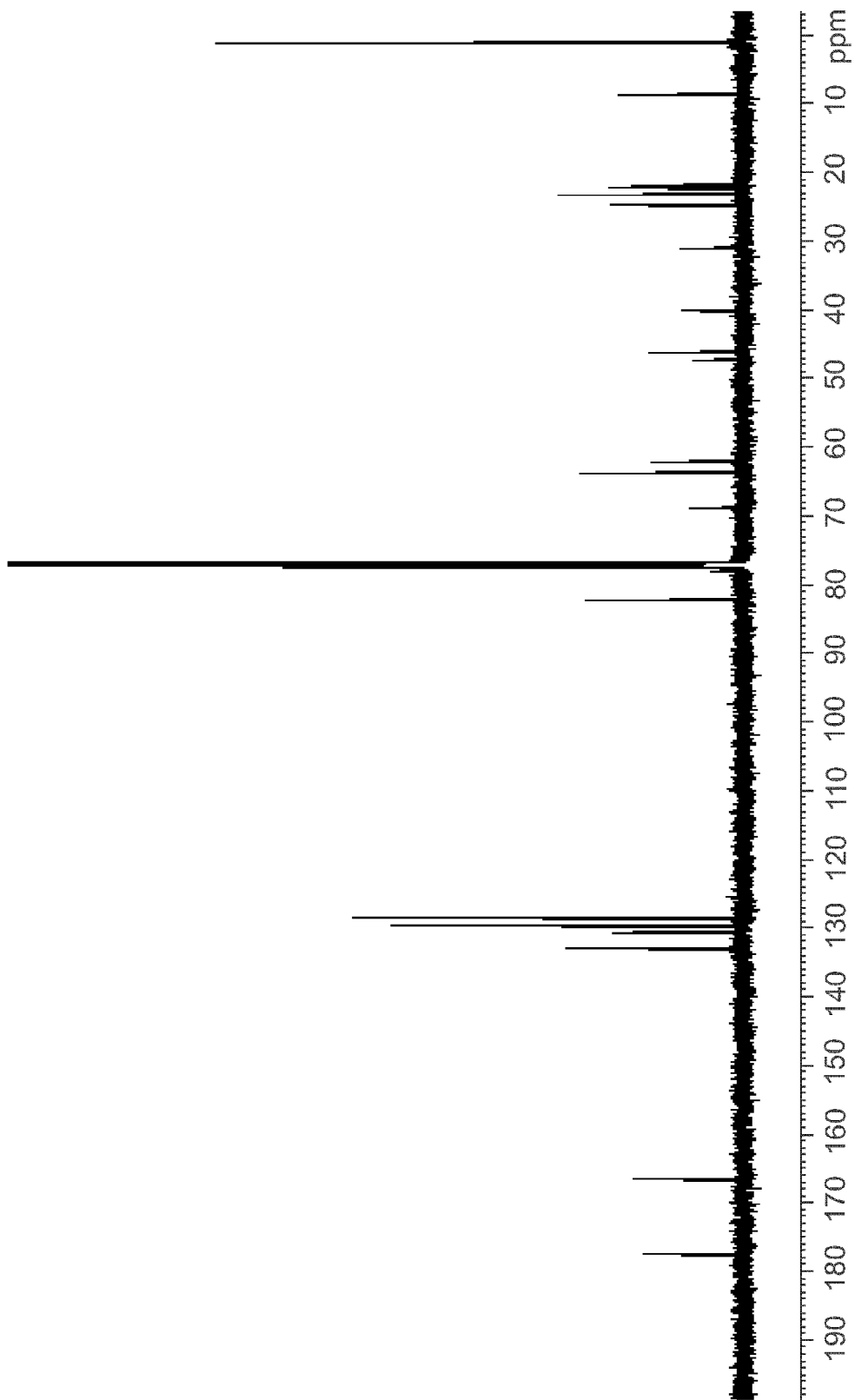
FIG. 38: $^{13}$C-NMR spectrum of the compound of formula (XXVp-1B-Bz-TMS) in $CDCl_3$

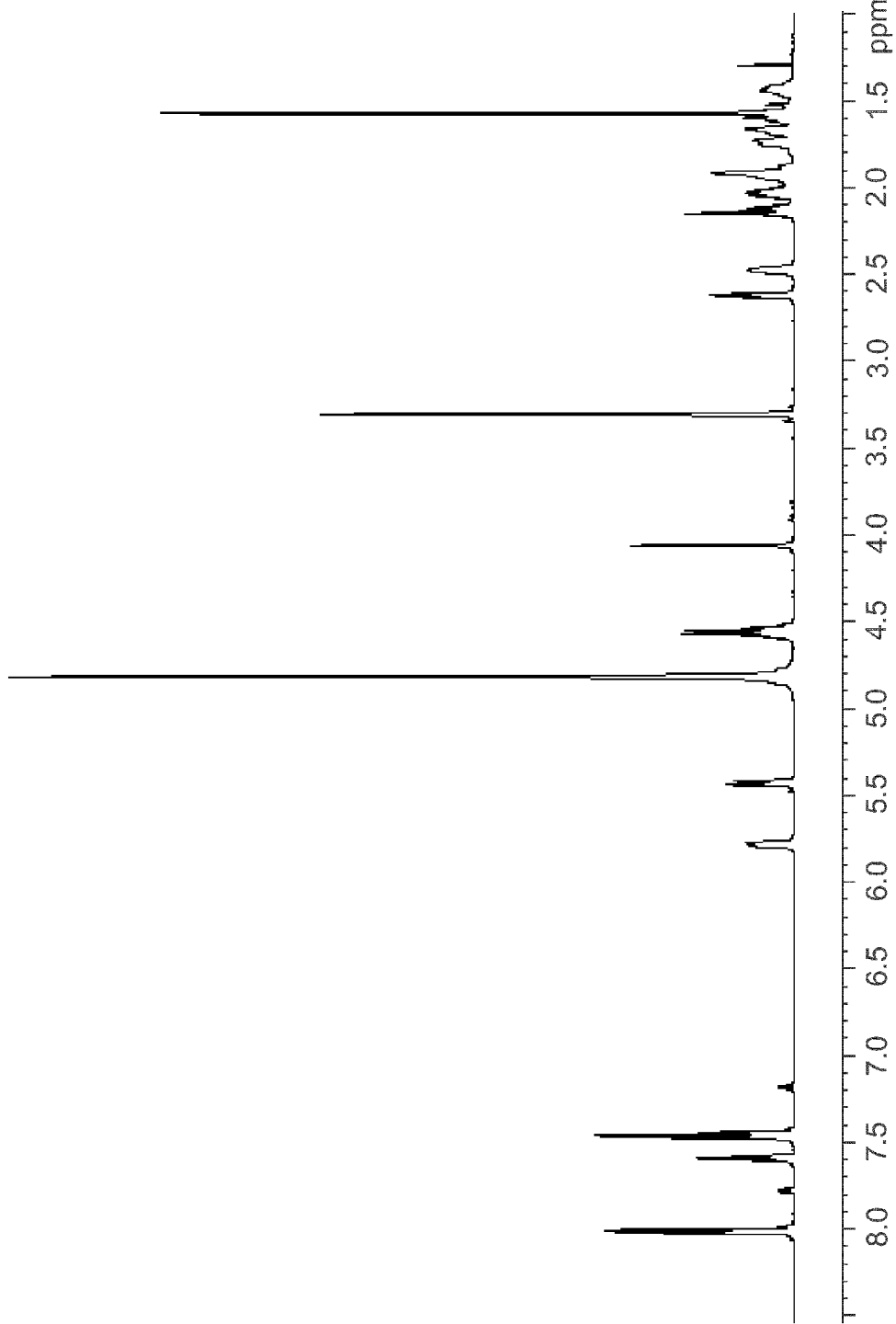
FIG. 39: ¹H-NMR of spectrum of the compound of formula (XXVI-1B-Bz) in CD₃OD

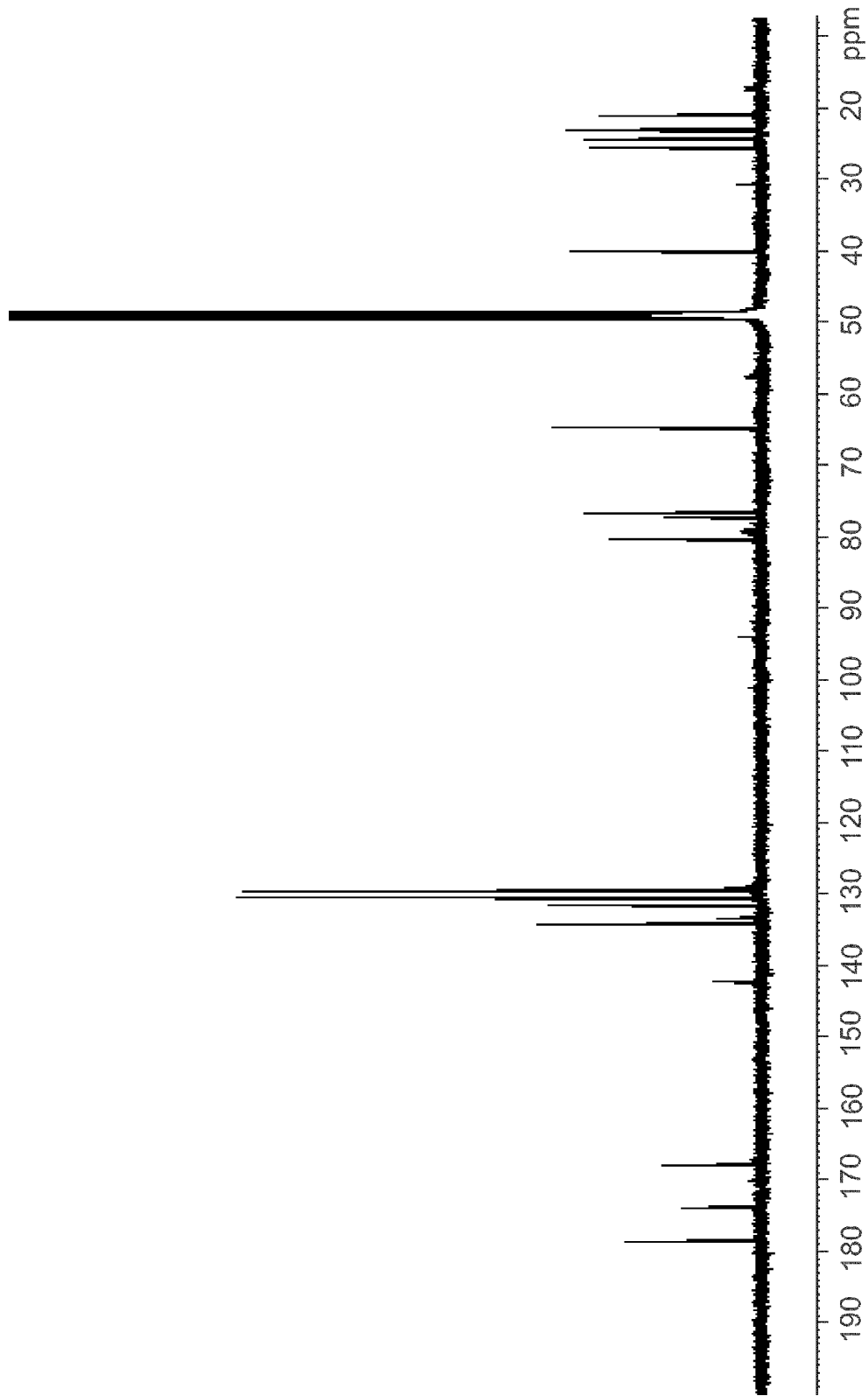
FIG. 40: $^{13}$C-NMR spectrum of the compound of formula (XXVI-1B-Bz) in CD$_3$OD

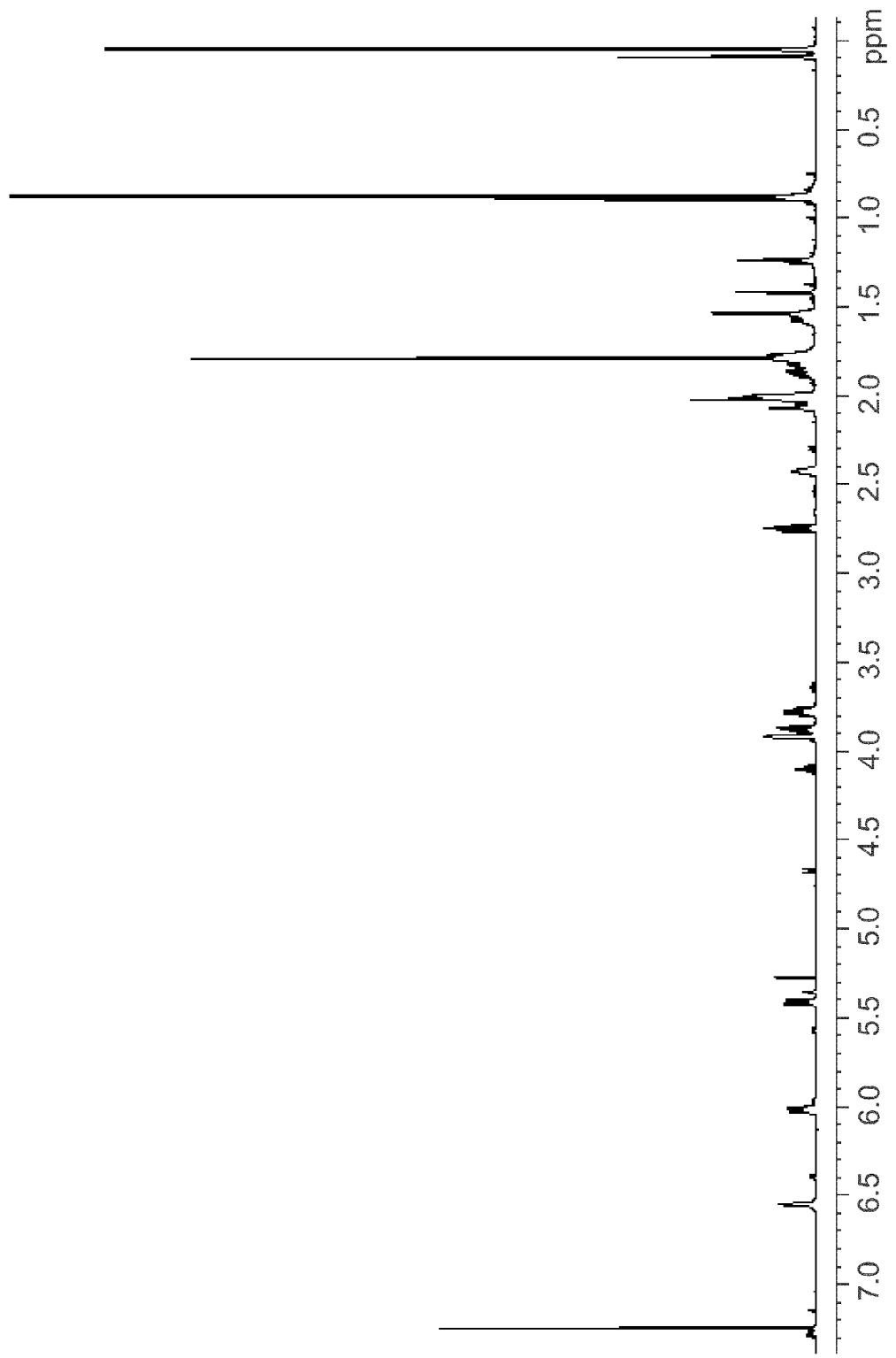
FIG. 41: $^1$H-NMR of spectrum of the compound of formula (XXVIII-1B-TBS) in CDCl$_3$

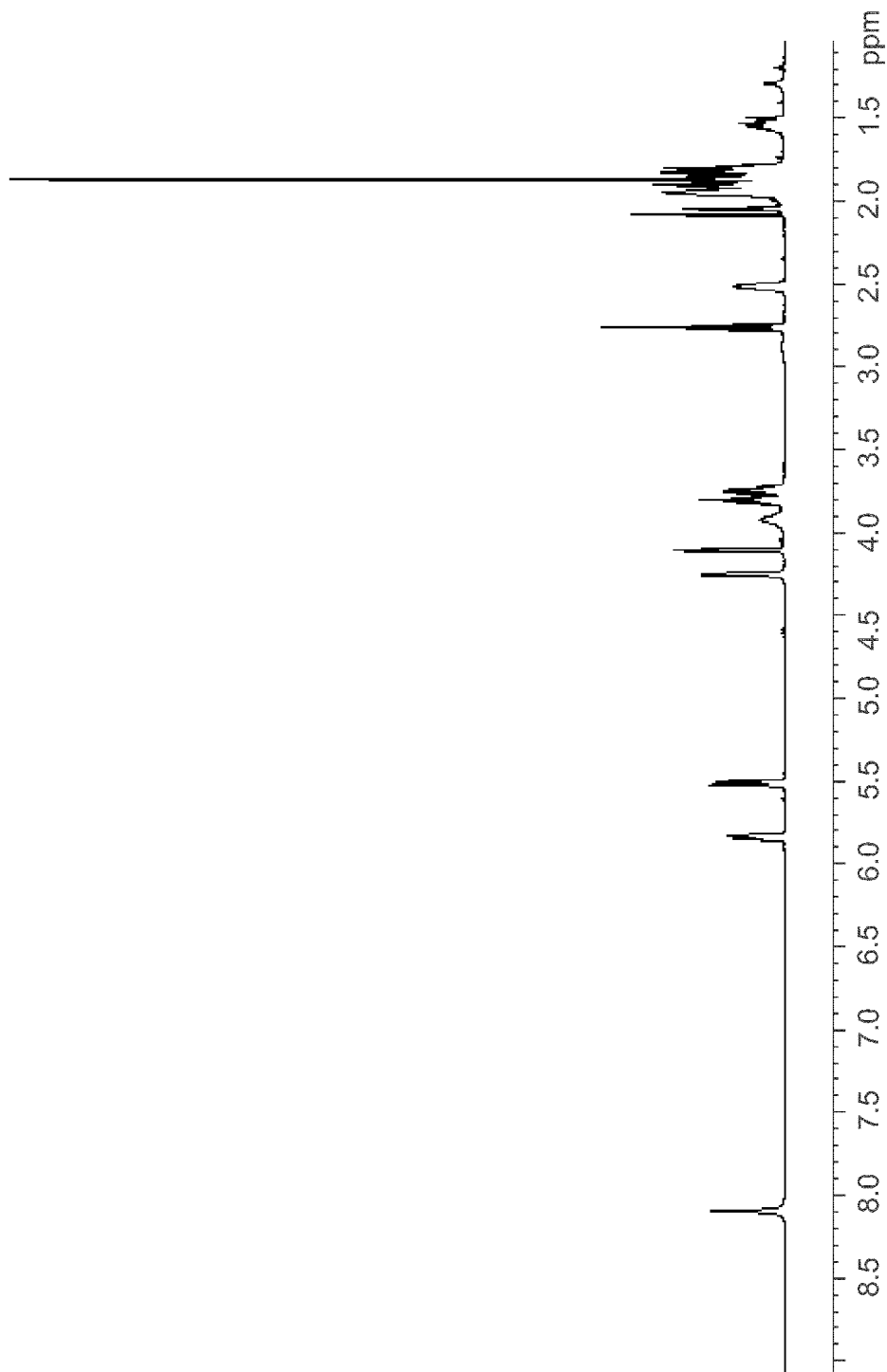

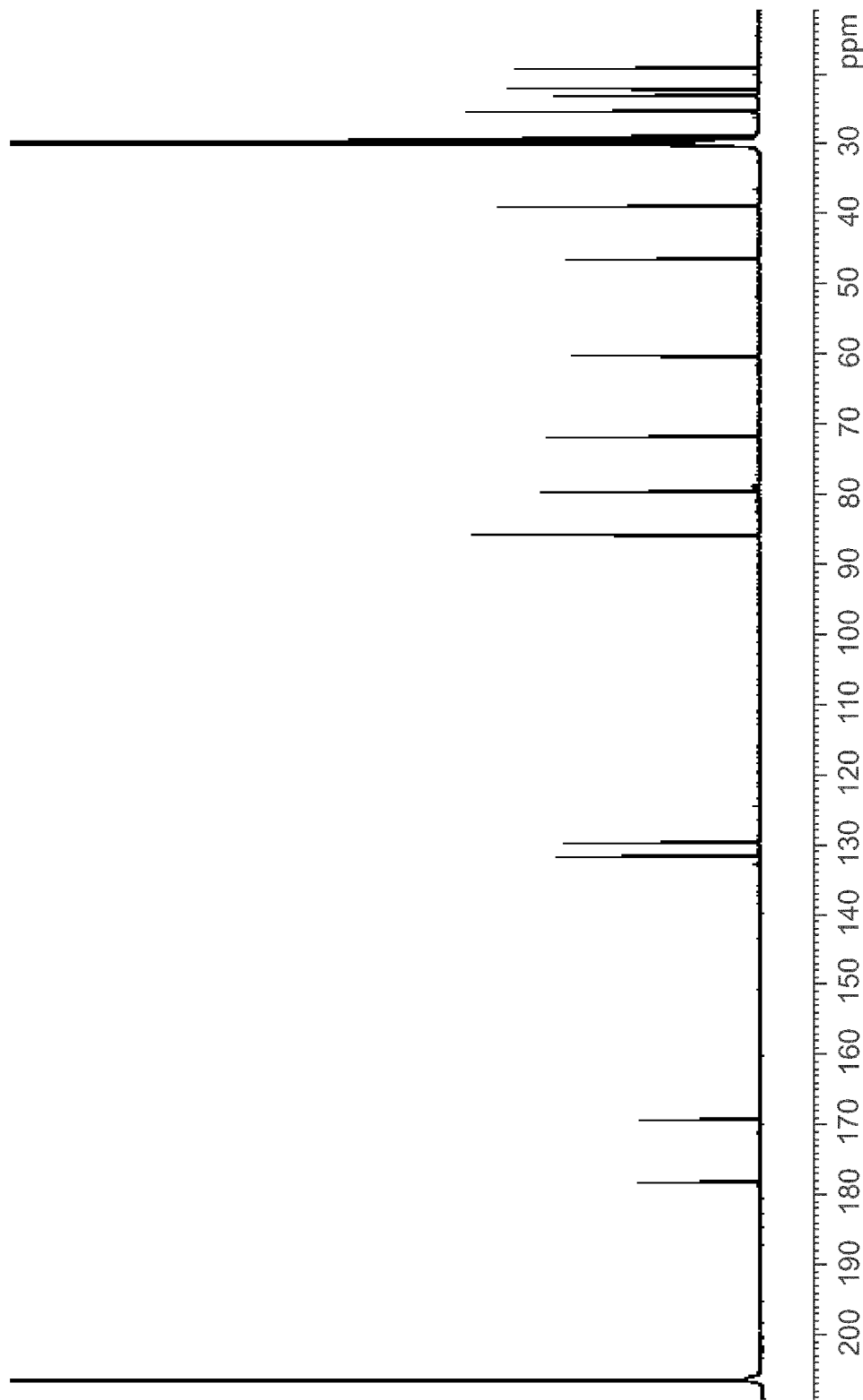
FIG. 43: $^{13}$C-NMR of Compound (XV-1B) in acetone-$d_6$

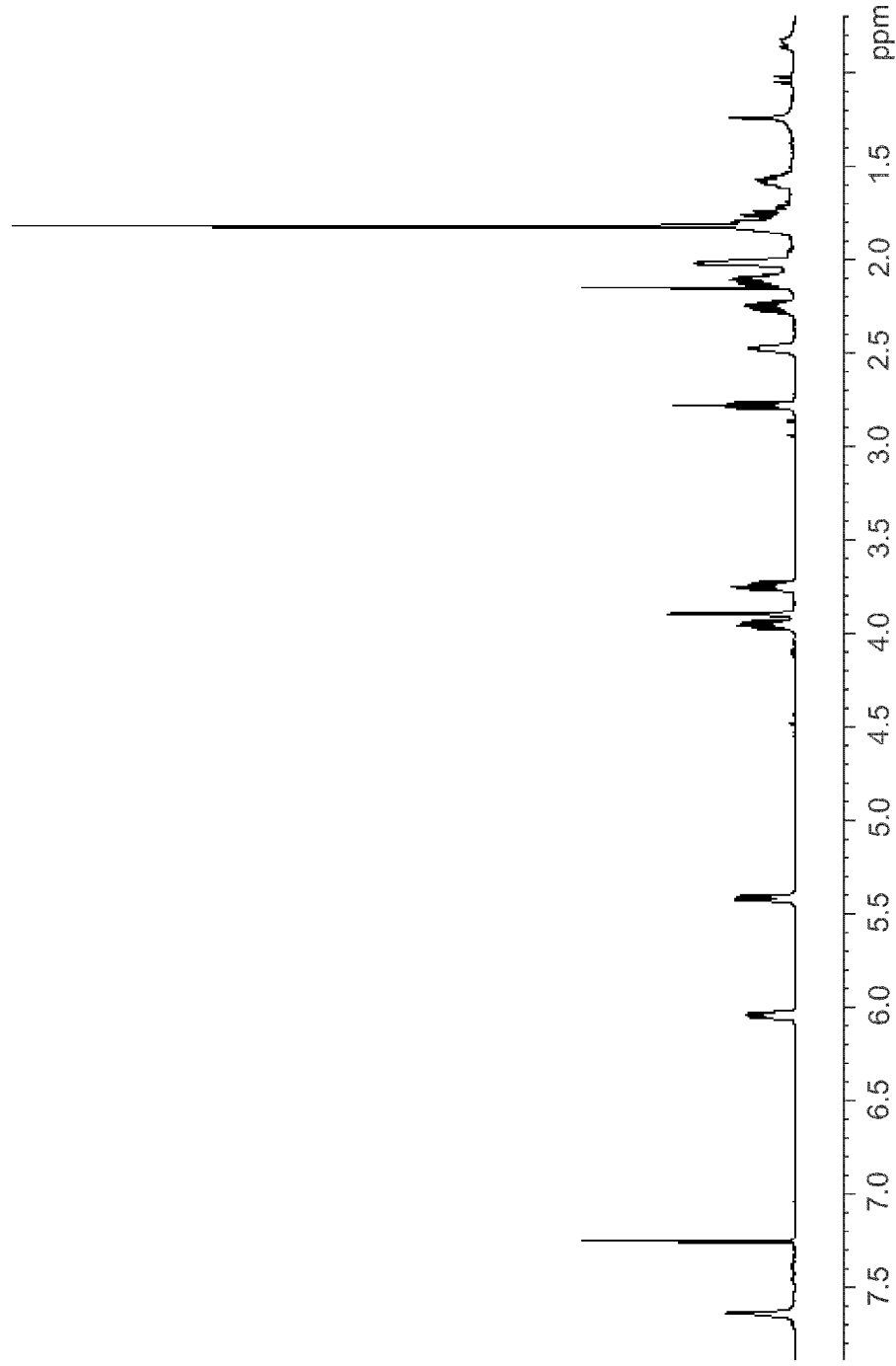
FIG. 44: $^1$H-NMR of Compound (XVI-1B) produced from Compound (XV-1B) obtained synthetically in CDCl$_3$

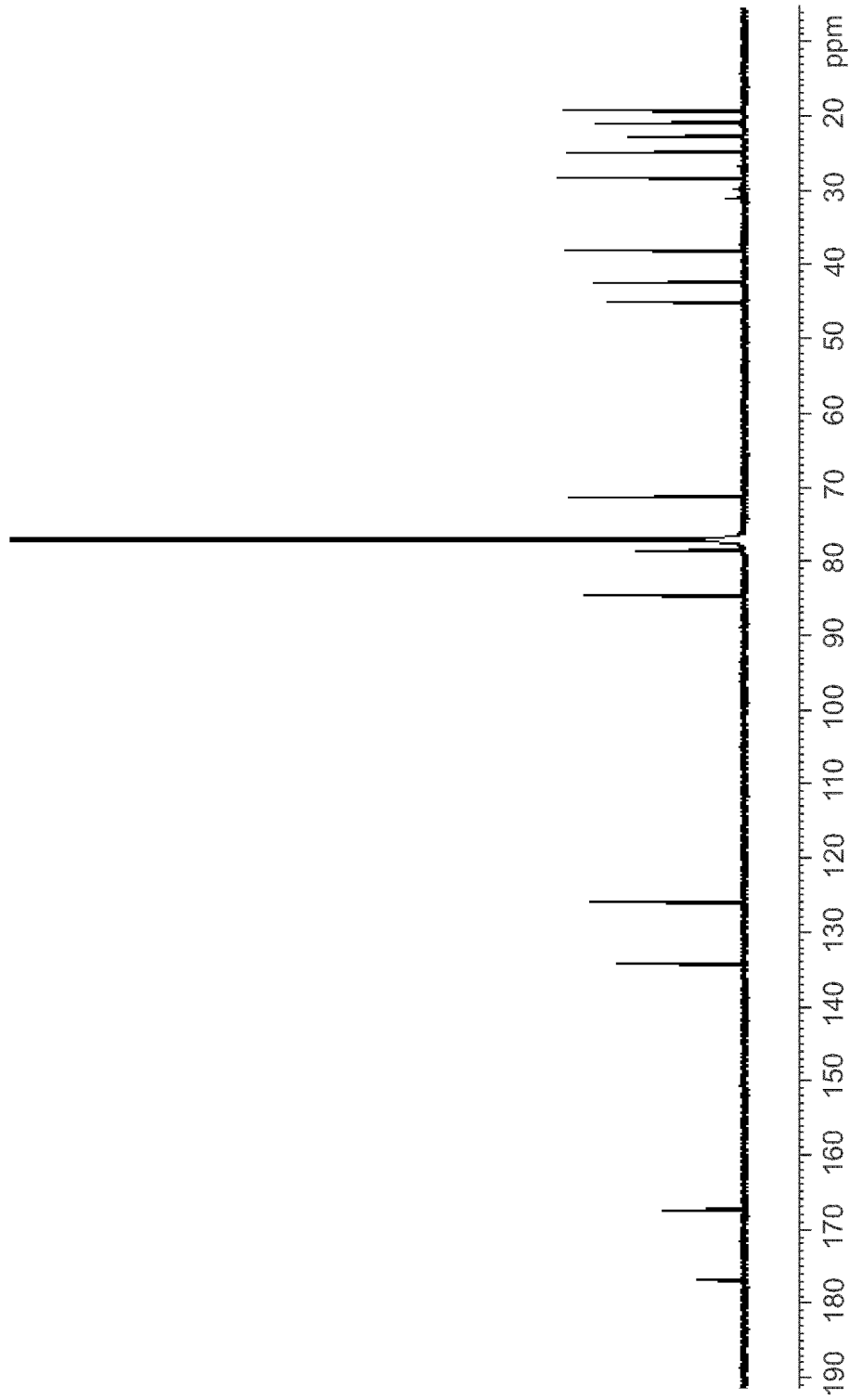
FIG. 45: $^{13}$C-NMR of Compound (XVI-1B) produced from Compound (XV-1B) obtained synthetically in CDCl$_3$

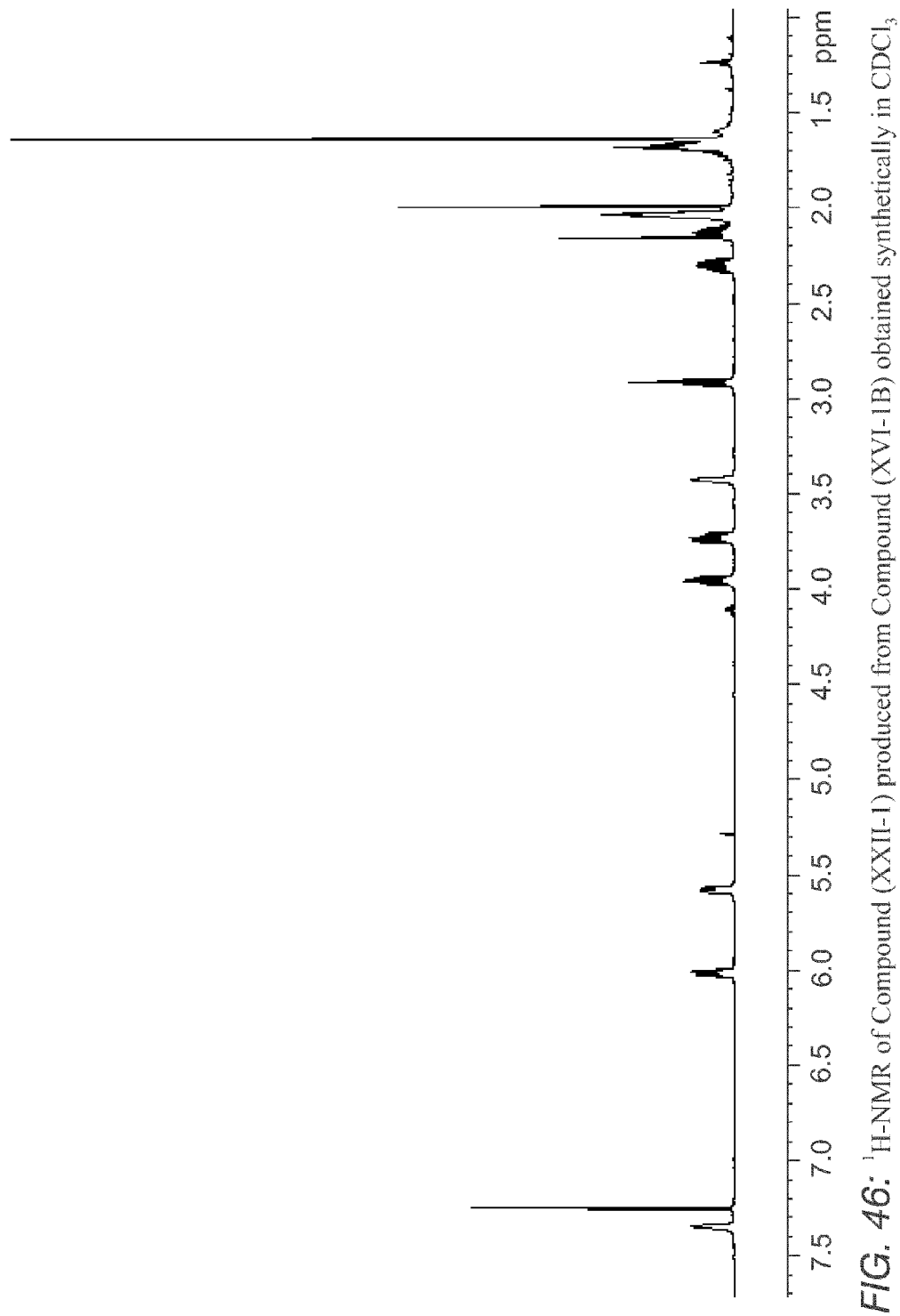
FIG. 46: $^1$H-NMR of Compound (XXII-1) produced from Compound (XVI-1B) obtained synthetically in CDCl$_3$

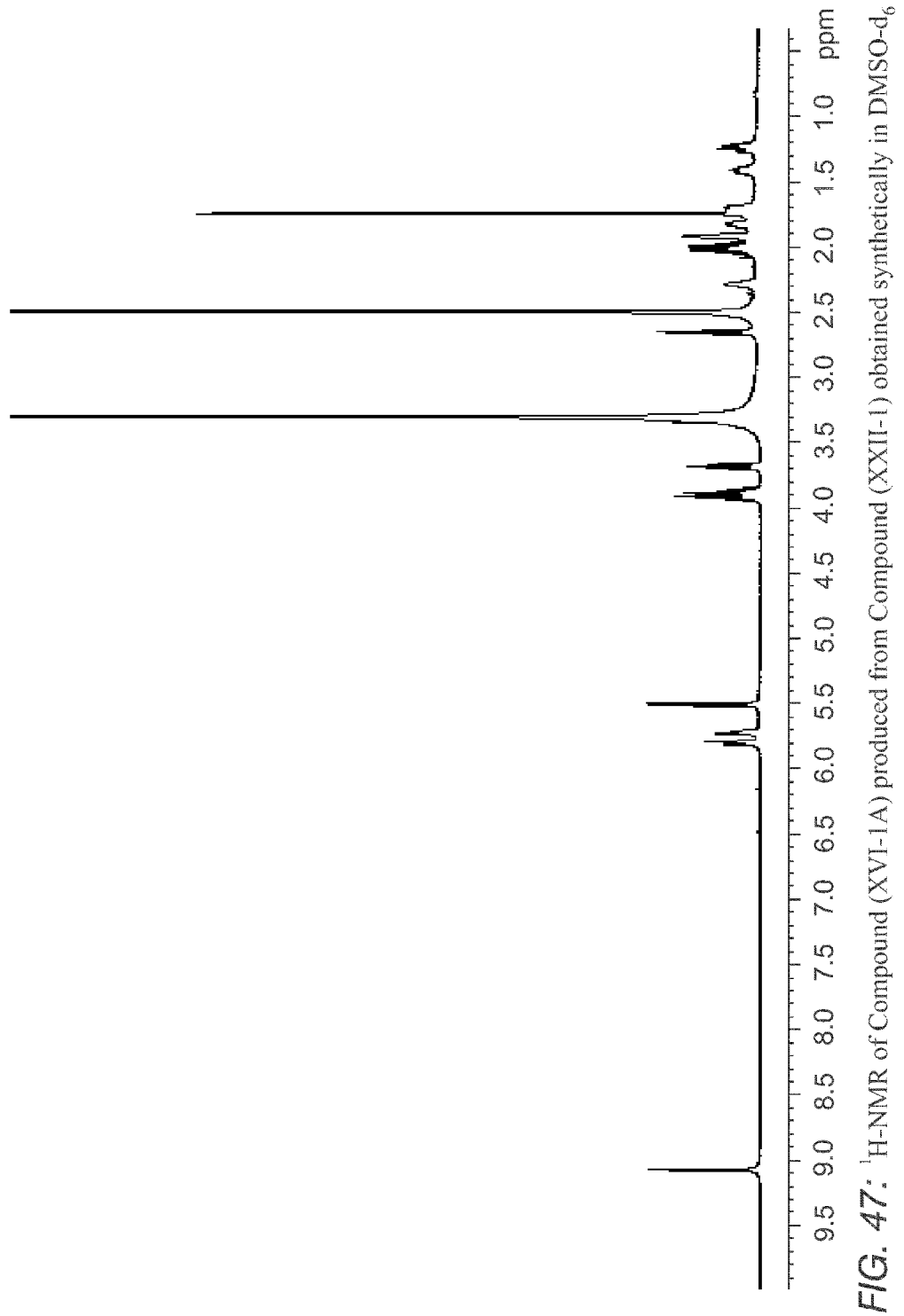
FIG. 47: ¹H-NMR of Compound (XVI-1A) produced from Compound (XXII-1) obtained synthetically in DMSO-d₆

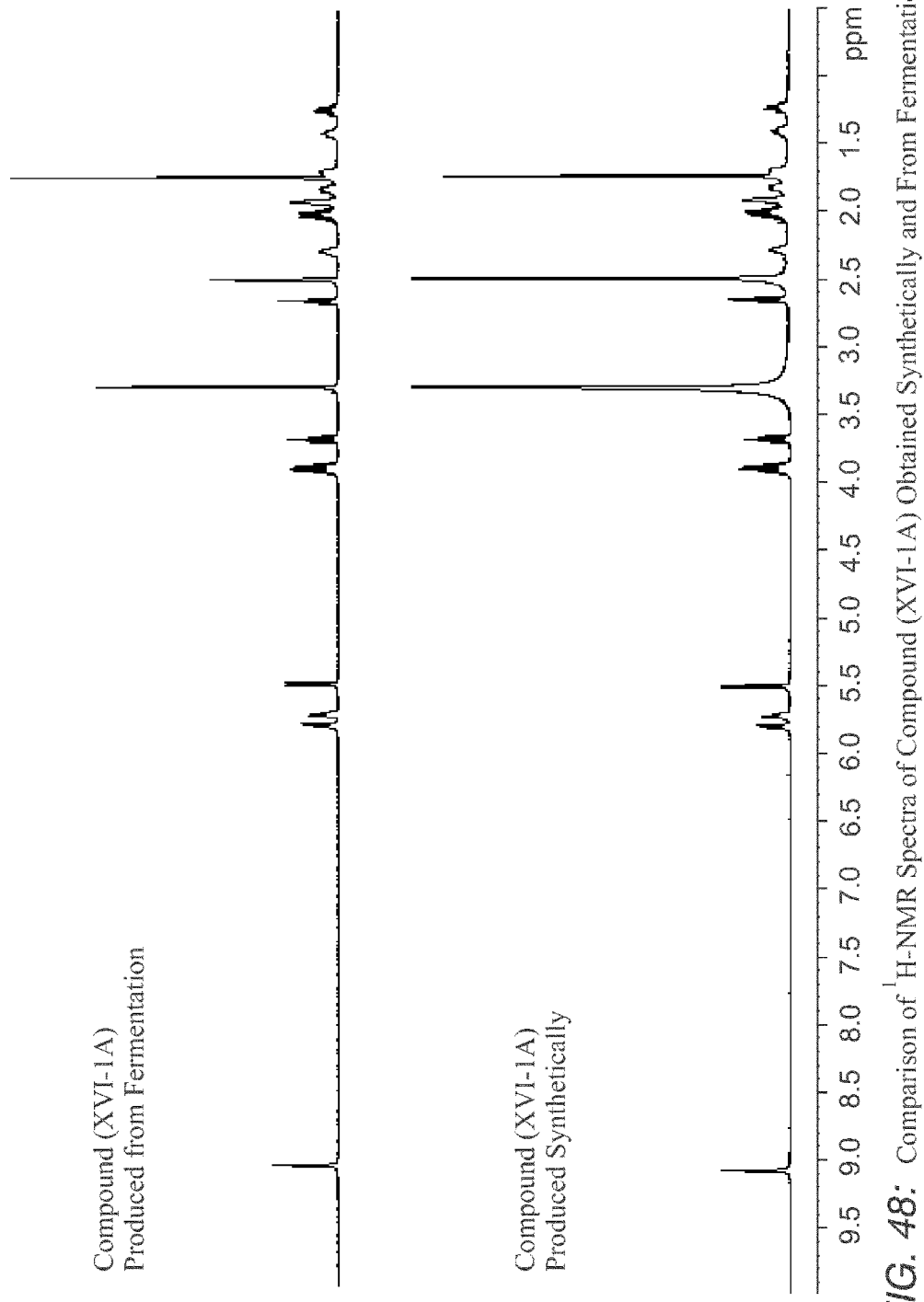
FIG. 48: Comparison of ¹H-NMR Spectra of Compound (XVI-1A) Obtained Synthetically and From Fermentation

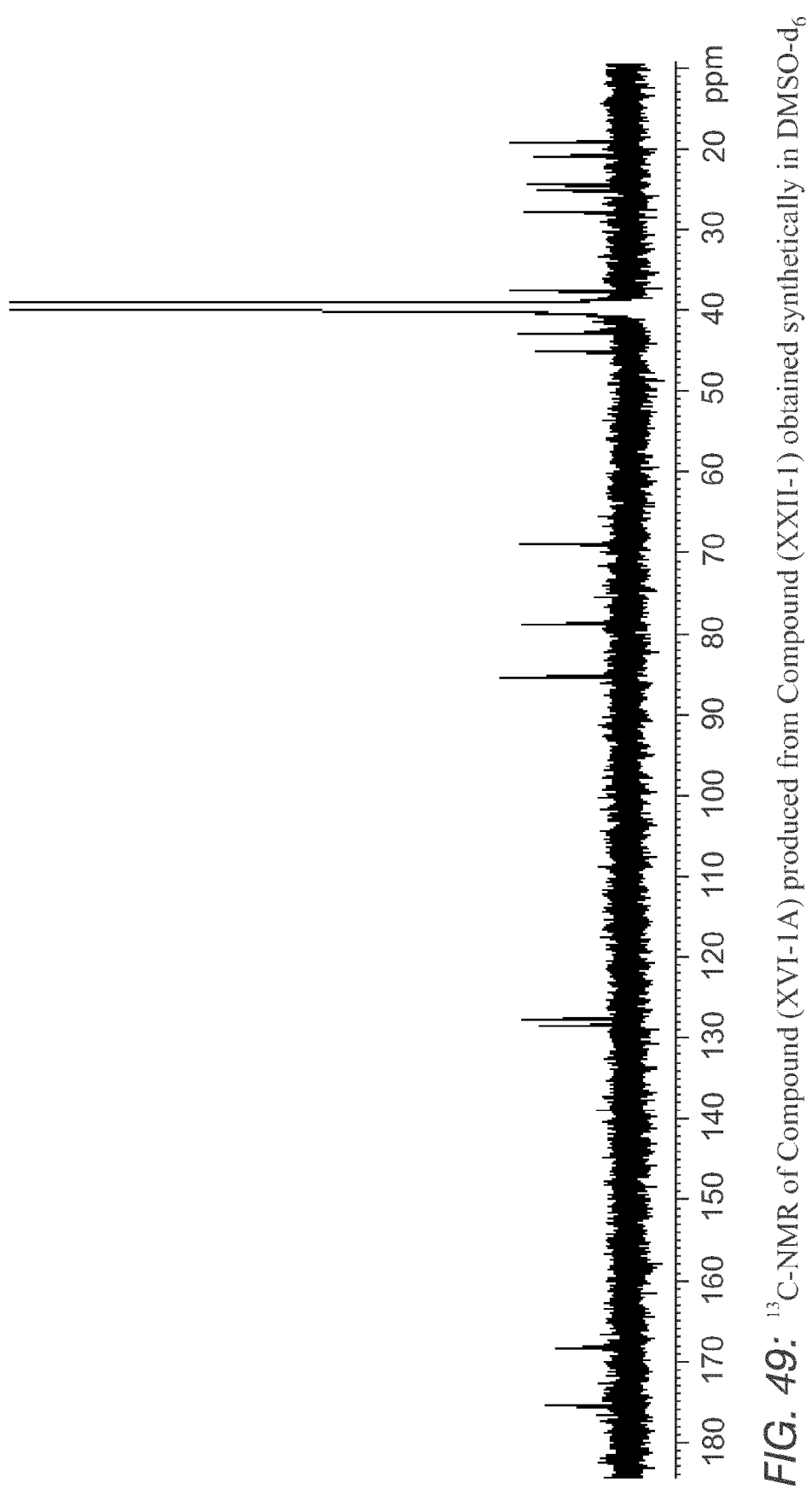
FIG. 49: $^{13}$C-NMR of Compound (XVI-1A) produced from Compound (XXII-1) obtained synthetically in DMSO-$d_6$

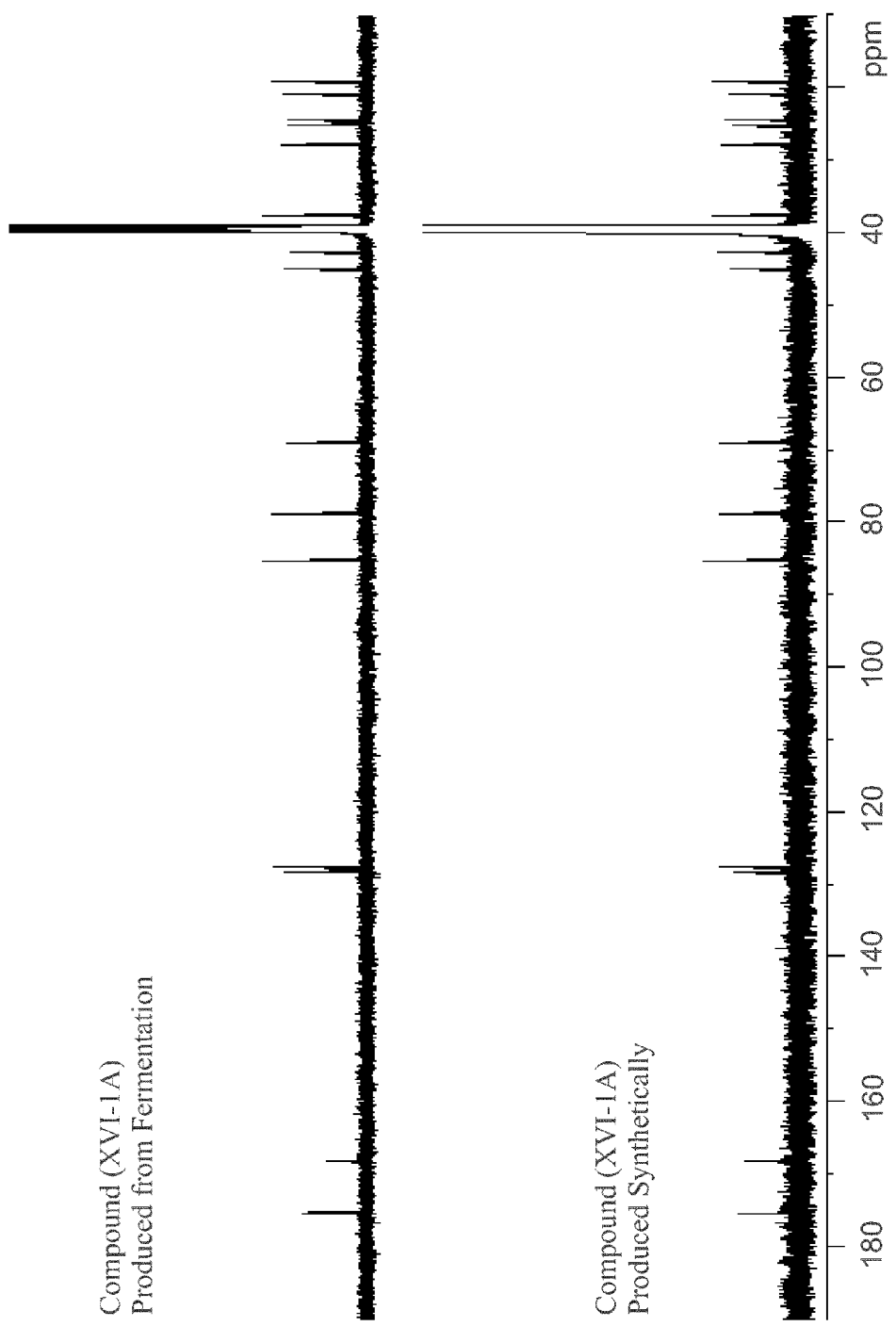
FIG. 50: Comparison of $^{13}$C-NMR Spectra of Compound (XVI-1A) Obtained Synthetically and From Fermentation

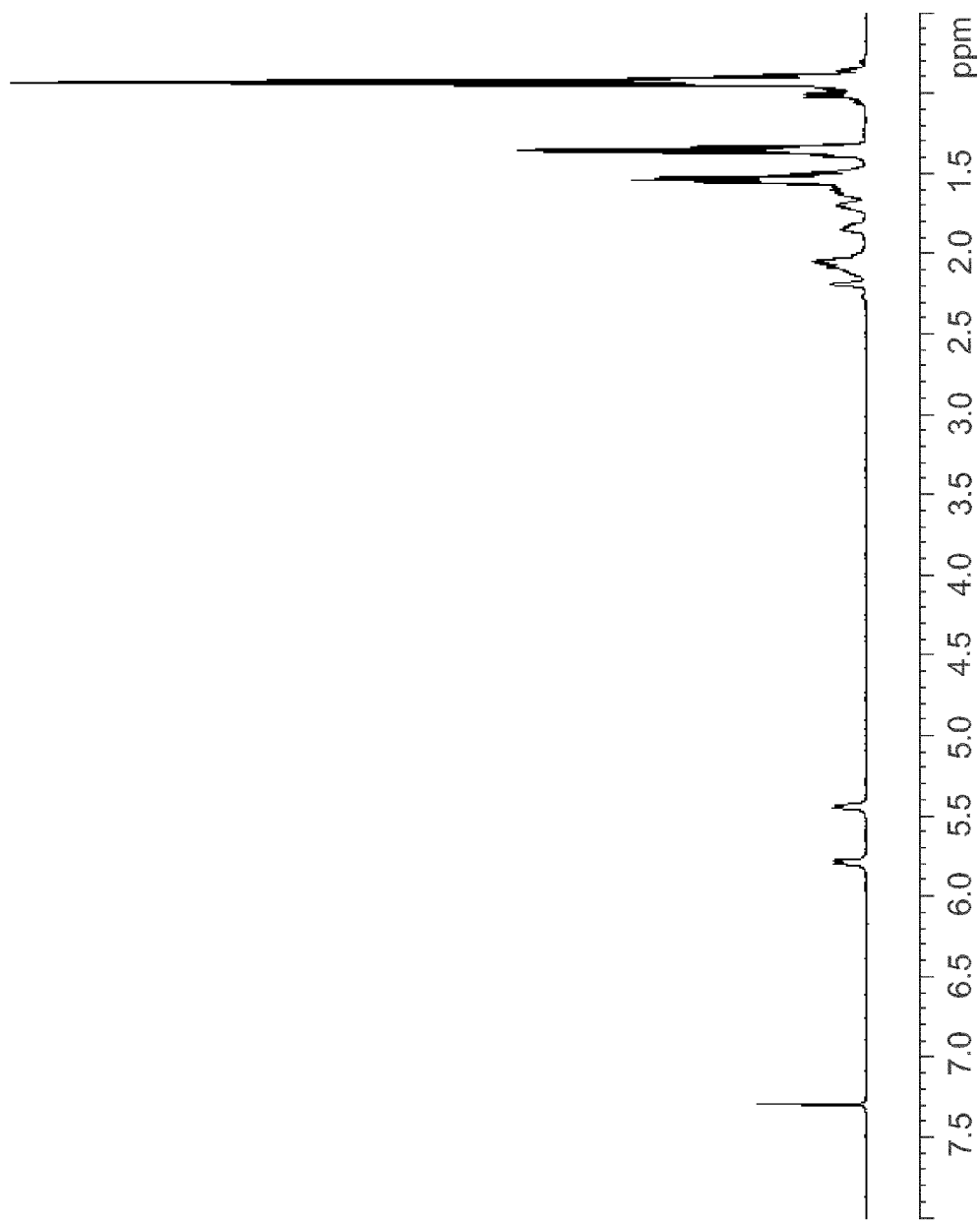
FIG. 51: ¹H-NMR of Cyclohexenyltributyltin in CDCl₃

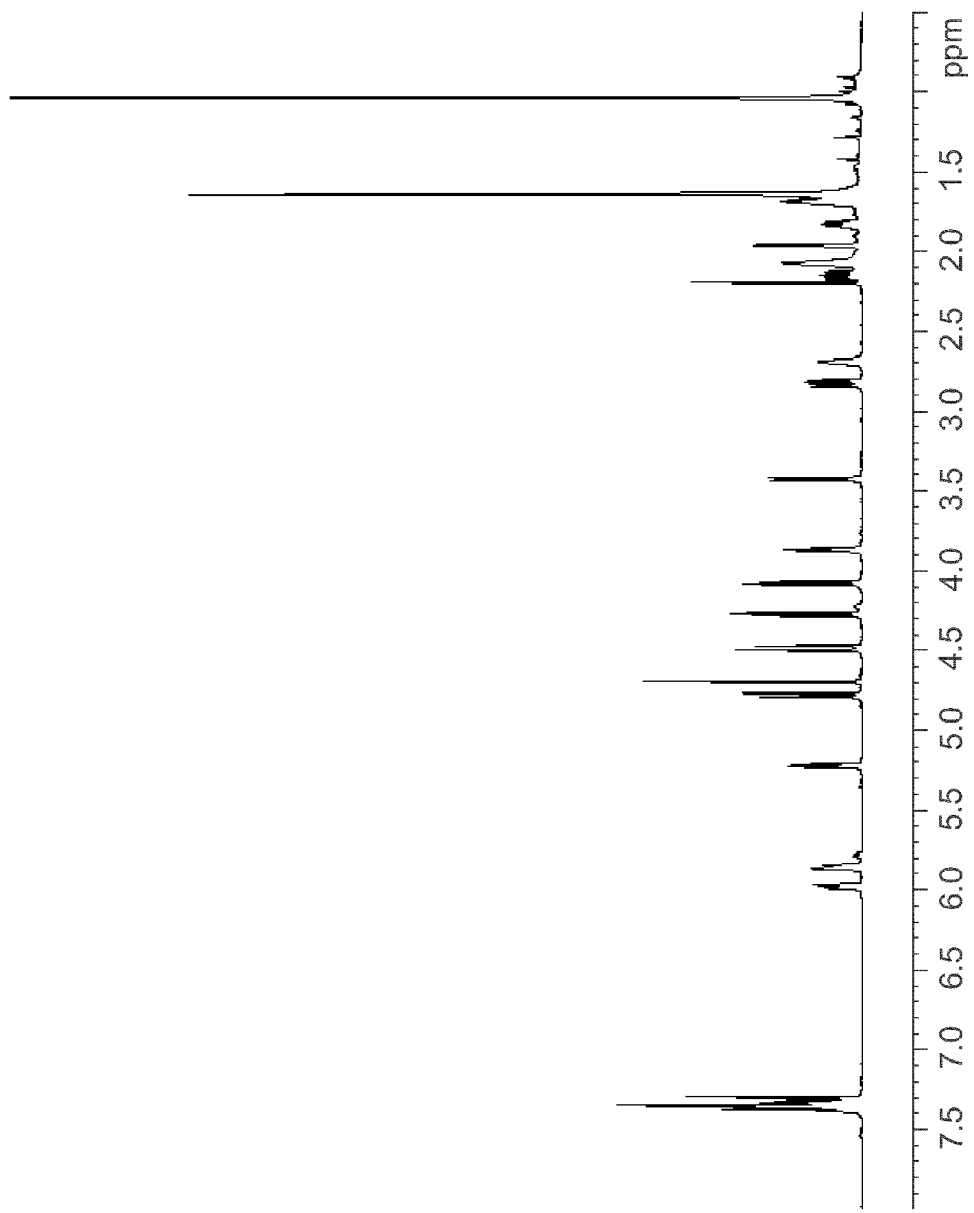
FIG. 52: $^1$H-NMR of Compound (X-1$_a$) in CDCl$_3$

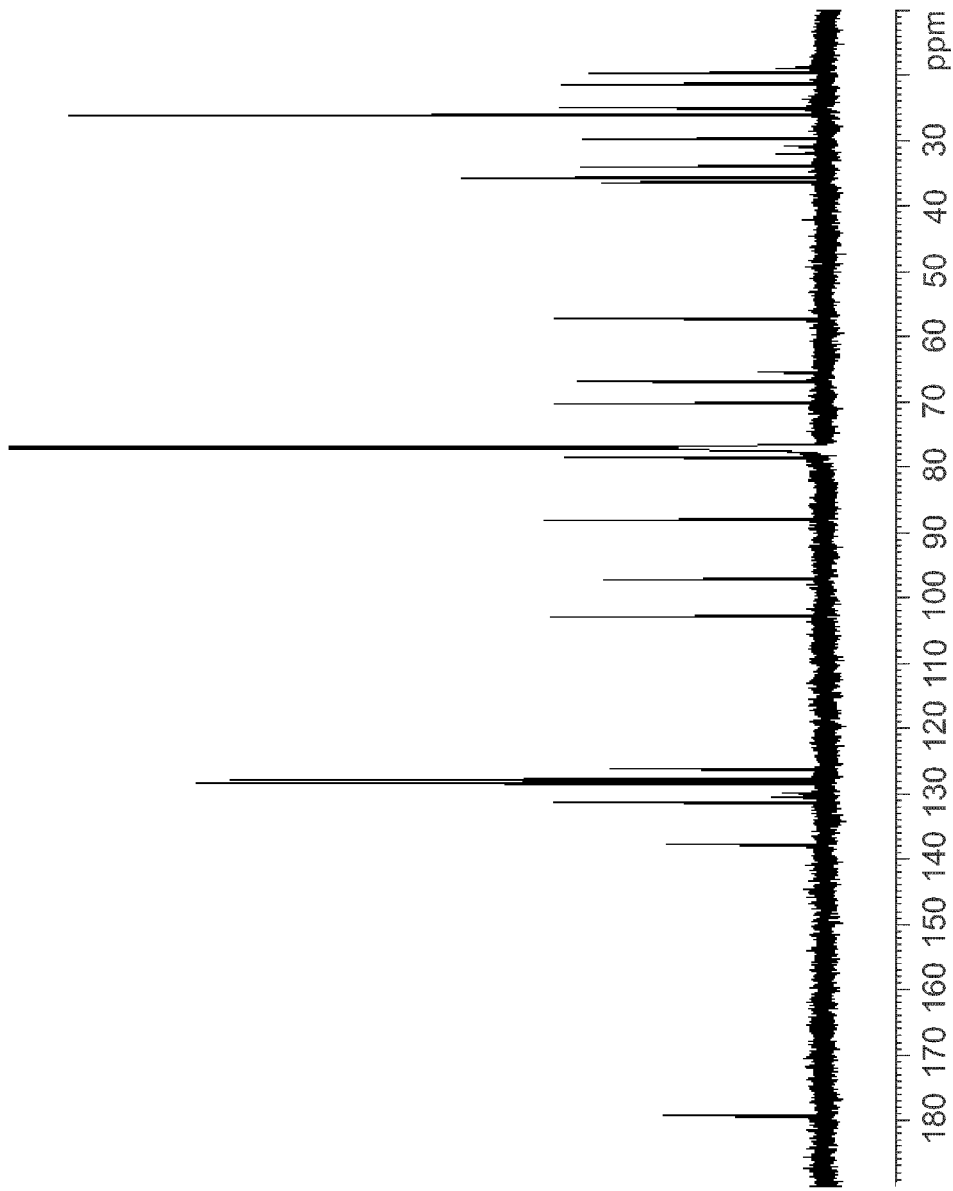
FIG. 53: $^{13}$C-NMR of Compound (X-1$_a$) in CDCl$_3$

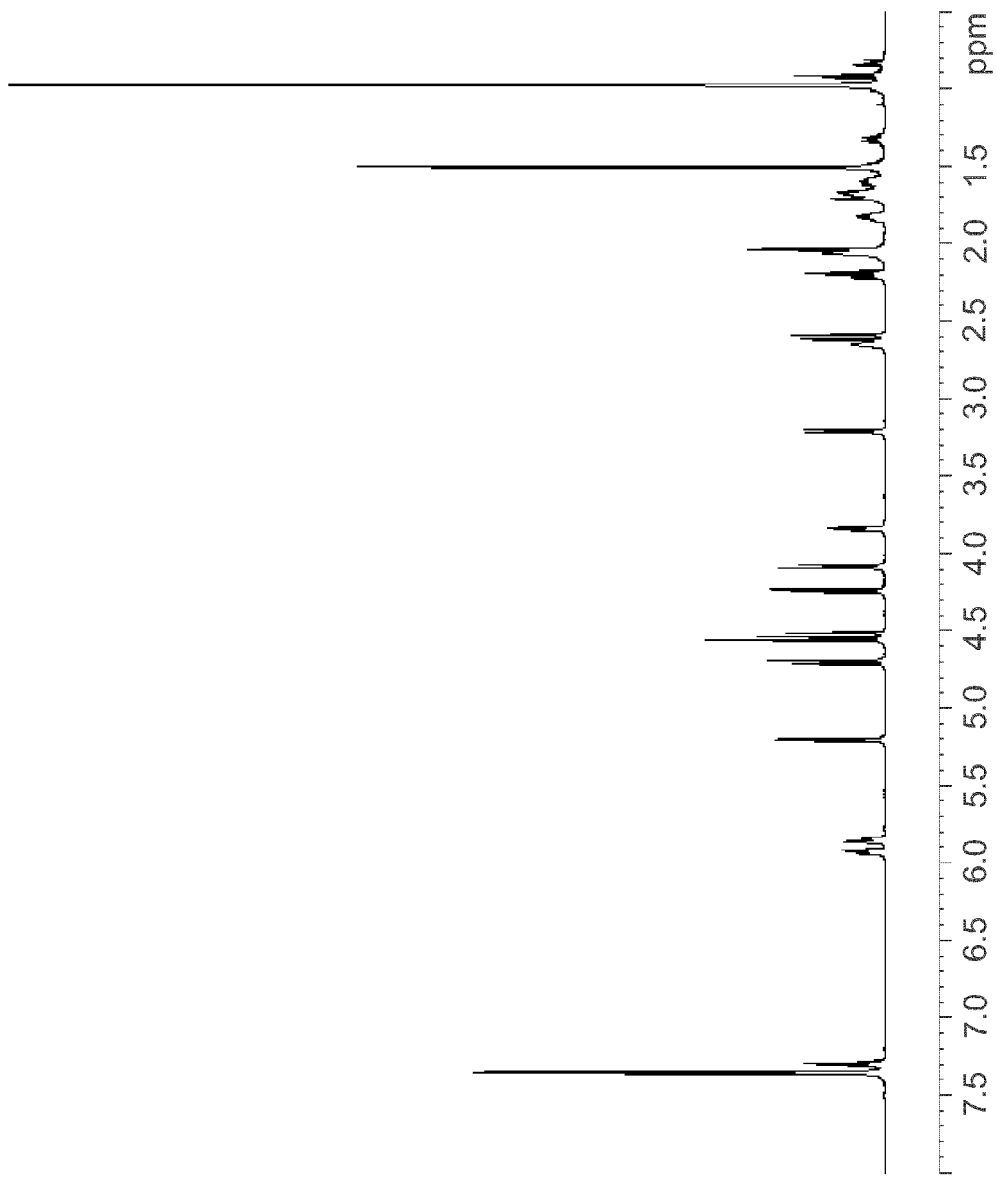
FIG. 54: $^1$H-NMR of Compound (X-1$_b$) in CDCl$_3$

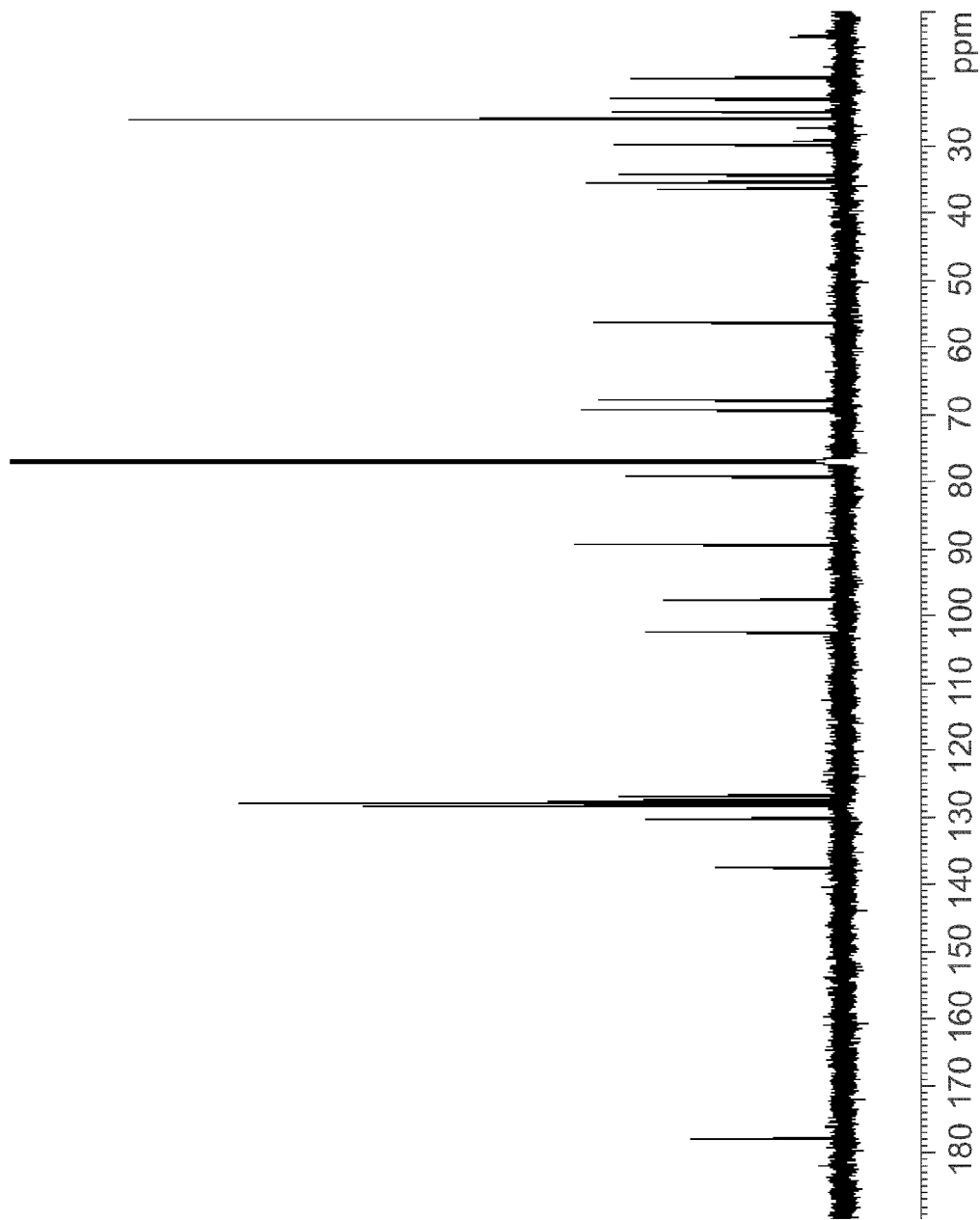
FIG. 55: $^{13}$C-NMR of Compound (X-1$_b$) in CDCl$_3$

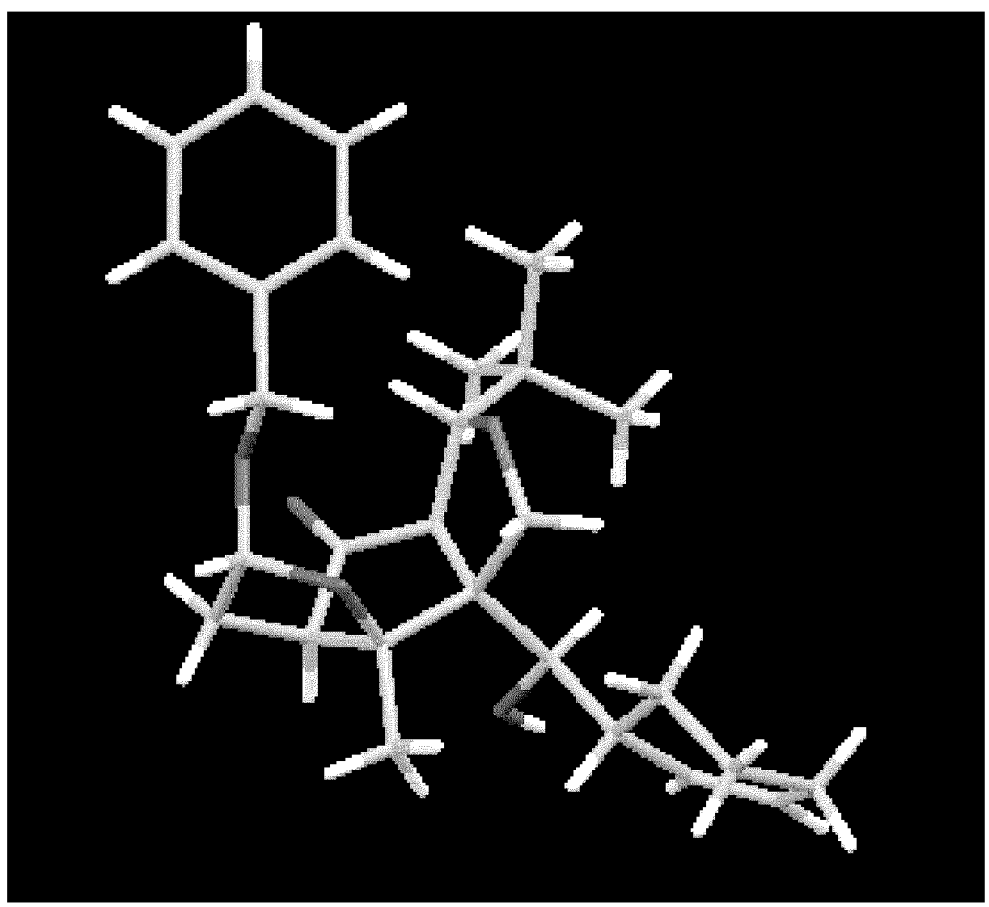
FIG. 56: Crystal Structure of Compound (X-1_b)

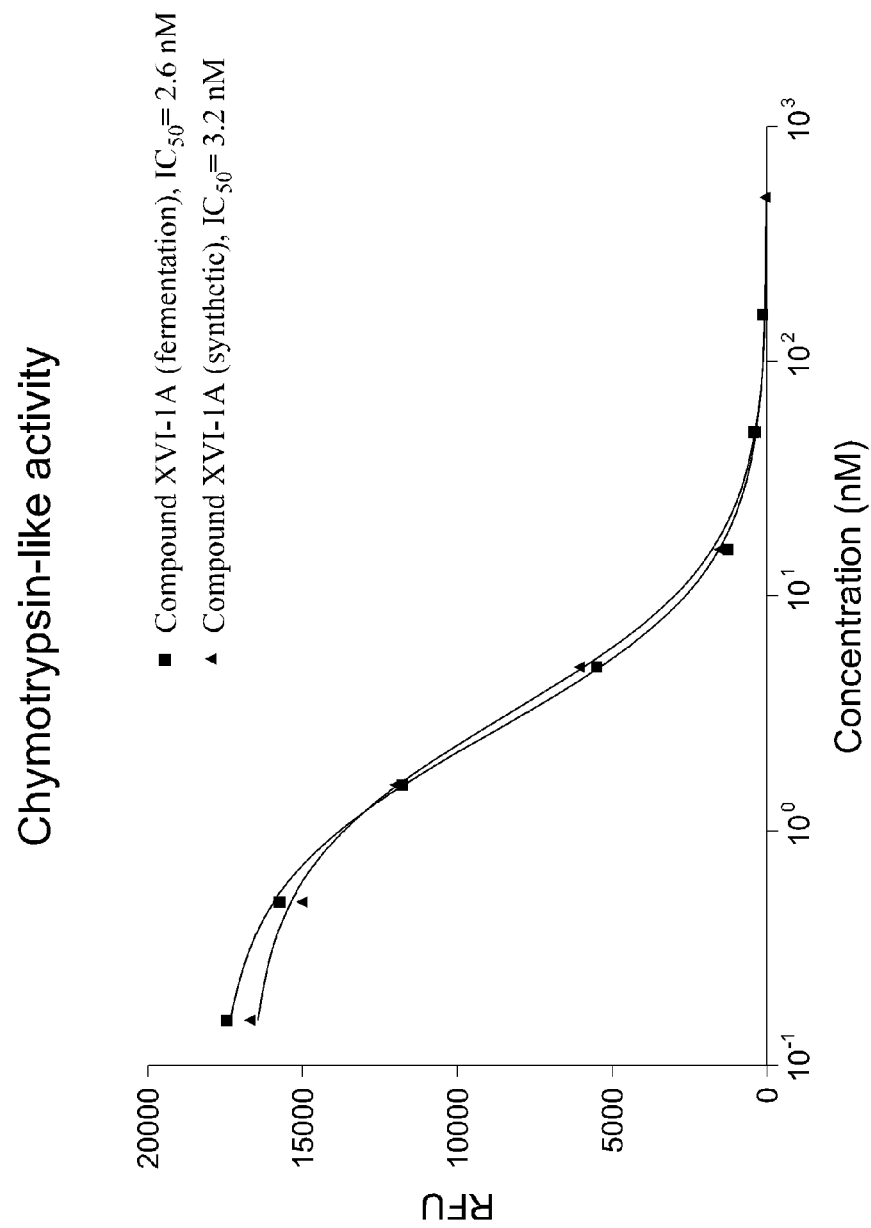
FIG. 57: Inhibition of the Chymotrypsin-like Activity of 20S Proteasomes by the Synthetic and Fermentation Compounds XVI-1A

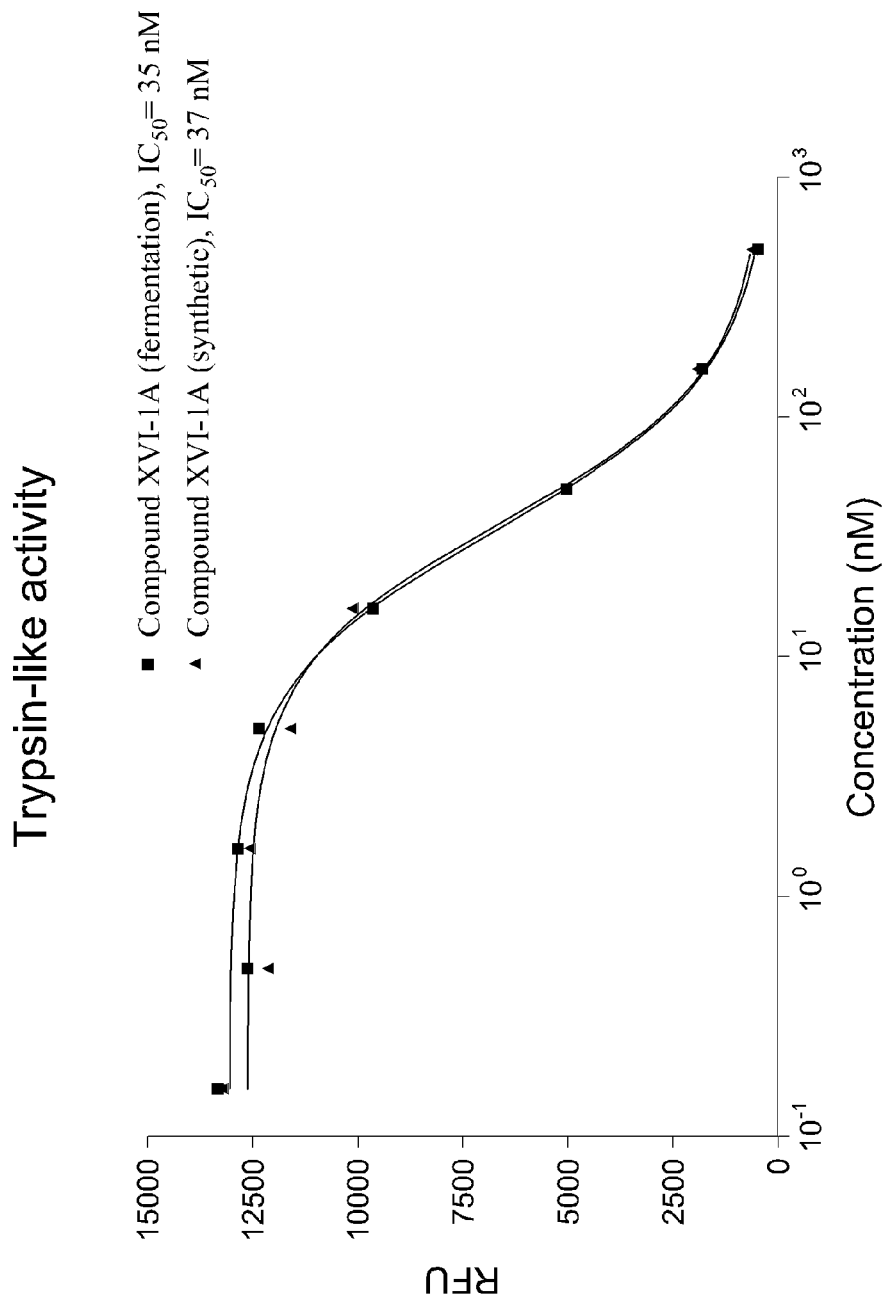
FIG. 58: Inhibition of the Trypsin-like Activity of 20S Proteasomes by the Synthetic and Fermentation Compounds XVI-1A

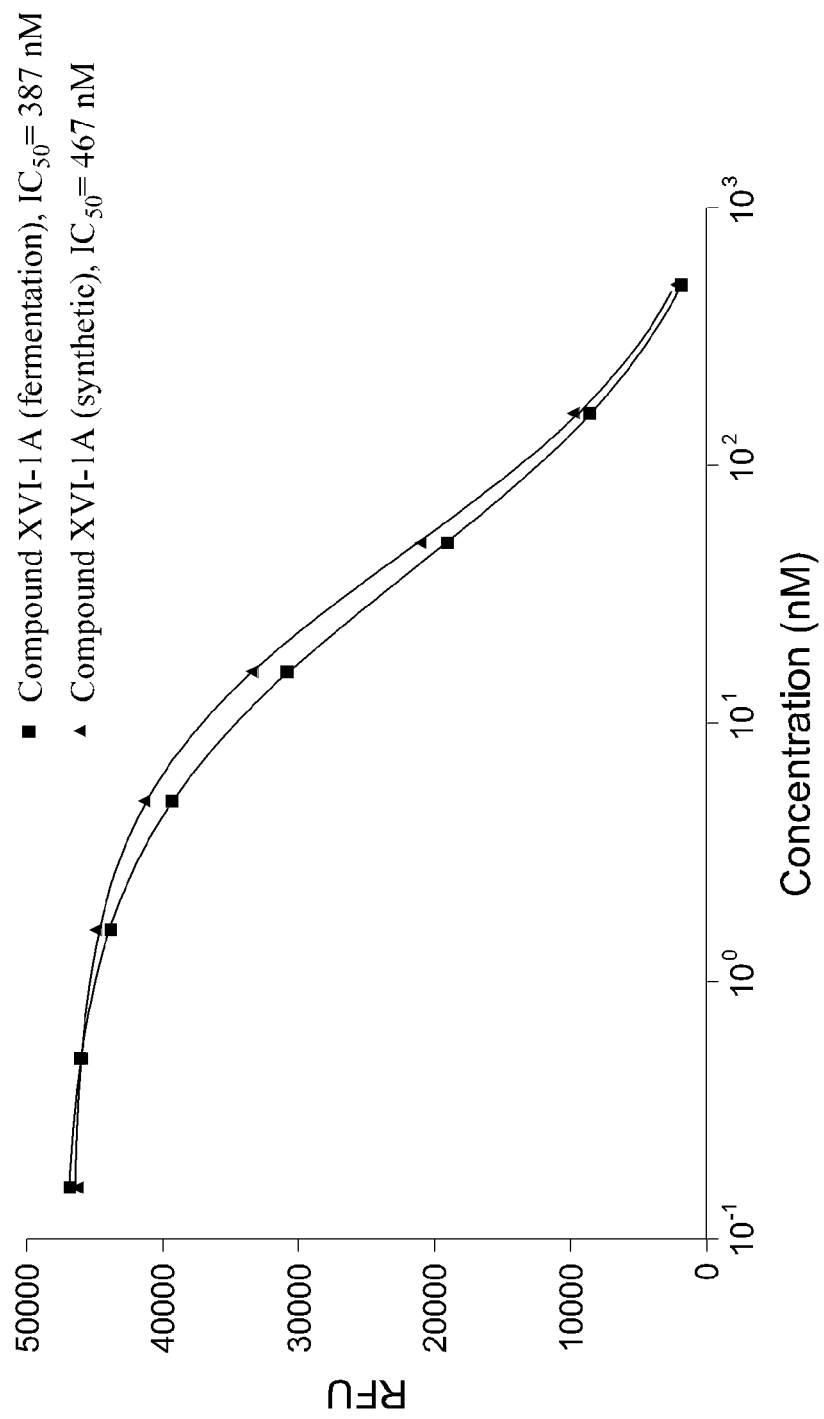
FIG. 59: Inhibition of the Caspase-like Activity of 20S Proteasomes by the Synthetic and Fermentation Compounds XVI-1A

TOTAL SYNTHESIS OF SALINOSPORAMIDE A AND ANALOGS THEREOF

CROSS-REFERENCE TO RELATED APPLICATIONS

This application is a divisional of U.S. patent application Ser. No. 11/697,689, entitled "Total Synthesis of Salinosporamide A and Analogs Thereof," filed Apr. 6, 2007, and claims priority to U.S. Provisional Patent Application Nos. 60/790,168, entitled "Total Synthesis of Salinosporamide A and Analogs Thereof," filed Apr. 6, 2006; 60/816,968, entitled "Total Synthesis of Salinosporamide A and Analogs Thereof," filed Jun. 27, 2006; 60/836,155, entitled "Total Synthesis of Salinosporamide A and Analogs Thereof," filed Aug. 7, 2006; 60/844,132, entitled "Total Synthesis of Salinosporamide A and Analogs Thereof," filed Sep. 12, 2006; and 60/885,379, entitled "Total Synthesis of Salinosporamide A and Analogs Thereof," filed Jan. 17, 2007, all of which are incorporated herein by reference in their entireties, including any drawings.

BACKGROUND OF THE INVENTION

1. Field of the Invention

The present invention relates to certain compounds and to methods for the preparation of certain compounds that can be used in the fields of chemistry and medicine.

2. Description of the Related Art

Cancer is a leading cause of death in the United States. Despite significant efforts to find new approaches for treating cancer, the primary treatment options remain surgery, chemotherapy and radiation therapy, either alone or in combination. Surgery and radiation therapy, however, are generally useful only for fairly defined types of cancer, and are of limited use for treating patients with disseminated disease. Chemotherapy is the method that is generally useful in treating patients with metastatic cancer or diffuse cancers such as leukemias. Although chemotherapy can provide a therapeutic benefit, it often fails to result in cure of the disease due to the patient's cancer cells becoming resistant to the chemotherapeutic agent. Due, in part, to the likelihood of cancer cells becoming resistant to a chemotherapeutic agent, such agents are commonly used in combination to treat patients.

Similarly, infectious diseases caused, for example, by bacteria, fungi and protozoa are becoming increasingly difficult to treat and cure. For example, more and more bacteria, fungi and protozoa are developing resistance to current antibiotics and chemotherapeutic agents. Examples of such microbes include *Bacillus, Leishmania, Plasmodium* and *Trypanosoma*.

Furthermore, a growing number of diseases and medical conditions are classified as inflammatory diseases. Such diseases include conditions such as asthma to cardiovascular diseases. These diseases continue to affect larger and larger numbers of people worldwide despite new therapies and medical advances.

Therefore, a need exists for additional chemotherapeutics, anti-microbial agents, and anti-inflammatory agents to treat cancer, inflammatory diseases and infectious disease. A continuing effort is being made by individual investigators, academia and companies to identify new, potentially useful chemotherapeutic and anti-microbial agents.

Marine-derived natural products are a rich source of potential new anti-cancer agents and anti-microbial agents. The oceans are massively complex and house a diverse assemblage of microbes that occur in environments of extreme variations in pressure, salinity, and temperature. Marine microorganisms have therefore developed unique metabolic and physiological capabilities that not only ensure survival in extreme and varied habitats, but also offer the potential to produce metabolites that would not be observed from terrestrial microorganisms (Okami, Y. 1993 *J Mar Biotechnol* 1:59). Representative structural classes of such metabolites include terpenes, peptides, polyketides, and compounds with mixed biosynthetic origins. Many of these molecules have demonstrable anti-tumor, anti-bacterial, anti-fungal, anti-inflammatory or immunosuppressive activities (Bull, A. T. et al. 2000 *Microbiol Mol Biol Rev* 64:573; Cragg, G. M. & D. J. Newman 2002 *Trends Pharmacol Sci* 23:404; Kerr, R. G. & S. S. Kerr 1999 *Exp Opin Ther Patents* 9:1207; Moore, B. S 1999 *Nat Prod Rep* 16:653; Faulkner, D. J. 2001 *Nat Prod Rep* 18:1; Mayer, A. M. & V. K. Lehmann 2001 *Anticancer Res* 21:2489), validating the utility of this source for isolating invaluable therapeutic agents. Further, the isolation of novel anti-cancer and anti-microbial agents that represent alternative mechanistic classes to those currently on the market will help to address resistance concerns, including any mechanism-based resistance that may have been engineered into pathogens for bioterrorism purposes.

SUMMARY OF THE INVENTION

The embodiments disclosed herein generally relate to the total synthesis of chemical compounds, including heterocyclic compounds and analogs thereof. Some embodiments are directed to the chemical compound and intermediate compounds. Other embodiments are directed to the individual methods of synthesizing the chemical compound and intermediate compounds.

An embodiment disclosed herein relates to a method for synthesizing Salinosporamide A and its analogs through an intermediate compound of formula (V):

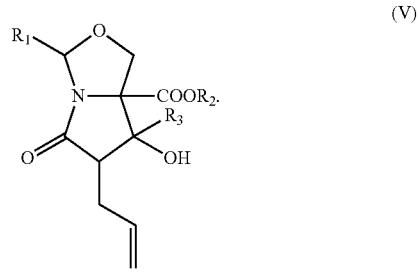

(V)

One embodiment described herein relates to a method for synthesizing an intermediate compound of formula (V).

Another embodiment described herein relates to a method for synthesizing an intermediate compound of formula (X).

Still another embodiment described herein relates to a method for synthesizing an intermediate compound of formula (XV).

Yet still another embodiment described herein relates to a method for synthesizing an intermediate compound of formula (XVII).

One embodiment described herein relates to a method for synthesizing Salinosporamide A and its analogs through an intermediate compound of formula (V).

Another embodiment described herein relates to a method for synthesizing Salinosporamide A and its analogs through an intermediate compound of formula (VI).

Still another embodiment described herein relates to a method for synthesizing Salinosporamide A and its analogs through an intermediate compound of formula (X).

Still another embodiment described herein relates to a method for synthesizing Salinosporamide A and its analogs through an intermediate compound of formula (Xp).

Yet still another embodiment described herein relates to a method for synthesizing Salinosporamide A and its analogs through an intermediate compound of formula (XI).

One embodiment described herein relates to a method for synthesizing Salinosporamide A and its analogs through an intermediate compound of formula (XV).

Another embodiment described herein relates to a method for synthesizing Salinosporamide A and its analogs through an intermediate compound of formula (XVII).

Still another embodiment described herein relates to a method for synthesizing Salinosporamide A and its analogs through an intermediate compound of formula (XVIIp).

Yet still another embodiment described herein relates to a method for synthesizing Salinosporamide A and its analogs through an intermediate compound of formula (XVIII).

One embodiment described herein relates to a method for synthesizing Salinosporamide A and its analogs through an intermediate compound of formula (XXIII).

Some embodiments described herein relate to the individual methods of synthesizing compounds of formula (III), (IV), (VI), (VI), (VII), (VIII), (IX), (X), (XV), (XVI), (XXII), (XXIII), (XXIV), (XXV), (XXVI), (XXVII), (XXVIII) and protected derivatives thereof.

Other embodiments described herein relate to the individual compounds of formula (III), (IV), (VI), (VI), (VII), (VIII), (IX), (X), (XV), (XVI), (XXII) (XXIII) (XXIV), (XXV) (XXVI), (XXVII), (XXVIII) and protected derivatives thereof.

One embodiment described herein relates to a method of forming a compound of formula (X) from a compound of formula (V) comprising the steps of: cleaving the carbon-carbon double bond of the compound of formula (V) and cyclizing the cleaved double bond with the tertiary hydroxy group; transforming —COOR$_2$ to an aldehyde; and adding R$_4$ to the aldehyde using an organometallic moiety containing at least one R$_4$, wherein R$_2$ and R$_4$ are described herein An embodiment described herein relates to a method of forming a compound of formula (XV) from a compound of formula (X) comprising the steps of: cleaving an aminal group; removing PG$_1$ and reductively opening the hemiacetal; and forming a four membered lactone ring, wherein PG$_1$ can be a protecting group moiety described herein. In some embodiments, the cleaving of the aminal group can occur before the removal of PG$_1$ and reductively opening the hemiacetal, and before the formation of the four membered lactone ring. In other embodiments, the cleaving of the aminal group can occur after the removal of PG$_1$ and reductively opening the hemiacetal, but before the formation of the four membered ring.

Another embodiment described herein relates to a method of forming a compound of formula (XVII) from a compound of formula (V) comprising the steps of: cleaving the carbon-carbon double bond of the compound of formula (V) and cyclizing the cleaved double bond with the tertiary hydroxy group; and adding R$_4$ after cyclization with the tertiary hydroxy group using an organometallic moiety containing at least one R$_4$, wherein R$_4$ is described herein;

On embodiment described herein relates to a method of forming a compound of formula (XXII) from a compound of formula (XVII) comprising the steps of: cleaving an aminal group; removing PG$_1$ and reductively opening the hemiac-etal; forming a four membered ring via a lactonization reaction; and removing any protecting groups on a ketone, wherein PG$_1$ can be a protecting group moiety described herein. In some embodiments, the cleaving of the aminal group can occur before the removal of PG$_1$ and reductively opening the hemiacetal, and before the formation of the four membered ring via a lactonization reaction. In other embodiments, the cleaving of the aminal group is after the removal of PG$_1$ and reductively opening the hemiacetal, but before the formation of the four membered ring via a lactonization reaction.

BRIEF DESCRIPTION OF THE DRAWINGS

The accompanying drawings, which are incorporated in and form part of the specification, merely illustrate certain preferred embodiments of the present invention. Together with the remainder of the specification, they are meant to serve to explain preferred modes of making certain compounds of the invention to those of skilled in the art. In the drawings:

FIG. 2 shows a $^1$H NMR spectrum of the compound of formula (I-1) in CDCl$_3$.

FIG. 3 shows a $^1$H NMR spectrum of the ester precursor to the compound of formula (II-1) in CDCl$_3$.

FIG. 4 shows a $^1$H NMR spectrum of the protected ester precursor of the compound of formula (II-1) in CDCl$_3$.

FIG. 5 shows a $^1$H NMR spectrum of the compound of formula (II-1) in CDCl$_3$.

FIG. 6a shows a $^1$H NMR spectrum of the compound of formula (III-1) in CDCl$_3$.

FIG. 6b shows a LC-MS of the compound of formula (III-1).

FIG. 7a shows a $^1$H NMR spectrum of the compound of formula (IV-1) in CDCl$_3$.

FIG. 7b shows a NOESY spectrum of the compound of formula (IV-1) in CDCl$_3$.

FIG. 7c shows a $^1$H NMR spectrum of the compound of formula (IV-1A) in CDCl$_3$.

FIG. 7d shows a $^1$H NMR spectrum of the compound of formula (IV-1B) in CDCl$_3$.

FIG. 7e shows a LC-MS of the compound of formula (IV-1).

FIG. 8 shows a $^1$H NMR spectrum of the compound of formula (V-1A) in CDCl$_3$.

FIG. 9 shows a $^{13}$C NMR spectrum of the compound of formula (V-1A) in CDCl$_3$.

FIG. 10 shows a $^1$H-$^1$H COSY NMR spectrum of the compound of formula (V-1A) in CDCl$_3$.

FIG. 11 shows the crystal structure of the compound of formula (V-1A).

FIG. 12 shows a $^1$H NMR spectrum of the compound of formula (VI-1) in CDCl$_3$.

FIG. 13 shows a $^1$H NMR spectrum of the compound of formula (VII-1$_a$) in CDCl$_3$.

FIG. 14 shows a $^1$H NMR spectrum of the compound of formula (VII-1$_b$) in CDCl$_3$.

FIG. 15 shows the crystal structure of the compound of formula (VII-1$_b$).

FIG. 16 shows a $^1$H NMR spectrum of the compound of formula (VIII-1$_b$) in CDCl$_3$.

FIG. 17 shows a $^1$H NMR of the compound of formula (VIII-1$_a$) in CDCl$_3$

FIG. 18 shows a $^1$H NMR spectrum of the compound of formula (IX-1$_b$) in CDCl$_3$ FIG. 19 shows a $^1$H NMR spectrum of the compound of formula (IX-1$_a$) in CDCl$_3$ FIG. 20 shows a $^1$H NMR spectrum of the compound of formula (X-1$_b$B) in CDCl$_3$ FIG. 21 shows a $^{13}$C NMR spectrum of the compound of formula (X-1$_b$B) in CDCl$_3$.

FIG. 22 shows the crystal structure of the compound of formula (X-1$_b$B).

FIG. 23 shows a $^1$H NMR spectrum of the compound of formula (X-1$_a$B) in CDCl$_3$.

FIG. 24 shows a $^{13}$C NMR spectrum of the compound of formula (X-1$_a$B) in CDCl$_3$.

FIG. 25 shows a $^1$H NMR spectrum of the compound of formula (V-1B) in CDCl$_3$.

FIG. 26 shows the crystal structure of the compound of formula (V-1B).

FIG. 27 shows a $^1$H NMR spectrum of the compound of formula (V-1C) in CDCl$_3$.

FIG. 28 shows a $^{13}$C NMR spectrum of the compound of formula (V-1C) in CDCl$_3$.

FIG. 29 shows a NOESY spectrum of the compound of formula (V-1C) in CDCl$_3$.

FIG. 30 shows a $^1$H NMR spectrum of the compound of formula (XXIX-1) in CDCl$_3$.

FIG. 31 shows a $^{13}$C NMR spectrum of the compound of formula (XXIX-1) in CDCl$_3$.

FIG. 32 shows a $^1$H NMR spectrum of the compound of formula (XXIII-1B) in CDCl$_3$.

FIG. 33 shows a $^{13}$C NMR spectrum of the compound of formula (XXIII-1B) in CDCl$_3$.

FIG. 34 shows a $^1$H NMR spectrum of the compound of formula (XXIV-1B-Bz) in CDCl$_3$.

FIG. 35 shows a $^1$H NMR spectrum of the compound of formula (XXV-1B-Bz) in CDCl$_3$.

FIG. 36 shows a $^{13}$C NMR spectrum of the compound of formula (XXV-1B-Bz) in CDCl$_3$.

FIG. 37 shows a $^1$H NMR spectrum of the compound of formula (XXVp-1B-Bz-TMS) in CDCl$_3$.

FIG. 38 shows a $^{13}$C NMR spectrum of the compound of formula (XXVp-1B-Bz-TMS) in CDCl$_3$.

FIG. 39 shows a $^1$H NMR spectrum of the compound of formula (XXVI-1B-Bz) in CD$_3$OD.

FIG. 40 shows a $^{13}$C NMR spectrum of the compound of formula (XXVI-1B-Bz) in CD$_3$OD.

FIG. 41 shows a $^1$H NMR spectrum of the compound of formula (XXVIII-1B-TBS) in CDCl$_3$.

FIG. 42 shows a $^1$H NMR spectrum of the compound of formula (XV-1B) in acetone-d$_6$.

FIG. 43 shows a $^{13}$C NMR spectrum of the compound of formula (XV-1B) in acetone-d$_6$.

FIG. 44 shows a $^1$H NMR spectrum of the compound of formula (XVI-1B) produced from the compound of formula (XV-1B) produced synthetically in CDCl$_3$.

FIG. 45 shows a $^{13}$C NMR spectrum of the compound of formula (XVI-1B) produced from the compound of formula (XV-1B) produced synthetically in CDCl$_3$.

FIG. 46 shows $^1$H NMR spectrum of the compound of formula (XXII-1) produced from the compound of formula (XVI-1B) obtained synthetically in CDCl$_3$.

FIG. 47 shows $^1$H NMR spectrum of the compound of formula (XVI-1A) produced from the compound of formula (XXII-1) obtained synthetically in DMSO-d$_6$.

FIG. 48 shows a comparison of $^1$H NMR spectra of compound (XVI-1A) produced synthetically and from fermentation.

FIG. 49 shows a $^{13}$C NMR spectrum of the compound of formula (XVI-1A) produced from the compound of formula (XXII-1) obtained synthetically in DMSO-d$_6$.

FIG. 50 shows a comparison of $^{13}$C NMR spectra of compound (XVI-1A) produced synthetically and from fermentation.

FIG. 51 shows a $^1$H NMR spectrum of cyclohexenyltributyltin in CDCl$_3$.

FIG. 52 shows a $^1$H NMR spectrum of the compound of formula (X-1$_a$) in CDCl$_3$.

FIG. 53 shows a $^{13}$C NMR spectrum of the compound of formula (X-1$_a$) in CDCl$_3$.

FIG. 54 shows a $^1$H NMR spectrum of the compound of formula (X-1$_b$) in CDCl$_3$.

FIG. 55 shows a $^{13}$C NMR spectrum of the compound of formula (X-1$_b$) in CDCl$_3$.

FIG. 56 shows the crystal structure of the compound of formula (X-1$_b$).

FIG. 57 shows a plot of the inhibition of the chymotrypsin-like activity of 20S proteasomes by the synthetic and fermentation compounds of formula (XVI-1A).

FIG. 58 shows a plot of the inhibition of the trypsin-like activity of 20S proteasomes by the synthetic and fermentation compounds of formula (XVI-1A).

FIG. 59 shows a plot of the inhibition of the caspase-like activity of 20S proteasomes by the synthetic and fermentation compounds of formula (XVI-1A).

DETAILED DESCRIPTION OF THE PREFERRED EMBODIMENT

Figure 1:
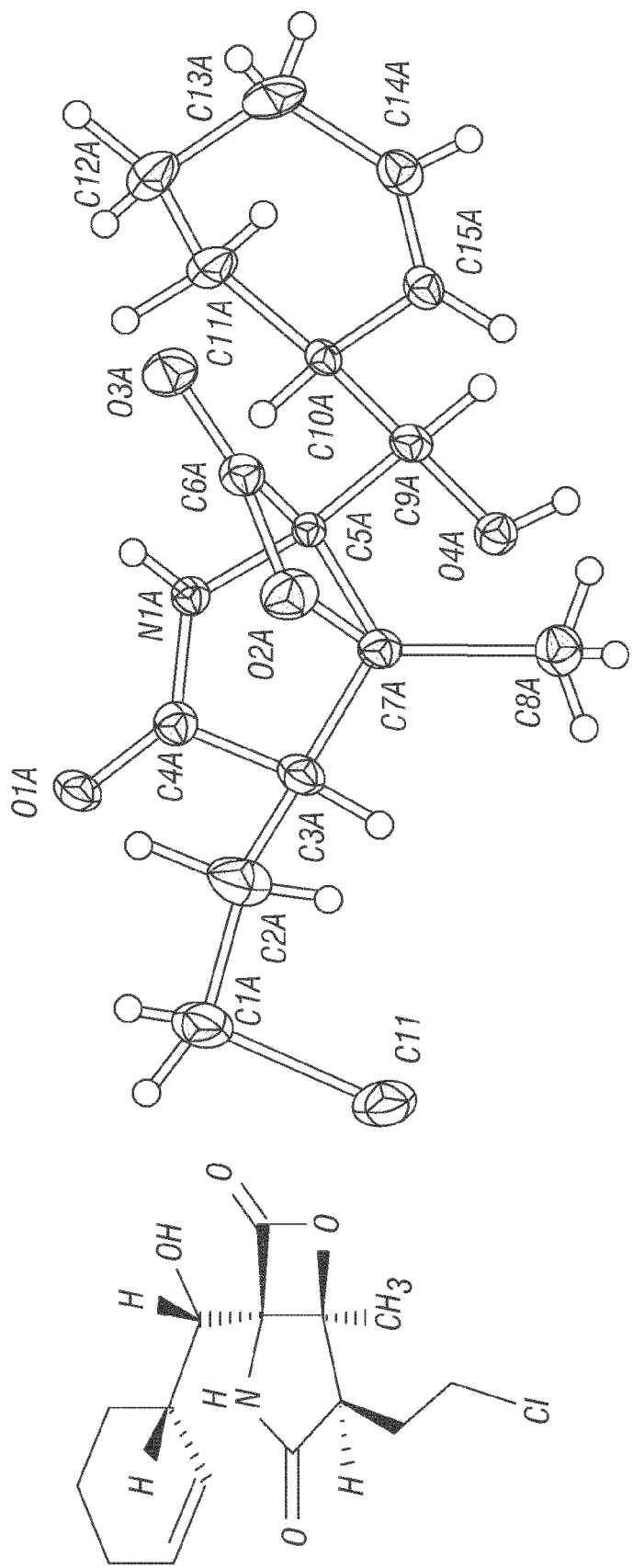
FIG. 1 shows the chemical structure of Salinosporamide A.

Numerous references are cited herein. The references cited herein, including the U.S. patents cited herein, are each to be considered incorporated by reference in their entirety into this specification.

Embodiments of the invention include, but are not limited to, methods for the preparation of various compounds and intermediates, and the compounds and intermediates themselves. In some embodiments, one or more substituents, one or more compounds, or groups of compounds can be specifically excluded in any one or more of the methods or compounds as described more fully below.

Salinosporamide A and its analogs thereof have various biological activities. For example, the compounds have chemosensitizing activity, anti-microbial, anti-inflammation, radiosensitizing, and anti-cancer activity. Studies have been conducted that show Salinosporamide A and its analogs have proteasome inhibitory activity, effect NF-κB/IκB signaling pathway, and have anti-anthrax activity. Salinosporamide A and several analogs, as well as biological activity of the same, are described in U.S. Provisional Patent Applications Nos. 60/480,270, filed Jun. 20, 2003; 60/566,952, filed Apr. 30, 2004; 60/627,461, filed Nov. 12, 2004; 60/633,379, filed Dec. 3, 2004; 60/643,922, filed Jan. 13, 2005; 60/658,884, filed Mar. 4, 2005; 60/676,533, filed Apr. 29, 2005; 60/567,336, filed Apr. 30, 2004; 60/580,838, filed Jun. 18, 2004; 60/591, 190, filed Jul. 26, 2004; 60/627,462, filed Nov. 12, 2004; 60/644,132, filed Jan. 13, 2005; and 60/659,385, filed Mar. 4, 2005; U.S. patent application Ser. Nos. 10/871,368, filed Jun. 18, 2004; 11/118,260, filed Apr. 29, 2005; 11/412,476, filed Apr. 27, 2006; and 11/453,374, filed Jun. 15, 2006; and International Patent Applications Nos. PCT/US2004/019543, filed Jun. 18, 2004; PCT/US2005/044091, filed Dec. 2, 2005; PCT/US2005/014846, filed Apr. 29, 2005; and PCT/US2006/016104, filed Apr. 27, 2006; each of which is hereby incorporated by reference in its entirety.

Provided herein are methods for synthesizing Salinosporamide A and its analogs through an intermediate compound of formula (V):

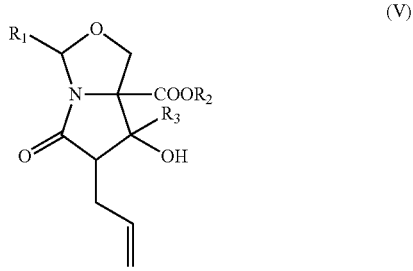

The compound of formula (V) can be synthesized from readily available starting materials, as described herein. The compound of formula (V) may be subsequently converted to Salinosporamide A or analogs thereof. For example Salinosporamide A or analogs thereof may be synthesized according to Scheme A.

Examples of suitable substituents include but are not limited to hydrogen, alkoxy, cycloalkyl, cycloalkenyl, acyl, acylamino, acyloxy, amino, alkyl amino, aminoacyl, aminoacyloxy, oxyacylamino, cyano, halogen, hydroxy, carboxyl, carboxylalkyl, keto, thioketo, thiol, thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$—H, —SO$_2$—OH, —SO$_2$-alkyl, —SO$_2$-substituted alkyl, —SO$_2$-aryl and —SO$_2$-heteroaryl, heteroaryl, boronate alkyl, boronic acid, (OH)$_2$B-alkyl, phosphate and phosphate esters, phosphonooxy, phosphonooxyalkyl, azido, azidoalkyl, ammonium, carboxyalkyl, a salt of a carboxyalkyl, alkylamino, a salt of an alkylamino, dialkylamino, a salt of a dialkylamino, alkylthio, arylthio, carboxy, cyano, alkanesulfonyl, alkanesulfinyl, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy)alkyl, phosphorylalkyl, a salt of a phosphorylalkyl, (alkylphosphoryl)alkyl, pyridinylalkyl, a salt of a pyridinylalkyl, a salt of a heteroary- Scheme A

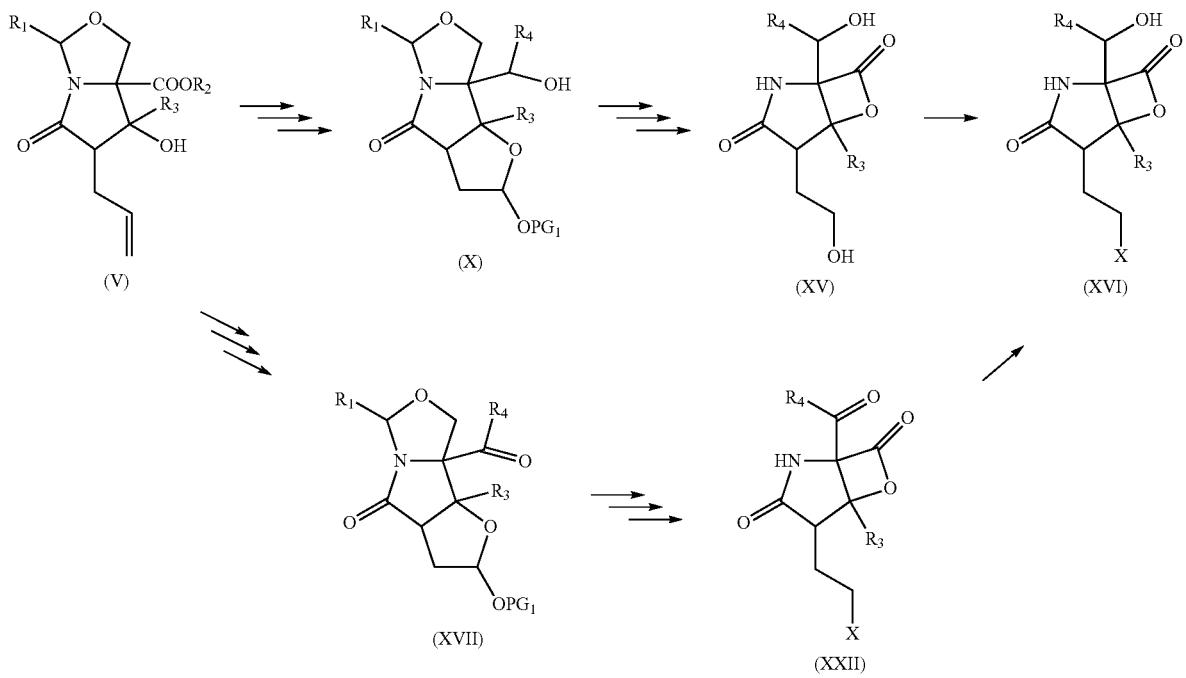

For the compounds described herein, each stereogenic carbon can be of R or S configuration. Although the specific compounds exemplified in this application can be depicted in a particular configuration, compounds having either the opposite stereochemistry at any given chiral center or mixtures thereof are also envisioned unless otherwise specified. When chiral centers are found in the derivatives of this invention, it is to be understood that the compounds encompasses all possible stereoisomers unless otherwise indicated.

The term "substituted" has its ordinary meaning, as found in numerous contemporary patents from the related art. See, for example, U.S. Pat. Nos. 6,509,331; 6,506,787; 6,500,825; 5,922,683; 5,886,210; 5,874,443; and 6,350,759; all of which are incorporated herein in their entireties by reference.

lalkyl guanidino, a salt of a guanidino, and guanidinoalkyl. Each of the substituents can be further substituted. The other above-listed patents also provide standard definitions for the term "substituted" that are well-understood by those of skill in the art.

Whenever a group is described as "optionally substituted" the group may be unsubstituted or substituted with one or more substituents as described herein.

As used herein, any "R" group(s) such as, without limitation, R, R$_1$, R$_2$, R$_3$, R$_4$, R$_5$, R$_6$, R$_7$, R$_8$, R$_A$ and R$_B$ represent substituents that can be attached to the indicated atom. An R group may be substituted or unsubstituted. If two "R" groups are covalently bonded to the same atom or to adjacent atoms, then they may be "taken together" as defined herein to form a cycloalkyl, aryl, heteroaryl or heterocycle. For example, without limitation, if $R_{1a}$ and $R_{1b}$ of an $NR_{1a}R_{1b}$ group are indicated to be "taken together," it means that they are covalently bonded to one another to form a ring:

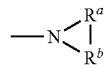

The term "alkyl," as used herein, means any unbranched or branched, substituted or unsubstituted, saturated hydrocarbon, with $C_1$-$C_{24}$ preferred, and $C_1$-$C_6$ hydrocarbons being preferred, with methyl, ethyl, propyl, isopropyl, butyl, isobutyl, and tert-butyl, and pentyl being most preferred.

The term "alkenyl," as used herein, means any unbranched or branched, substituted or unsubstituted, unsaturated hydrocarbon containing one or more double bonds. Some examples of alkenyl groups include allyl, homo-allyl, vinyl, crotyl, butenyl, pentenyl, hexenyl, heptenyl and octenyl.

The term "alkynyl" as used herein, means any unbranched or branched, substituted or unsubstituted, unsaturated hydrocarbon with one or more triple bonds The term "cycloalkyl" refers to any non-aromatic, substituted or unsubstituted, hydrocarbon ring, preferably having five to twelve atoms comprising the ring. Furthermore, in the present context, the term "cycloalkyl" comprises fused ring systems such that the definition covers bicyclic and tricyclic structures.

The term "cycloalkenyl" refers to any non-aromatic, substituted or unsubstituted, hydrocarbon ring that includes a double bond, preferably having five to twelve atoms comprising the ring. Furthermore, in the present context, the term "cycloalkenyl" comprises fused ring systems such that the definition covers bicyclic and tricyclic structures.

The term "cycloalkynyl" refers to any non-aromatic, substituted or unsubstituted, hydrocarbon ring that includes a triple bond, preferably having five to twelve atoms comprising the ring. Furthermore, in the present context, the term "cycloalkynyl" comprises fused ring systems such that the definition covers bicyclic and tricyclic structures.

The term "acyl" refers to hydrogen, lower alkyl, lower alkenyl, or aryl connected, as substituents, via a carbonyl group. Examples include formyl, acetyl, propanoyl, benzoyl, and acryl. An acyl may be substituted or unsubstituted.

In the present context the term "aryl" is intended to mean a carbocyclic aromatic ring or ring system. Moreover, the term "aryl" includes fused ring systems wherein at least two aryl rings, or at least one aryl and at least one $C_{3-8}$-cycloalkyl share at least one chemical bond. Some examples of "aryl" rings include optionally substituted phenyl, naphthalenyl, phenanthrenyl, anthracenyl, tetralinyl, fluorenyl, indenyl, and indanyl. An aryl group may be substituted or unsubstituted.

In the present context, the term "heteroaryl" is intended to mean a heterocyclic aromatic group where one or more carbon atoms in an aromatic ring have been replaced with one or more heteroatoms selected from the group comprising nitrogen, sulfur, phosphorous, and oxygen. Furthermore, in the present context, the term "heteroaryl" comprises fused ring systems wherein at least one aryl ring and at least one heteroaryl ring, at least two heteroaryl rings, at least one heteroaryl ring and at least one heterocyclyl ring, or at least one heteroaryl ring and at least one $C_{3-8}$-cycloalkyl ring share at least one chemical bond. A heteroaryl can be substituted or unsubstituted.

The terms "heterocycle" and "heterocyclyl" are intended to mean three-, four-, five-, six-, seven-, and eight-membered rings wherein carbon atoms together with from 1 to 3 heteroatoms constitute said ring. A heterocycle may optionally contain one or more unsaturated bonds situated in such a way, however, that an aromatic π-electron system does not arise. The heteroatoms are independently selected from oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides, cyclic carbamates, and the like. Heterocyclyl rings may optionally also be fused to at least other heterocyclyl ring, at least one $C_{3-8}$-cycloalkyl ring, at least one $C_{3-8}$-cycloalkenyl ring and/or at least one $C_{3-8}$-cycloalkynyl ring such that the definition includes bicyclic and tricyclic structures. Examples of benzo-fused heterocyclyl groups include, but are not limited to, benzimidazolidinone, tetrahydroquinoline, and methylenedioxybenzene ring structures. Some examples of "heterocycles" include, but are not limited to, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyridine, pyridinium, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. A heterocycle group of this invention may be substituted or unsubstituted.

The term "alkoxy" refers to any unbranched, or branched, substituted or unsubstituted, saturated or unsaturated ether, with $C_1$-$C_6$ unbranched, saturated, unsubstituted ethers being preferred, with methoxy being preferred, and also with dimethyl, diethyl, methyl-isobutyl, and methyl-tert-butyl ethers also being preferred.

The term "cycloalkoxy" refers to any non-aromatic hydrocarbon ring comprising an oxygen heteroatom, preferably having five to twelve atoms comprising the ring. A cycloalkoxy can be substituted or unsubstituted.

The term "alkoxy carbonyl" refers to any linear, branched, cyclic, saturated, unsaturated, aliphatic or aromatic alkoxy attached to a carbonyl group. The examples include methoxycarbonyl group, ethoxycarbonyl group, propyloxycarbonyl group, isopropyloxycarbonyl group, butoxycarbonyl group, sec-butoxycarbonyl group, tert-butoxycarbonyl group, cyclopentyloxycarbonyl group, cyclohexyloxycarbonyl group, benzyloxycarbonyl group, allyloxycarbonyl group, phenyloxycarbonyl group, pyridyloxycarbonyl group, and the like. An alkoxy carbonyl may be substituted or unsubstituted.

The term "(cycloalkyl)alkyl is understood as a cycloalkyl group connected, as a substituent, via a lower alkylene. The (cycloalkyl)alkyl group and lower alkylene of a (cycloalkyl) alkyl group may be substituted or unsubstituted.

The terms "(heterocycle)alkyl" and "(heterocyclyl)alkyl" are understood as a heterocycle group connected, as a substituent, via a lower alkylene. The heterocycle group and the lower alkylene of a (heterocycle)alkyl group may be substituted or unsubstituted.

The term "arylalkyl" is intended to mean an aryl group connected, as a substituent, via a lower alkylene, each as defined herein. The aryl group and lower alkylene of an arylalky may be substituted or unsubstituted. Examples include benzyl, substituted benzyl, 2-phenylethyl, 3-phenylpropyl, and naphthylalkyl.

The term "heteroarylalkyl" is understood as heteroaryl groups connected, as substituents, via a lower alkylene, each as defined herein. The heteroaryl and lower alkylene of a heteroarylalkyl group may be substituted or unsubstituted. Examples include 2-thienylmethyl, 3-thienylmethyl, furylmethyl, thienylethyl, pyrrolylalkyl, pyridylalkyl, isoxazolylalkyl, imidazolylalkyl, and their substituted as well as benzo-fused analogs.

The term "halogen atom," as used herein, means any one of the radio-stable atoms of column 7 of the Periodic Table of the Elements, i.e., fluorine, chlorine, bromine, or iodine, with bromine and chlorine being preferred.

As employed herein, the following terms have their accepted meaning in the chemical literature.

| | |
|---|---|
| 9-BBN | 9-borabicyclo[3.3.1]nonane |
| BF$_3$•Et$_2$O | borontrifluoride diethyl etherate |
| Bn | benzyl |
| BnOH | benzyl alcohol |
| BOPCl | bis(2-oxo-3-oxazolidinyl)phosphinic chloride |
| t-BuOH | tert-butanol/tert-butyl alcohol |
| t-BuOK | potassium tert-butoxide |
| Bz | benzoyl |
| DMIPS | Dimethyl iso-propylsilyl |
| ESI | electrospray ionization |
| EtOAc | ethyl acetate |
| FDH | formate dehydroganase |
| GDH | glucose dehydrogenase |
| ID | internal diameter |
| IPA | isopropyl alcohol |
| LC-MS | liquid chromatography-mass spectrometry |
| LDA | lithium diisopropylamide |
| MS | mass spectrum |
| MsCl | methanesulfonyl chloride |
| NaOMe | sodium methoxide |
| NaOEt | sodium ethoxide |
| NMO | N-methylmorpholine N-oxide |
| NMR | nuclear magnetic resonance |
| Pb(OAc)$_4$ | lead tetraacetate |
| PCC | pyridinium chlorochromate |
| PDC | pyridinium dicromate |
| PPTS | pyridinium p-toluene sulfonate |
| PTSA | p-toluene sulfonic acid |
| RT | room temperature |
| SAR | structure-activity relationship |
| TMS | trimethylsilyl |
| TBS | t-butyldimethylsilyl |
| TES | triethylsilyl |
| THF | tetrahydrofuran |
| TFA | trifluoroacetic acid |
| TPAP | tetrapropylammonium perruthenate |

The terms "organometallic moiety" and "organometallic moieties" as used herein refer to any chemical compound that contains a metal-element bond(s) of a largely covalent character. The term "metal" as used herein include those elements traditionally classified as metals (e.g., lithium, magnesium, zinc, and tin) and those elements classified as metalloids (e.g., boron).

The terms "protecting group moiety" and "protecting group moieties" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis,* 3. Ed. John Wiley & Sons, 1999, and in J. F. McOmie, *Protective Groups in Organic Chemistry* Plenum Press, 1973, both of which are hereby incorporated by reference. The protecting group moiety may be chosen in such a way, that they are stable to the reaction conditions applied and readily removed at a convenient stage using methodology known from the art. A non-limiting list of protecting groups include benzyl; substituted benzyl; alkylcarbonyls (e.g., t-butoxycarbonyl (BOC)); arylalkylcarbonyls (e.g., benzyloxycarbonyl, benzoyl); substituted methyl ether (e.g. methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g. benzoate ester); carbonates (e.g. methoxymethylcarbonate); sulfonates (e.g. tosylate, mesylate); acyclic ketal (e.g. dimethyl acetal); cyclic ketals (e.g., 1,3-dioxane or 1,3-dioxolanes); acyclic acetal; cyclic acetal; acyclic hemiacetal; cyclic hemiacetal; and cyclic dithioketals (e.g., 1,3-dithiane or 1,3-dithiolane). As used herein, any "PG" group(s) such as, without limitation, PG$_1$, PG$_2$ and PG$_3$ represent a protecting group moiety.

The terms "pure," "purified," "substantially purified," and "isolated" as used herein refer to the compound of the embodiment being free of other, dissimilar compounds with which the compound, if found in its natural state, would be associated in its natural state. In certain embodiments described as "pure," "purified," "substantially purified," or "isolated" herein, the compound may comprise at least 0.5%, 1%, 5%, 10%, or 20%, and most preferably at least 50% or 75% of the mass, by weight, of a given sample.

The terms "derivative," "variant," or other similar term refers to a compound that is an analog of the other compound.

As shown in Schemes 1-4, the starting compounds of formulae (I) and (II) may be synthesized from readily available materials. As shown in Scheme 1-1, a compound of formula (I) can be synthesized from a serine ester salt, an aldehyde (e.g. t-butyl aldehyde) and a base (e.g., triethylamine) at elevated temperatures. In some embodiments, the serine ester salt can be a D-serine methylester salt which can form a compound of formula (I) with the stereochemistry shown in Scheme 1-2.

Scheme 1-1

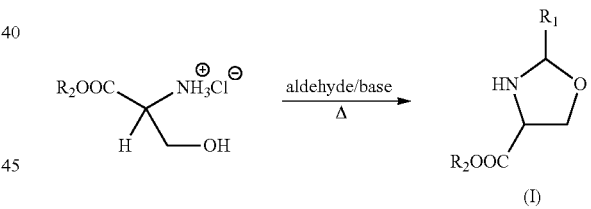

(I)

Scheme 1-2

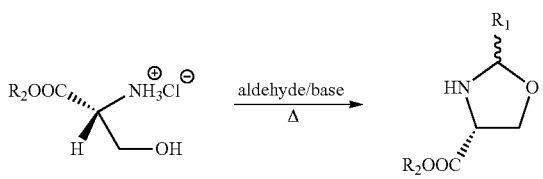

In some embodiments, a compound of formula (I) can have the structure shown above wherein R$_1$ can be hydrogen or unsubstituted or substituted C$_{1-6}$ alkyl; and R$_2$ can be hydrogen, or substituted or unsubstituted variants of the following: C$_{1-6}$ alkyl, aryl or arylalkyl. In an embodiment when R$_1$ is hydrogen, one skilled in the art would recognize that the stereochemistry at C-4 may not be retained upon conversion of a compound of formula (IV) to a compound of formula (V)

shown below. In an embodiment when $R_1$ is an unsubstituted or substituted $C_{1-6}$ alkyl, one skilled in the art would recognize that the stereochemistry at C-4 would be retained upon conversion of a compound of formula (IV) to a compound of formula (V) shown below. As an example, a compound of formula (I) can have the following structure and stereochemistry:

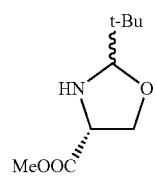
(I-1)

A compound of formula (II) can be synthesized according to Schemes 2, 3 and 4. The ester precursor of the compound of Formula II can be prepared according to Scheme 2, starting with a β-ketoester and a base (e.g., t-BuOK or NaH) and then adding an allyl halide.

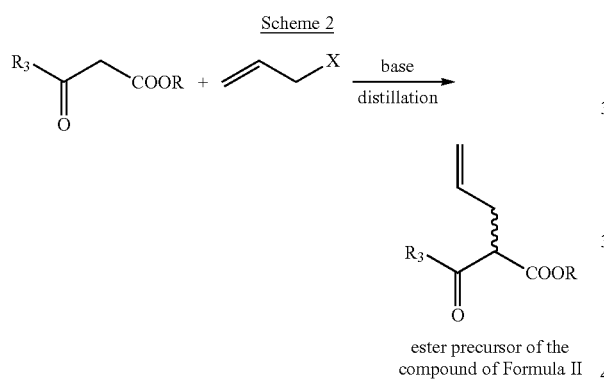

Scheme 2 ester precursor of the compound of Formula II

In some embodiments, the ester precursor of the compound of formula (II) can have the structure shown above wherein R can be hydrogen or substituted or unsubstituted variants of the following: $C_{1-6}$ alkyl, aryl or arylalkyl; and $R_3$ can be substituted or unsubstituted variants of the following: $C_{1-6}$ alkyl, $C_{3-6}$ cycloalkyl, $C_{2-6}$ alkenyl, $C_{3-6}$ cycloalkenyl, aryl, or arylalkyl. An exemplary ester precursor is the compound having the following structure:

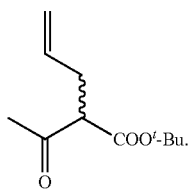

The protected ester precursor of the compound of formula (II) can be prepared according to Scheme 3. The ketone carbonyl of the ester precursor can be protected using a suitable protecting group moiety/moieties, as described herein. One method for protecting the ketone carbonyl is shown in Scheme 3.

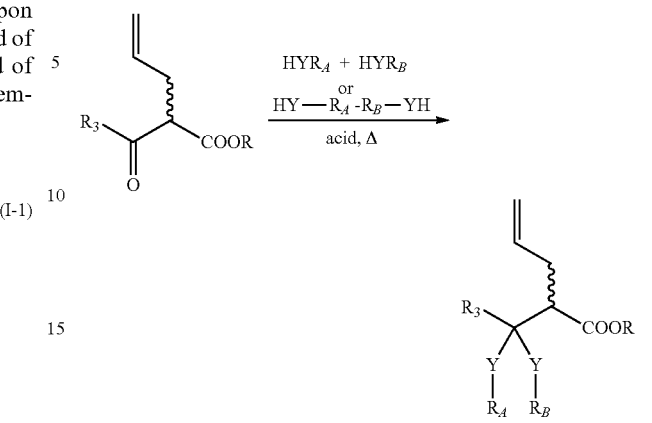

Scheme 3 protected ester precursor of the compound of formula II

In some embodiments, the protected ester precursor of the compound of formula (II) can have structure shown in Scheme 3 wherein R can be hydrogen or substituted or unsubstituted variants of the following: $C_{1-6}$ alkyl, aryl or arylalkyl; $R_3$ can be substituted or unsubstituted variants of the following: $C_{1-6}$ alkyl, $C_{3-6}$ cycloalkyl, $C_{2-6}$ alkenyl, $C_{3-6}$ cycloalkenyl, aryl, or arylalkyl; each Y can be an oxygen or sulfur; and $R_A$ and $R_B$ can be each independently selected from the group consisting of substituted or unsubstituted variants of the following: $C_{1-6}$ alkyl, $C_{2-6}$ alkenyl and $C_{2-6}$ alkynyl, wherein $R_A$ and $R_B$ can be optionally bound together to form an optionally substituted 5, 6, 7, or 8 membered heterocyclyl.

For example, the ketone carbonyl may be protected by reacting the ester precursor with 1,2 dihydroxyethane to form a 1,3-dioxolane heterocyclic ring as shown below:

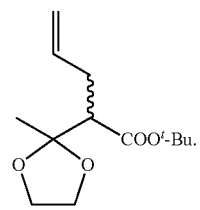

As shown in Scheme 4, the protected ester precursor of a compound of formula (II) can then be hydrolyzed to the carboxylic acid equivalent using an appropriate acid such as TFA or PTSA to form a compound of formula (II).

Scheme 4

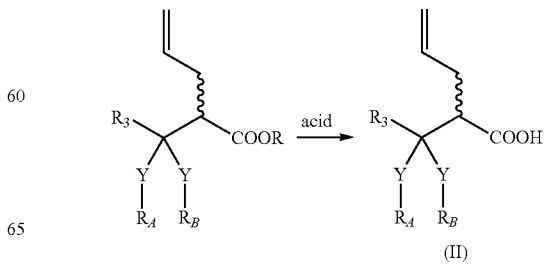
(II)

In some embodiments, a compound of formula (II) can have the structure shown in Scheme 4 wherein $R_3$ can be substituted or unsubstituted variants of the following: $C_{1-6}$ alkyl, $C_{3-6}$ cycloalkyl, $C_{2-6}$ alkenyl, $C_{3-6}$ cycloalkenyl, aryl, or arylalkyl; each Y can be an oxygen or sulfur; and $R_A$ and $R_B$ can be each independently selected from the group consisting of substituted or unsubstituted variants of the following: $C_{1-6}$ alkyl, $C_{2-6}$ alkenyl and $C_{2-6}$ alkynyl, wherein $R_A$ and $R_B$ can be optionally bound together to form an optionally substituted 5, 6, 7, or 8 membered heterocyclyl. As an example, the compound of formula (II) can have the following structure:

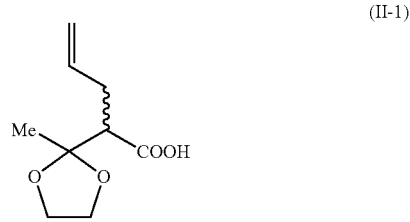

(II-1)

A method of preparing a compound of formula (V) from the starting compounds of formulae (I) and (II) is shown below in Scheme 5.

Scheme 5

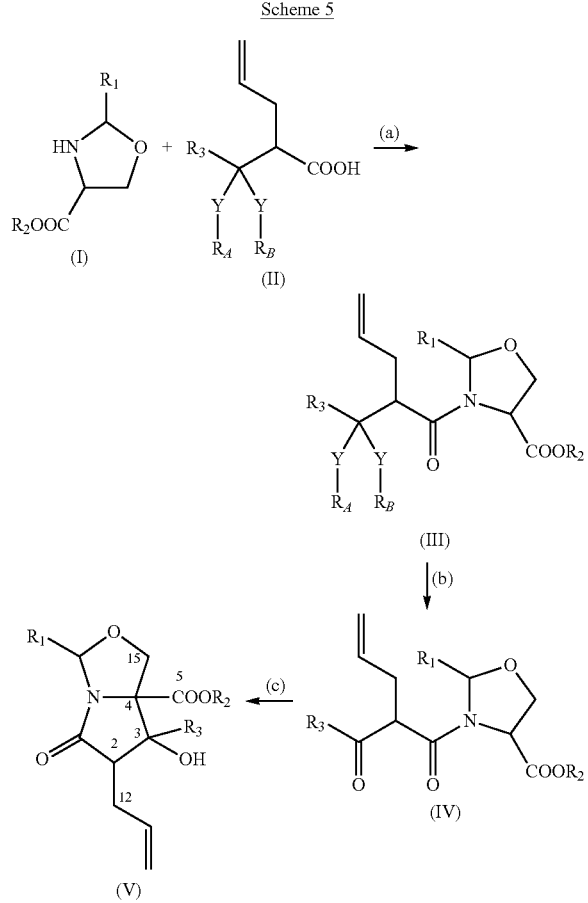

In step (a) of Scheme 5, a compound of formula (III) can be formed by reacting a compound of formula (I) with a compound of formula (II) under suitable conditions wherein $R_1$ can be hydrogen or unsubstituted or substituted $C_{1-6}$ alkyl; $R_2$ can be hydrogen, or substituted or unsubstituted variants of the following: $C_{1-6}$ alkyl, aryl or arylalkyl; $R_3$ can be substituted or unsubstituted variants of the following: $C_{1-6}$ alkyl, $C_{3-6}$ cycloalkyl, $C_{2-6}$ alkenyl, $C_{3-6}$ cycloalkenyl, aryl, or arylalkyl; each Y can be an oxygen or sulfur; and $R_A$ and $R_B$ can be each independently selected from the group consisting of substituted or unsubstituted variants of the following: $C_{1-6}$ alkyl, $C_{2-6}$ alkenyl and $C_{2-6}$ alkynyl, wherein $R_A$ and $R_B$ can be optionally bound together to form an optionally substituted 5, 6, 7, or 8 membered heterocyclyl. For example, a compound of formula (I) can be added to a mixture containing a compound of formula (II), a mild base (e.g., triethylamine or N-methyl piperidine) and an acylating agent such as methanesulfonyl chloride, trifluoromethanesulfonyl chloride or chloromethylformate.

As an example, the compounds of formulae (I), (II) and (III) may have the following structures and stereochemistry:

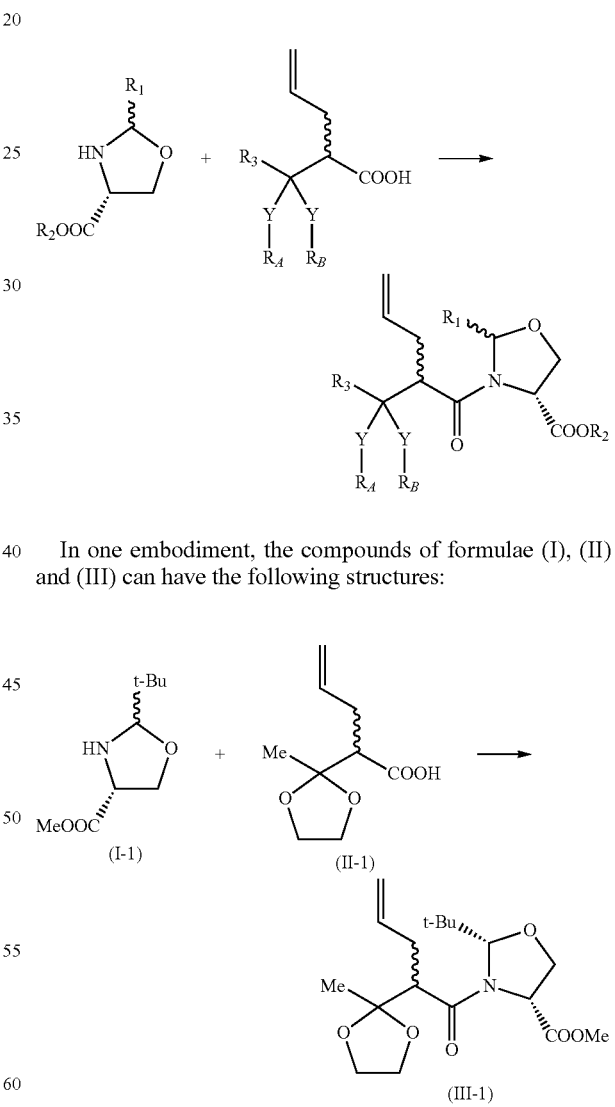

In one embodiment, the compounds of formulae (I), (II) and (III) can have the following structures:

The compound of formula (III) can be deprotected to form a compound of formula (IV), as shown in step (b) of Scheme 5, wherein: $R_1$ can be hydrogen or unsubstituted or substituted $C_{1-6}$ alkyl; $R_2$ can be hydrogen, or substituted or unsubstituted variants of the following: $C_{1-6}$ alkyl, aryl or arylalkyl;

$R_3$ can be substituted or unsubstituted variants of the following: $C_{1-6}$ alkyl, $C_{3-6}$ cycloalkyl, $C_{2-6}$ alkenyl, $C_{3-6}$ cycloalkenyl, aryl, or arylalkyl; each Y can be an oxygen or sulfur; and $R_A$ and $R_B$ can be each independently selected from the group consisting of substituted or unsubstituted variants of the following: $C_{1-6}$ alkyl, $C_{2-6}$ alkenyl and $C_{2-6}$ alkynyl, wherein $R_A$ and $R_B$ can be optionally bound together to form an optionally substituted 5, 6, 7, or 8 membered heterocyclyl. One method for removing the ketone carbonyl protecting group (e.g., 1,3-dioxolane) includes reacting a compound of formula (III) with sodium iodide and a Lewis base such as cerium (III) chloride heptahydrate. A second method includes reacting a compound of formula (III) with iodine in acetone at an elevated temperature. Alternatively, a compound of formula (III) can be reacted with lithium tetrafluoroboride at an elevated temperature to form a compound of formula (IV). If Y is sulfur, the ketone carbonyl protecting group can be removed using various hydrolytic, oxidative and/or solid-state methods such as those described and cited in Habibi et al., *Molecules*, (2003) 8, 663-9, which is incorporated by reference in its entirety.

Exemplary structures and stereochemistry of compounds of formulae (III) and (IV) are shown below:

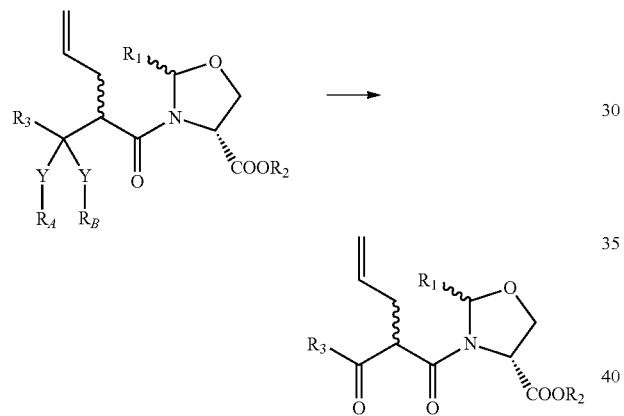

For example, the compounds of formulae (III) and (IV) can have the following structures:

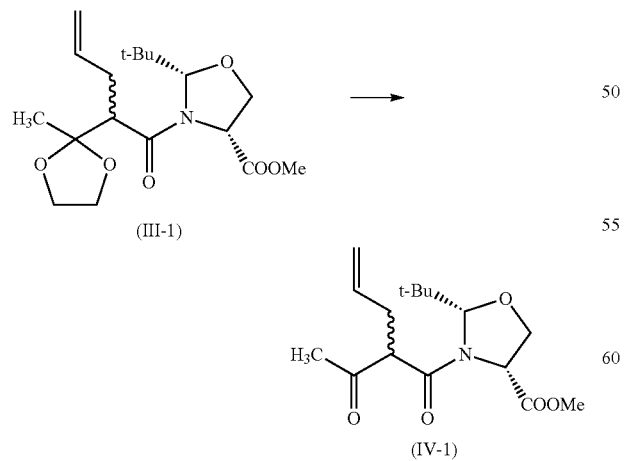

As shown in step (c) of Scheme 5, treatment of a compound of formula (IV) with an appropriate base (e.g., t-BuOK, NaOMe, NaOEt or LDA) can induce an intramolecular aldol reaction to form a compound of formula (V) wherein $R_1$ can be hydrogen or unsubstituted or substituted $C_{1-6}$ alkyl; $R_2$ can be hydrogen, or substituted or unsubstituted variants of the following: $C_{1-6}$ alkyl, aryl or arylalkyl; and $R_3$ can be substituted or unsubstituted variants of the following: $C_{1-6}$ alkyl, $C_{3-6}$ cycloalkyl, $C_{2-6}$ alkenyl, $C_{3-6}$ cycloalkenyl, aryl, or arylalkyl.

As an example, the compounds of formulae (IV) and (V) may have the following structures and stereochemistry:

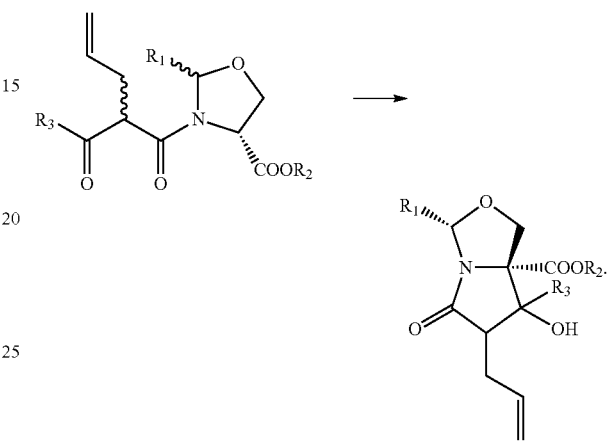

More specifically, compounds of formula (V) may adopt one of the following stereochemical structures:

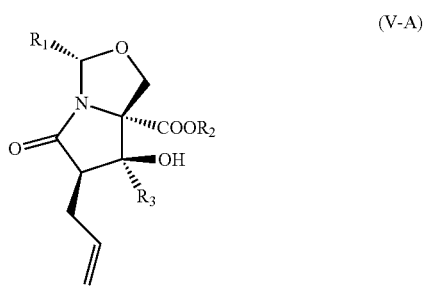

(V-A)

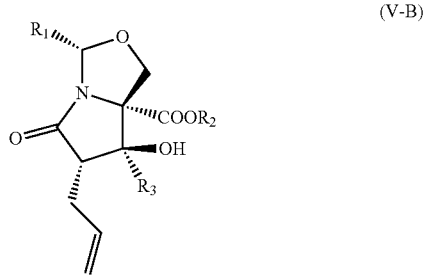

(V-B)

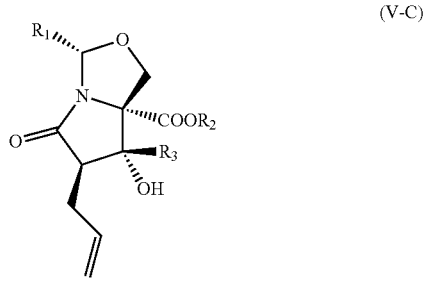

(V-C)

Exemplary structures of compounds formulae (IV) and (V) are shown below:

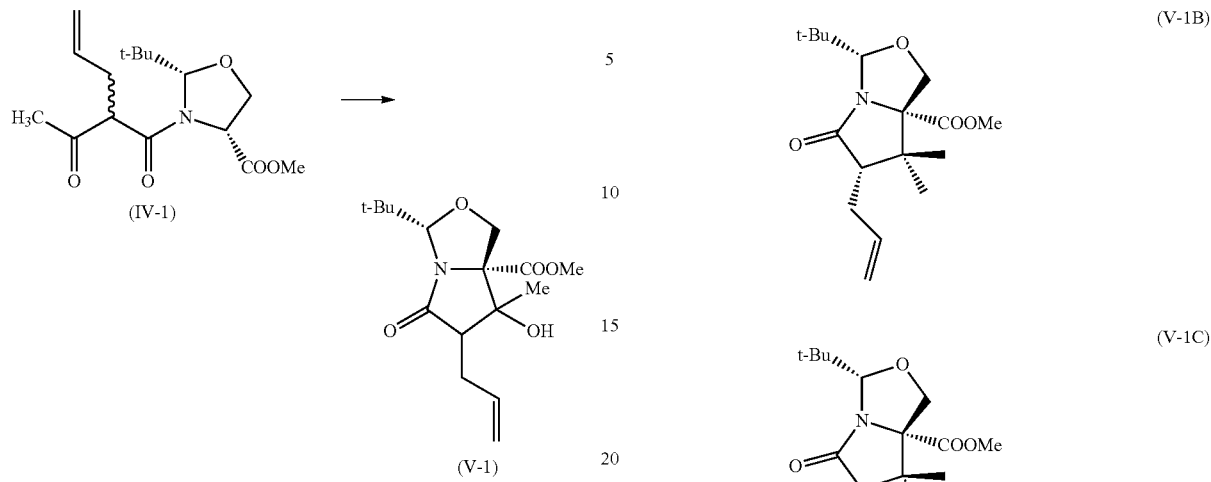

More specifically, a compound of formula (V) may adopt one of the following stereochemical structures:

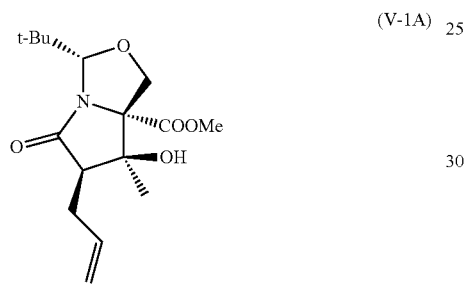

A compound of formula (V) can be used to synthesize heterocyclic compounds such as Salinosporamide A and analogs thereof. One method can proceed through a compound of formula (X), which can then be transformed to Salinosporamide A and analogs thereof, as shown in the schemes herein. In an embodiment, a compound of formula (X) can be produced from a compound of formula (V) as shown in Scheme 6.

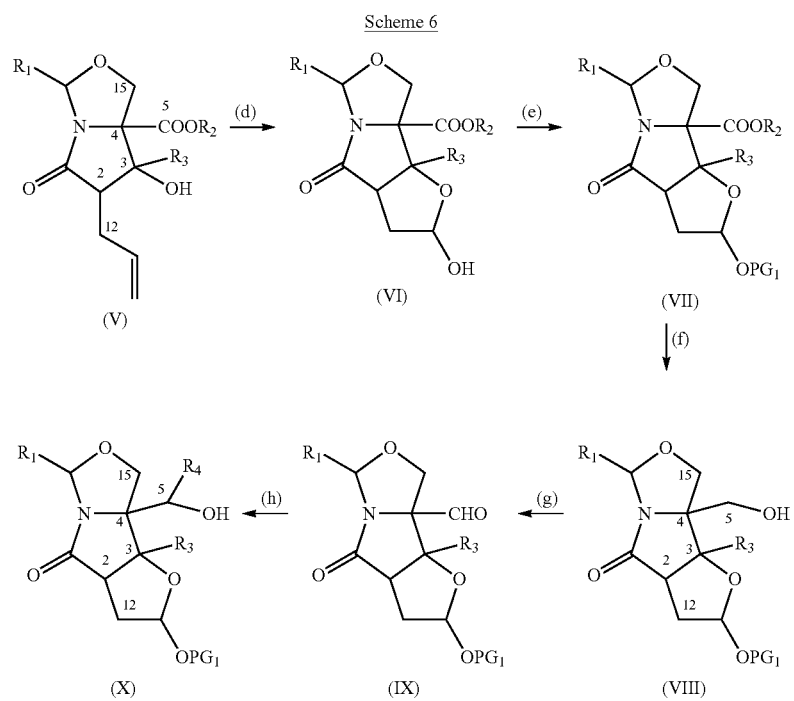

In step (d) of Scheme 6, the carbon-carbon double bond of the compound of formula (V) can be oxidatively cleaved and then cyclized to form a hemiacetal with the tertiary hydroxy group to form a compound of formula (VI), wherein $R_1$ can be hydrogen or unsubstituted or substituted $C_{1-6}$ alkyl; $R_2$ can be hydrogen, or substituted or unsubstituted variants of the following: $C_{1-6}$ alkyl, aryl or arylalkyl; and $R_3$ can be substituted or unsubstituted variants of the following: $C_{1-6}$ alkyl, $C_{3-6}$ cycloalkyl, $C_{2-6}$ alkenyl, $C_{3-6}$ cycloalkenyl, aryl, or arylalkyl. An exemplary method for preparing a compound of formula (VI) includes reacting a compound of formula (V) with a suitable oxidant or oxidant combination, such as $OsO_4$ and NMO for several hours and then adding an additional oxidant (e.g., $NaIO_4$ or $Pb(OAc)_4$) to the reaction mixture. The reaction can be quenched using suitable salt solutions.

Exemplary structures and stereochemistry of compounds of formulae (V) and (VI) are shown below:

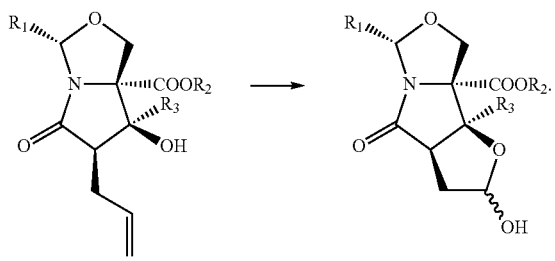

Examples of compounds of formulae (V) and (VI) are as follows:

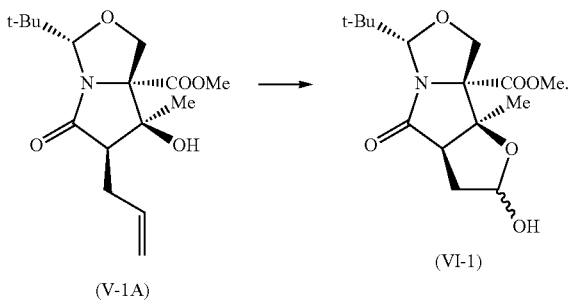

(V-1A)

(VI-1)

If desired, the hemiacetal of a compound of formula (VI) can be protected by forming an acetal using a protecting group moiety (e.g. benzyl, substituted benzyl, silyl, or methoxylmethyl) to form a compound of formula (VII), as shown in step (e) of Scheme 6. In some embodiments, $R_1$, $R_2$, and $R_3$ can be the same as described with respect to the compound of formula (VI); and $PG_1$ can be a protecting group moiety. Examples of suitable protecting group moieties are described herein.

As an example, the compounds of formulae (VI) and (VII) may have the following structures and stereochemistry:

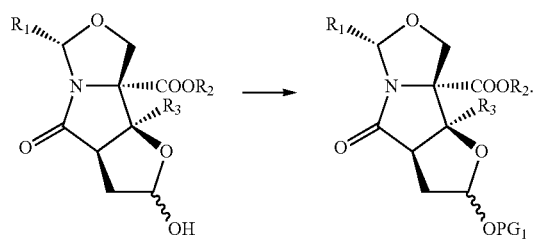

Exemplary structures of compounds of formulae (VI) and (VII) are shown below:

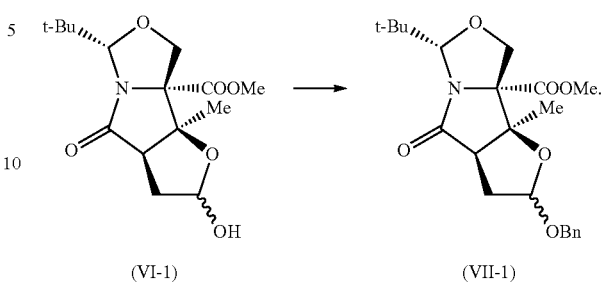

(VI-1)

(VII-1)

As shown in step (f) of Scheme 6, the $COOR_2$ group of a compound of formula (VII) can be reduced to an alcohol to form a compound of formula (VIII), wherein $R_1$, $R_3$, and $PG_1$ can be the same as described with respect to the compound of formula (VII). For example, the $COOR_2$ group can be reduced to an alcohol using a suitable reducing reagent (e.g., diisobutylaluminum hydride, lithium borohydride, lithium aluminum hydride, superhydride) and known techniques.

Exemplary structures and stereochemistry of compounds of formulae (VII) and (VIII) are shown below:

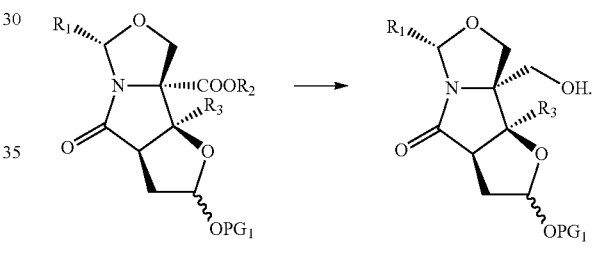

For example, compounds of formulae (VII) and (VIII) can have the following structures:

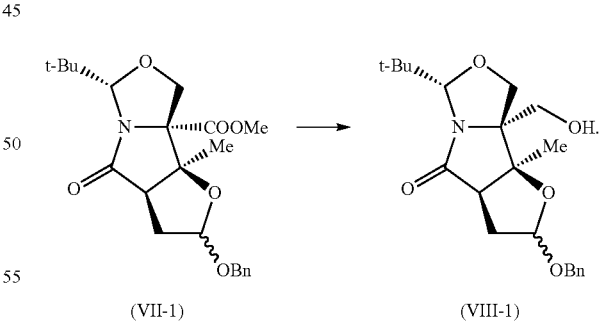

(VII-1)

(VIII-1)

In step (g) of Scheme 6, the C-5 alcohol of the compound of formula (VIII) can be oxidized using an appropriate oxidizing agent to form the compound of formula (IX), wherein $R_1$, $R_3$, and $PG_1$ can be the same as described with respect to the compound of formula (VII). For example, an alcohol can be oxidized to an aldehyde using an oxidant such as Dess-Martin periodinane, TPAP/NMO, Swern oxidation reagent, PCC, or PDC.

Compounds of formulae (VIII) and (IX) may have the following structures and stereochemistry:

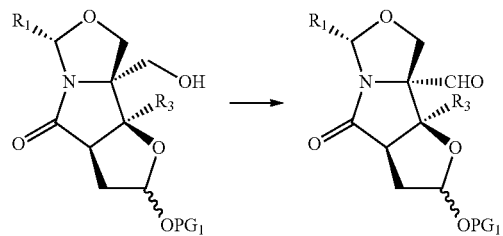

Examples of compounds of formulae (VIII) and (IX) are as follows:

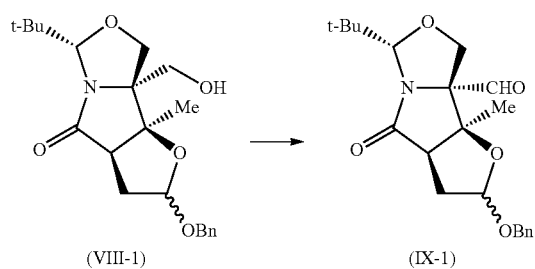

(VIII-1)         (IX-1)

In another embodiment, the COOR$_2$ group of a compound of formula (VII) can be reduced directly to an aldehyde to give a compound of formula (IX) in a single step.

As shown in step (h) of Scheme 6, a compound of formula (X) can be synthesized by reacting an organometallic moiety containing at least one R$_4$ with a compound of formula (IX), wherein R$_1$, R$_3$, and PG$_1$ can be the same as described with respect to the compound of formula (VII); and R$_4$ can be selected from the group consisting of substituted or unsubstituted variants of the following: C$_1$-C$_{12}$ alkyl, C$_2$-C$_{12}$ alkenyl, C$_2$-C$_{12}$ alkynyl, C$_3$-C$_{12}$ cycloalkyl, C$_3$-C$_{12}$ cycloalkenyl, C$_3$-C$_{12}$ cycloalkynyl, C$_3$-C$_{12}$ heterocyclyl, aryl, heteroaryl, arylalkyl, heteroarylalkyl, (cycloalkyl)alkyl, (heterocyclyl)alkyl, acyl, acylalkyl, alkyloxycarbonyloxy, carbonylacyl, aminocarbonyl, azido, azidoalkyl, aminoalkyl, salt of an aminoalkyl, carboxyalkyl, salt of a carboxyalkyl, alkylaminoalkyl, salt of an alkylaminoalkyl, dialkylaminoalkyl, salt of a dialkylaminoalkyl, phenyl, alkylthioalkyl, arylthioalkyl, carboxy, cyano, alkanesulfonylalkyl, alkanesulfinylalkyl, alkoxysulfinylalkyl, thiocyanoalkyl, boronic acidalkyl, boronic esteralkyl, guanidinoalkyl, salt of guanidinoalkyl, sulfoalkyl, salt of a sulfoalkyl, alkoxysulfonylalkyl, sulfooxyalkyl, salt of a sulfooxyalkyl, alkoxysulfonyloxyalkyl, phosphonooxyalkyl, salt of a phosphonooxyalkyl, (alkylphosphooxy)alkyl, phosphorylalkyl, salt of a phosphorylalkyl, (alkylphosphoryl)alkyl, pyridinylalkyl, salt of a pyridinylalkyl, salt of a heteroarylalkyl and halogenated alkyl including polyhalogenated alkyl. In some embodiments, R$_4$ can be selected from the group consisting of: substituted or unsubstituted variants of the following: C$_3$-C$_{12}$ heterocyclyl, aryl, heteroaryl, heteroarylalkyl, (cycloalkyl)alkyl, (heterocyclyl)alkyl, acyl, acylalkyl, alkyloxycarbonyloxy, carbonylacyl, aminocarbonyl, azido, azidoalkyl, aminoalkyl, salt of an aminoalkyl, carboxyalkyl, salt of a carboxyalkyl, alkylaminoalkyl, salt of an alkylaminoalkyl, dialkylaminoalkyl, salt of a dialkylaminoalkyl, phenyl, alkylthioalkyl, arylthioalkyl, carboxy, cyano, alkanesulfonylalkyl, alkanesulfinylalkyl, alkoxysulfinylalkyl, thiocyanoalkyl, boronic acidalkyl, boronic esteralkyl, guanidinoalkyl, salt of guanidinoalkyl, sulfoalkyl, salt of a sulfoalkyl, alkoxysulfonylalkyl, sulfooxyalkyl, salt of a sulfooxyalkyl, alkoxysulfonyloxyalkyl, phosphonooxyalkyl, salt of a phosphonooxyalkyl, (alkylphosphooxy)alkyl, phosphorylalkyl, salt of a phosphorylalkyl, (alkylphosphoryl)alkyl, pyridinylalkyl, salt of a pyridinylalkyl, salt of a heteroarylalkyl and halogenated alkyl including polyhalogenated alkyl.

A non-limiting list of suitable organometallic moieties include organomagnesium compounds, organolithium compounds, organotin compounds, organocuprates compounds, organozinc, and organopalladium compounds, metal carbonyls, metallocenes, carbine complexes, and organometalloids (e.g., organoboranes and organosilanes). In some embodiments, the organometallic moiety can be selected from the group consisting of R$_4$—MgR$_7$, R$_4$—ZnR$_7$, R$_4$—Li, (R$_4$)$_p$—B(R$_7$)$_{3-p}$, and (R$_4$)$_q$—Sn(R$_7$)$_{4-q}$; wherein R$_7$ can selected from the group consisting of halogen, or substituted or unsubstituted variants of the following: alkyl, alkenyl, cycloalkyl, aryl, arylalkyl, isopinocampheyl, hydroxy, alkoxy, and carbonylalkoxy, wherein if more than one R$_7$ is present, the R$_7$ groups can optionally be bond together to form an optionally substituted cycloalkyl (e.g., 9-BBN), optionally substituted cycloalkenyl, optionally substituted heteroalkyl or optionally substituted heteroalkenyl ring; p can be an integer from 1 to 3; and q can be an integer from 1 to 4. In an embodiment, the organometallic moiety is (R$_4$)$_p$—B(R$_7$)$_{3-p}$. In certain embodiments, the organometallic moiety is (R$_4$)$_p$—B(R$_7$)$_{3-p}$, wherein R$_4$ is 2-cyclohexenyl. In some embodiments, the organometallic moiety is (R$_4$)$_p$—B(R$_7$)$_{3-p}$, wherein R$_4$ is 2-cyclohexenyl, p is 1, and the two R$_7$ groups are taken together to form an optionally substituted cycloalkyl. In another embodiment, the organometallic moiety is R$_4$—MgR$_7$. In certain embodiments, the organometallic moiety is R$_4$—MgR$_7$, wherein R$_4$ is 2-cyclohexenyl. In some embodiments, the organometallic moiety is R$_4$—MgR$_7$, wherein R$_4$ is 2-cyclohexenyl and R$_7$ is a halogen (e.g., chlorine).

As an example, the compounds of formulae (IX) and (X) may have the following structures and stereochemistry:

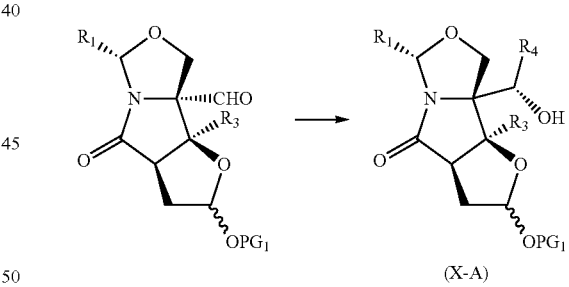

(X-A)

As another example, the compounds of formulae (IX) and (X) may have the following structures and stereochemistry.

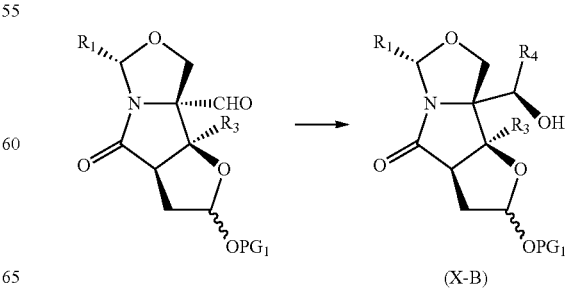

(X-B)

Exemplary structures of compounds of formulae (IX) and (X) are shown below:
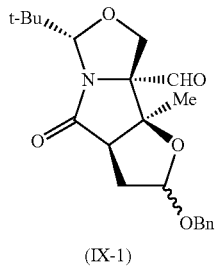
(IX-1)
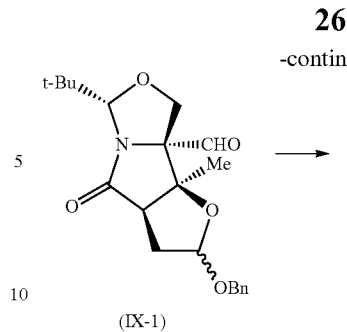
(IX-1)
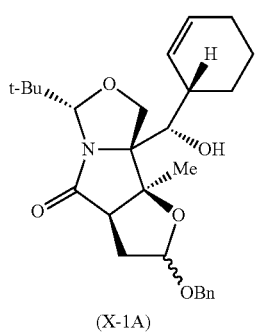
(X-1A)
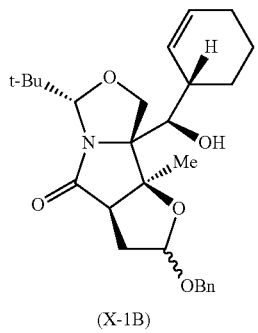
(X-1B)
Various synthetic routes can be used to transform a compound of formula (X) to Salinosporamide A and analogs thereof. In an embodiment, the synthesis can proceed through the intermediate compound of formula (XV). Exemplary synthetic routes are shown Schemes 7-1 to 7-5.
Scheme 7-1
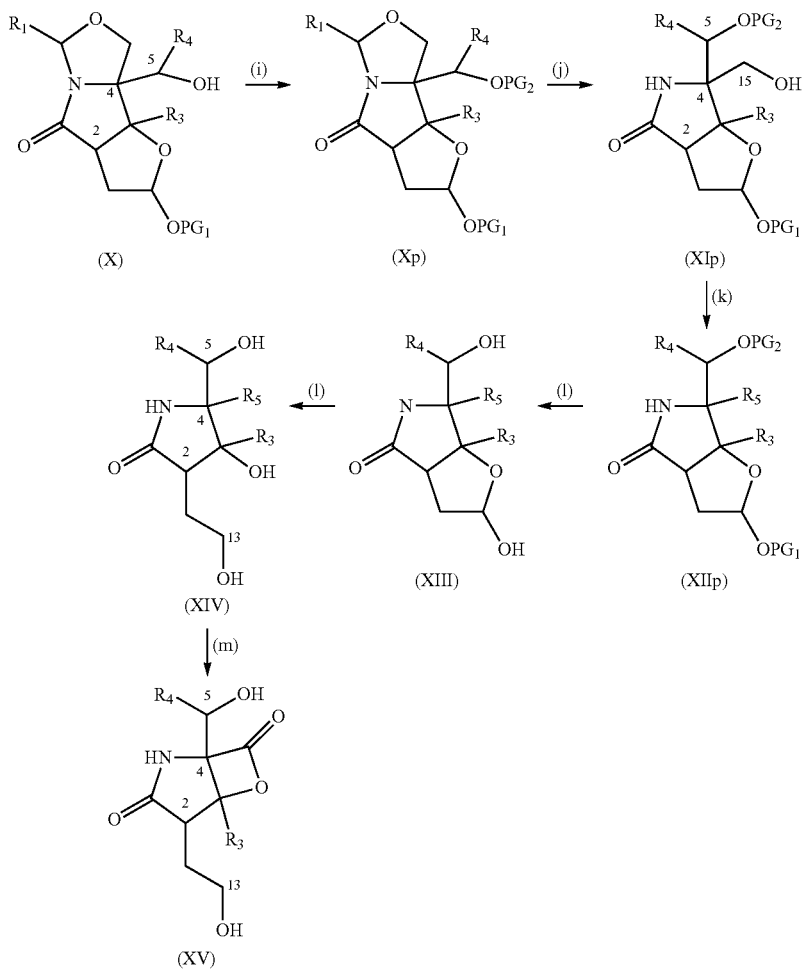

Scheme 7-2

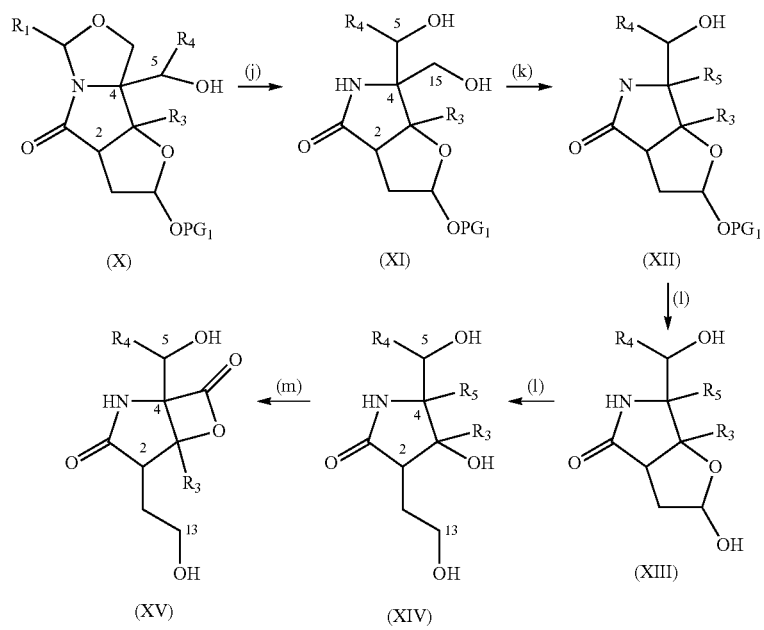

As shown in step (i) of Scheme 7-1, the C-5 secondary hydroxy group of a compound of formula (X) can be protected with a suitable protecting group moiety to form a compound of formula (Xp), wherein $R_1$, $R_3$, $R_4$ and $PG_1$ can be the same as described with respect to the compound of formula (X); and $PG_2$ can be a protecting group moiety. A non-limiting list of suitable protecting group moieties that can be used to protect the C-5 secondary hydroxy group of a compound of formula (X) include a substituted methyl ether (e.g. methoxymethyl), a substituted ethyl, a substituted benzylethyl, tetrahydropyranyl, a silyl ether (e.g. trimethylsilyl, triethylsilyl, triisopropylsilyl, t-butyldimethylsilyl, or t-butyldiphenylsilyl), an ester (e.g. benzoate ester), or a carbonate (e.g. methoxymethylcarbonate). Alternatively, in some embodiments, the C-5 secondary hydroxy group of a compound of formula (X) can remain unprotected, as shown in Scheme 7-2.

Compounds of formulae (X) and (Xp) may have the following structures and stereochemistry:

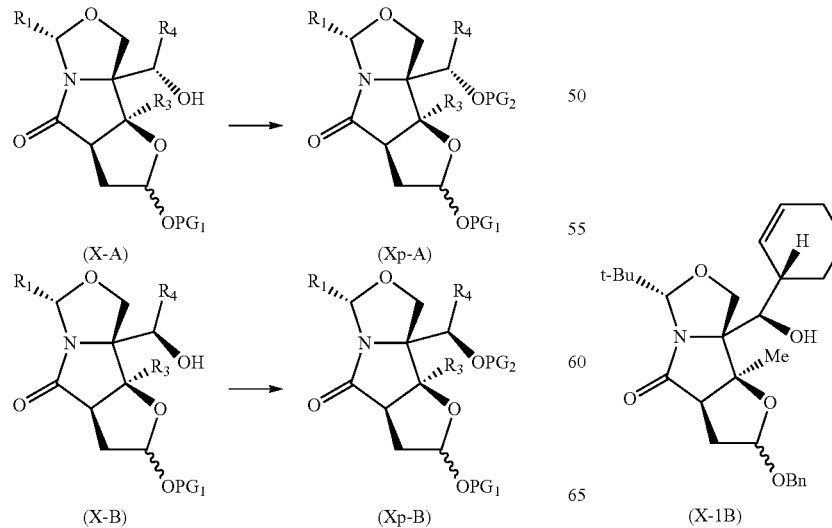

As examples, compounds of formulae (X) and (Xp) can have the following structures:

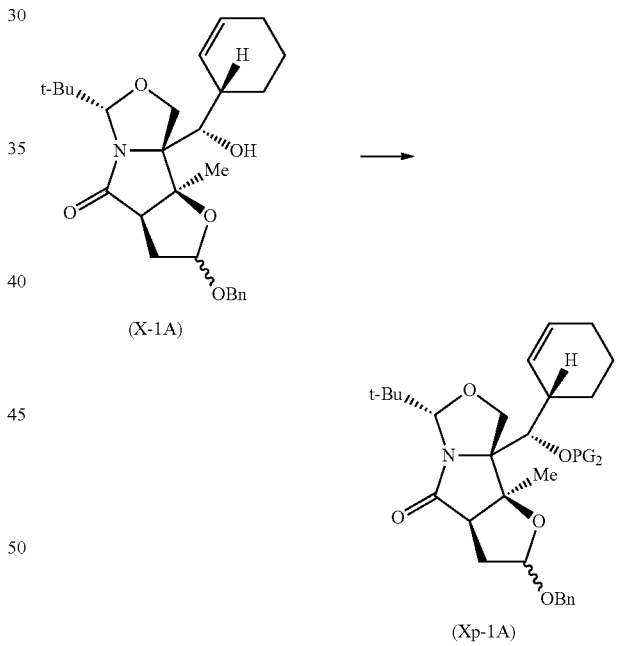

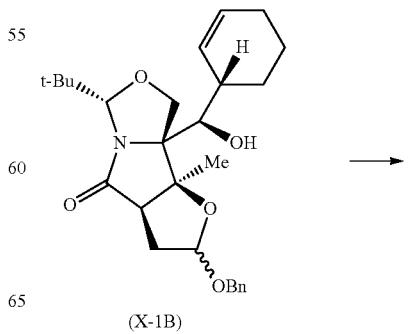

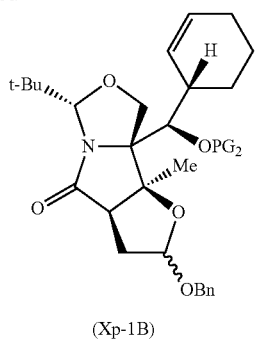

(Xp-1B)

The aminal of a compound of formula (Xp) can be cleaved using a suitable acid (e.g. triflic acid, HCl, PTSA, PPTS, TFA, camphor sulfonic acid) to form a compound of formula (XIp), as shown in Scheme 7-1. In instances in which the C-5 secondary hydroxy is unprotected, the same or another acid can be used to form a compound of formula (XI) from a compound of formula (X). See Scheme 7-2. The substituents and protecting group moieties ($R_1$, $R_3$, $R_4$, $PG_1$, and $PG_2$ where applicable) for compounds of formula (XI) and (XIp) can be the same as described with respect to the compound of formula (Xp).

Exemplary structures and stereochemistry of compounds of formulae (X), (Xp), (XI), and (XIp) are shown below:

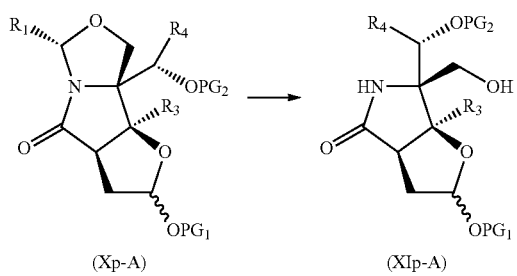

(Xp-A) → (XIp-A)

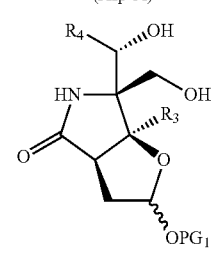

(X-A) → (XI-A)

As another example, the compounds of formulae (X), (Xp), (XI), and (XIp) can have the following structures and stereochemistry:

(Xp-B) → (XIp-B)

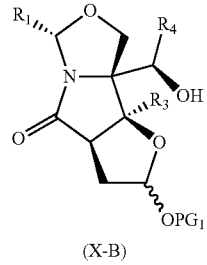 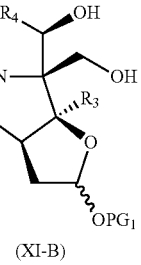

(X-B) → (XI-B)

For example, compounds of formulae (X), (Xp), (XI) and (XIp) can have the following structures:

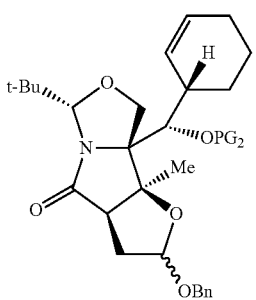 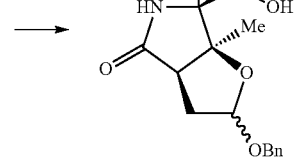

(Xp-1A) → (XIp-1A)

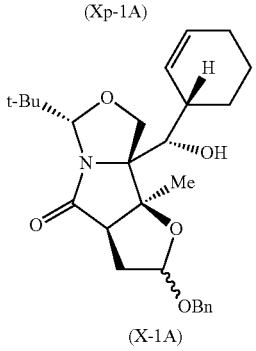 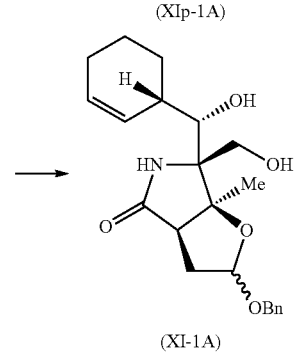

(X-1A) → (XI-1A)

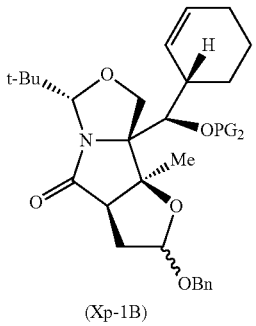 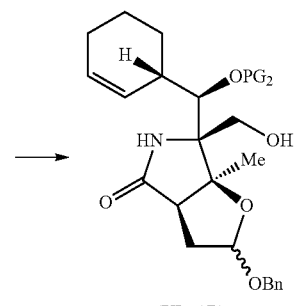

(Xp-1B) → (XIp-1B)

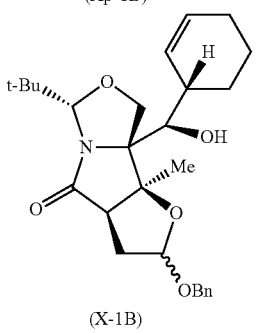 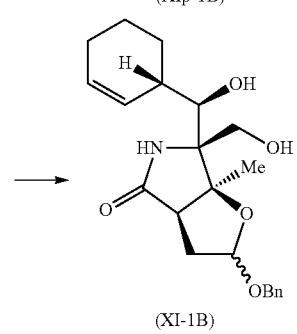

(X-1B) → (XI-1B)

As shown in Scheme 7-1, step (k), the C-15 primary alcohol group of a compound of formula (XIp) can be transformed to $R_5$ to form a compound of formula (XIIp). Similarly when the C-5 secondary hydroxy group is unprotected, the C-15 primary alcohol group of a compound of formula (XI) can be transformed to $R_5$ to form a compound of formula (XII). See Scheme 7-2. $R_3$, $R_4$, $PG_1$, (and $PG_2$, where applicable) of the compounds of formulae (XII) and (XIIp) can be the same as described with respect to the compound of formula (Xp); and $R_5$ can be selected from the group consisting of —C(=O) $OR_6$, —C(=O)$SR_6$, —C(=O)$NR_6R_6$, —C(=O)Z wherein each $R_6$ can be independently selected from the group consisting of hydrogen, halogen, or substituted or unsubstituted variants of the following: $C_1$-$C_{24}$ alkyl, acyl, alkylacyl, arylacyl, aryl, arylalkyl, p-nitrophenyl, pentafluorophenyl, pentafluoroethyl, trifluoroethyl, trichloroethyl, and heteroaryl; and Z can be a halogen. For example, the primary alcohol group can be converted to a carboxylic acid using appropriate oxidation conditions such as Jones oxidation. Alternatively, the carboxylic acid group can be prepared from the primary alcohol group of the compound of formula (XI) or (XIp) through an aldehyde. The primary alcohol group of the compound of formula (XI) or (XIp) can first be converted to aldehyde using appropriate oxidant such as Dess-Martin periodinane, TPAP, Swern oxidation reagent, PCC, or PDC and then the resulting aldehyde can be oxidized further to carboxylic acid using appropriate oxidants such as a combination of sodium chlorite/sodium phosphate dibasic/2-methyl-2-butene. If desired, the carboxylic acid can then be further converted to an ester, a thioester, acid halides (e.g., acid chloride) or an anhydride using an appropriate alcohol, thiol (e.g., thiophenol, cystine), thionyl or oxalyl chlorides, carboxylic acid (e.g., acetic acid, benzoic acid), and/or anhydride (e.g., acetic anhydride).

As an example, the compounds of formulae (XI), (XIp), (XII) and (XIIp) may have the following structures and stereochemistry:

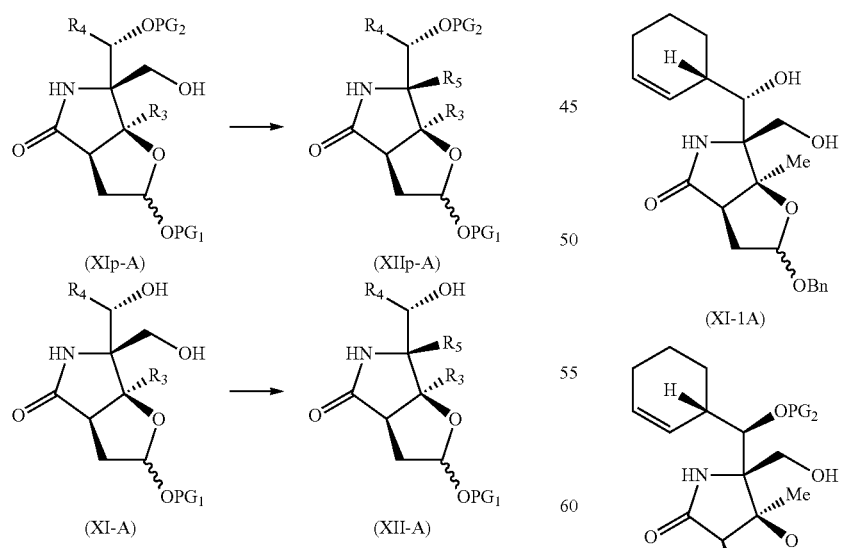

Other exemplary structures and stereochemistry of the compounds of formulae (XI), (XIp), (XII) and (XIIp) include following structures and stereochemistry:

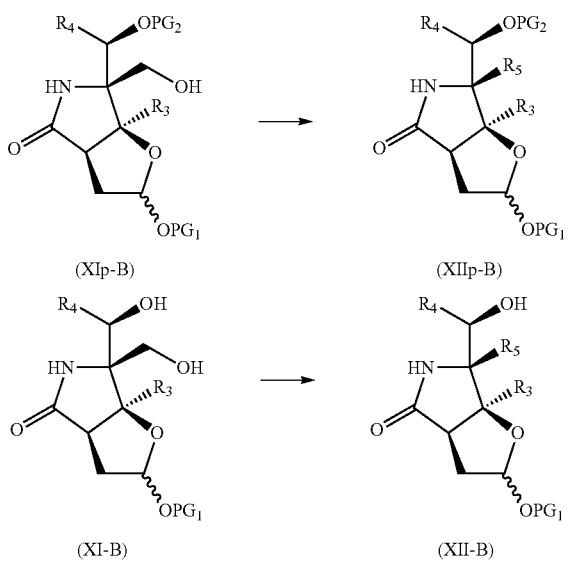

Exemplary structures of compounds of formulae (XI), (XIp), (XII), and (XIIp) are as follows:

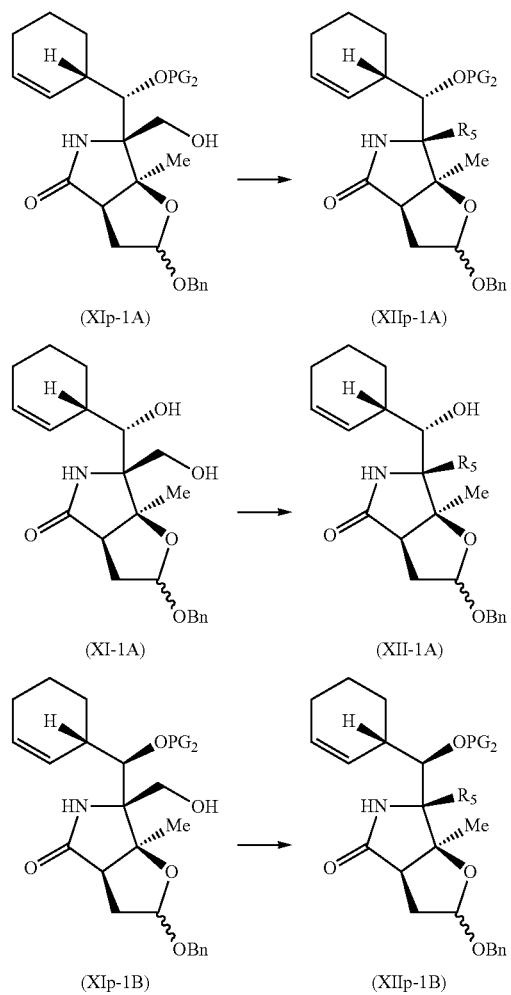

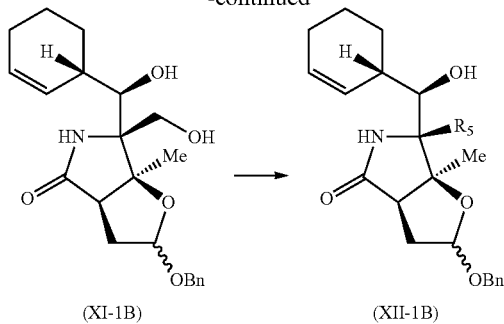

(XI-1B) (XII-1B)

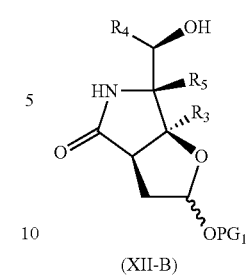

In some embodiments, a compound of formula (XII) can have the structure shown in Scheme 7-2, with the proviso that if a compound of formula (XII) has the structure and stereochemistry of the compound of formula (XII-1A), then $R_5$ cannot be —C(=O)$OR_6$, wherein $R_6$ is t-butyl.

A compound of formula (XIV) can be synthesized by removing any protecting group moieties on the compound of formula (XII) and/or (XIIp) to form a compound of formula (XIII) and then cleaving the hemiacetal of the compound of formula (XIII). In some embodiments, $R_3$, $R_4$, and $R_5$ of the compounds of formulae (XIII) and (XIV) can be the same as described with respect to the compound of formula (XIIp). One method for reductively cleaving the hemiacetal can be using a suitable reducing reagent such as sodium borohydride. In one embodiment, the formation of a compound of formula (XIV) from a compound of formula (XII) or (XIIp) can be accomplished in a single step. In another embodiment, the protecting group moiety $PG_1$ on the compound of formula (XII) can be initially removed to form a compound of formula (XIII) and then the resulting hemiacetal can be reductively cleaved to form a compound of formula (XIV). In another embodiment, the protecting group moieties $PG_1$ and $PG_2$ on the compound of formula (XIIp) can be removed simultaneously or sequentially to form a compound of formula (XIII) and then the resulting hemiacetal can be reductively cleaved to form a compound of formula (XIV). If the protecting group moieties on the compound of formula (XIIp) are removed sequentially, they can be removed in any order to form a compound of formula (XIII).

Compounds of formulae (XII), (XIIp), (XIII), and (XIV) may have the following structures and stereochemistry:

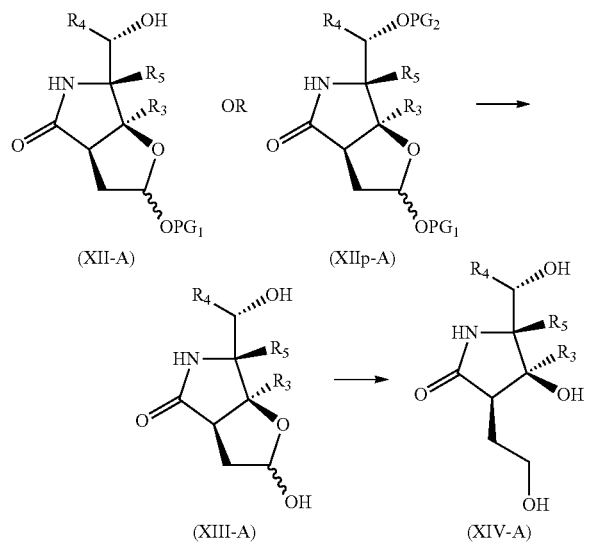

Exemplary structures of compounds of formulae (XII), (XIIp), (XIII), and (XIV) are shown below:

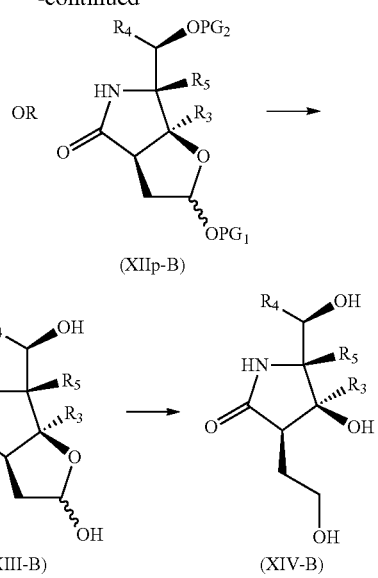

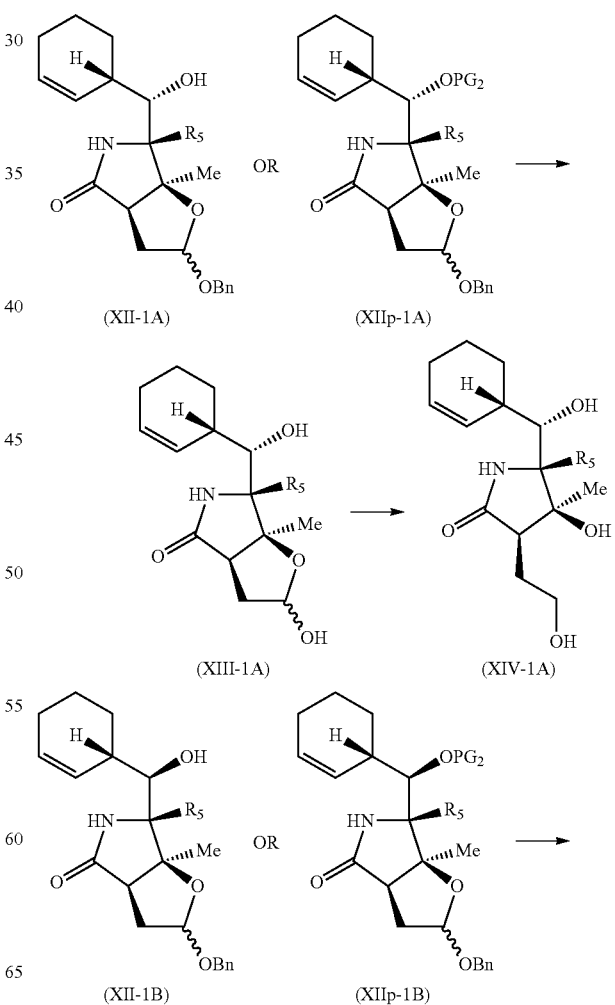

-continued

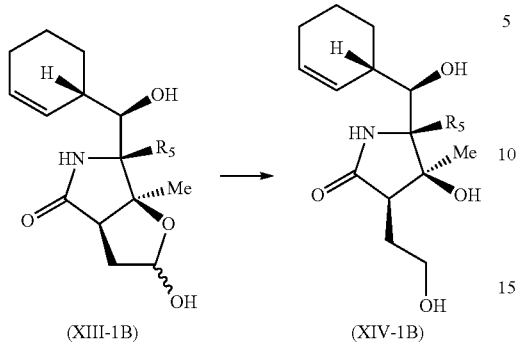

(XIII-1B)   (XIV-1B)

In some embodiments, a compound of formula (XIV) can be synthesized by removing any protecting group moieties on the compound of formula (XII) and/or (XIIp) and reductively cleaving the resulting hemiacetal of the compound of formula (XIII) with the proviso that if the compound of formula (XII) has the structure and stereochemistry of the compounds of formula (XII-1A), then $R_5$ cannot be —C(=O)OR$_6$, wherein $R_6$ is t-butyl. In other embodiments, a compound of formula (XIV) can be synthesized by removing any protecting group moieties on the compound of formula (XII) and/or (XIIp) and reductively cleaving the resulting hemiacetal of the compound of formula (XIII) with the proviso that if the compound of formula (XIII) has the structure and stereochemistry of the compounds of formula (XIII-1A), then $R_5$ cannot be —C(=O)OR$_6$, wherein $R_6$ is t-butyl.

In one embodiment, a compound of formula (XIII) can have the structure and stereochemistry of a compound of formula (XIII-1A), with the proviso that $R_5$ cannot be —C(=O)OR$_6$, wherein $R_6$ is t-butyl. In an embodiment, a compound of formula (XIV) can have structure shown herein, with the proviso that if the compound of formula (XIV) has the structure and stereochemistry of the compound of formula (XIV-1A), then $R_5$ cannot be —C(=O)OR$_6$, wherein $R_6$ is hydrogen, methyl, or t-butyl.

Finally, in step (m) of Schemes 7-1 and 7-2, a compound of formula (XV) can be formed by treating a compound of formula (XIV) with an appropriate base (e.g., BOPCl/pyridine, triethylamine) to induce a lactonization reaction and form the 4-membered heterocyclic ring, wherein $R_3$, $R_4$, and $R_5$ can be same as described with respect to the compound of formula (XII) or (XIIp). In an embodiment, if $R_5$ is an ester, it can first be transformed to a carboxylic acid, an activated acid (e.g., acid halide), or an activated ester (e.g., p-nitrophenyl ester, pentafluorophenyl ester, pentafluoroethyl ester, trifluoroethyl ester, trichloroethyl ester, a thioester, etc.) before being treated with an appropriate reagent to induce the lactonization reaction. For example, when $R_5$ is carboxylic acid, it can be treated with an appropriate base to affect the lactonization reaction. In some embodiments, if $R_5$ is an amide, it can first be transformed to a carboxylic acid, an activated acid, or an activated ester such as those described herein before being treated with an appropriate base to induce the lactonization reaction.

As an example, the compounds of formulae (XIV) and (XV) may have the following structures and stereochemistry:

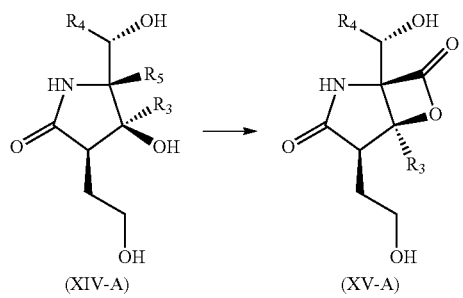

(XIV-A)   (XV-A)

In another example, the compounds of formulae (XIV) and (XV) may have the following structures and stereochemistry:

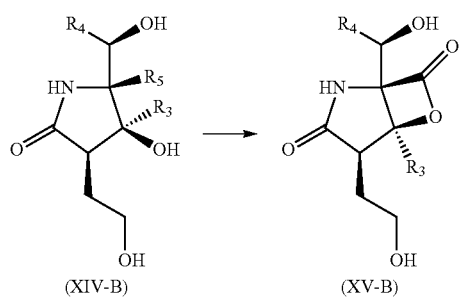

(XIV-B)   (XV-B)

Exemplary structures of compounds of formulae (XIV) and (XV) are as follows:

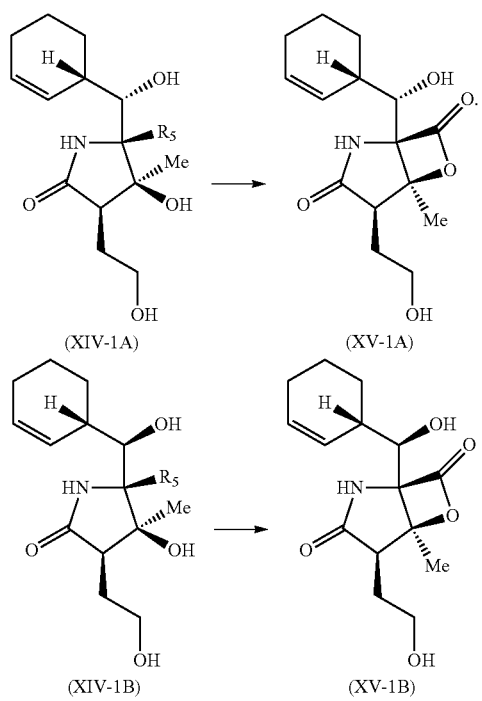

(XIV-1A)   (XV-1A)

(XIV-1B)   (XV-1B)

In an embodiment, $R_5$ of the compound of formula (XIV-1A) can be a carboxylic acid. In some embodiments, $R_5$ of the compound of formula (XIV-1A) can be an activated acid (e.g., acid chloride). In certain embodiments, $R_5$ of the compound of formula (XIV-1A) can be an activated ester such as p-nitrophenyl ester, pentafluorophenyl ester, pentafluoroethyl ester, trifluoroethyl ester, trichloroethyl ester, thioester, etc. In an embodiment, $R_5$ of the compound of formula (XIV-1B) can be a carboxylic acid. In some embodiments, $R_5$ of the compound of formula (XIV-1B) can be an activated acid (e.g., acid chloride). In certain embodiments, $R_5$ of the compound of formula (XIV-1B) can be an activated ester such as p-nitrophenyl ester, pentafluorophenyl ester, pentafluoroethyl ester, trifluoroethyl ester, trichloroethyl ester, thioester, etc.

In some embodiments, a compound of formula (XV) can be synthesized by performing a lactonization reaction on a compound of formula (XIV) with the proviso that if the compounds of formulae (XIV) and (XV) have the same structures and stereochemistry as the compounds of formulae (XIV-1A) and (XV-1A), then $R_5$ cannot be —C(=O)OR$_6$, wherein $R_6$ is hydrogen. In other embodiments, the lactonization reaction includes the further proviso that $R_6$ cannot be methyl or t-butyl when the compounds of formulae (XIV) and (XV) have the structures and stereochemistry of the compounds of formulae (XIV-1A) and (XV-1A). In some embodiments, a compound of formula (XV) can be synthesized by performing a lactonization reaction on a compound of formula (XIV) and/or (XIV-A) with the proviso that if $R_5$ is —C(=O)OR$_6$, wherein $R_6$ is hydrogen, methyl or t-butyl then $R_4$ cannot be isopropyl. In an embodiment, a compound of formula (XV) can have the structure shown herein with the proviso that if the compound of formula (XV) has the structure and stereochemistry of the compound of formula (XV-A) and $R_3$ is methyl then $R_4$ cannot be 2-cyclohexenyl. In some embodiments, a compound of formula (XV) can have the structure shown herein with the proviso that if $R_3$ is methyl then $R_4$ cannot be isopropyl, cyclohexyl, or phenyl. In one embodiment, a compound of formula (XV) can have the structure shown herein with the proviso that if the compound of formula (XV) has the structure and stereochemistry of the compound of formula (XV-A) and $R_3$ is methyl then $R_4$ cannot be isopropyl.

A compound of formula (XV) can also be synthesized from a compound of formula (X) as shown in Scheme 7-3. By modifying the protection/deprotection sequence, a compound of formula (XV) can also be obtained from a compound of formula (X) as shown in Schemes 7-4 and 7-5.

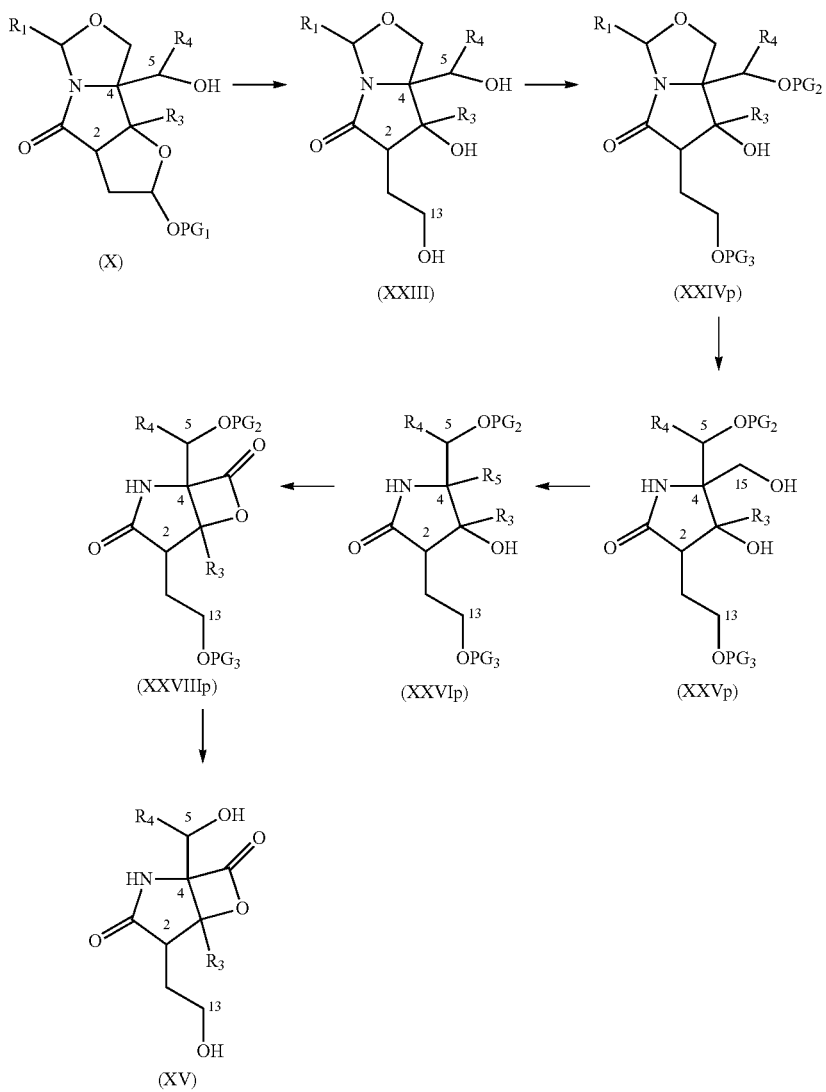

Scheme 7-3

Scheme 7-4
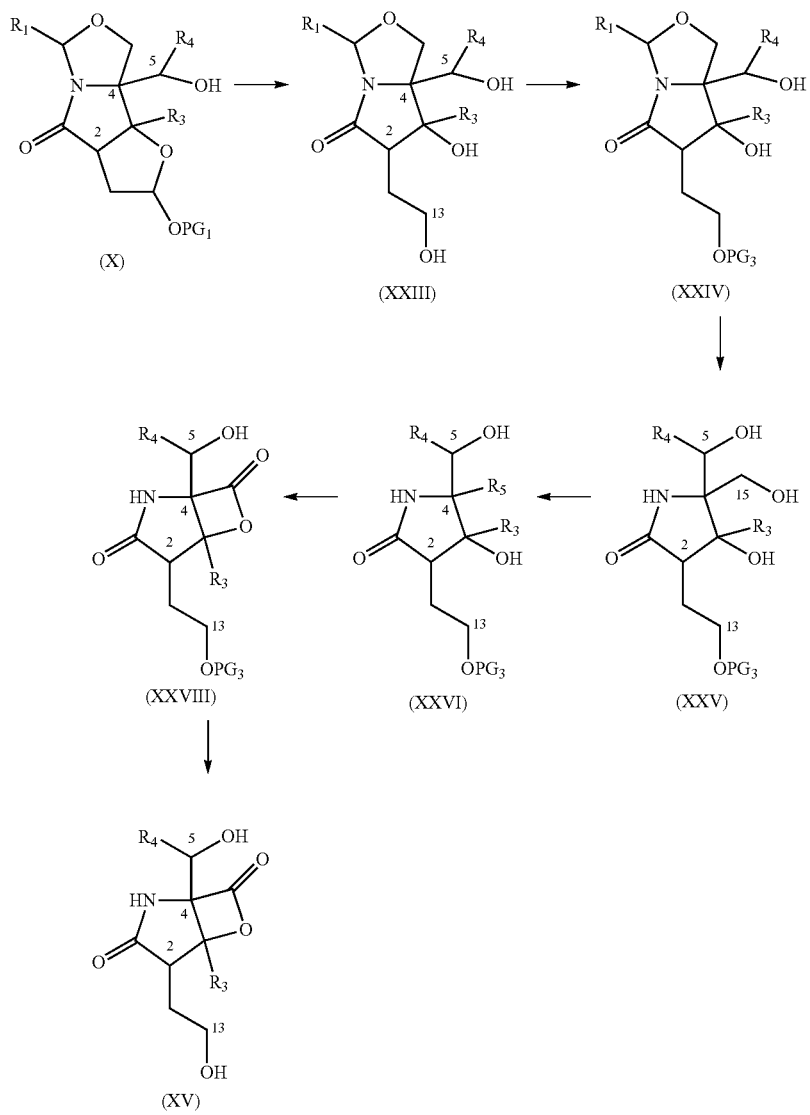
Scheme 7-5
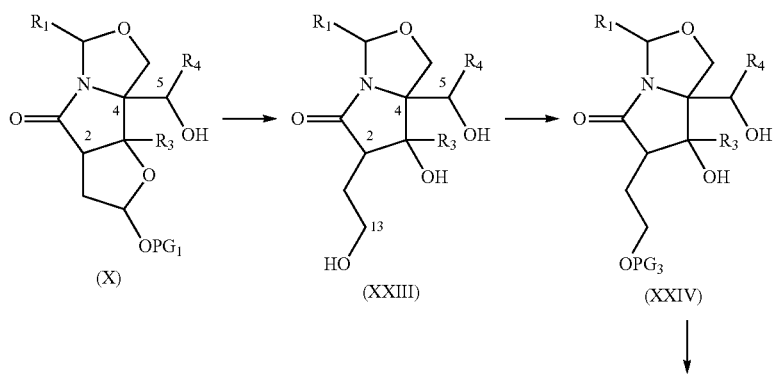

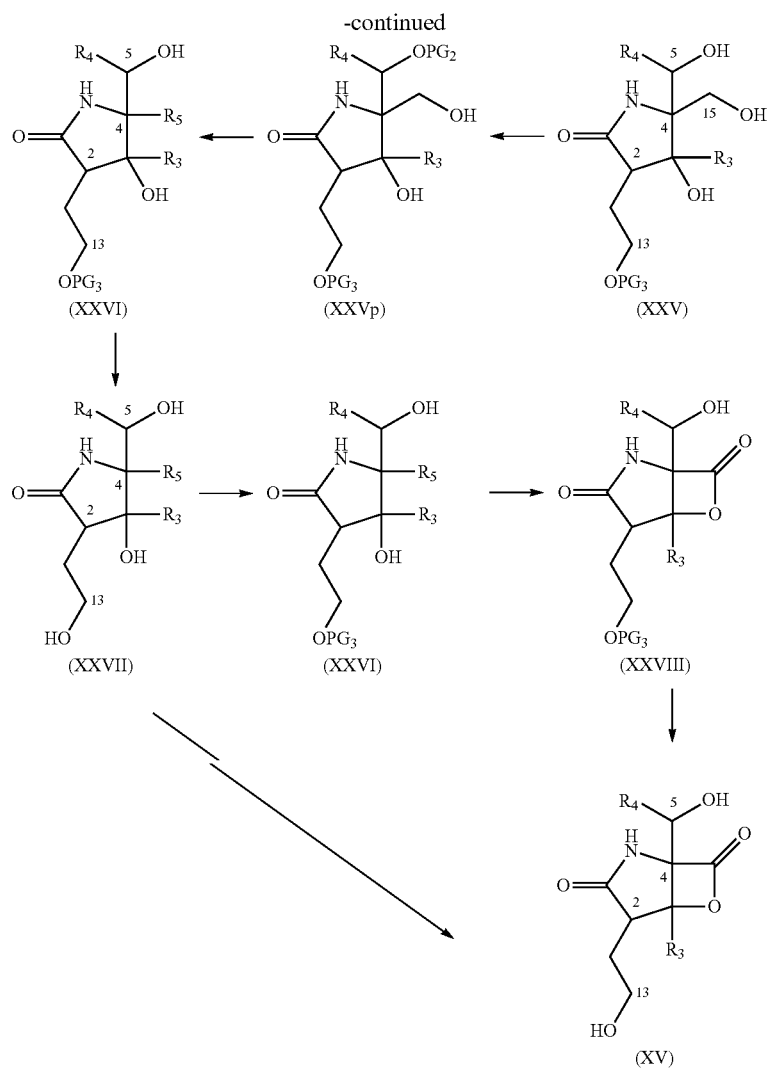

*PG₃ can be the same or different in the two compounds of formula XXVI shown above A compound of formula (XXIII) can be synthesized by removing the protecting group moiety on the compound of formula (X) and reductively opening the hemiacetal. The protecting group moiety can be removed using known methods and the hemiacetal can be reductively opened using a reducing agent (e.g., sodium borohydride). In some embodiments, the substituents (and protecting group moiety where applicable) ($R_1$, $R_3$, $R_4$, and $PG_1$) for compound of formulae (X) and (XXIII) can be selected from the following: $R_1$ can be hydrogen or an unsubstituted or substituted $C_{1-6}$ alkyl; $R_3$ can be substituted or unsubstituted variants of the following: $C_{1-6}$ alkyl, $C_{3-6}$ cycloalkyl, $C_{2-6}$ alkenyl, $C_{3-6}$ cycloalkenyl, aryl, or arylalkyl; $R_4$ can be selected from the group consisting of substituted or unsubstituted variants of the following: $C_1$-$C_{12}$ alkyl, $C_2$-$C_{12}$ alkenyl, $C_2$-$C_{12}$ alkynyl, $C_3$-$C_{12}$ cycloalkyl, $C_3$-$C_{12}$ cycloalkenyl, $C_3$-$C_{12}$ cycloalkynyl, $C_3$-$C_{12}$ heterocyclyl, aryl, heteroaryl, arylalkyl, heteroarylalkyl, (cycloalkyl)alkyl, (heterocyclyl)alkyl, acyl, acylalkyl, alkyloxycarbonyloxy, carbonylacyl, aminocarbonyl, azido, azidoalkyl, aminoalkyl, salt of an aminoalkyl, carboxyalkyl, salt of a carboxyalkyl, alkylaminoalkyl, salt of an alkylaminoalkyl, dialkylaminoalkyl, salt of a dialkylaminoalkyl, phenyl, alkylthioalkyl, arylthioalkyl, carboxy, cyano, alkanesulfonylalkyl, alkanesulfinylalkyl, alkoxysulfinylalkyl, thiocyanoalkyl, boronic acidalkyl, boronic esteralkyl, guanidinoalkyl, salt of guanidinoalkyl, sulfoalkyl, salt of a sulfoalkyl, alkoxysulfonylalkyl, sulfooxyalkyl, salt of a sulfooxyalkyl, alkoxysulfonyloxyalkyl, phosphonooxyalkyl, salt of a phosphonooxyalkyl, (alkylphosphooxy)alkyl, phosphorylalkyl, salt of a phosphorylalkyl, (alkylphosphoryl)alkyl, pyridinylalkyl, salt of a pyridinylalkyl, salt of a heteroarylalkyl and halogenated alkyl including polyhalogenated alkyl.

Compounds of formulae (X) and (XXIII) may have the following structures and stereochemistry:

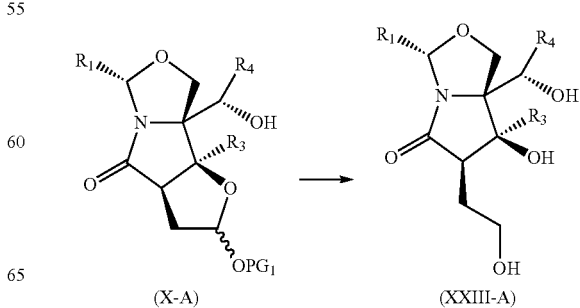

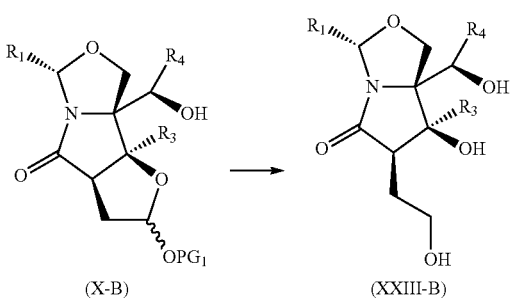

As examples, compounds of formulae (X) and (XXIII) can have the following structures:

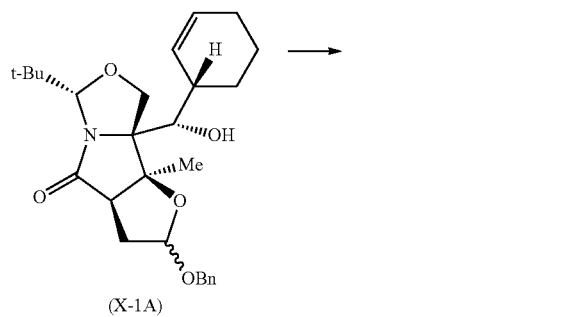

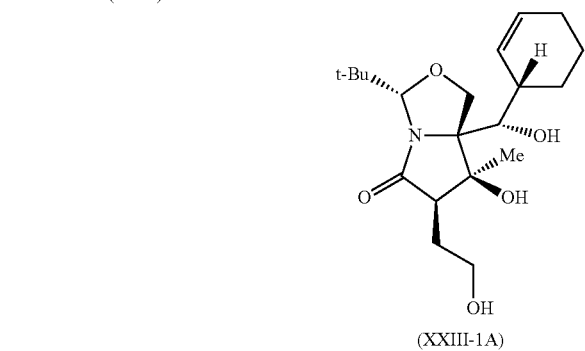

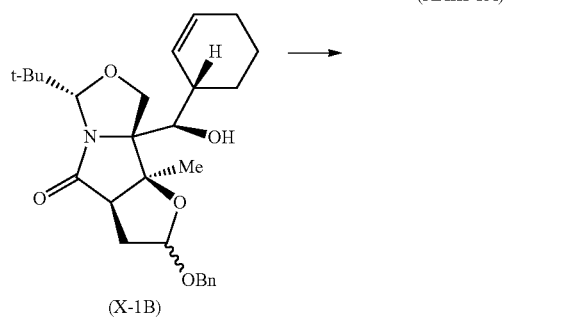

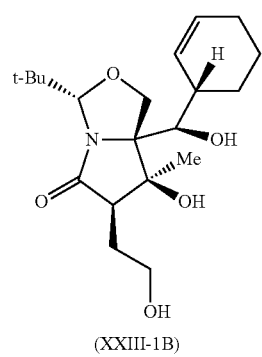

If desired, the C-13 primary and C-5 secondary hydroxy groups of a compound of formula (XXIII) can be protected using suitable protecting group moieties as described herein to form a compound of formula (XXIVp), as shown in Scheme 7-3. Alternatively, only the C-13 primary hydroxy group of a compound of formula (XXIII) can be protected to form a compound of formula (XXIV), as shown in Scheme 7-4 and 7-5. In some embodiments, $R_1$, $R_3$, and $R_4$ of the compound of formula (XXIV) can be the same as described with respect to the compound of formula (X) and $PG_3$ can be a protecting group moiety. In certain embodiments, $PG_3$ can be selected from the group consisting of substituted or unsubstituted arylcarbonyls (e.g., benzoyl); substituted or unsubstituted alkyl carbonyl (e.g. acetyl); substituted methyl ether (e.g. methoxymethyl); substituted ethyl ether; substituted or substituted benzyl ether (e.g. benzyl, 4-methoxybenzyl); tetrahydropyranyl ether; silyl ethers (e.g., trimethylsilyl, triethylsilyl, triisopropylsilyl, t-butyldimethylsilyl, or t-butyldiphenylsilyl); carbonates (e.g. methoxymethylcarbonate); and sulfonates (e.g. mesylate, tosylate). In an embodiment, $R_1$, $R_3$ and $R_4$ of the compound of formula (XXIVp) can be the same as described with respect to the compound of formula (X), and $PG_2$ and $PG_3$ can be protecting group moieties. In some embodiments, $PG_3$ cannot be an alkyl carbonyl (e.g., $-C(=O)CH_2CH_3$). In other embodiments, $PG_3$ cannot be a sulfonate (e.g., methylate).

As an example, the compounds of formulae (XXIII), (XXIV), and (XXIVp) may have the following structures and stereochemistry:

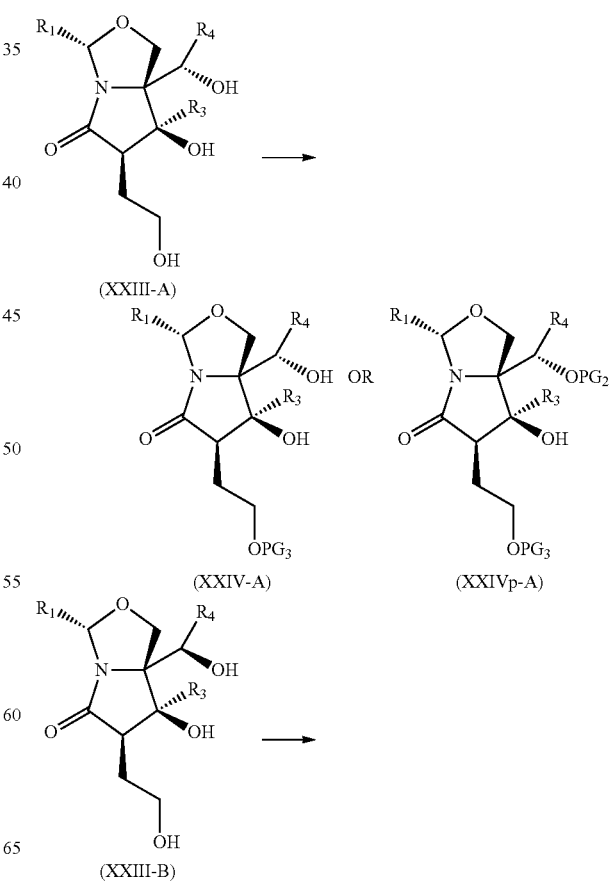

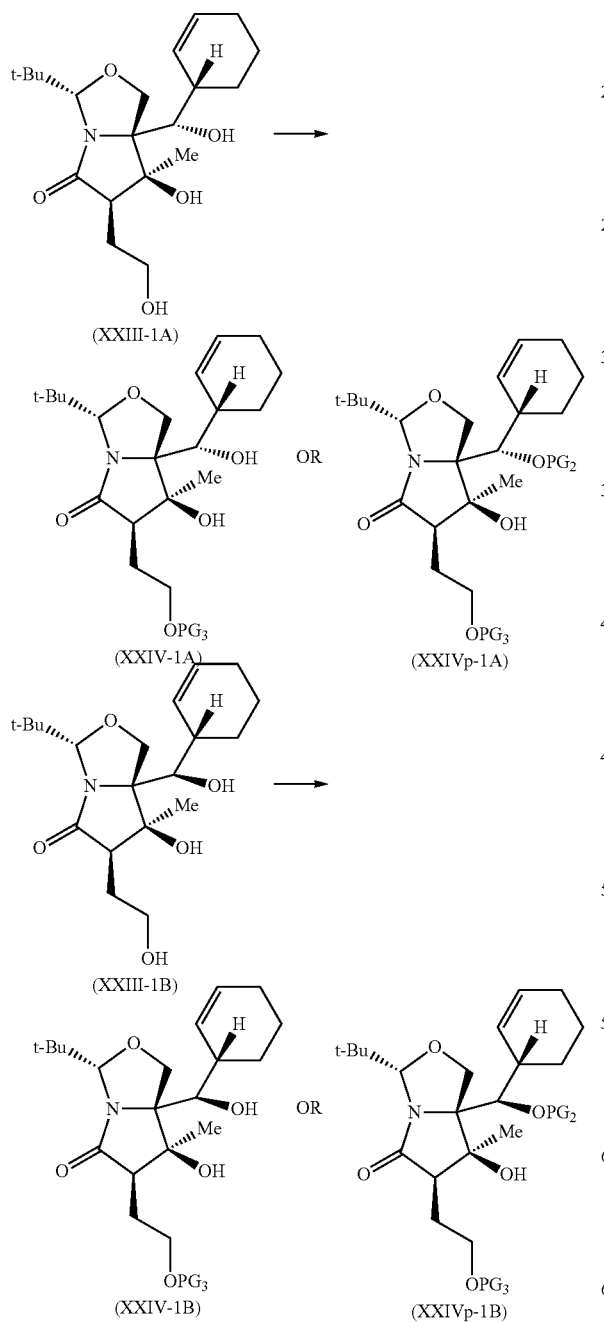

Other examples of the structures and stereochemistry of the compounds of formulae (XXIII), (XXIV), and (XXIVp) include the following:

Similar to step (j) of Schemes 7-1 and 7-2, the aminal of a compound of formula (XXIV) can be cleaved using a suitable acid as described herein to form a compound of formula (XXV). In the case where the C-5 secondary hydroxy has been protected, the aminal of a compound of formula (XXIVp) can also be cleaved using a suitable acid to form a compound of formula (XXVp). In some embodiments, $R_3$, and $R_4$ of the compound of formula (XXV) can be the same as described with respect to the compound of formula (X), and $PG_3$ can be a protecting group moiety. In some embodiments, $R_3$ and $R_4$, and $PG_2$ for compound of formula (XXVp) can be the same as described with respect to the compound of formula (X), and $PG_2$ and $PG_3$ can be protecting group moieties.

Exemplary structures and stereochemistry of compounds of formulae (XXIV) and (XXV) are shown below:

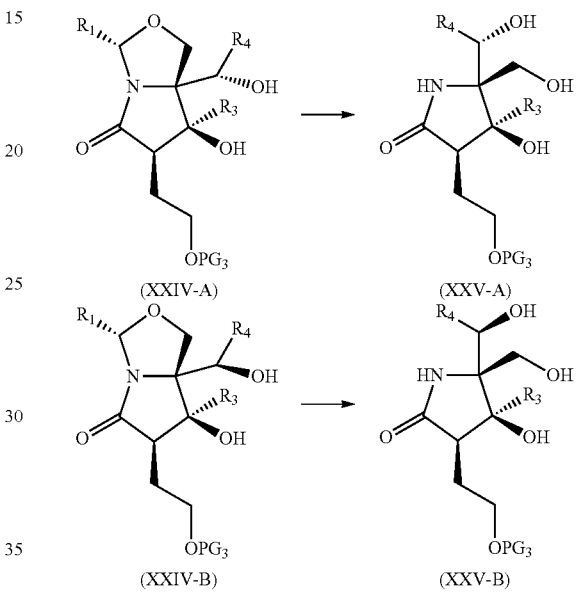

Additional examples of the structures and stereochemistry of compounds of formulae (XXIVp), and (XXVp) can be as follows:

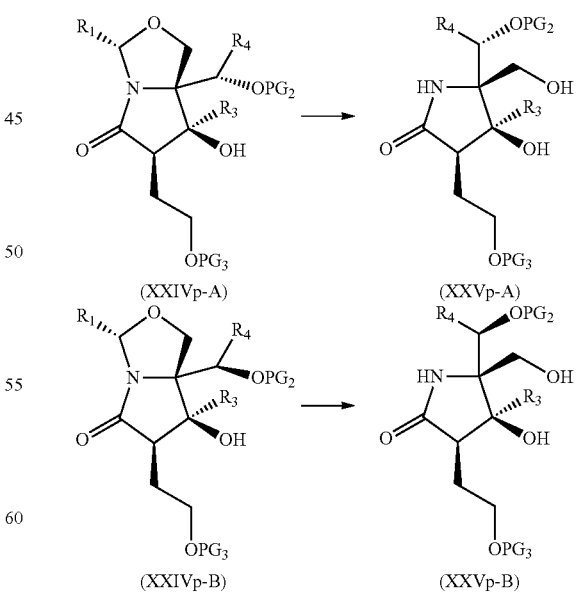

Compounds of formulae (XXIV), (XXIVp), (XXV), and (XXVp) may also have the following structures and stereochemistry:

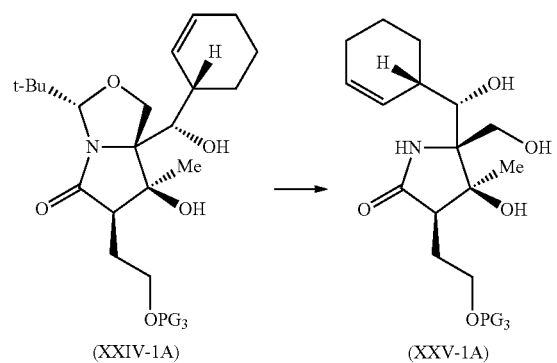

(XXIV-1A)    (XXV-1A)

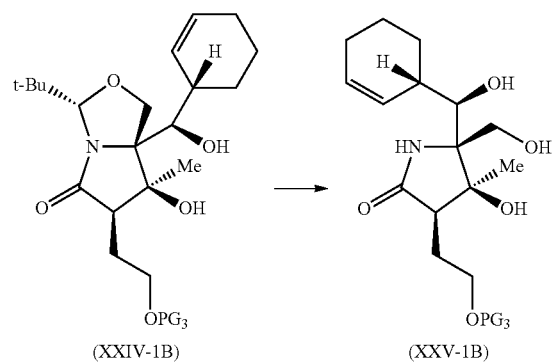

(XXIV-1B)    (XXV-1B)

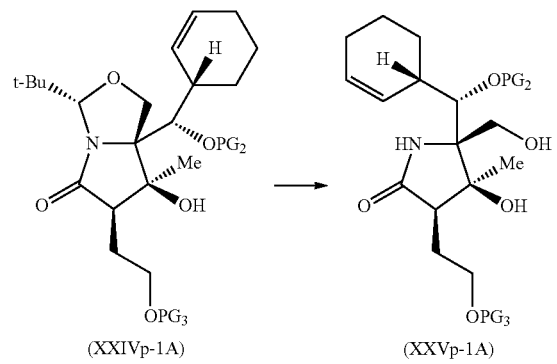

(XXIVp-1A)    (XXVp-1A)

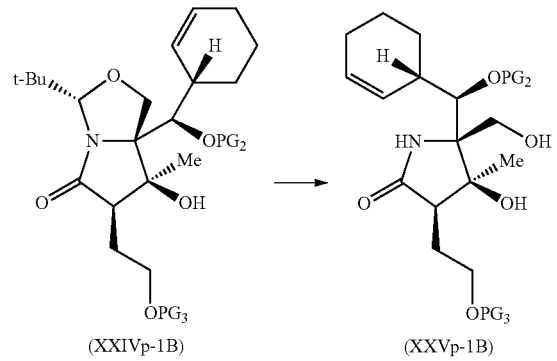

(XXIVp-1B)    (XXVp-1B)

As shown in Scheme 7-5, the aminal of the compound of formula (XXIV) can first be cleaved using one of methods described herein to form a compound of formula (XXV). The C-5 secondary hydroxy group of the compound of formula (XXV) can then be protected with an appropriate protecting group moiety to form a compound of formula (XXVp). In some embodiments, $R_3$, $R_4$, $PG_2$, and $PG_3$ of the compounds of formulae (XXV) and (XXVp) can be the same as described in the preceding paragraphs.

Exemplary structures of compounds of formulae (XXV) and (XXVp) are as follows:

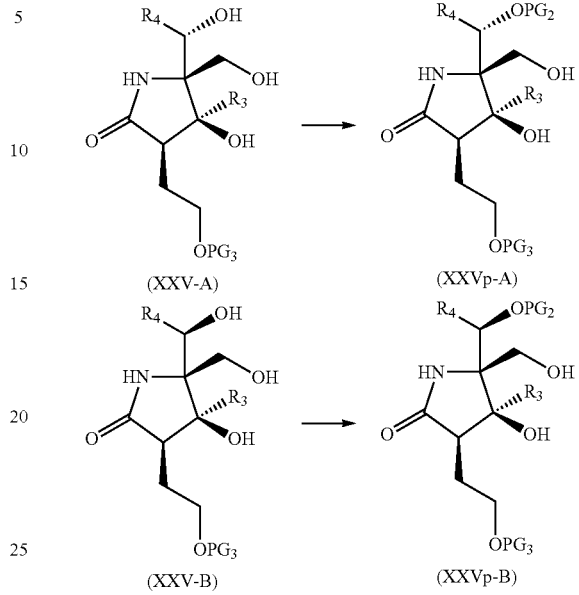

(XXV-A)    (XXVp-A)

(XXV-B)    (XXVp-B)

As an example, the compounds of formulae (XXV) and (XXVp) may have the following structures and stereochemistry:

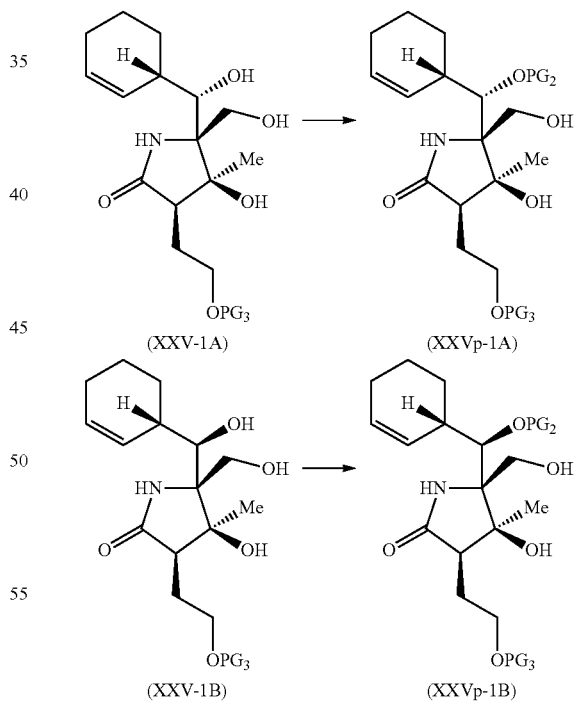

(XXV-1A)    (XXVp-1A)

(XXV-1B)    (XXVp-1B)

In an embodiment, the primary alcohol group of the compound of formula (XXV) and/or (XXVp) can be transformed to $R_5$ to form a compound of formula (XXVI) and/or (XXVIp), respectively (see Schemes 7-3 and 7-4, respectively).

In some embodiments, the compound of formula (XXVp) can be transformed directly to a compound of formula (XXVI) as shown in Scheme 7-5. In an embodiment, the protecting group moiety, PG$_2$, on the compound of formula (XXVp) can be removed simultaneously with the transformation of the C-15 primary alcohol to R$_5$ group to form a compound of formula (XXVI). Alternatively, in an embodiment, PG$_2$ can be removed before or after the transformation of the primary alcohol.

The transformation of the C-15 primary alcohol group to an R$_5$ group can be achieved using the same or a similar method to the one described in step (k) of Schemes 7-1 and/or 7-2. In some embodiments, R$_3$, R$_4$, and R$_5$ of the compounds of formulae (XXVI) and (XXVIp) can be the same as described with respect to the compound of formulae (XII) or (XIIp) of Schemes 7-1 and/or 7-2, and PG$_2$ and PG$_3$ can be a protecting group moieties.

Exemplary structures and stereochemistry of the compounds of formulae (XXV), (XXVp), (XXVI), and (XXVIp) can have the following structures and stereochemistry:

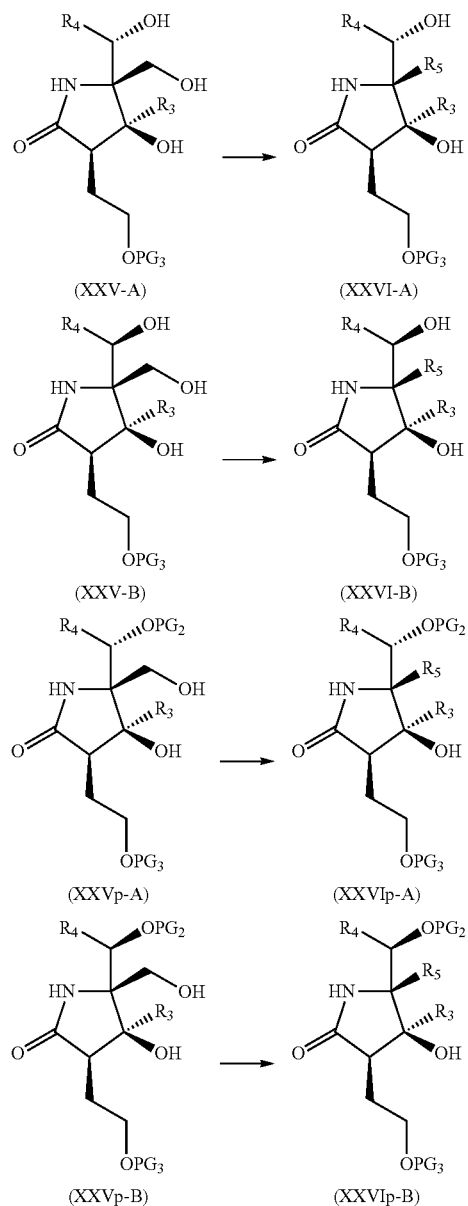

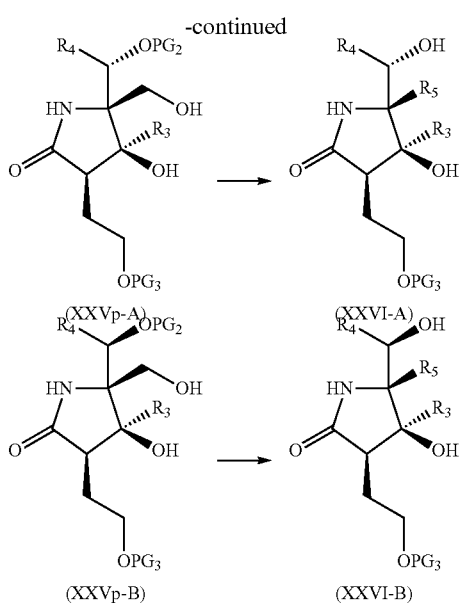

Other examples of the structures and stereochemistry of the compounds of formulae (XXV), (XXVp), (XXVI), and (XXVIp) are shown below:

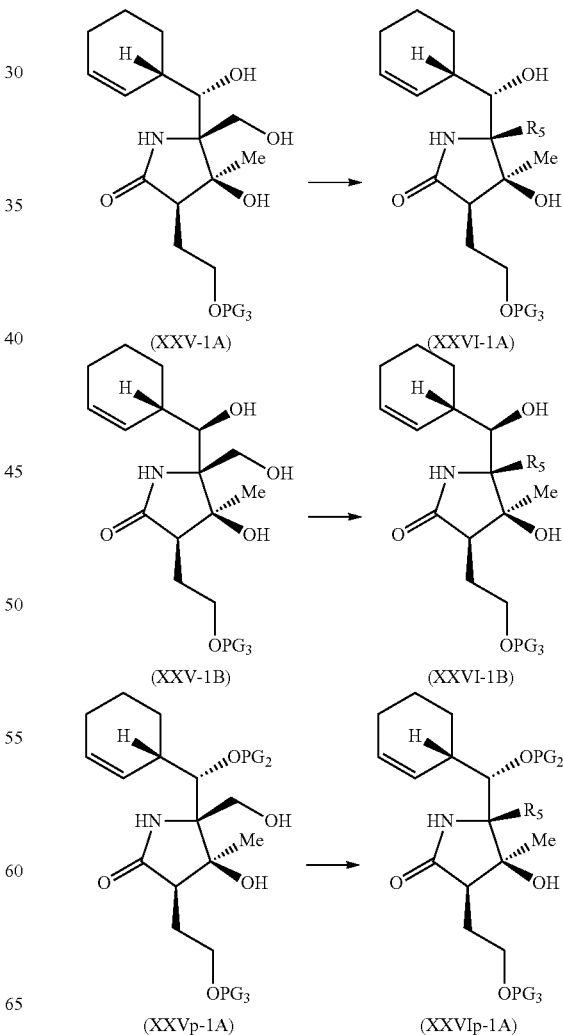

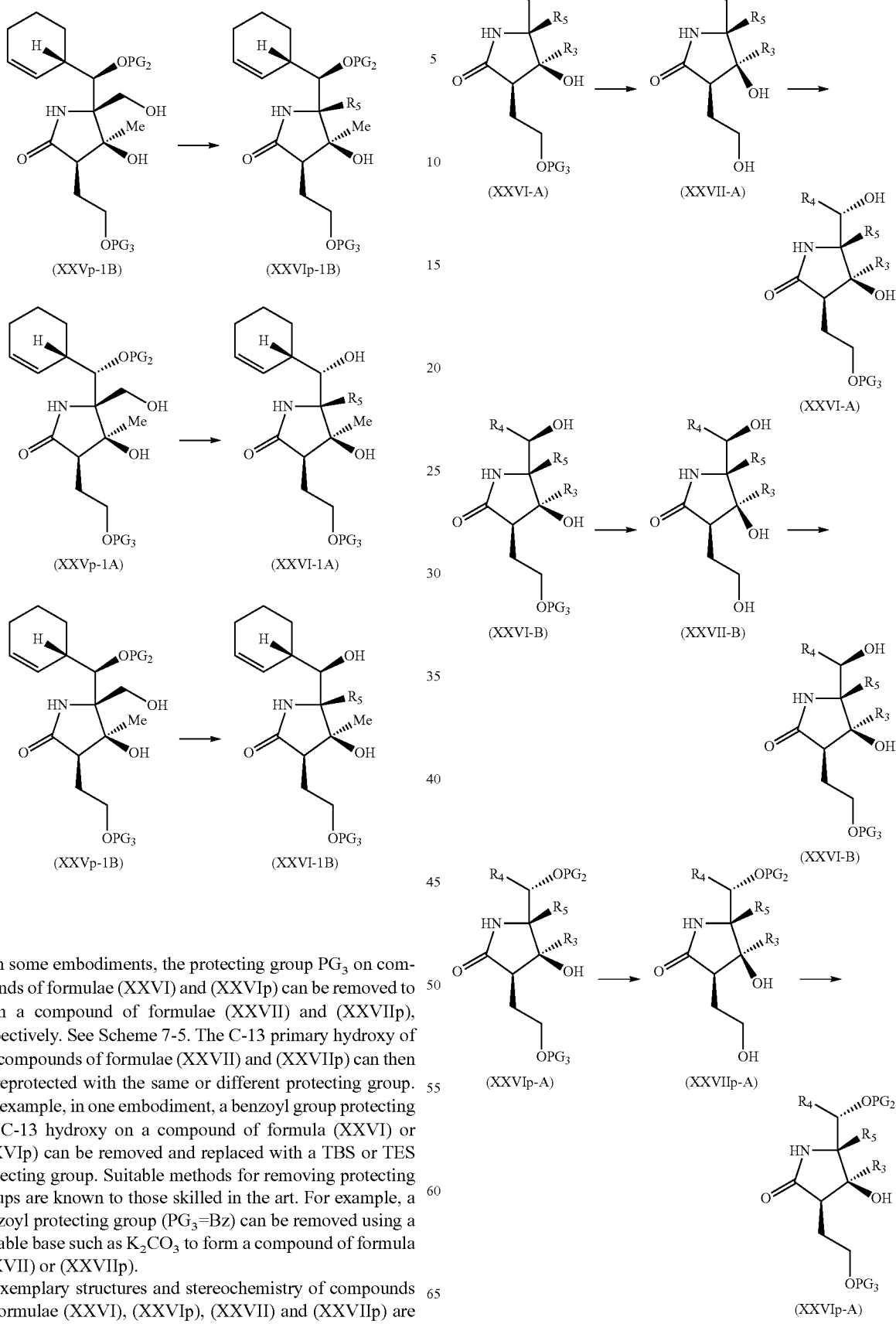

In some embodiments, the protecting group PG₃ on compounds of formulae (XXVI) and (XXVIp) can be removed to form a compound of formulae (XXVII) and (XXVIIp), respectively. See Scheme 7-5. The C-13 primary hydroxy of the compounds of formulae (XXVII) and (XXVIIp) can then be reprotected with the same or different protecting group. For example, in one embodiment, a benzoyl group protecting the C-13 hydroxy on a compound of formula (XXVI) or (XXVIp) can be removed and replaced with a TBS or TES protecting group. Suitable methods for removing protecting groups are known to those skilled in the art. For example, a benzoyl protecting group (PG₃=Bz) can be removed using a suitable base such as $K_2CO_3$ to form a compound of formula (XXVII) or (XXVIIp).

Exemplary structures and stereochemistry of compounds of formulae (XXVI), (XXVIp), (XXVII) and (XXVIIp) are shown below:

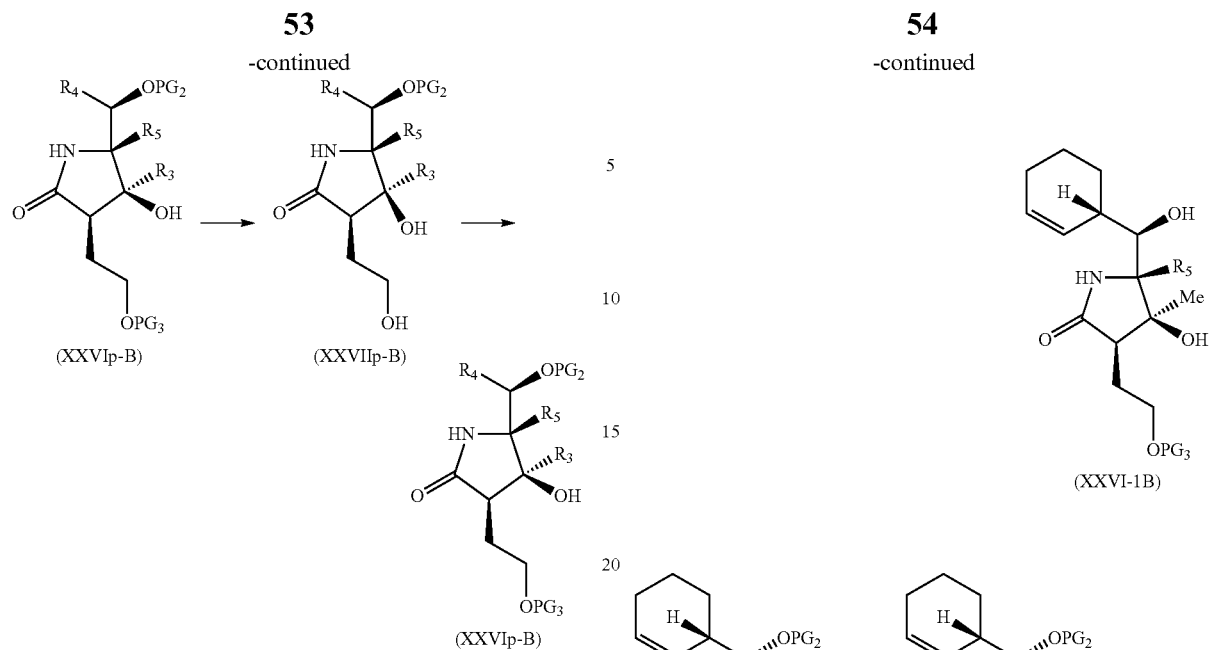
Additional examples of the structures and stereochemistry of compounds of formulae (XXVI), (XXVIp), (XXVII) and (XXVIIp) can be as follows:
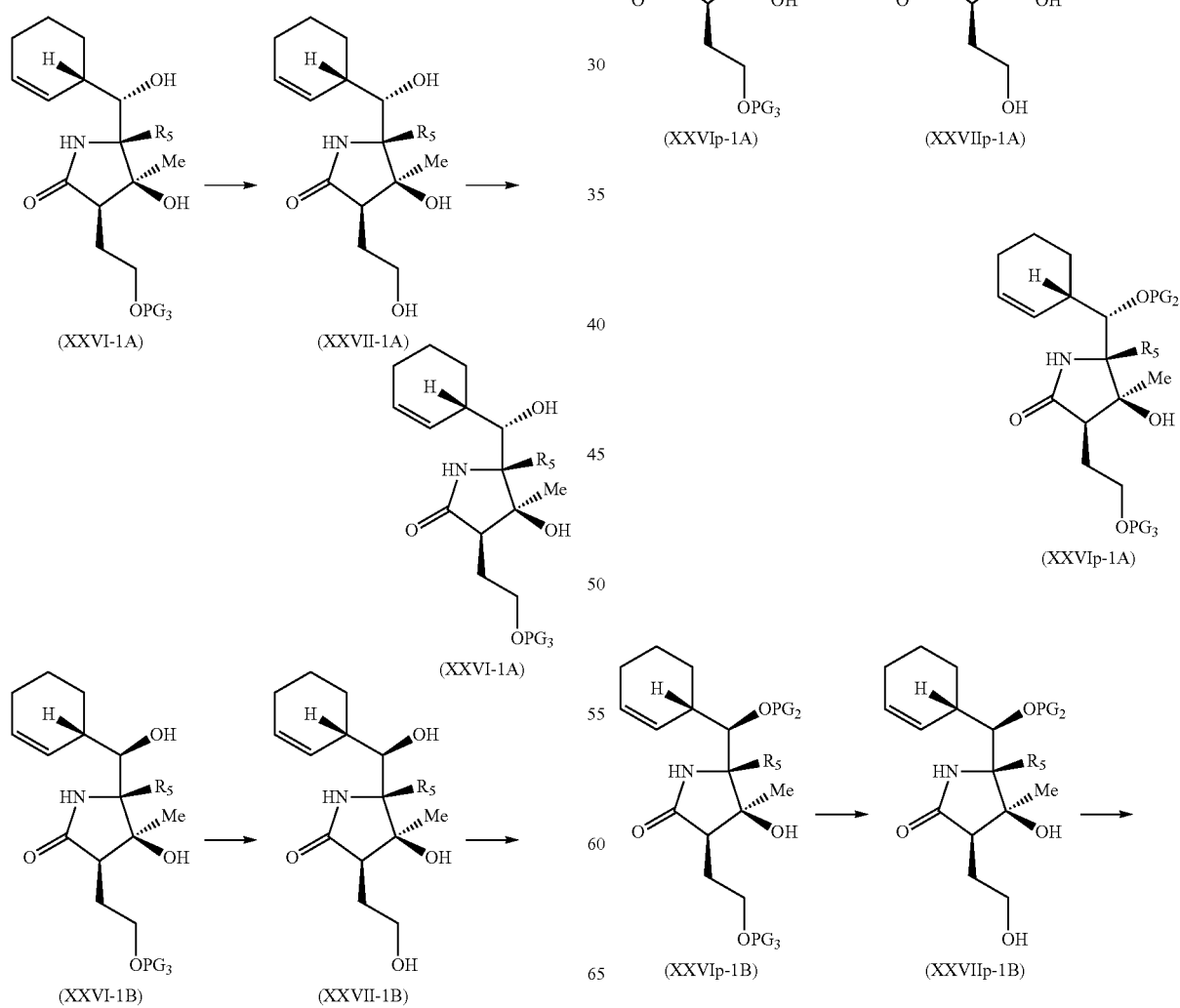

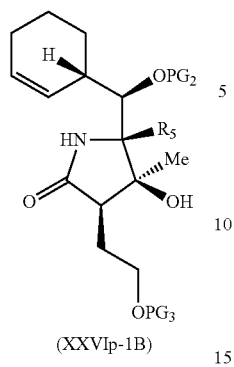
(XXVIp-1B)
Further examples of the structures and stereochemistry of compounds of formulae (XXVI), (XXVIp), (XXVII) and (XXVIIp) can be as follows:
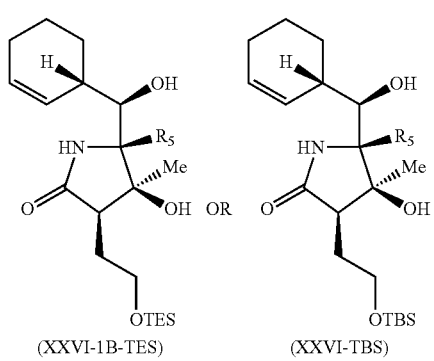
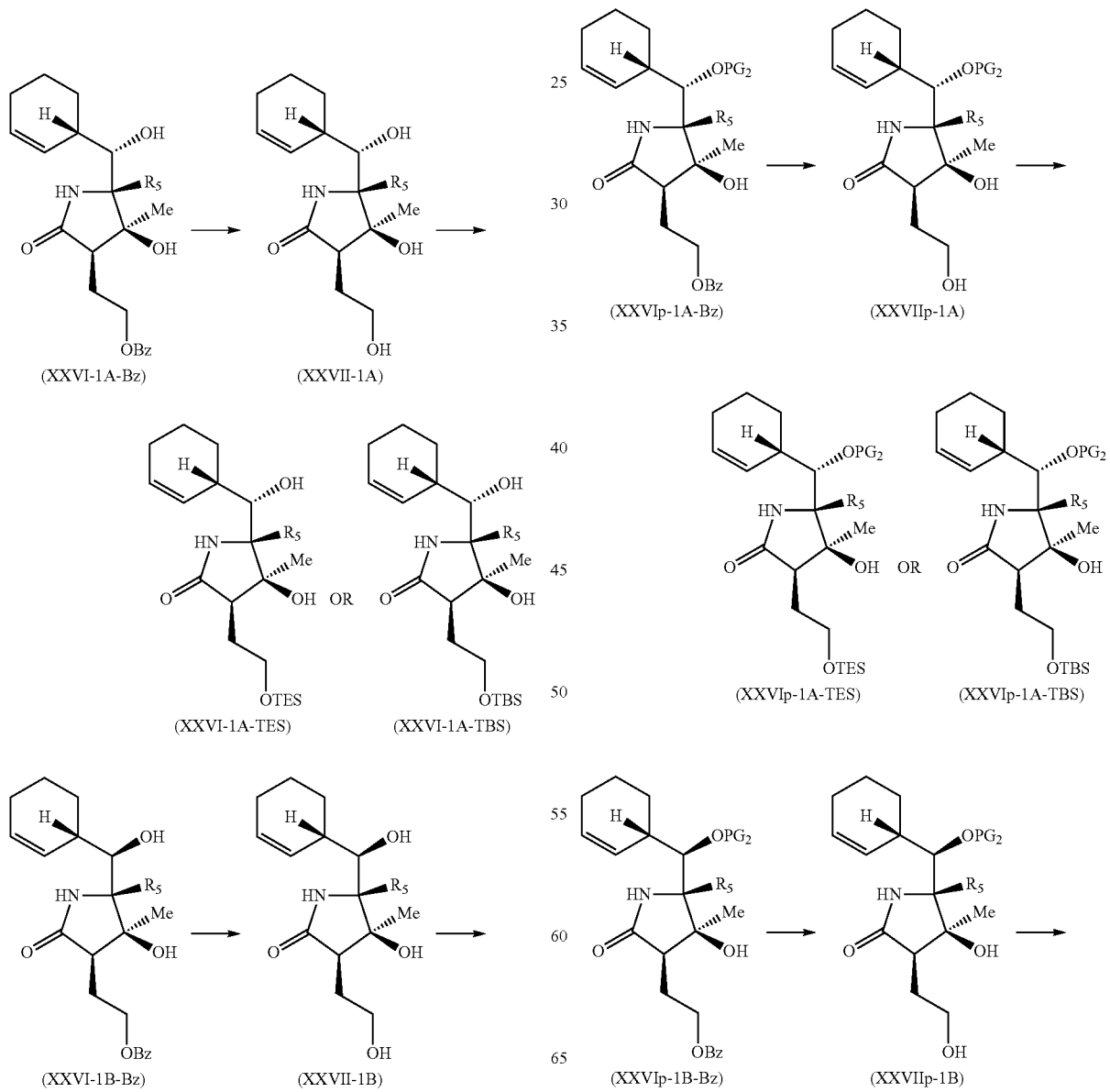

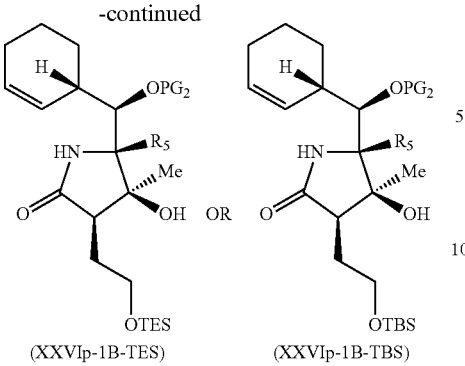

(XXVIp-1B-TES) OR (XXVIp-1B-TBS)

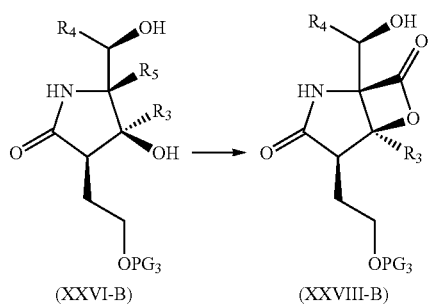

(XXVI-B) (XXVIII-B)

Using an appropriate base, a compound of formula (XXVIII) and/or (XXVIIIp) can be synthesized via a lactonization reaction from a compound of formula (XXVI) and (XXVIp), respectively. See Schemes 7-3, 7-4 and 7-5. In some embodiments, $R_3$, $R_4$, $R_5$ (and $PG_2$, where relevant) for compounds of formulae (XXVIII) and (XXVIIIp) can be the same as described with respect to the compound of formulae (XXVI) and (XXVIp), and $PG_3$ can be a protecting group moiety. In some embodiment, $R_5$ of the compound of formula (XXVI) or (XXVIp) can be a carboxylic acid. In an embodiment, $R_5$ of the compound of formula (XXVI) or (XXVIp) can be an activated acid (e.g., acid chloride). In certain embodiments, $R_5$ of the compound of formula (XXVI) or (XXVIp) can be an activated ester such as p-nitrophenyl ester, pentafluorophenyl ester, pentafluoroethyl ester, trifluoroethyl ester, trichloroethyl ester, thioester, etc.

In some embodiments, a compound of formula (XXVIII) can be synthesized by performing a lactonization reaction on a compound of formula (XXVI) with the proviso that if the compounds of formulae (XXVIII) and (XXVI) have the same structures and stereochemistry of the compounds of formulae (XXVIII-1A) and (XXVI-1A), then $R_5$ cannot be —C(=O)OR$_6$, wherein $R_6$ is hydrogen. In other embodiments, the lactonization reaction includes the further the proviso that $R_6$ cannot be methyl or t-butyl when the compounds of formulae (XXVIII) and (XXVI) have the structures and stereochemistry of the compounds of formulae (XXVIII-1A) and (XXVI-1A). In an embodiment, the compound of formula (XXVIII) can have the structure shown herein with the proviso that if $R_4$ is 2-cyclohexenyl and $R_3$ is methyl, then $PG_3$ cannot be —C(=O)CH$_2$CH$_3$ and/or mesylate. In an embodiment, if the compound of formula (XXVIII) has the structure and stereochemistry of the compound of formula (XXVIII-A) and if $R_4$ is 2-cyclohexenyl and $R_3$ is methyl, then $PG_3$ cannot be —C(=O)CH$_2$CH$_3$ and/or mesylate.

As an example, compounds of formulae (XXVI) and (XXVIII) can have the structures and stereochemistry shown below:

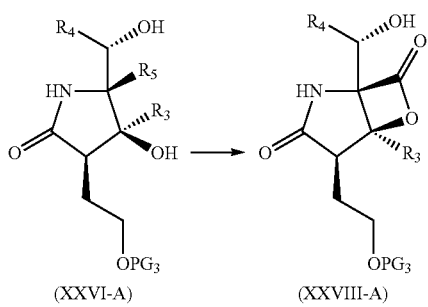

(XXVI-A) (XXVIII-A)

Other exemplary structures and stereochemistry of compounds of formulae (XXVIp) and (XXVIIIp) are as follows:

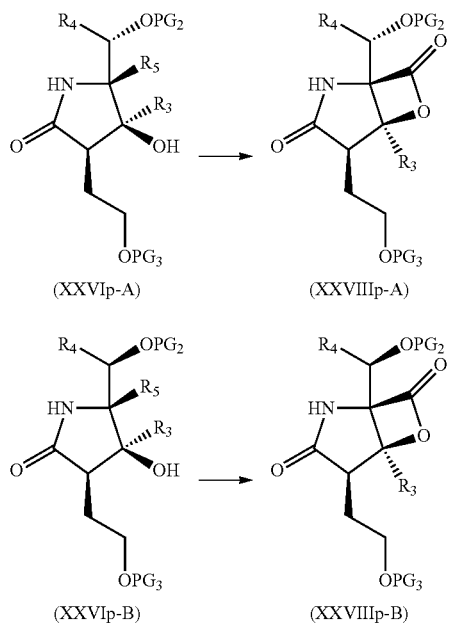

(XXVIp-A) (XXVIIIp-A)

(XXVIp-B) (XXVIIIp-B)

Additional examples of the structures and stereochemistry of compounds of formulae (XXVI), (XXVIp), (XXVIII), and (XXVIIIp) are shown below:

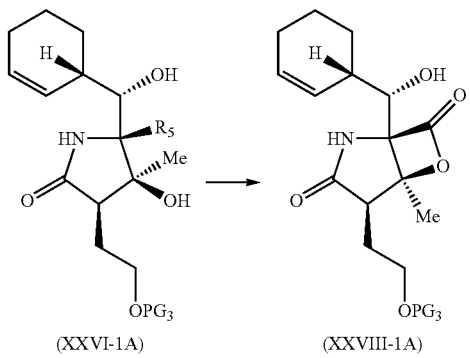

(XXVI-1A) (XXVIII-1A)

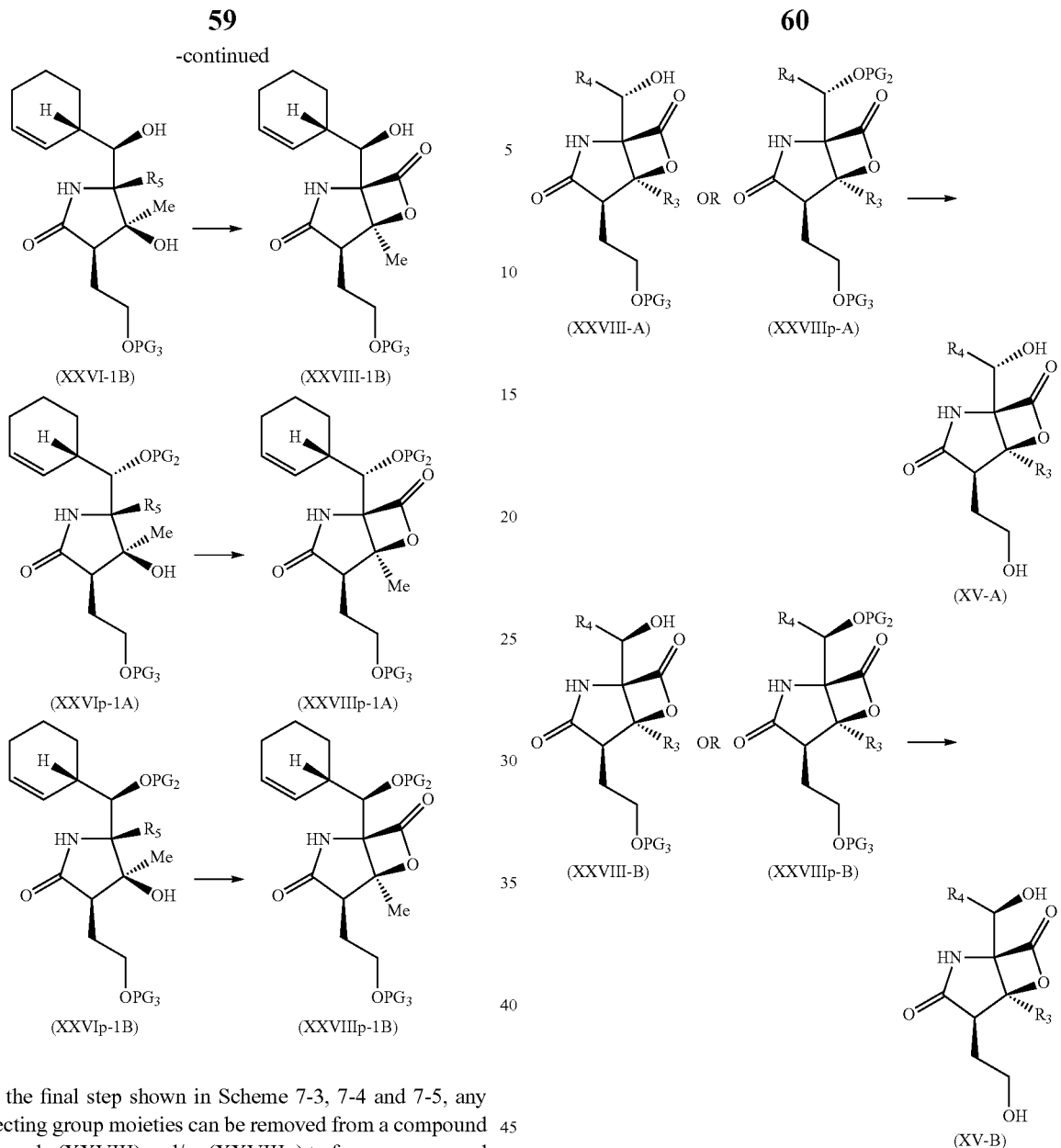

In the final step shown in Scheme 7-3, 7-4 and 7-5, any protecting group moieties can be removed from a compound of formula (XXVIII) and/or (XXVIIIp) to form a compound of formula (XV), respectively. In some embodiments, $R_3$ and $R_4$ (and $PG_2$, where relevant) of the compounds (XXVIII), (XXVIIIp) and (XV) can be the same as described with respect to the compound of formulae (XXVI) or (XXVIp), and $PG_3$ can be a protecting group moiety. In another embodiment, the protecting groups $PG_2$ and $PG_3$ can be removed from a compound of formula (XXVIIIp) in a stepwise fashion to form a compound of formula (XV); the protecting groups can be removed in any order. In yet another embodiment, the protecting groups $PG_2$ and $PG_3$ are simultaneously removed from a compound of formula (XXVIIIp) to form a compound of formula (XV). In an embodiment, a compound of formula (XV) can have the structure shown herein with the proviso that if the compound of formula (XV) has the structure and stereochemistry of the compound of formula (XV-A) and $R_3$ is methyl then $R_4$ cannot be 2-cyclohexenyl.

Compounds of formulae (XXVIII), (XXVIIIp) and (XV) can have the following structures and stereochemistry:

In addition, compounds of formula (XXVIII), (XXVIIIp) and (XV) can have the structures and stereochemistry shown below:

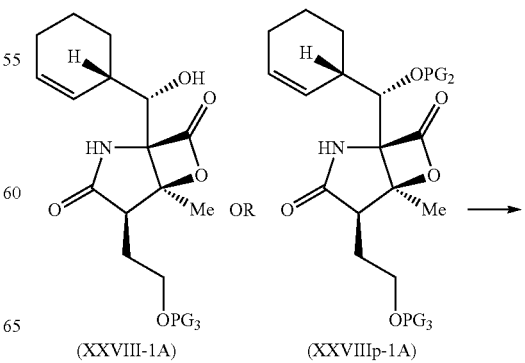

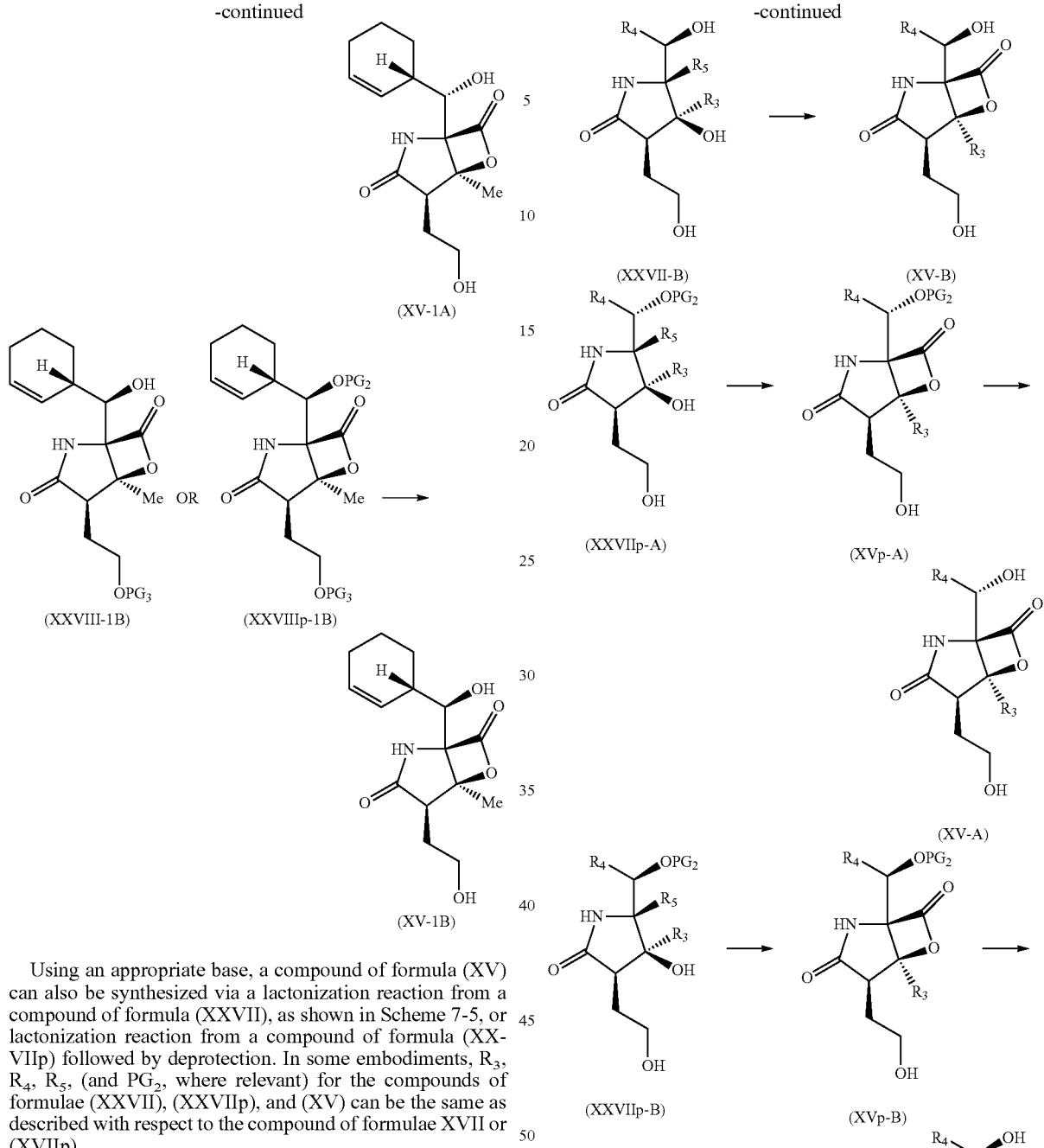

Using an appropriate base, a compound of formula (XV) can also be synthesized via a lactonization reaction from a compound of formula (XXVII), as shown in Scheme 7-5, or lactonization reaction from a compound of formula (XXVIIp) followed by deprotection. In some embodiments, $R_3$, $R_4$, $R_5$, (and $PG_2$, where relevant) for the compounds of formulae (XXVII), (XXVIIp), and (XV) can be the same as described with respect to the compound of formulae XVII or (XVIIp).

As an example, compounds of formulae (XXVII), (XXVIIp), (XVp) and (XV) can have the structures and stereochemistry shown below:

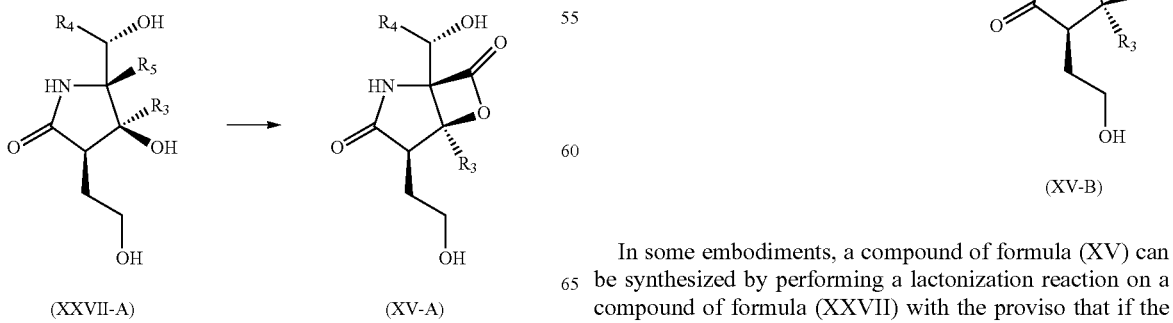

In some embodiments, a compound of formula (XV) can be synthesized by performing a lactonization reaction on a compound of formula (XXVII) with the proviso that if the compounds of formulae (XXVII) and (XV) have the same structures and stereochemistry as the compounds of formulae (XXVII-1A) and (XV-1A), then $R_5$ cannot be —C(=O)OR$_6$, wherein $R_6$ is hydrogen. In other embodiments, the lactonization reaction includes the further proviso that $R_6$ cannot be methyl or t-butyl when the compounds of formulae (XXVII) and (XV) have the structures and stereochemistry of the compounds of formulae (XXVII-1A) and (XV-1A). In some embodiments, a compound of formula (XV) can be synthesized by performing a lactonization reaction on a compound of formula (XXVII) and/or (XXVII-A) with the proviso that if $R_5$ is —C(=O)OR$_6$, wherein $R_6$ is hydrogen, methyl or t-butyl then $R_4$ cannot be isopropyl. In an embodiment, a compound of formula (XV) can have the structure shown herein with the proviso that if the compound of formula (XV) has the structure and stereochemistry of the compound of formula (XV-A) and $R_3$ is methyl then $R_4$ cannot be 2-cyclohexenyl. In an embodiment, a compound of formula (XV) can have the structure shown herein with the proviso that if the compound of formula (XV) has the structure and stereochemistry of the compound of formula (XV-A) and $R_3$ is methyl then $R_4$ cannot be isopropyl. In an embodiment, a compound of formula (XVp) can have the structure shown herein with the proviso that if $R_3$ is methyl and $R_4$ is isopropyl then PG$_2$ cannot be DMIPS or TBS. In some embodiments, a compound of formula (XVp) can have the structure shown herein with the proviso that if the compound of formula (XVp) has the structure and stereochemistry of the compound of formula (XVp-A) and $R_3$ is methyl and $R_4$ is isopropyl then PG$_2$ cannot be DMIPS or TBS.

In an embodiment, a compound of formula (XXVII) can have the structure shown herein with the proviso that if the compound of formula (XXVII) has the structure and stereochemistry of the compound of formula (XXVII-A), $R_3$ is methyl, and $R_5$ is —C(=O)OR$_6$, wherein $R_6$ is methyl, H or t-butyl, then $R_4$ cannot be 2-cyclohexenyl. In one embodiment, a compound of formula (XXVIIp) can have the structure shown herein with the proviso that if the compound of formula (XXVIIp) has the structure and stereochemistry of the compound of formula (XXVIIp-A); $R_3$ is methyl; $R_5$ is —C(=O)OR$_6$, wherein $R_6$ is hydrogen or methyl; and PG$_2$ is TBS or DMIPS then $R_4$ cannot be isopropyl.

Other exemplary structures and stereochemistry of compounds of formulae (XXVII), (XXVIIp), (XVp) and (XV) are as follows:

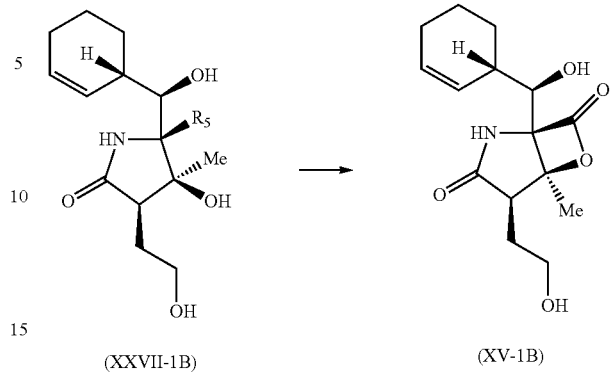

(XXVII-1B)    (XV-1B)

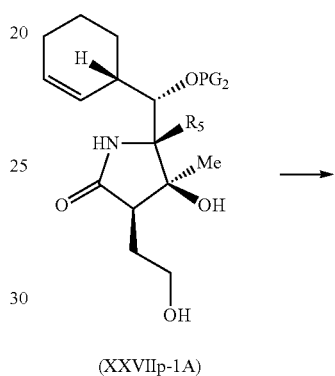

(XXVIIp-1A)

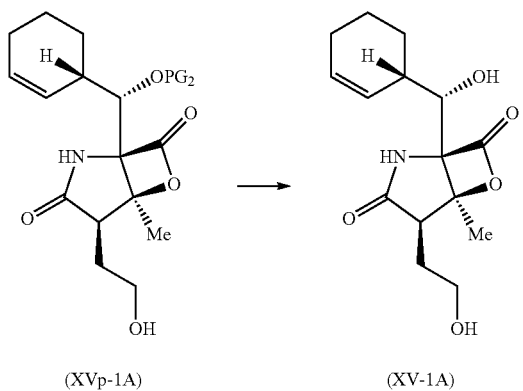

(XVp-1A)    (XV-1A)

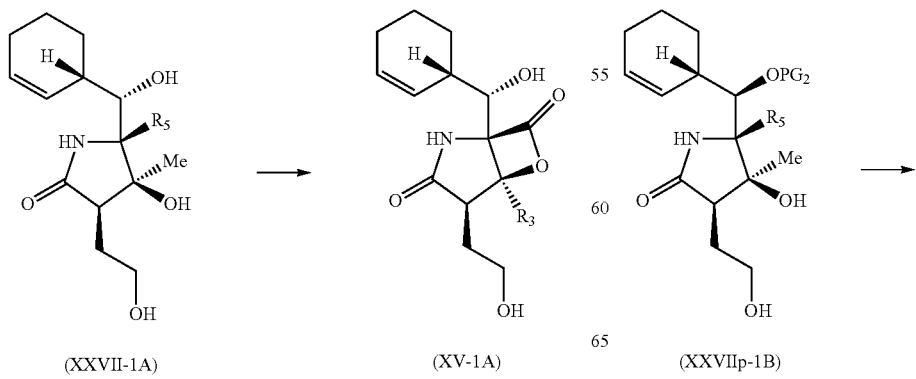

(XXVII-1A)    (XV-1A)    (XXVIIp-1B)

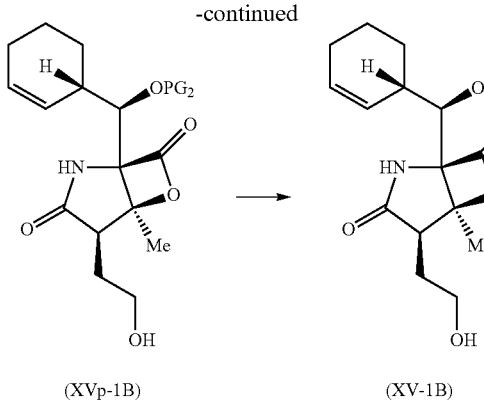

(XVp-1B)　　　　　(XV-1B)

As shown in Scheme 7-6, a compound of formula (XV) can further be transformed by replacing the C-13 primary hydroxy group of the compound of formula (XV) to form a compound of formula (XVI), wherein $R_3$ and $R_4$ can be the same as described with respect to the compound of formula (X) and X can be a halogen (e.g., F, Cl, Br, and I). If desired or necessary, $R_4$, in some embodiments, can be protected and/or deprotected one or several times in any of the synthetic steps described herein.

Scheme 7-6

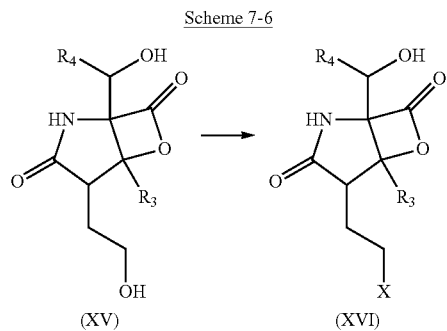

(XV)　　　　　(XVI)

Examples of the structures and stereochemistry of compounds of formulae (XV) and (XVI) are shown below:

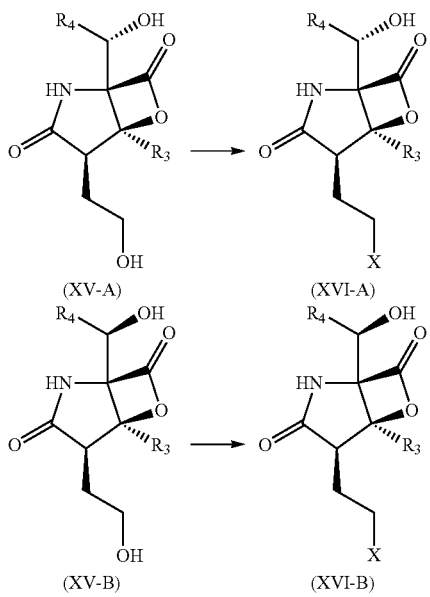

(XV-A)　　　　　(XVI-A)

(XV-B)　　　　　(XVI-B)

Further examples of the structures and stereochemistry of the compounds of formula (XV) and (XVI) are shown below:

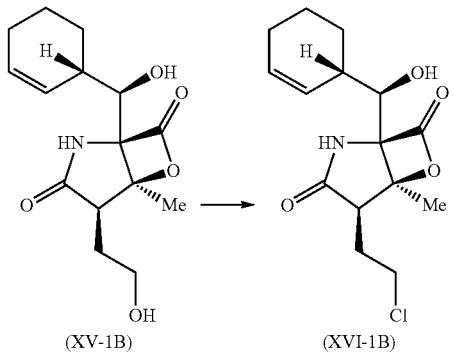

(XV-1B)　　　　　(XVI-1B)

In one embodiment, Salinosporamide A can be synthesized by chlorinating a compound of formula (XV), wherein $R_4$ is 2-cyclohexenyl and $R_3$ is methyl.

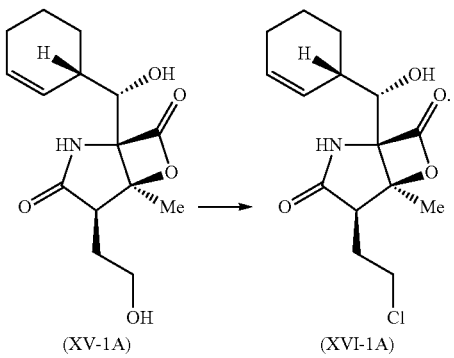

(XV-1A)　　　　　(XVI-1A)

In some embodiments, a compound of formula (XVI) can be prepared by substituting the C-13 primary hydroxy group of the compound of formula (XV), with the proviso that the compounds of formula (XV) and (XVI) cannot be the compounds of formula (XV-1A) and (XVI-1A). In certain embodiments, if the compound of formula (XVI) has the structure and stereochemistry of the compound of formula (XVI-A), then $R_4$ cannot be isopropyl or 2-cyclohexenyl when $R_3$ is methyl and X is chlorine.

In an embodiment, the C-13 primary hydroxy group of the compound of formula (XV) can be converted to a leaving group, as shown in Scheme 7-7. A non-limiting list of suitable leaving groups (LG) includes sulfonate leaving groups (e.g. tosylate, (OTs), mesylate (OMs), triflate (OTO, tripsylate (OTps), and mesitylate (OMst)). In an embodiment, $R_3$ and $R_4$ can be the same as described with respect to the compound of formula (X). If desired, the C-5 secondary hydroxy can be protected or oxidized before converting the C-13 secondary hydroxy group of the compound of formula (XV). After the leaving group has been added, the C-5 center can be deprotected and/or reduced to a hydroxy group.

Scheme 7-7

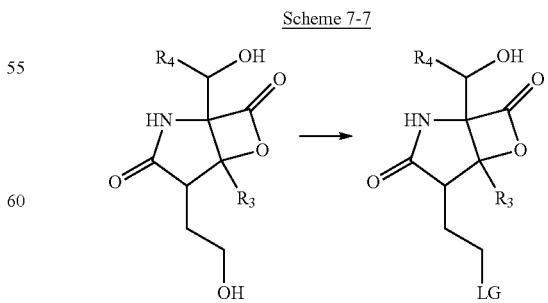

Examples of the structures and stereochemistry of compounds of formulae (XV) and (XXXX) with a leaving group attached to the C-13 oxygen are shown below:

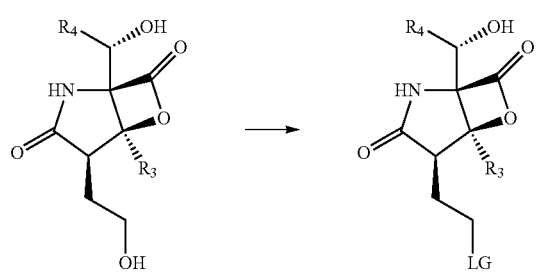

(XV-A) → (XXXX-A)

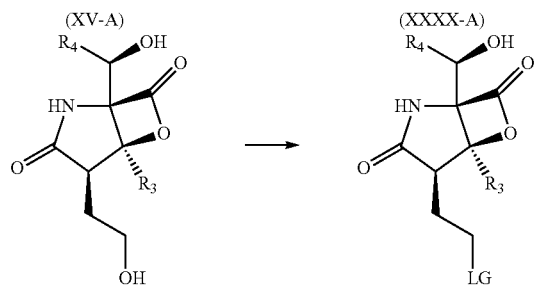

(XV-B) → (XXXX-B)

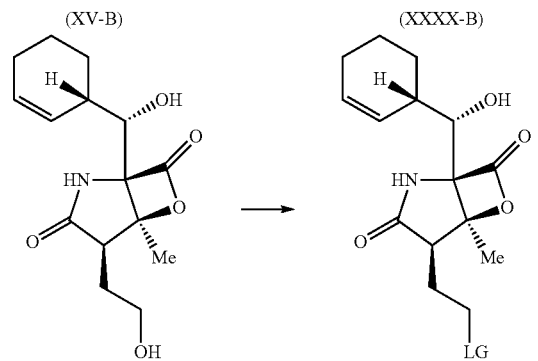

(XV-1A) → (XXXX-1A)

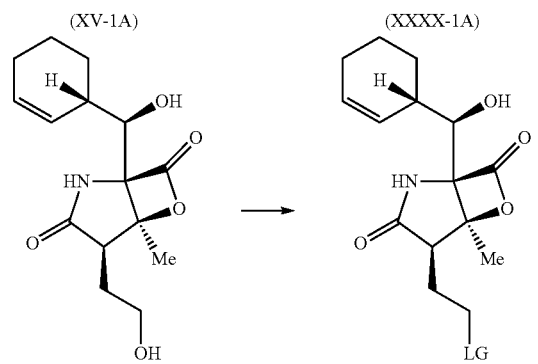

(XV-1B) → (XXXX-1B)

The leaving group of compounds of formula (XXXX) can be displaced with a nucleophile (Nu) using methods known to those skilled in the art to form a compound of formula (XXXXI). See Scheme 7-8. In an embodiment, $R_3$ and $R_4$ can be the same as described with respect to the compound of formula (XXXX). Suitable nucleophiles include but are not limited to $R_9S^-$, $CN^-$, $R_9O^-$, halide anion, $NR_{9a}R_{9b}^-$, $N_3^-$, $-CO_2R_9$, $R_9OH$, and $R_9SH$ wherein $R_9$, $R_{9a}$ and $R_{9b}$ can each be independently selected from the group consisting of hydrogen, or substituted or unsubstituted variants of the following: $C_1$-$C_{12}$ alkyl, $C_2$-$C_{12}$ alkenyl, $C_2$-$C_{12}$ alkynyl, $C_3$-$C_{12}$ cycloalkyl, $C_3$-$C_{12}$ cycloalkenyl, $C_3$-$C_{12}$ cycloalkynyl, $C_3$-$C_{12}$ heterocyclyl, aryl, heteroaryl, arylalkyl, heteroarylalkyl, (cycloalkyl)alkyl, (heterocyclyl)alkyl, acyl, and alkyl acyl, wherein $R_{9a}$ and $R_{9b}$ can be taken together to form an optionally substituted cycloalkyl.

Scheme 7-8

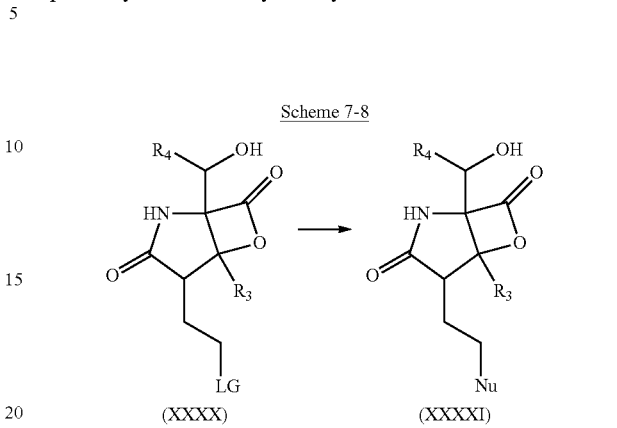

(XXXX) → (XXXXI)

Exemplary structures and stereochemistry of compounds of formulae (XXXX) and (XXXXI) include:

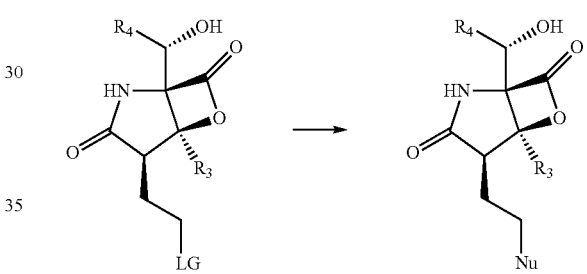

(XXXX-A) → (XXXXI-A)

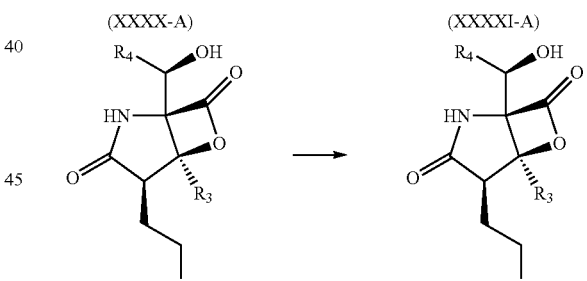

(XXXX-B) → (XXXXI-B)

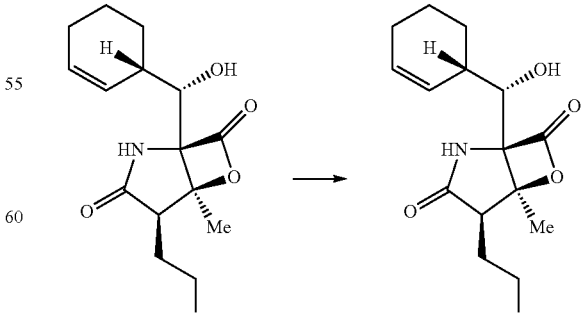

(XXXX-1A) → (XXXXI-1A)

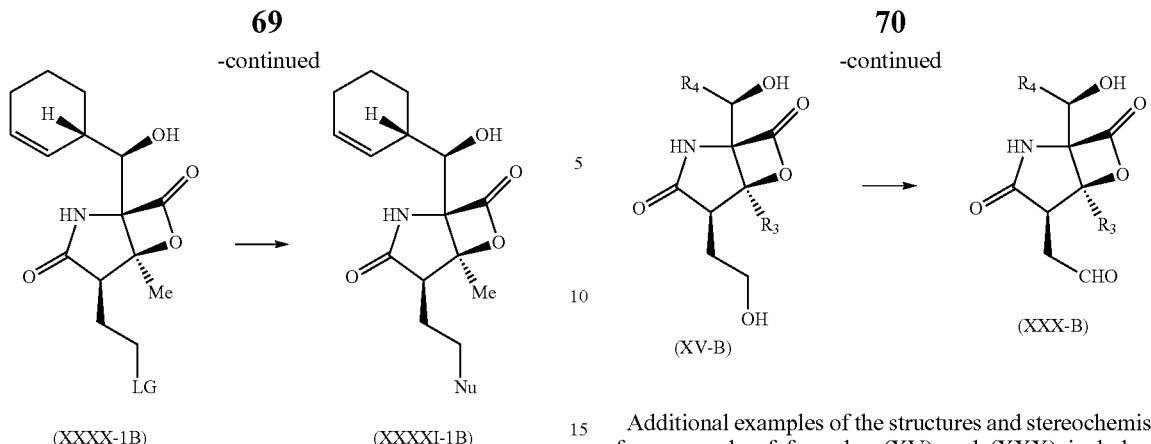

(XXXX-1B) (XXXXI-1B)

In some embodiments, the C-13 primary hydroxy group of the compound of formula (XV) can be oxidized. For example, in one embodiment, the C-13 primary hydroxy group can be oxidized to an aldehyde to form a compound of formula (XXX). See Scheme 7-9. In an embodiment, $R_3$ and $R_4$ of a compound of formula (XXX) can be the same as described with respect to the compound of formula (XVII). If desired, the C-5 secondary hydroxy can be protected or remained unprotected during the oxidation.

Scheme 7-9

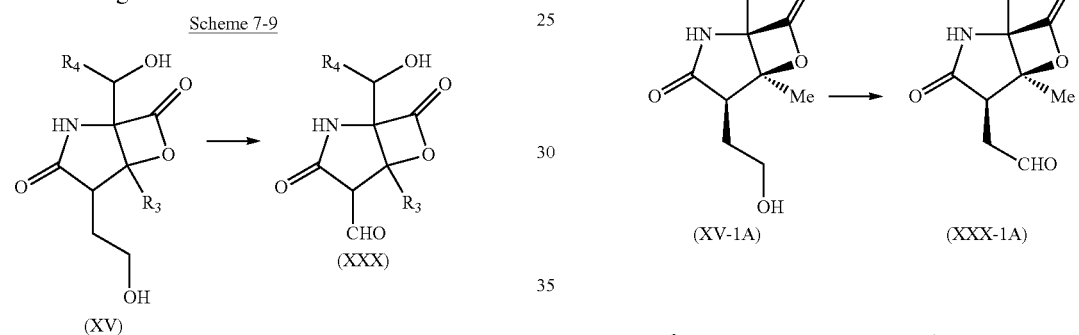

(XV) (XXX)

Exemplary structures and stereochemistry of compounds of formulae (XV) and (XXX) are shown below:

(XV-A) (XXX-A)

Additional examples of the structures and stereochemistry of compounds of formulae (XV) and (XXX) include the following:

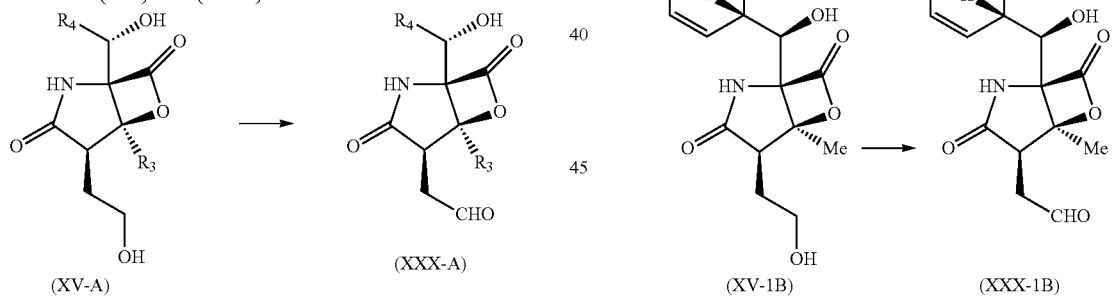

(XV-1A) (XXX-1A)

(XV-1B) (XXX-1B)

Scheme 7-10

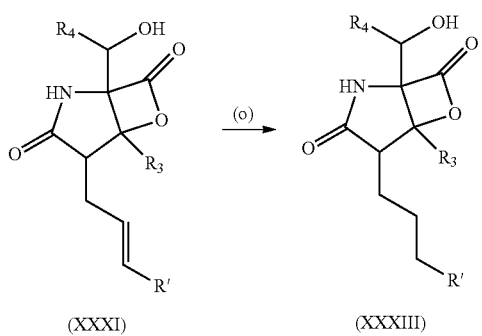

(XXXI) (XXXIII)

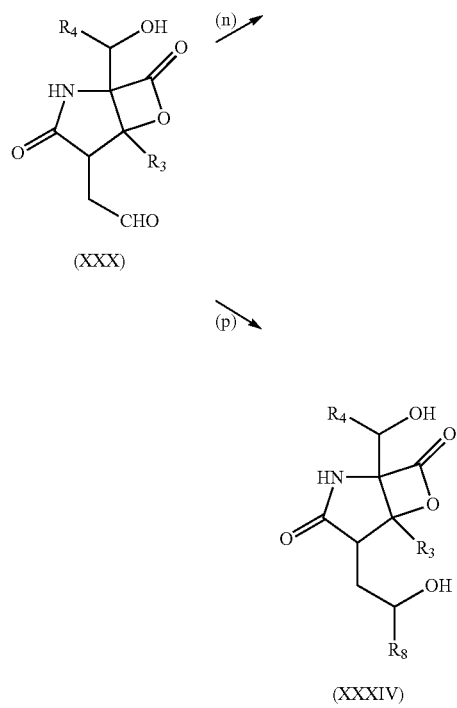

A compound of formula (XXX) can further be transformed as shown in step (n) of Scheme 7-10. In one embodiment, a Wittig reaction can be used to convert a compound of formula (XXX) to compounds of formulae (XXXI), wherein $R_3$ and $R_4$ can be the same as described with respect to the compound of formula (XXX), R' can be hydrogen, halogen, —C(=O)R", —C(=O)OR", —C(=O)N(R")$_2$, —C(=O)SR", —CN, —(CH$_2$)$_n$OH, and —(CH$_2$)$_n$X; R" can be a hydrogen or a substituted or unsubstituted variant of the following: alkyl, alkenyl, alkoxy, aryloxy, and arylalkoxy, and when more than one R" is present, they may be the same or different; X can be a halogen; and n can be 0, 1, 2, 3, or 4. Appropriate conditions and reagents are known to those skilled in the art and include Wittig reagents such as triphenyl phosphonium ylides). In an embodiment, n can be 0. In another embodiment, n can be 1. In still another embodiment, n can be 2. In yet still another embodiment, n can be 3. In an embodiment, n can be 4.

Examples of the structures and stereochemistry of compounds of formulae (XXX), and (XXXI) are shown below:

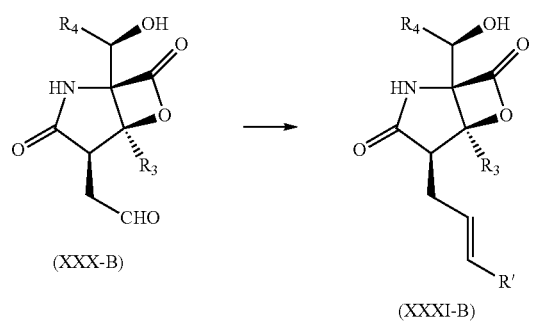

-continued

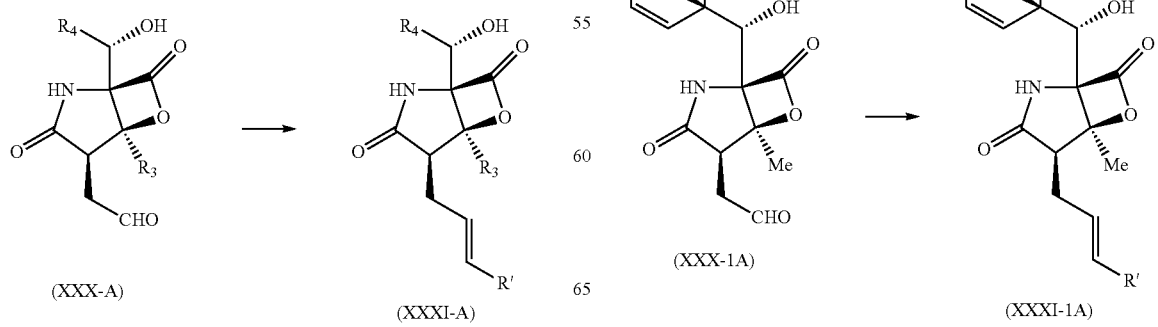

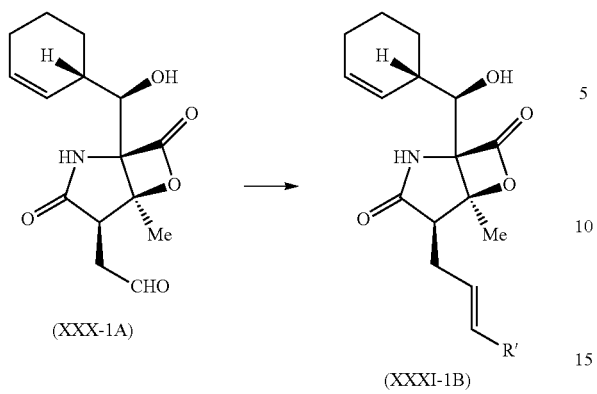

(XXX-1A) → (XXXI-1B)

Selective hydrogenation of the side chain double bond of compound of formula (XXXI) can form a compound of formula (XXXIII), as shown in step (o) of Scheme 7-10. In an embodiment, $R_3$, $R_4$ and R' of a compound of formula (XXXIII) can be the same as described with respect to the compound of formula (XXXI). In some embodiments, a compound of formula (XXXIII) can have the structure shown herein with the proviso that if $R_3$ is methyl and R' is hydrogen or chlorine then $R_4$ cannot be isopropyl, cyclohexyl, or phenyl.

Exemplary structures and stereochemistry of compounds of formulae (XXXI), and (XXXIII) are shown below:

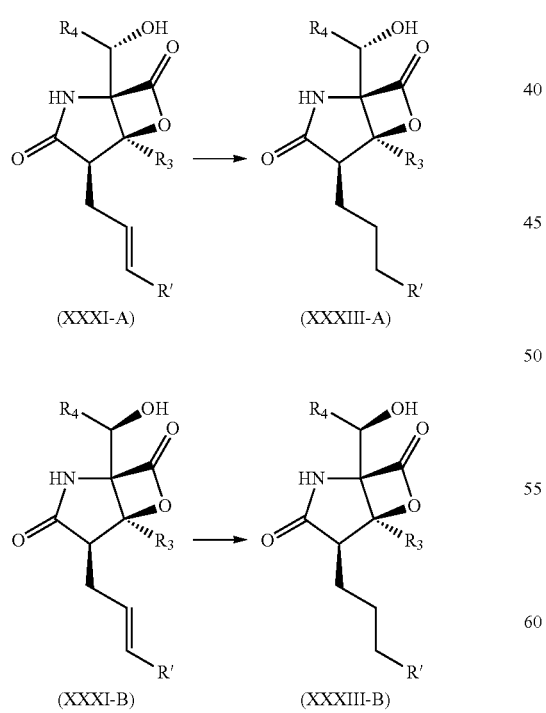

(XXXI-A) → (XXXIII-A)

(XXXI-B) → (XXXIII-B)

In certain embodiments, compounds of formulae (XXXI) and (XXXIII) can have the following structures and stereochemistry:

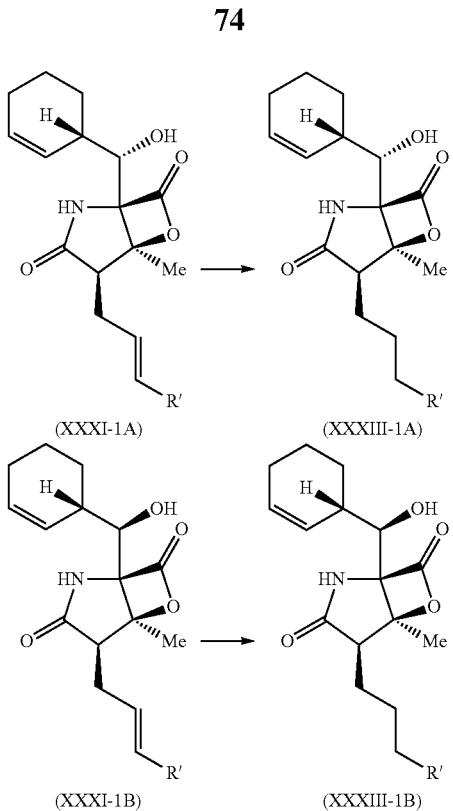

(XXXI-1A) → (XXXIII-1A)

(XXXI-1B) → (XXXIII-1B)

In another embodiment, nonselective reduction of the compound of formula (XXX1-A) or (XXX1-B) can be used to obtain the compounds of formulae (XXXII), respectively. In some embodiments, a compound of formula (XXXII) can have the structure shown herein with the proviso that R' cannot be hydrogen or chlorine.

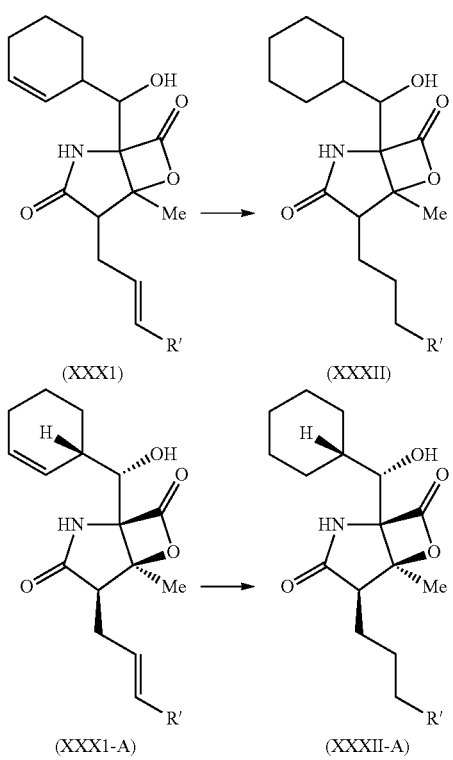

(XXX1) → (XXXII)

(XXX1-A) → (XXXII-A)

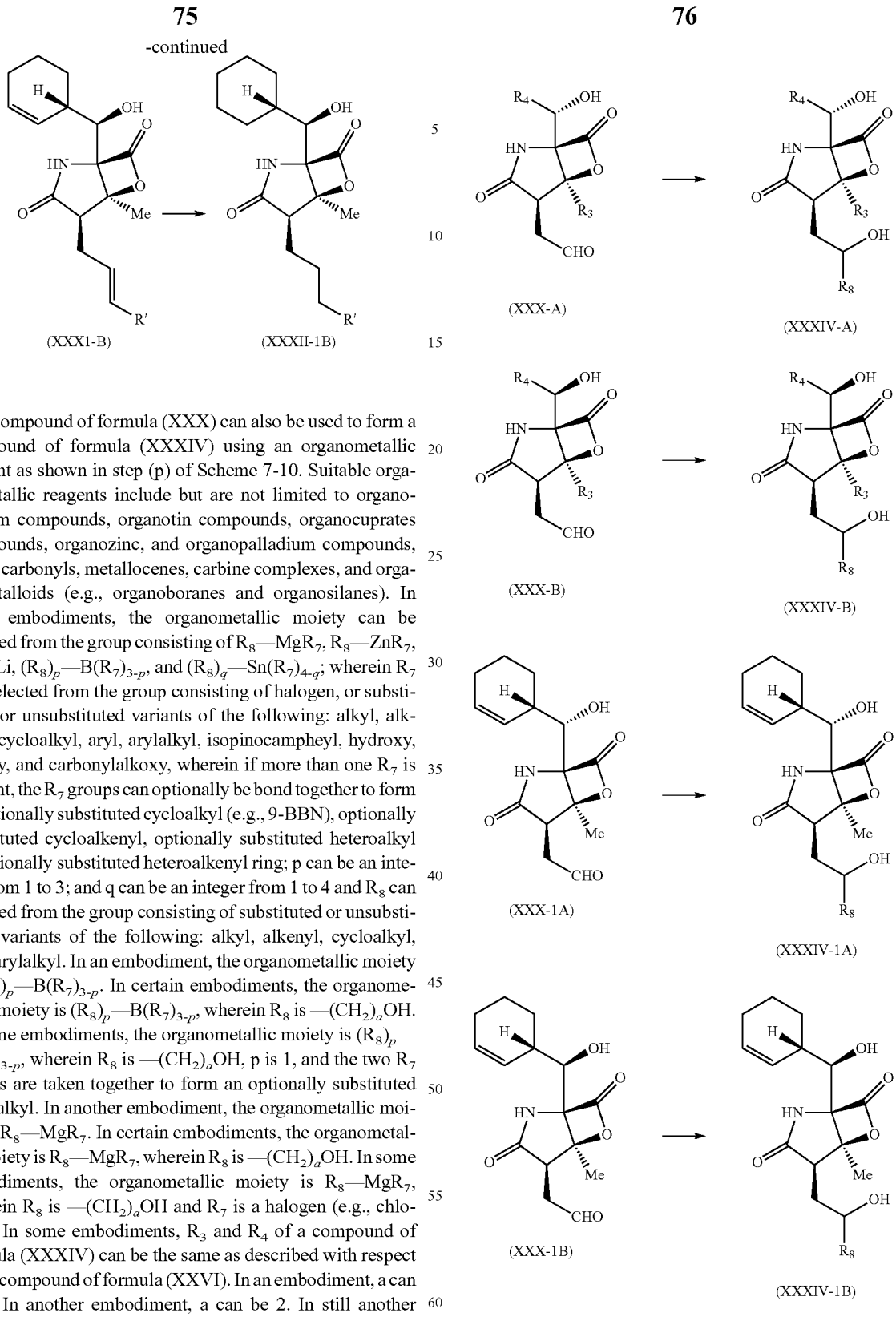

A compound of formula (XXX) can also be used to form a compound of formula (XXXIV) using an organometallic reagent as shown in step (p) of Scheme 7-10. Suitable organometallic reagents include but are not limited to organolithium compounds, organotin compounds, organocuprates compounds, organozinc, and organopalladium compounds, metal carbonyls, metallocenes, carbine complexes, and organometalloids (e.g., organoboranes and organosilanes). In some embodiments, the organometallic moiety can be selected from the group consisting of $R_8$—$MgR_7$, $R_8$—$ZnR_7$, $R_8$—Li, $(R_8)_p$—$B(R_7)_{3-p}$, and $(R_8)_q$—$Sn(R_7)_{4-q}$; wherein $R_7$ can selected from the group consisting of halogen, or substituted or unsubstituted variants of the following: alkyl, alkenyl, cycloalkyl, aryl, arylalkyl, isopinocampheyl, hydroxy, alkoxy, and carbonylalkoxy, wherein if more than one $R_7$ is present, the $R_7$ groups can optionally be bond together to form an optionally substituted cycloalkyl (e.g., 9-BBN), optionally substituted cycloalkenyl, optionally substituted heteroalkyl or optionally substituted heteroalkenyl ring; p can be an integer from 1 to 3; and q can be an integer from 1 to 4 and $R_8$ can selected from the group consisting of substituted or unsubstituted variants of the following: alkyl, alkenyl, cycloalkyl, aryl, arylalkyl. In an embodiment, the organometallic moiety is $(R_8)_p$—$B(R_7)_{3-p}$. In certain embodiments, the organometallic moiety is $(R_8)_p$—$B(R_7)_{3-p}$, wherein $R_8$ is —$(CH_2)_a OH$. In some embodiments, the organometallic moiety is $(R_8)_p$—$B(R_7)_{3-p}$, wherein $R_8$ is —$(CH_2)_a OH$, p is 1, and the two $R_7$ groups are taken together to form an optionally substituted cycloalkyl. In another embodiment, the organometallic moiety is $R_8$—$MgR_7$. In certain embodiments, the organometallic moiety is $R_8$—$MgR_7$, wherein $R_8$ is —$(CH_2)_a OH$. In some embodiments, the organometallic moiety is $R_8$—$MgR_7$, wherein $R_8$ is —$(CH_2)_a OH$ and $R_7$ is a halogen (e.g., chlorine). In some embodiments, $R_3$ and $R_4$ of a compound of formula (XXXIV) can be the same as described with respect to the compound of formula (XXVI). In an embodiment, a can be 1. In another embodiment, a can be 2. In still another embodiment, a can be 3. In yet still another embodiment, a can be 4. In an embodiment, a can be 5. In an embodiment, a can be 6. In still another embodiment, In an embodiment, a can be $\geq 7$ Examples of the structures and stereochemistry of compounds of formulae (XXX) and (XXXIV) are shown below:

In certain embodiments, $R_8$ can be —$(CH_2)_a OH$, wherein a can be selected from the group consisting of 1, 2, 3, 4, 6, or 7. Examples of the structures and stereochemistry of compounds of formulae (XXXIV-1B) when $R_8$ is —$(CH_2)_a OH$ is shown below:

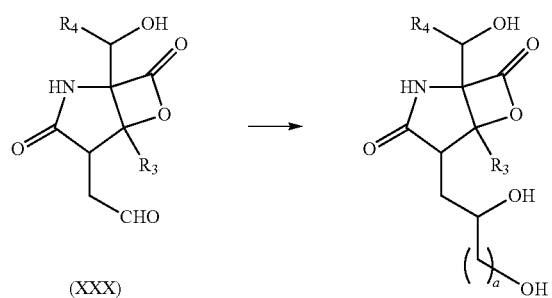

(XXX)

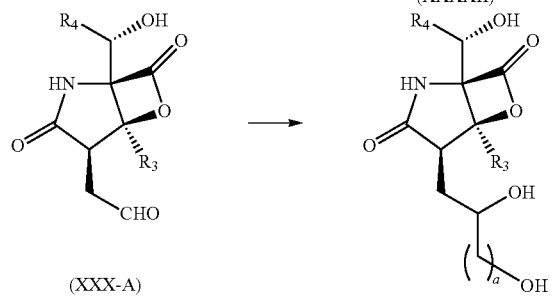

(XXX-A)

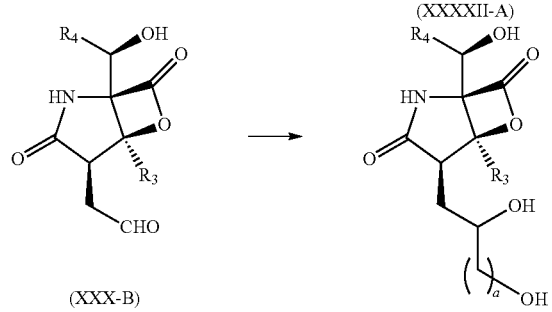

(XXX-B)

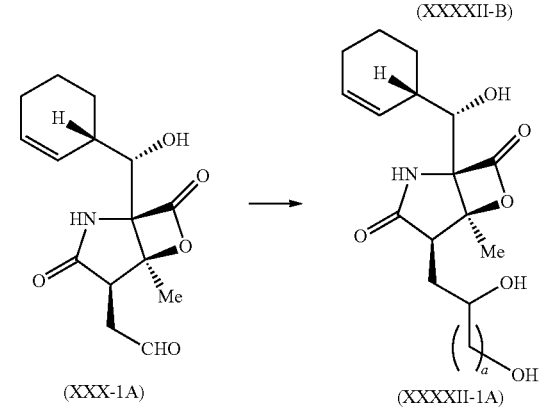

(XXX-1A)

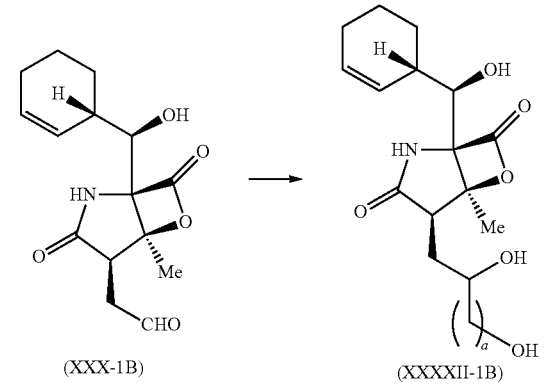

(XXX-1B)

(XXXXII)

(XXXXII-A)

(XXXXII-B)

(XXXXII-1A)

(XXXXII-1B)

When $R_8$ is —$(CH_2)_aOH$, a compound of formula (XXXIV) can be halogenated to form a compound of formula (XXXV), wherein X is a halogen (e.g., F, Cl, Br, and I), as shown in Scheme 7-11. In some embodiments, $R_3$ and $R_4$ of a compound of formula (XXXV) can be the same as described with respect to the compound of formula (XXVI). In an embodiment, a can be 1. In another embodiment, a can be 2. In still another embodiment, a can be 3. In yet still another embodiment, a can be 4. In an embodiment, a can be 5. In another embodiment, a can be 6. In still another embodiment, a can be 6. In yet still another embodiment, a can be $\geq 7$.

Scheme 7-11

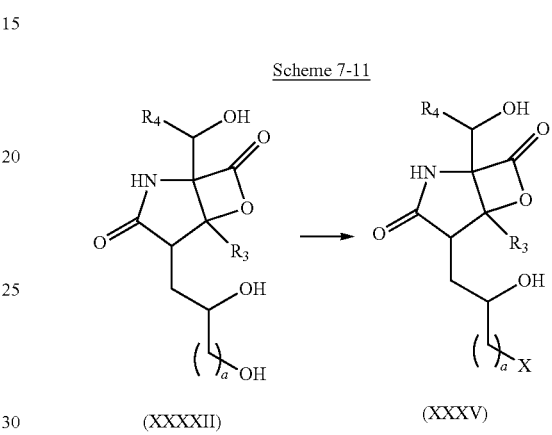

(XXXXII)     (XXXV)

Examples of the structures and stereochemistry of compounds of formulae (XXXXII) and (XXXV) are shown below:

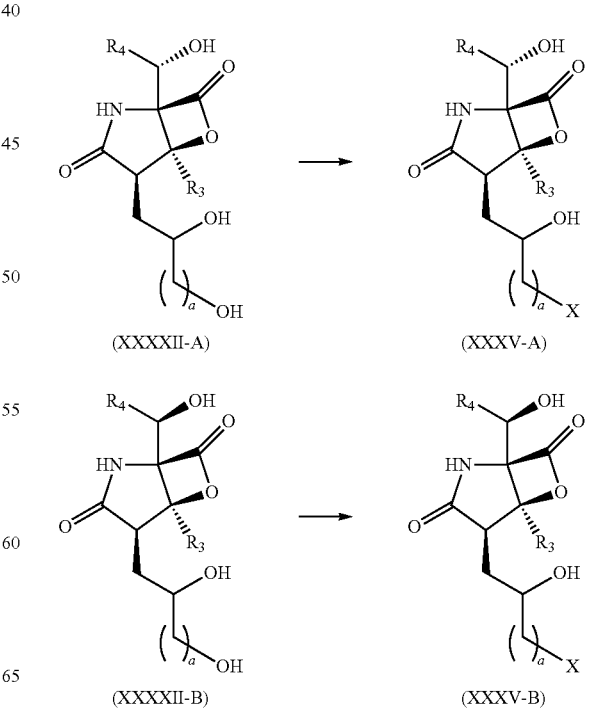

(XXXXII-A)     (XXXV-A)

(XXXXII-B)     (XXXV-B)

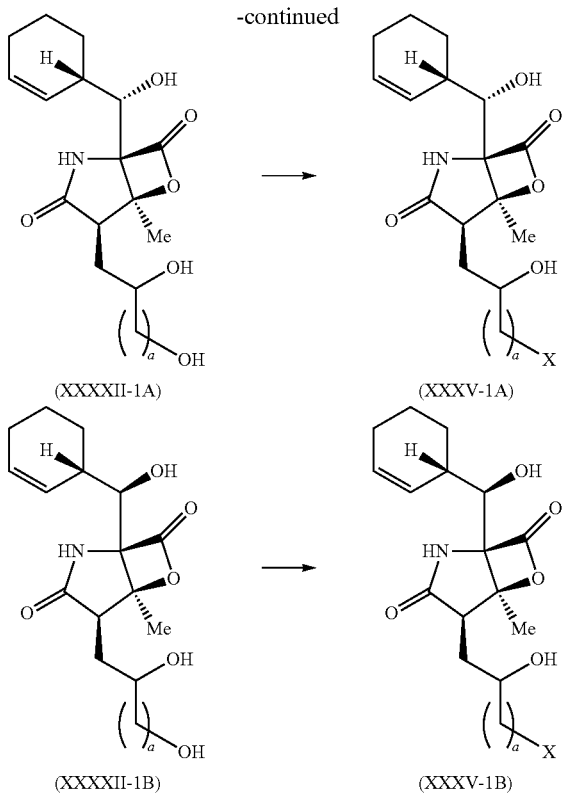

The stereochemistry of the secondary hydroxy group of the compound of formula (XVI-B) can be inverted (e.g., by a Mitsunobu transformation) to form a compound of formula (XVI-A).

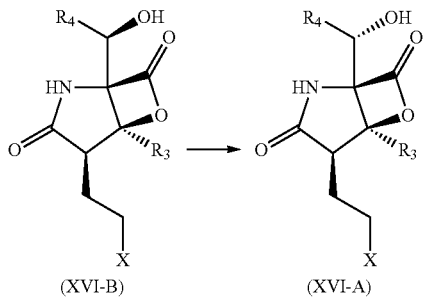

In one embodiment, Salinosporamide A can be synthesized from a compound with the structure and stereochemistry of formula (XVI-1B) as shown below:

Alternatively, the stereochemistry of the C-5 secondary hydroxy can be inverted via a multistep process, for example, by oxidizing the secondary hydroxy to a ketone and then reducing the ketone to a secondary hydroxy of opposite stereochemistry. In one method, the compound of formula (XVI-B) can be oxidized with a suitable oxidizing agent (e.g., Dess-Martin periodinane, TPAP/NMO, Swern oxidation reagent, PCC, or PDC) to form the compound of formula (XXII). In some embodiments of the compound of formula (XXII), $R_4$ cannot be substituted or unsubstituted cyclohexenyl, unsubstituted cyclohexa-1,3-dienyl, TMSO substituted cyclohexa-1,3-dienyl, unsubstituted phenyl, TMSO substituted phenyl, when $R_3$ is methyl and X is halogen. In an embodiment, if the compound of formula (XXII) has the structure and stereochemistry of the compound of formula (XXII-A), then $R_4$ cannot be substituted or unsubstituted cyclohexenyl, unsubstituted cyclohexa-1,3-dienyl, TMSO substituted cyclohexa-1,3-dienyl, unsubstituted phenyl, TMSO substituted phenyl, when $R_3$ is methyl and X is halogen. The compound of formula (XXII) can then be reduced to a compound of formula (XVI-A) using a suitable chemical reagent such as sodium borohydride. In some embodiments, the reduction can be accomplished via selective enzymatic transformation. In certain embodiments, the reducing enzyme is a ketoreductase such as KRED-EXP-C1A and/or KRED-EXP-B1Y.

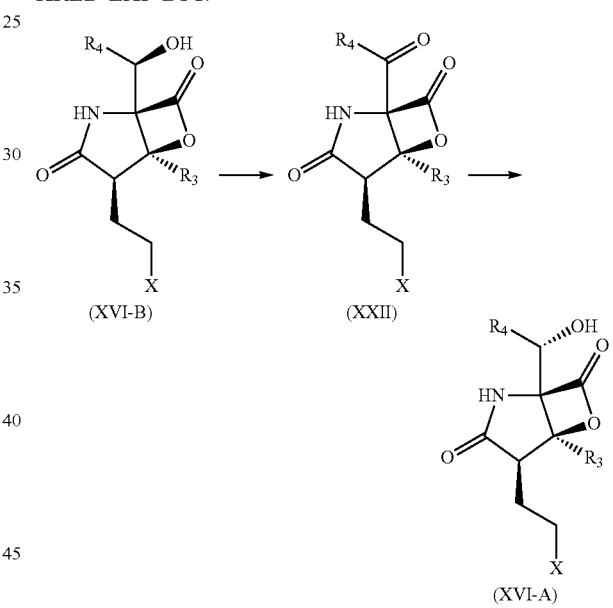

In another embodiment, Salinosporamide A can be synthesized from a compound with the structure and stereochemistry of formula (XVI-1B) as follows:

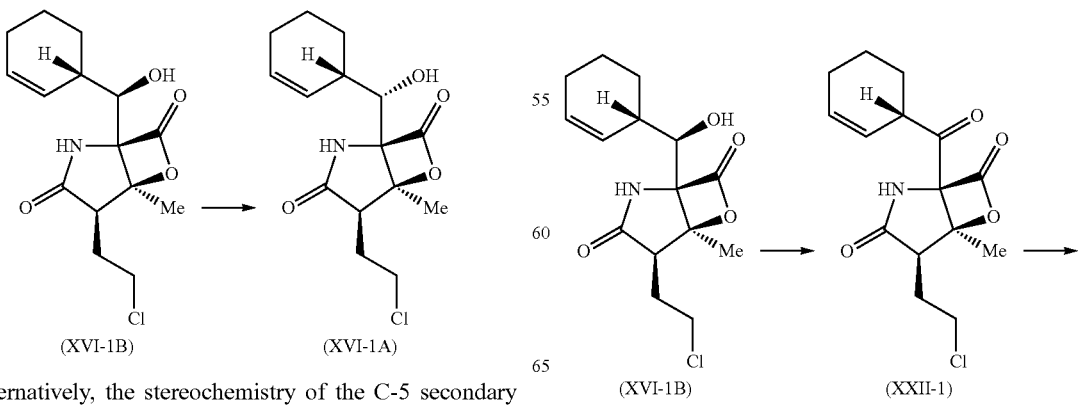

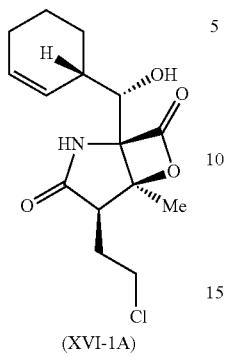

(XVI-1A)

Moreover, the stereochemistry of the C-5 secondary hydroxy can be inverted at any time after the addition of the $R_4$ group to the compound of formula (X). For example, the stereochemistry of the C-5 secondary hydroxy can be inverted in the compounds of formulae (X), (Xp), (XI), (XIp), (XII), (XIIp), (XIII), (XIV), (XV), (XXIII), (XXIV), (XXIVp), (XXV), (XXVp), (XXVI), (XXVIp), (XXII), (XXVIII), and (XXVIIIp) In an embodiment, the stereochemistry of the C-5 secondary hydroxy can be inverted in a one step process as described herein (e.g., by a Mitsunobu transformation). The inversion can also take place in multistep process. In an embodiment, the C-5 secondary hydroxy group can be oxidized using an appropriate oxidizing agent (e.g., Dess-Martin periodinane, TPAP/NMO, Swern oxidation reagent, PCC, or PDC) to a keto group and then reduced to a hydroxy group using a suitable reducing agent such as sodium borohydride. In another embodiment, the keto group can be reduced via selective enzymatic transformation. In certain embodiments, the reducing enzyme is a ketoreductase such as KRED-EXP-C1A and/or KRED-EXP-B1Y.

An alternative method for synthesizing Salinosporamide A and its analogs from the compound of formula (V) can proceed through a compound of formula (XVII). Scheme 8-1 shows a method of synthesizing a compound of formula (XVII) from a compound of formula (V). Scheme 8-2 shows a method of synthesizing a compound of formula (XVII) from a compound of formula (X). Schemes 9-1 and 9-2 show methods of synthesizing Salinosporamide A and its analogs from a compound of formula (XVII).

Scheme 8-1

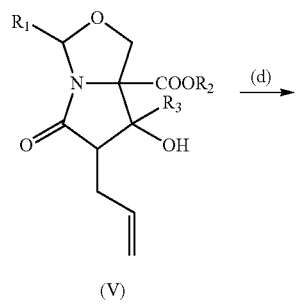

(V)

For some of the embodiments described herein, steps (d) and (e) of Scheme 8-1 can be the same as described above with respect to Scheme 6.

In step ($f_2$) of Scheme 8-1, $R_4$ can be added to a compound of formula (VII) using an organometallic moiety containing at least one $R_4$ to form a compound of formula (XVII), wherein $R_1$ can be hydrogen or unsubstituted or substituted $C_{1-6}$ alkyl; $R_2$ can be a hydrogen substituted or unsubstituted variants of the following: $C_{1-6}$ alkyl, aryl or arylalkyl; $R_3$ can be a substituted or unsubstituted variants of the following: $C_{1-6}$ alkyl, a $C_{3-6}$ cycloalkyl, a $C_{2-6}$ alkenyl, $C_{3-6}$ cycloalkenyl, aryl, or arylalkyl; $PG_1$ can be a protecting group moiety; and $R_4$ can be selected from the group consisting of substituted or unsubstituted variants of the following: $C_1$-$C_{12}$ alkyl, $C_2$-$C_{12}$ alkenyl, $C_2$-$C_{12}$ alkynyl, $C_3$-$C_{12}$ cycloalkyl, $C_3$-$C_{12}$ cycloalkenyl, $C_3$-$C_{12}$ cycloalkynyl, $C_3$-$C_{12}$ heterocyclyl, aryl, heteroaryl, arylalkyl, heteroarylalkyl, (cycloalkyl)alkyl, (heterocyclyl)alkyl, acyl, acylalkyl, alkyloxycarbonyloxy, carbonylacyl, aminocarbonyl, azido, azidoalkyl, aminoalkyl, salt of an aminoalkyl, carboxyalkyl, salt of carboxyalkyl, alkylaminoalkyl, salt of an alkylaminoalkyl, dialkylaminoalkyl, salt of a dialkylaminoalkyl, phenyl, alkylthioalkyl, arylthioalkyl, carboxy, cyano, alkanesulfonylalkyl, alkanesulfinylalkyl, alkoxysulfinylalkyl, thiocyanoalkyl, boronic acidalkyl, boronic esteralkyl, guanidinoalkyl, salt of a guanidinoalkyl, sulfoalkyl, salt of a sulfoalkyl, alkoxysulfonylalkyl, sulfooxyalkyl, salt of a sulfooxyalkyl, alkoxysulfonyloxyalkyl, phosphonooxyalkyl, salt of a phosphonooxyalkyl, (alkylphosphooxy)alkyl, phosphorylalkyl, salt of a phosphorylalkyl, (alkylphosphoryl)alkyl, pyridinylalkyl, salt of a pyridinylalkyl, salt of a heteroarylalkyl and halogenated alkyl including polyhalogenated alkyl. In some embodiments, $R_4$ can be selected from the group consisting of: substituted or unsubstituted variants of the following: $C_3$-$C_{12}$ heterocyclyl, aryl, heteroaryl, heteroarylalkyl, (cycloalkyl)alkyl, (heterocyclyl)alkyl, acyl, acylalkyl, alkyloxycarbonyloxy, carbonylacyl, aminocarbonyl, azido, azidoalkyl, aminoalkyl, salt of an aminoalkyl, carboxyalkyl, salt of a carboxyalkyl, alkylaminoalkyl, salt of an alkylaminoalkyl, dialkylaminoalkyl, salt of a dialkylaminoalkyl, phenyl, alkylthioalkyl, arylthioalkyl, carboxy, cyano, alkanesulfonylalkyl, alkanesulfinylalkyl, alkoxysulfinylalkyl, thiocyanoalkyl, boronic acidalkyl, boronic esteralkyl, guanidinoalkyl, salt of guanidinoalkyl, sulfoalkyl, salt of a sulfoalkyl, alkoxysulfonylalkyl, sulfooxyalkyl, salt of a sulfooxyalkyl, alkoxysulfonyloxyalkyl, phosphonooxyalkyl, salt of a phosphonooxyalkyl, (alkylphosphooxy)alkyl, phosphorylalkyl, salt of a phosphorylalkyl, (alkylphosphoryl)alkyl, pyridinylalkyl, salt of a pyridinylalkyl, salt of a heteroarylalkyl and halogenated alkyl including polyhalogenated alkyl. Suitable organometallic moieties are described herein.

Exemplary structures and stereochemistry of compounds of formulae (VII) and (XVII) are shown below:

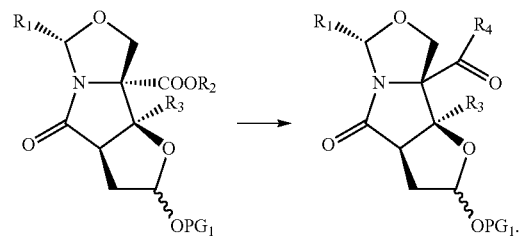

Examples of the structures of compounds of formulae (VII) and (XVII) are shown below:

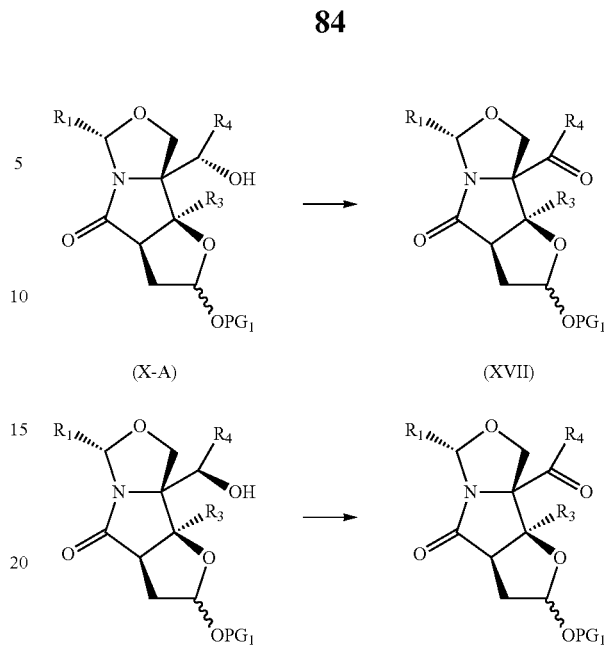

A compound of formula (XVII) can also be synthesized from a compound of formula (X) by oxidizing the secondary alcohol group of the compound of formula (X), according to Scheme 8-2. The compound of formula (X) can be synthesized as described in Scheme 6.

Scheme 8-2:

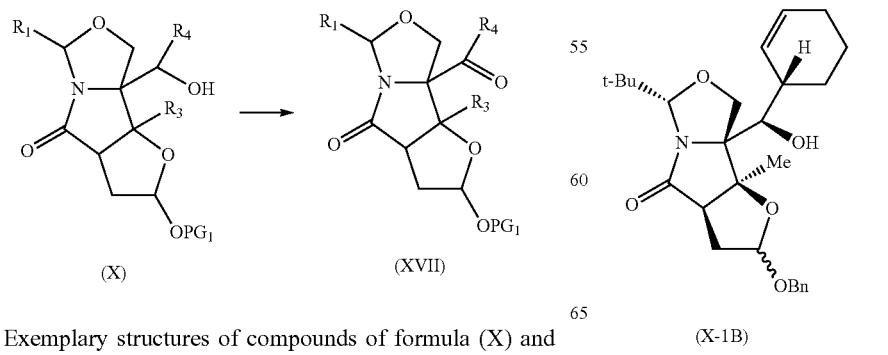

Exemplary structures of compounds of formula (X) and (XVII) are as follows:

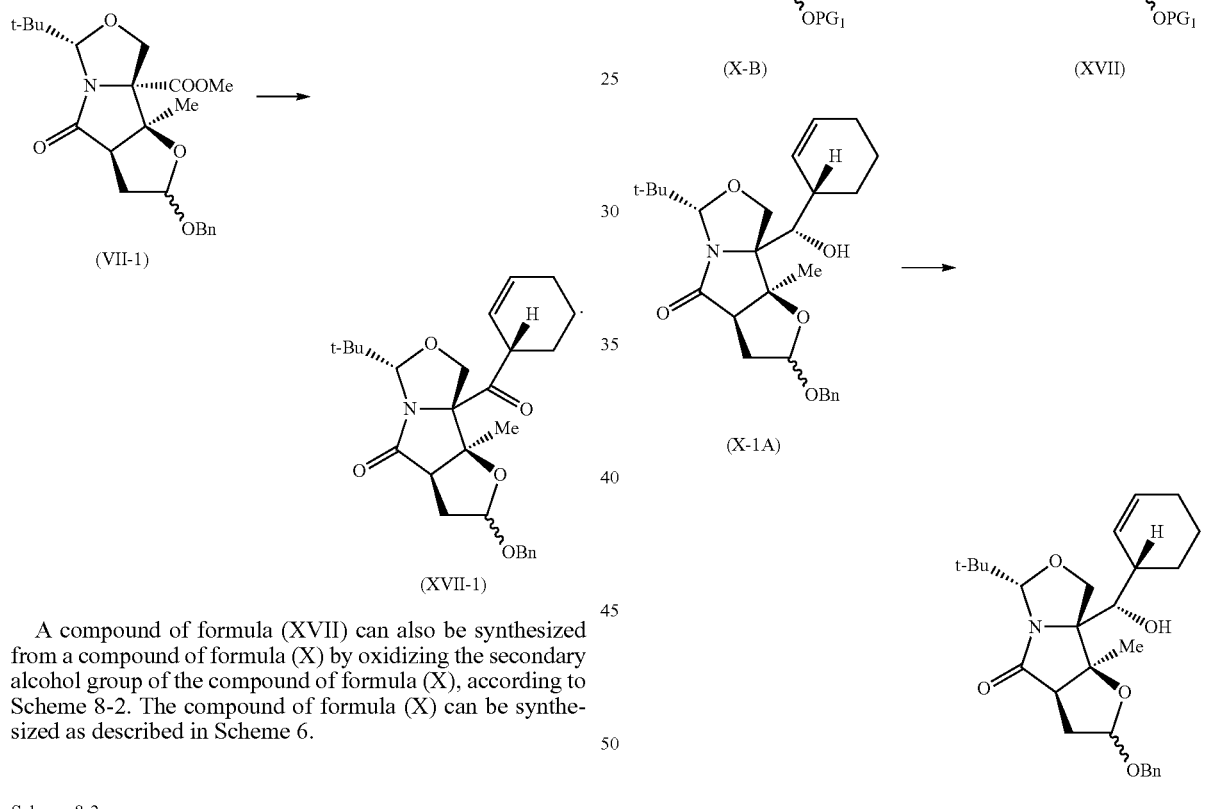

Examples of the structures of compounds of formula (VII) and (XXXVI) are shown below:

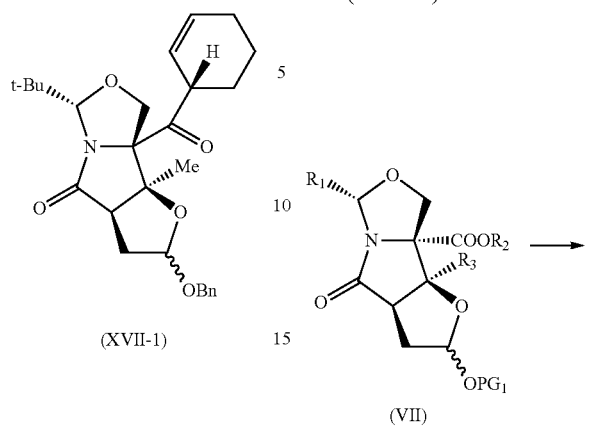

Additionally, a compound of formula (XVII) can be obtained via the synthetic Scheme 8-3.

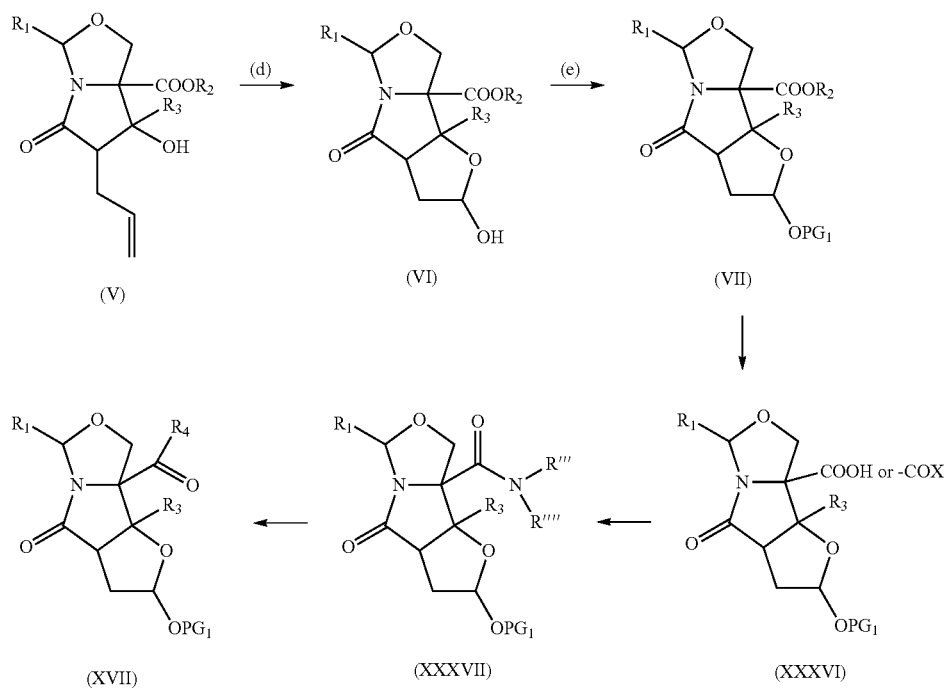

A compound of formula (VII) can be synthesized from a compound of formula (V) via steps (d) and (e) of Scheme 8-3 that are described above with respect to Scheme 6. The ester of the compound of formula (VII) can be transformed to a carboxylic acid using methods known to those skilled in the art (e.g., hydrolysis by LiOH, alkaline thioates such as LiSMe, NaSMe, LiSC$_2$H$_5$, etc.) which can be further transformed to acid halide using a suitable reagent (e.g. Oxalyl chloride, SOCl$_2$ etc.) to form a compound of formula (XXXVI). In an embodiment, $R_1$, $R_3$ and $PG_1$ of the compound of formula (XXXVI) can be the same as described with respect to the compound of formula (VII) and X is a halogen.

-continued

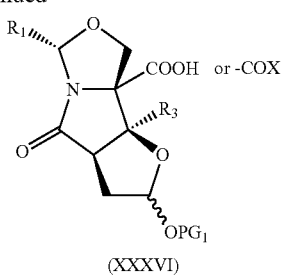

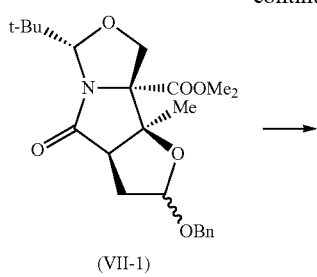

(VII-1)

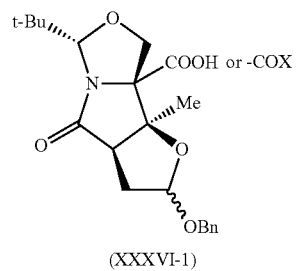

(XXXVI-1)

The carboxylic acid/acid halide of the compound of formula (XXXVI) can be reacted with an appropriate N,O-dimethylhydroxylamine hydrochloride [HCl.HNMe(OMe)] to form the corresponding Weinreb amide, wherein $R_1$, $R_3$ and $PG_1$ can be the same as described with respect to the compound of formula (VII) and R''' and R'''' can each independently be selected from the group consisting of alkyl (e.g. methyl), alkoxy (e.g. methoxy).

Exemplary structures of compounds of formula (XXXVI) and (XXXVII) are as follows:

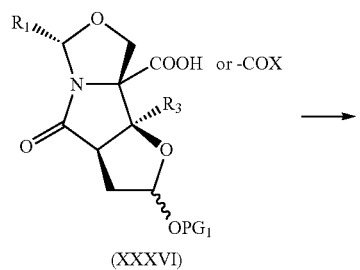

(XXXVI)

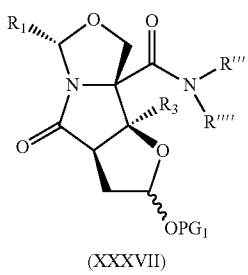

(XXXVII)

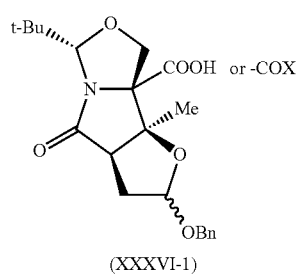

(XXXVI-1)

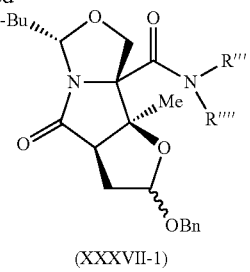

(XXXVII-1)

The Weinreb amide of the compound of formula (XXXVII) can be reacted with an appropriate organometallic moiety containing at least one $R_4$ to form a compound of formula (XVII). In an embodiment, $R_1$, $R_3$ and $PG_1$ can be the same as described with respect to the compound of formula (VII) and $R_4$ can be selected from the group consisting of substituted or unsubstituted variants of the following: $C_1$-$C_{12}$ alkyl, $C_2$-$C_{12}$ alkenyl, $C_2$-$C_{12}$ alkynyl, $C_3$-$C_{12}$ cycloalkyl, $C_3$-$C_{12}$ cycloalkenyl, $C_3$-$C_{12}$ cycloalkynyl, $C_3$-$C_{12}$ heterocyclyl, aryl, heteroaryl, arylalkyl, heteroarylalkyl, (cycloalkyl)alkyl, (heterocyclyl)alkyl, acyl, acylalkyl, alkyloxycarbonyloxy, carbonylacyl, aminocarbonyl, azido, azidoalkyl, aminoalkyl, salt of an aminoalkyl, carboxyalkyl, salt of carboxyalkyl, alkylaminoalkyl, salt of an alkylaminoalkyl, dialkylaminoalkyl, salt of a dialkylaminoalkyl, phenyl, alkylthioalkyl, arylthioalkyl, carboxy, cyano, alkanesulfonylalkyl, alkanesulfinylalkyl, alkoxysulfinylalkyl, thiocyanoalkyl, boronic acidalkyl, boronic esteralkyl, guanidinoalkyl, salt of a guanidinoalkyl, sulfoalkyl, salt of a sulfoalkyl, alkoxysulfonylalkyl, sulfooxyalkyl, salt of a sulfooxyalkyl, alkoxysulfonyloxyalkyl, phosphonooxyalkyl, salt of a phosphonooxyalkyl, (alkylphosphooxy)alkyl, phosphorylalkyl, salt of a phosphorylalkyl, (alkylphosphoryl)alkyl, pyridinylalkyl, salt of a pyridinylalkyl, salt of a heteroarylalkyl and halogenated alkyl including polyhalogenated alkyl. In some embodiments, $R_4$ can be selected from the group consisting of: substituted or unsubstituted variants of the following: $C_3$-$C_{12}$ heterocyclyl, aryl, heteroaryl, heteroarylalkyl, (cycloalkyl)alkyl, (heterocyclyl)alkyl, acyl, acylalkyl, alkyloxycarbonyloxy, carbonylacyl, aminocarbonyl, azido, azidoalkyl, aminoalkyl, salt of an aminoalkyl, carboxyalkyl, salt of a carboxyalkyl, alkylaminoalkyl, salt of an alkylaminoalkyl, dialkylaminoalkyl, salt of a dialkylaminoalkyl, phenyl, alkylthioalkyl, arylthioalkyl, carboxy, cyano, alkanesulfonylalkyl, alkanesulfinylalkyl, alkoxysulfinylalkyl, thiocyanoalkyl, boronic acidalkyl, boronic esteralkyl, guanidinoalkyl, salt of guanidinoalkyl, sulfoalkyl, salt of a sulfoalkyl, alkoxysulfonylalkyl, sulfooxyalkyl, salt of a sulfooxyalkyl, alkoxysulfonyloxyalkyl, phosphonooxyalkyl, salt of a phosphonooxyalkyl, (alkylphosphooxy)alkyl, phosphorylalkyl, salt of a phosphorylalkyl, (alkylphosphoryl)alkyl, pyridinylalkyl, salt of a pyridinylalkyl, salt of a heteroarylalkyl and halogenated alkyl including polyhalogenated alkyl. Suitable organometallic moieties are described herein.

In certain embodiments, compounds of formulae (XXXVII) and (XVII) can have the following structures and stereochemistry:

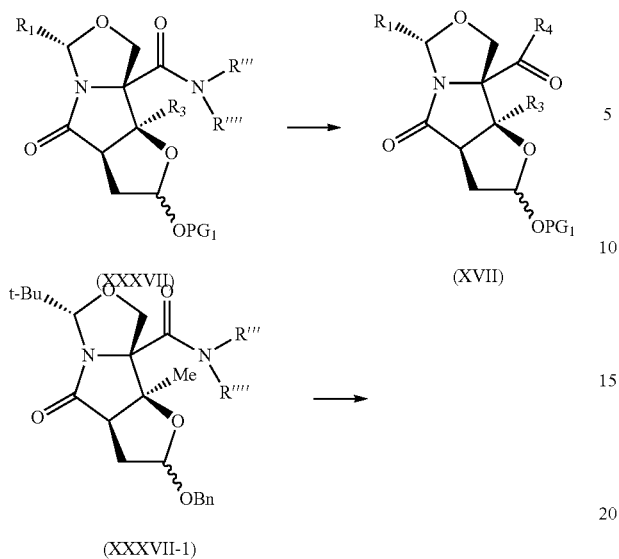
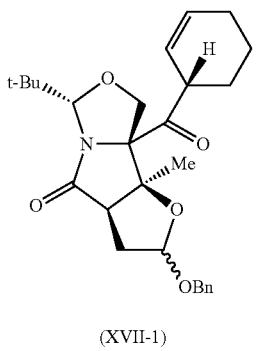
One method for obtaining Salinosporamide A and analogs thereof from a compound of formula (XVII) is shown in Scheme 9-1:
Scheme 9-1
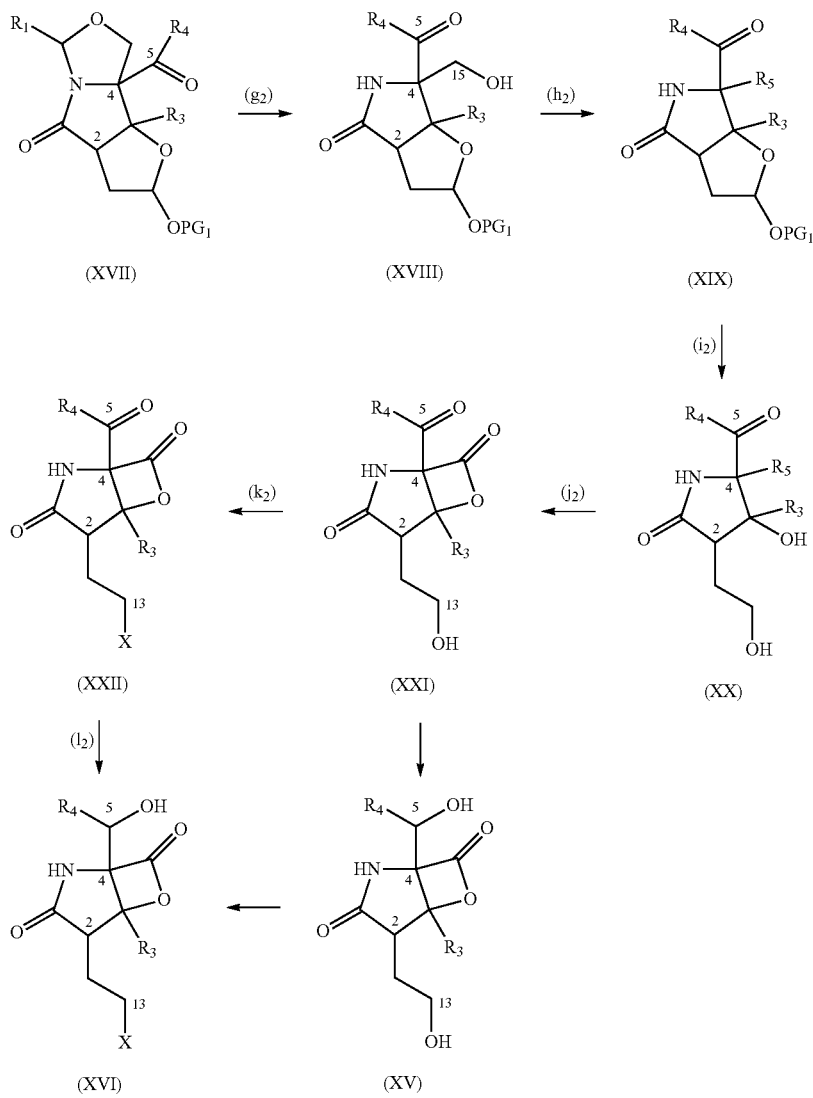

As shown in step (g$_2$) of Scheme 9-1, the aminal of a compound of formula (XVII) can be cleaved to form a compound of formula (XVIII) using an acid reagent (e.g., triflic acid or HCl). In some embodiments, R$_1$, R$_3$, R$_4$ and PG$_1$ of a compound of formula (XVIII) can be the same as described with respect to the compound of formula (XVII).

As an example, the compounds of formula (XVII) and (XVIII) may have the following structures and stereochemistry:

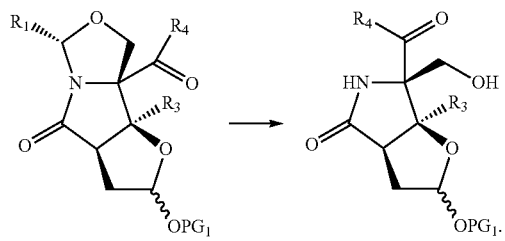

Exemplary structures of compounds of formula (XVII) and (XVIII) are shown below:

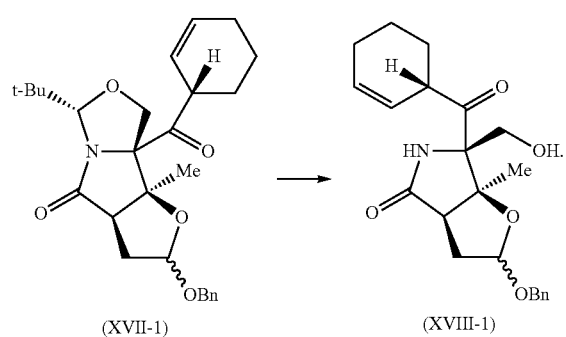

In step (h$_2$), the C-15 primary alcohol group of a compound of formula (XVIII) can be converted to R$_5$, which can be selected from the group consisting of —C(=O)OR$_6$, —C(=O)SR$_6$, —C(=O)NR$_6$R$_6$ and —C(=O)Z, wherein each R$_6$ can be independently selected from the group consisting of hydrogen, halogen, or substituted or unsubstituted variants of the following: C$_1$-C$_{24}$ alkyl, acyl, alkylacyl, arylacyl, aryl, arylalkyl, p-nitrophenyl, pentafluorophenyl, pentafluoroethyl, trifluoroethyl, trichloroethyl, and heteroaryl; and Z can be a halogen. The conversion of the primary alcohol group to R$_5$ may be achieved by converting the alcohol group to a carboxylic acid (R$_6$=H) using an appropriate oxidation conditions such as Jones oxidation. Alternatively the carboxylic acid group can be prepared from the primary alcohol group of the compound of formula (XVIII) through an aldehyde. The primary alcohol group of the compound of formula (XVIII) can first be converted to aldehyde using appropriate oxidant such as Dess-Martin periodinane, TPAP, Swern oxidation reagent, PCC, or PDC and then the resulting aldehyde can be oxidized further to carboxylic acid using appropriate oxidants such as a combination of sodium chlorite/sodium phosphate dibasic/2-methyl-2-butene. If desired the carboxylic acid can then be converted to an ester, a thioester, or an anhydride to form a compound of formula (XIX) using an appropriate alcohol, thiol (e.g. thiophenol, cystine), carboxylic acid (e.g. acetic acid, benzoic acid), or anhydride (e.g. acetic anhydride). In some embodiments, R$_3$ and R$_4$ of a compound of formula (XIX) can be the same as described with respect to the compound of formula (XVIII).

Compounds of formula (XVIII) and (XIX) may have the following structures and stereochemistry:

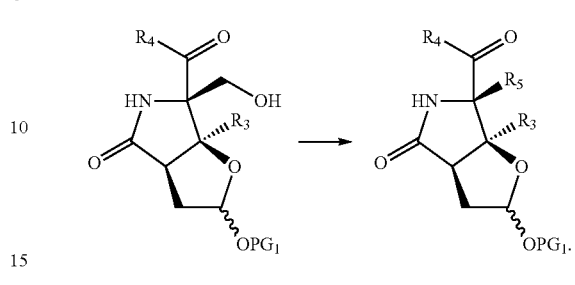

For example the compounds of formula (XVIII) and (XIX) may have the following structures:

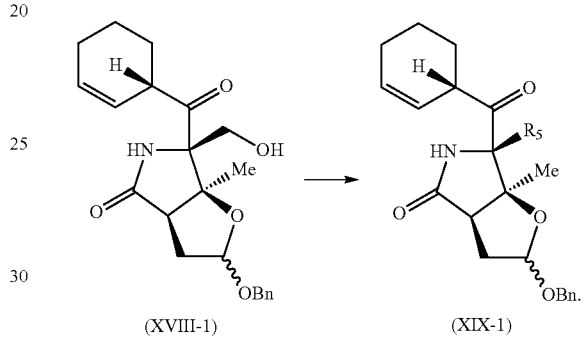

In step (i$_2$) of Scheme 9-1, a compound of formula (XX) can be synthesized by removing the protecting group moiety on the compound of formula (XIX) and reductively opening the resulting hemiacetal. As an example, the hemiacetal can be reductively opened using a reducing agent (e.g., sodium borohydride). In some embodiments, R$_3$, R$_4$, and R$_5$ of a compound of formula (XX) can be the same as described with respect to the compound of formula (XIX).

Exemplary structures and stereochemistry of compounds of formula (XIX) and (XX) can be as follows:

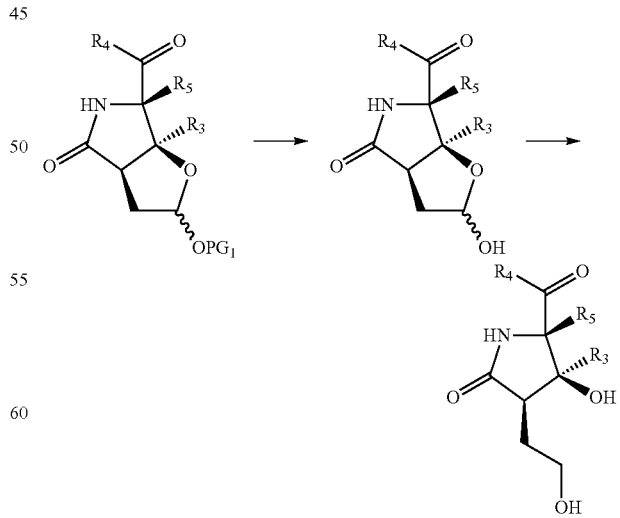

For example, compounds of formula (XIX) and (XX) can have the following structures:

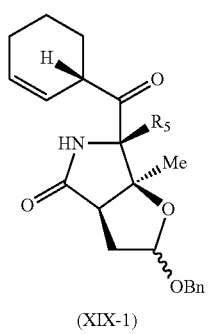

(XIX-1)

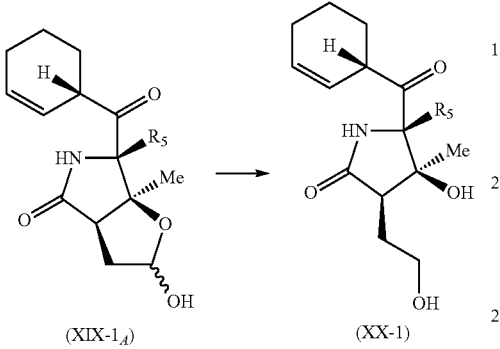

(XIX-1$_A$)  (XX-1)

Using an appropriate base (e.g. BOPCl/pyridine), a compound of formula (XXI) can be synthesized from a compound of formula (XX) via a lactonization reaction, as shown in step ($j_2$) of Scheme 9-1. In an embodiment, $R_3$, $R_4$, and $R_5$ of a compound of formula (XXI) can be the same as described with respect to the compound of formula (XX).

Examples of the structures and stereochemistry of compounds of formula (XX) and (XXI) are shown below:

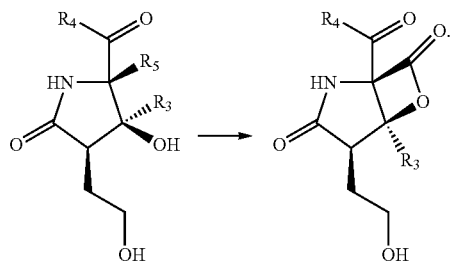

For example, compounds of formula (XX) and (XXI) can have the following structures:

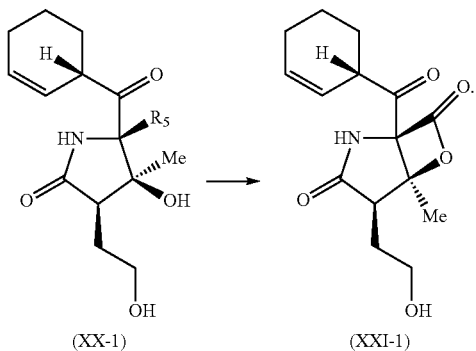

(XX-1)  (XXI-1)

As shown in step ($k_2$) of Scheme 9-1, a compound of formula (XXI) can further be transformed by substituting the primary hydroxy of the compound of formula (XXI) to form a compound of formula (XXII). In some embodiments, $R_3$ and $R_4$ of a compound of formula (XXII) can be the same as described with respect to the compound of formula (XXI), and X can be a halogen.

Exemplary structures and stereochemistry of compounds of formula (XXI) and (XXII) are shown below:

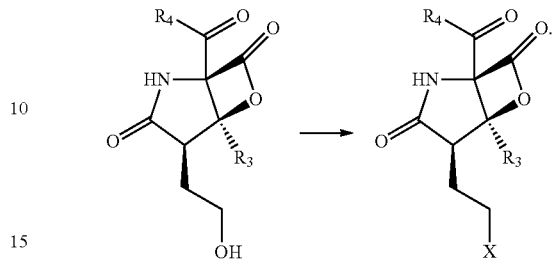

For example, compounds of formula (XXI) and (XXII) can have the following structures:

(XXI-1)  (XXII-1)

As shown step ($l_2$) of Scheme 9-1, the C-5 ketone group attached to the carbon adjacent to $R_4$ of a compound of formula (XXII) can be reduced to a secondary hydroxy group using a suitable reducing agent (e.g., sodium borohydride) or an enzyme to form a compound of formula (XVI). In one embodiment, the compound of formula (XXII) can be reduced to the compound of formula (XVI-A) and/or (XVI-B).

Examples of the structures and stereochemistry of compounds of formula (XXII) and (XVI) are shown below:

(XXII)

(XVI-A)  AND/OR  (XVI-B)

As another example, the compounds of formula (XXII) and (XVI) may have the following structures and stereochemistry:

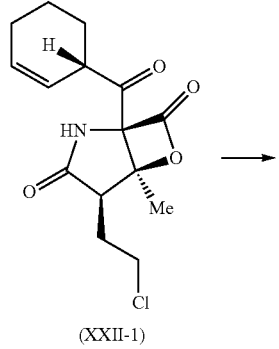

(XXII-1)

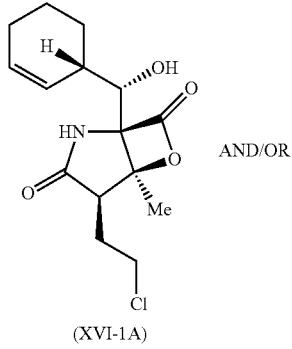 AND/OR 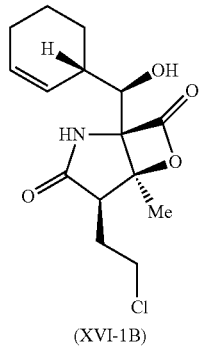

(XVI-1A)    (XVI-1B)

If desired, the stereochemistry of the secondary hydroxy of the compound of formula (XVI-B) can be inverted in a single step or a multistep process, as described herein.

A compound of formula (XXI) can also be used to synthesize a compound of formula (XV), as shown in Scheme 9-1. The C-5 keto group of the compound of formula (XXI) can be reduced using an appropriate reducing agent such as those described herein to form a compound of formula (XV). The C-13 primary hydroxy of the compound of formula (XV) can be used to obtain Salinosporamide A or analogs thereof following Schemes 7-6, 7-7, 7-8, 7-9, 7-10 and 7-11 described herein. The stereochemistry of the secondary hydroxy of the compound of formula (XVI-B) can be inverted in a single step or a multistep process, such as those described.

In certain embodiments, the compounds of formulae (XXI), (XV), and (XVI) can have the following structures and stereochemistry:

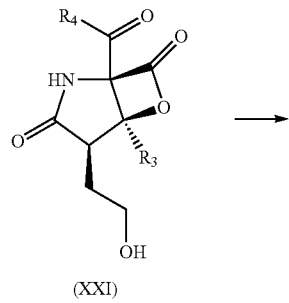

(XXI)

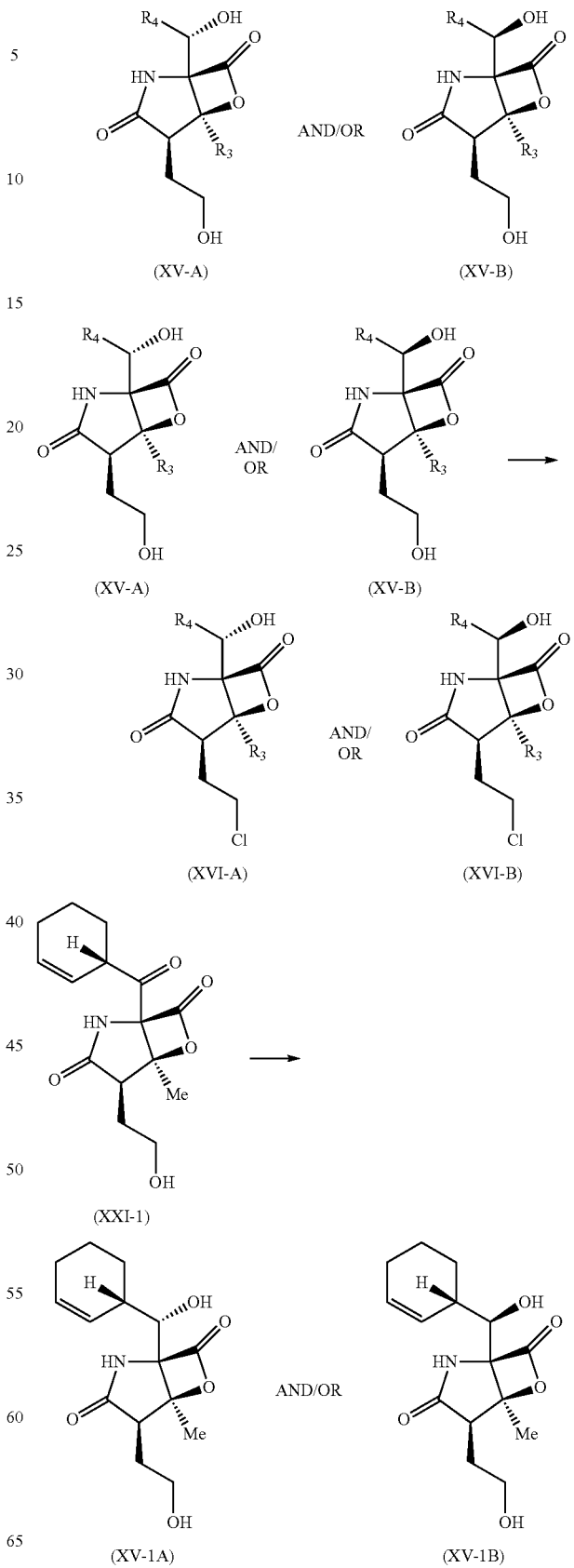

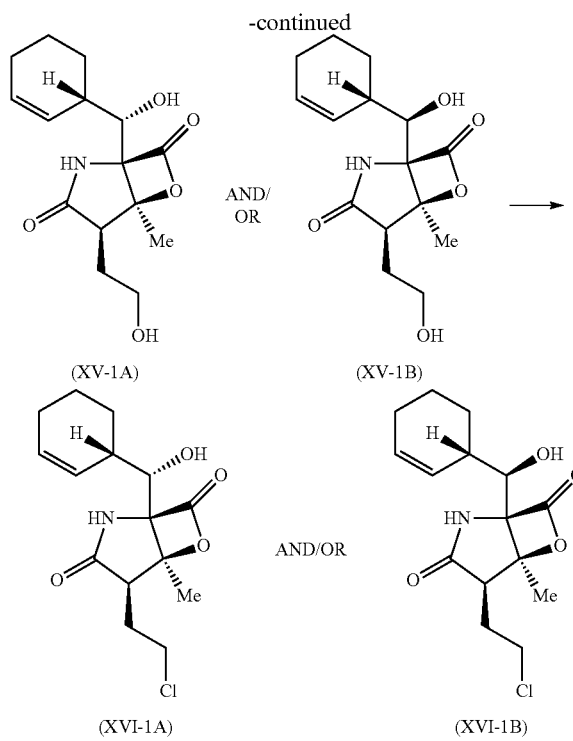

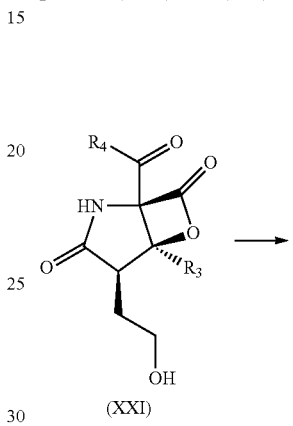

In some embodiments, compounds of formula (XV) can be synthesized via Scheme 9-2.

A compound of formula (XXI) can be synthesized from a compound of formula (XVII) via steps ($g_2$), ($h_2$), ($i_2$) and ($j_2$) of Scheme 9-2 that are described above with respect to Scheme 9-1. The C-5 keto group of the compound of formula (XXI) can be reduced to a secondary hydroxy group using a suitable reducing agent (e.g., sodium borohydride) or an enzyme to form a heterocyclic compound of formula (XV), for example, compounds (XV-A) and/or (XV-B), wherein $R_3$, $R_4$, and X can be the same as described with respect to the compound of formula (XXII).

Exemplary structures and stereochemistry of the compounds (XXI) and (XV) are shown below:

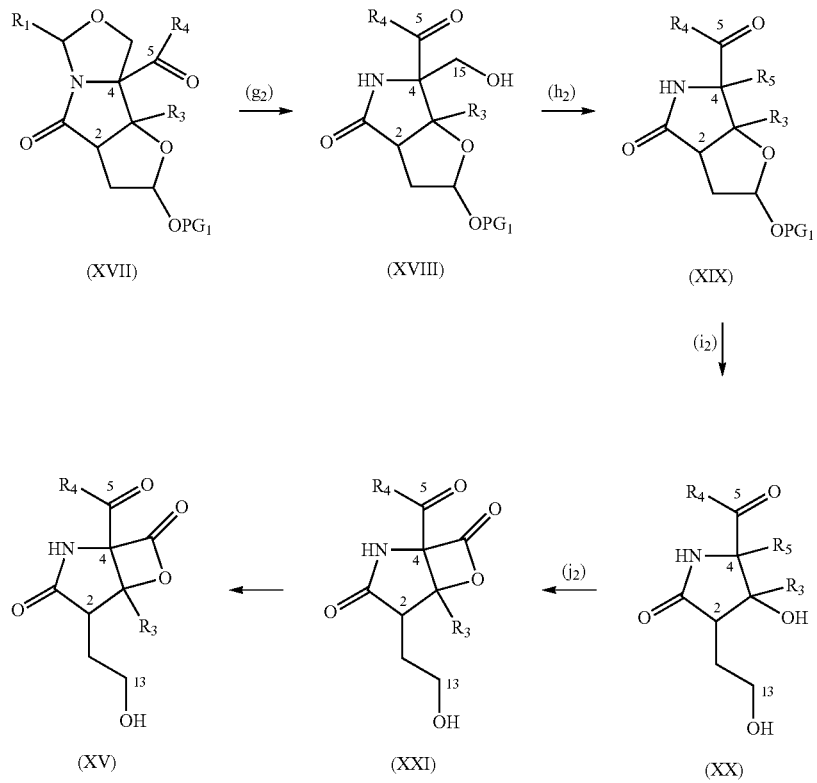

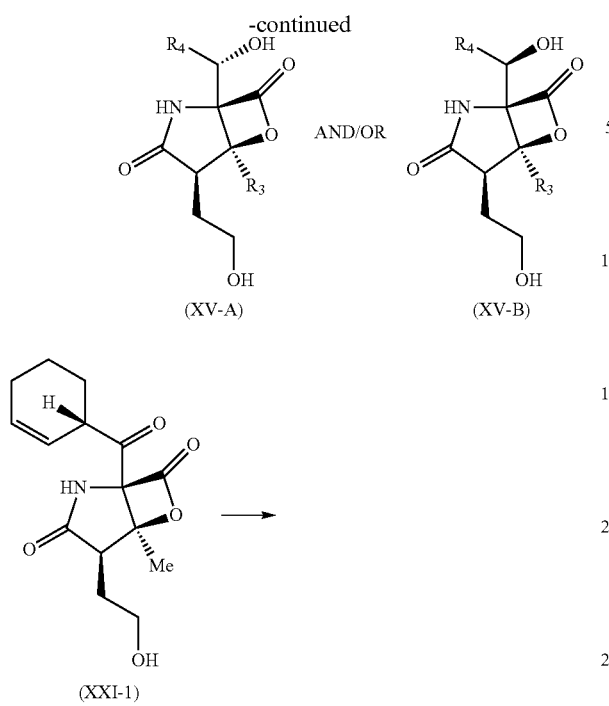
The compound of formula (XV) can then be used to obtain Salinosporamide A or analogs thereof following Schemes 7-6, 7-7, 7-8, 7-9, 7-10 and 7-11 described herein.
Another method for obtaining Salinosporamide A and analogs thereof from a compound of formula (XVII) is shown in Scheme 9-3.
Scheme 9-3
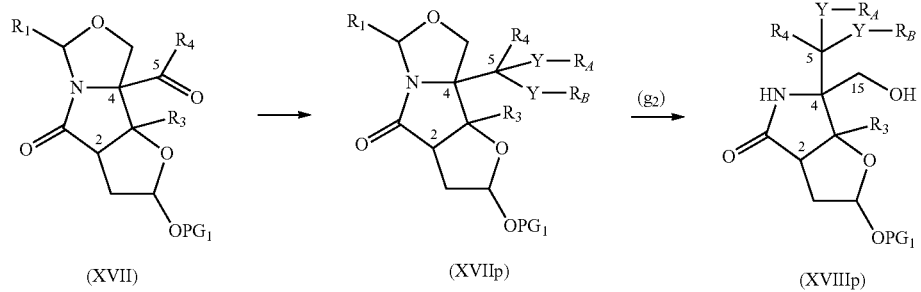
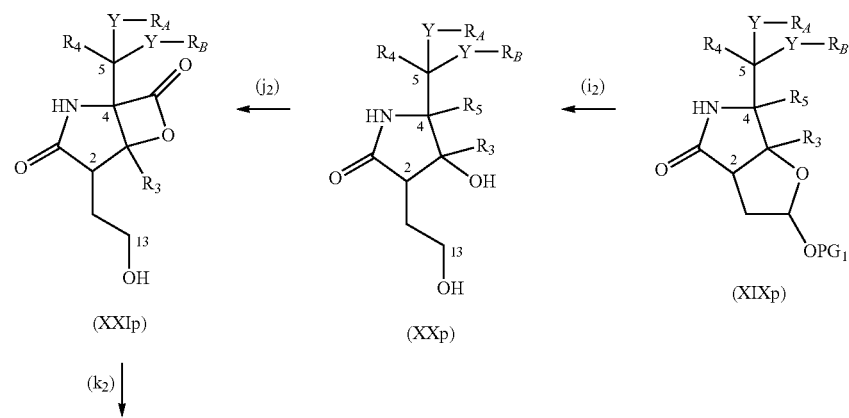

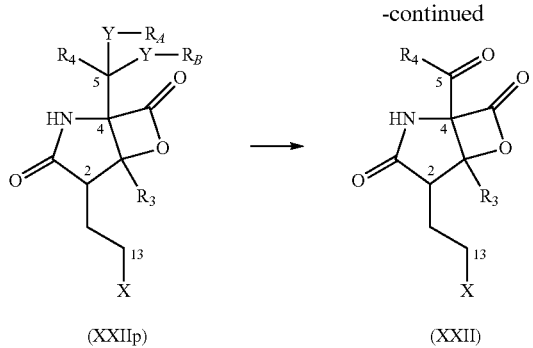
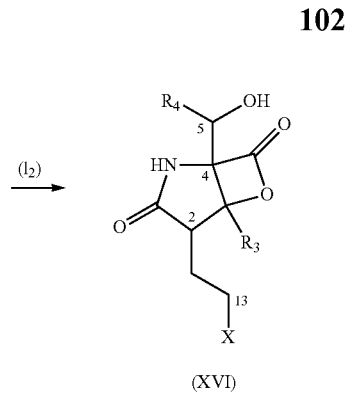

Preceding the cleavage of the aminal, the ketone group of a compound of formula (XVII) can be protected using a suitable protecting group moiety/moieties to form a compound of formula (XVIIp). In some embodiments, $R_1$, $R_3$, $R_4$, and $PG_1$ can be the same as described with respect to the compound of formula (XVII), each Y can be an oxygen or sulfur, and $R_A$ and $R_B$ can be each independently selected from the group consisting of $C_{1-6}$ alkyl, $C_{2-6}$ alkenyl and $C_{2-6}$ alkynyl, wherein $R_A$ and $R_B$ can be optionally bound together to form an optionally substituted 5, 6, 7, or 8 membered heterocyclyl.

As shown in Scheme 9-3, a compound of formula (XVIIp) can be transformed to a compound of formula (XXIIp) following the methods as described with respect to steps ($g_2$), ($h_2$), ($i_2$), ($j_2$), and ($k_2$) of Scheme 9-1. As shown in Scheme 9-3, the protecting group moiety/moieties, Y—$R_A$ and Y—$R_B$, can be removed from a compound of formula (XXIIp) using a suitable method to obtain a compound of formula (XXII). For each step, the substituents of the ketone protected compounds can be selected from the same groups as those described with respect to the corresponding unprotected compounds. For example, $R_3$, $R_4$, $PG_1$ and $R_5$ of a compound of formula (XIXp) can be selected from the same groups as a compound of formula (XIX). In some embodiments, the compounds of formula (XVIIp), (XVIIIp), (XIXp), (XXp), (XXIp) and (XXIIp), can have the same structures and/or stereochemistry as the corresponding non-protected compounds of Scheme 9-1 except that the keto carbonyl group is protected with a suitable protecting group(s).

Finally, the ketone group attached to the carbon adjacent to $R_4$ of a compound of formula (XXII) can be reduced to a hydroxy group using a suitable reducing agent (e.g., sodium borohydride) or an enzyme to form a compound of formula (XVI), including (XVI-A) and/or (XVI-B), wherein $R_3$, $R_4$, and X can be the same as described with respect to the compound of formula (XXII).

In an embodiment, compounds of formula (XV) can be synthesized from a compound of formula (XVII) is shown in Scheme 9-4.

Scheme 9-4

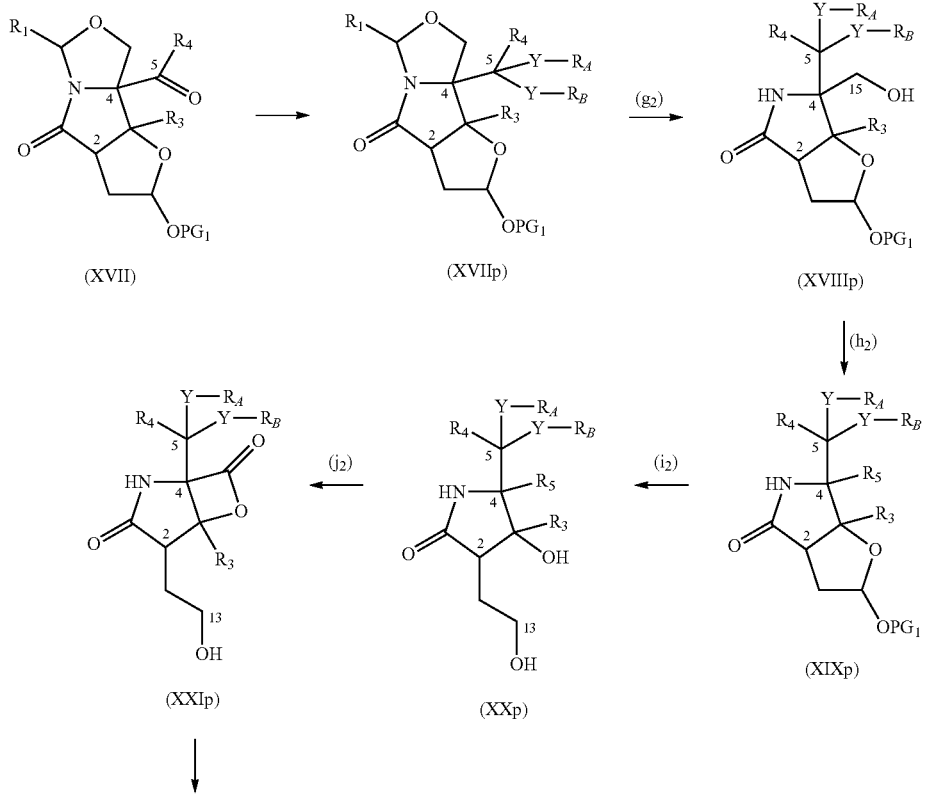

A compound of formula (XXIp) can be synthesized from a compound of formula (XVII) via steps (g₂), (h₂), (i₂) and (j₂) of Scheme 9-4 that are described above with respect to Scheme 9-1. The protecting group moiety/moieties, Y—$R_A$ and Y—$R_B$, can be removed from a compound of formula (XXIp) using a suitable method to obtain a compound of formula (XXI). In an embodiment, $R_3$ and $R_4$ can be the same as described with respect to the compound of formula (XVII). The C-5 keto group of the compound of formula (XXI) can be reduced to a secondary hydroxy group using a suitable reducing agent (e.g., sodium borohydride) or an enzyme to form a compound of formula (XV), including (XV-A) and/or (XV-B), wherein $R_3$ and $R_4$ can be the same as described with respect to the compound of formula (XXII). The compound of formula (XV) can then be used to obtain Salinosporamide A or analogs thereof following Schemes 7-6, 7-7, 7-8, 7-9, 7-10, and 7-11 described herein.

In certain embodiments, the compounds of formulae (XXIp), (XXI), and (XV) can have the following structures and stereochemistry:

Additional methods for synthesizing Salinosporamide A and analogs thereof are shown below in Schemes 9-5 and 9-6. The $PG_1$ of the compound of formula (XVII) or (XVIIp) can be removed and the resulting hemiacetal can be reductively opened as described above to form compounds of formulae (XXXVIII) and (XXXVIIIp), respectively. The aminal of the compounds of formulae (XXXVIII) and (XXXVIIIp) can be cleaved as described herein to form compounds of formula (XXXIX) and (XXXIXp), respectively. The C-15 primary alcohol group of the compounds of formula (XXXIX) and (XXXIXp) can be converted to $R_5$ using the methods described herein, wherein $R_5$ which can be selected from the group consisting of —C(=O)$OR_6$, —C(=O)$SR_6$, —C(=O)$NR_6R_6$ and —C(=O)Z, each $R_6$ can be independently selected from the group consisting of hydrogen, halogen, or substituted or unsubstituted variants of the following: each $R_6$ can be independently selected from the group consisting of hydrogen, halogen, or substituted or unsubstituted variants of the following: $C_1$-$C_{24}$ alkyl, acyl, alkylacyl, arylacyl, aryl, arylalkyl, p-nitrophenyl, pentafluorophenyl, pentafluoroethyl, trifluoroethyl, trichloroethyl, and heteroaryl, and Z can be a halogen. After the transformation of $R_5$, a compound of formula (XVI) can be formed as described above with respect to Schemes 9-1 and 9-3. If desired, the C-13 primary hydroxy group can be protected during the oxidation of C-15 hydroxy group of compounds of formulae (XXXIX) and (XXXIXp) and then removed if desired.

Scheme 9-5
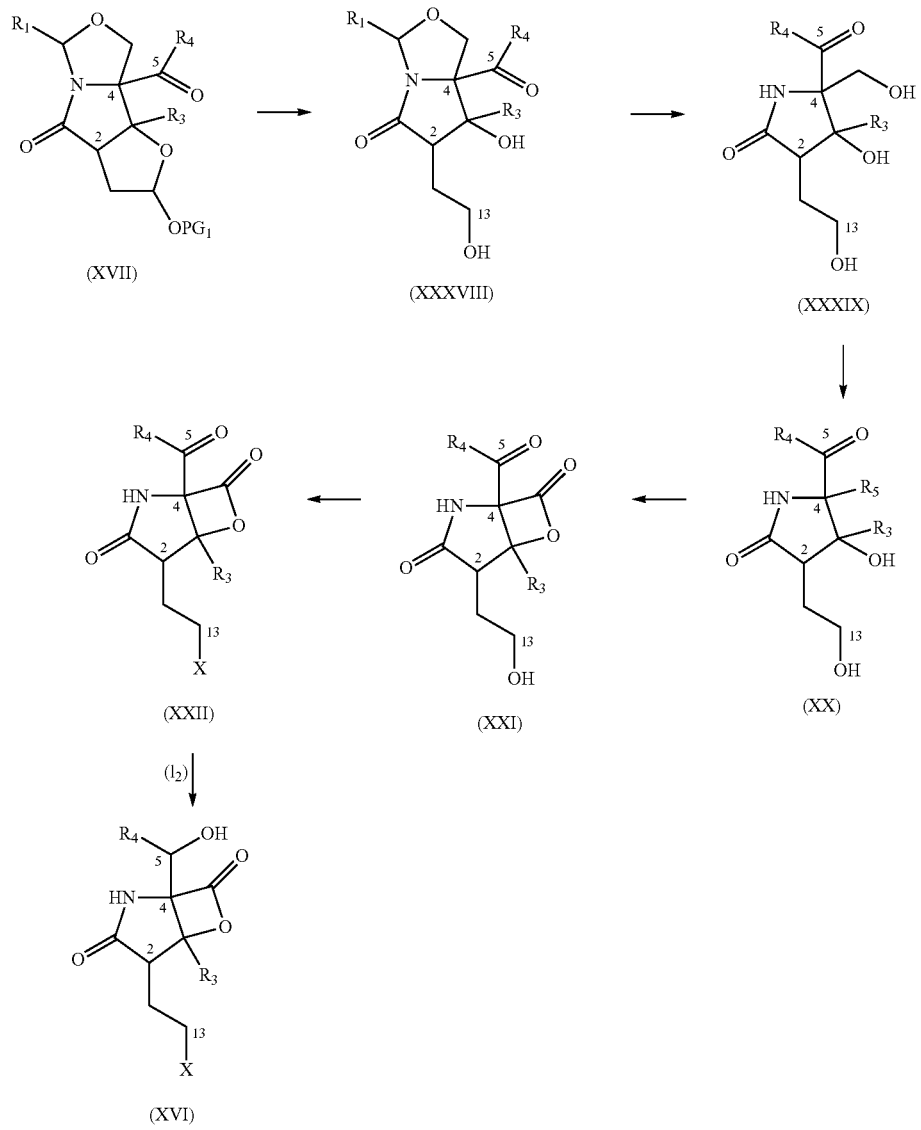
Scheme 9-6
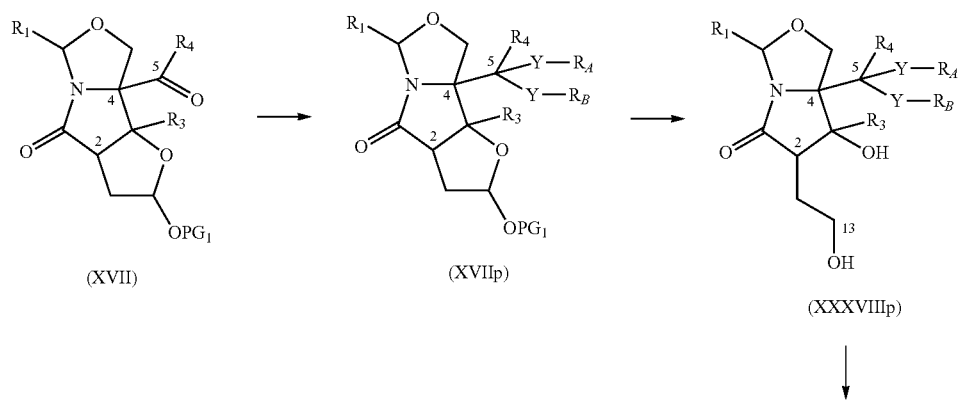

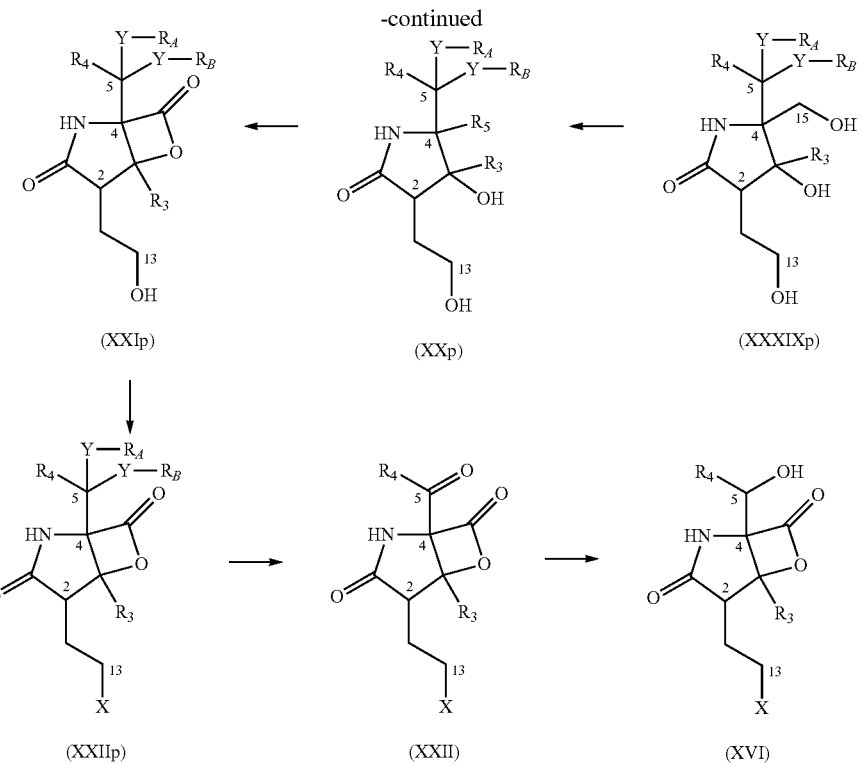

Additional methods of synthesizing compounds of formula (XV) are shown in Schemes 9-7 and 9-8. The $PG_1$ of the compound of formula (XVII) or (XVIIp) can be removed and the resulting hemiacetal can be reductively opened as described above to form compounds of formulae (XXXVIII) and (XXXVIIIp), respectively. The aminal of the compounds of formulae (XXXVIII) and (XXXVIIIp) can be cleaved as described herein to form compounds of formula (XXXIX) and (XXXIXp), respectively. The C-15 primary alcohol group of the compounds of formula (XXXIX) and (XXXIXp) can be converted to $R_5$ using the methods described herein, wherein $R_5$ which can be selected from the group consisting of —C(=O)$OR_6$, —C(=O)$SR_6$, —C(=O)$NR_6R_6$—C(=O)Z; each $R_6$ can be independently selected from the group consisting of hydrogen, halogen, or substituted or unsubstituted variants of the following: $C_1$-$C_{24}$ alkyl, acyl, alkylacyl, arylacyl, aryl, arylalkyl, p-nitrophenyl, pentafluorophenyl, pentafluoroethyl, trifluoroethyl, trichloroethyl, and heteroaryl, and Z can be a halogen. After the transformation of $R_5$, a compound of formula (XVI) can be formed as described above with respect to Schemes 9-1, 9-2, 9-3, and 9-4. A compound of formula (XV) obtained via the methods of Schemes 9-7 and/or 9-8 can then used to synthesize Salinosporamide A or analogs thereof following Schemes 7-6, 7-7, 7-8, 7-9, 7-10, and 7-11 as described herein.

Scheme 9-7

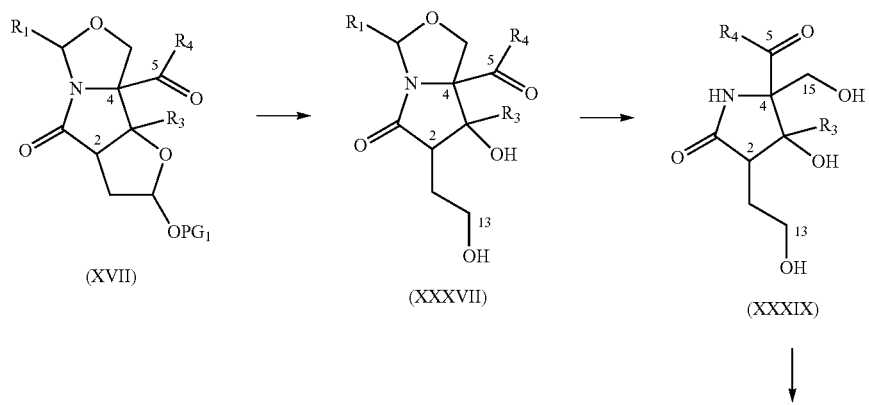

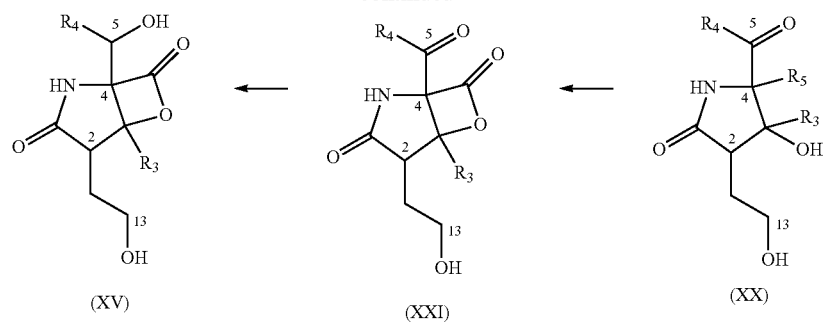
Scheme 9-8
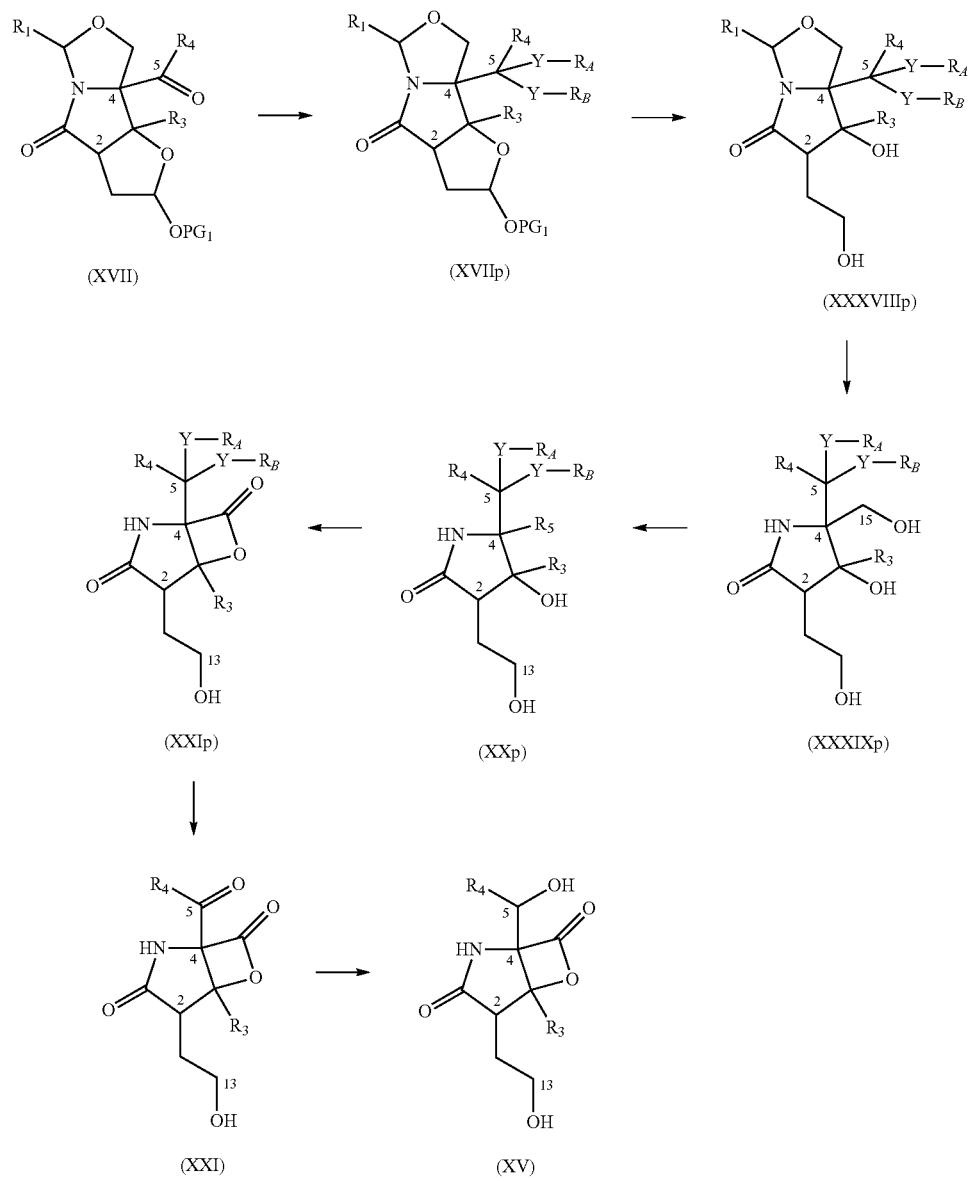

111

Examples of the structures and stereochemistry of the compounds of formulae (XXXVIII) and (XXXIX) (XXXIXp) are shown below:

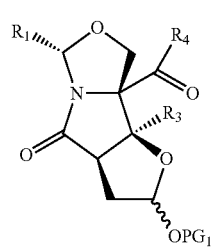

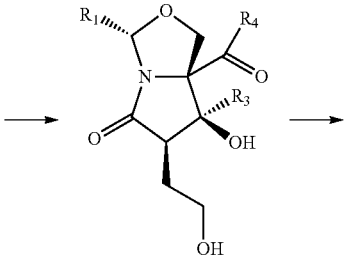

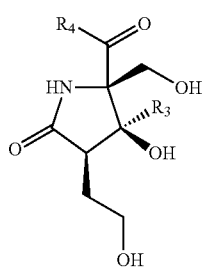

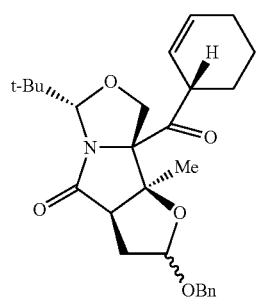

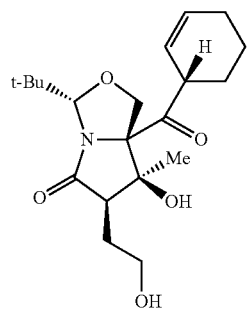 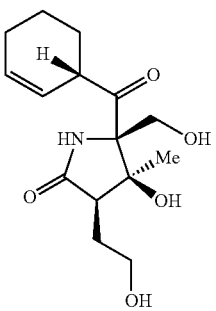

In some embodiments, the compounds of formula (XXX-VIIIp) and (XXXIXp) can have the same structures and/or stereochemistry as the corresponding non-protected compounds of formulae (XXXVIII) and (XXXIX) except that the keto carbonyl group is protected with a suitable protecting group(s).

In one embodiment, Salinosporamide A (compound XVI-1A) can be obtained from a compound of formula (XXII), wherein $R_4$ is 2-cyclohexenyl, $R_3$ is methyl and X is chlorine.

112

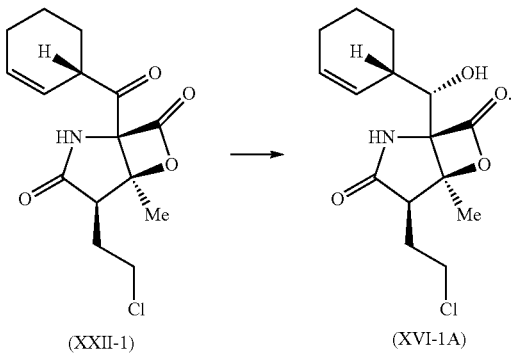

(XXII-1)   (XVI-1A)

In another embodiment, the compound of formula (XXII-1) can be converted to a compound of formula (XVI-B). If desired, the stereochemistry of the C-5 secondary hydroxy of the compound of formula (XVI-B) can be inverted in a single step or a multistep process to give a compound of formula (XVI-A), as previously described herein.

Salinosporamide A or analogs thereof can also be obtained from the compound of formula (XXI) and/or (XXIp). In an embodiment, the C-13 primary hydroxy of the compounds of formulae (XXI) and (XXIp) can be modified following the procedures shown in Schemes 7-6, 7-7, 7-8, 7-9, 7-10, and 7-11 described herein. Reduction of the C-5 keto group to a hydroxy group using an appropriate reducing agent (e.g., sodium borohydride) to produce Salinosporamide A or analogs thereof can take place at any step shown in Schemes 7-6, 7-7, 7-8, 7-9, 7-10, and 7-11.

The stereochemistry of the C-5 secondary hydroxy can be inverted at any time using one of the methods described herein or one known to those skilled in the art. For example, the stereochemistry of the C-5 secondary hydroxy can be inverted in the compound of formula (XV). In an embodiment, the stereochemistry of the C-5 secondary hydroxy can be inverted in a one step process as described herein (e.g., by a Mitsunobu transformation). The inversion can also take place in multistep process. In an embodiment, the C-5 secondary hydroxy group can be oxidized using an appropriate oxidizing agent (e.g., Dess-Martin periodinane, TPAP/NMO, Swern oxidation reagent, PCC, or PDC) to a keto group and then reduced to a hydroxy group using a suitable reducing agent such as sodium borohydride. In another embodiment, the keto group can be reduced via selective enzymatic transformation. In certain embodiments, the reducing enzyme is a ketoreductase such as KRED-EXP-C1A and/or KRED-EXP-B1Y.

In some embodiments, $R_4$ cannot be 2-cyclohexenyl in any of the compounds and methods described herein. In other embodiments, $R_4$ is 2-cyclohexenyl in any of the compounds and methods described herein. In some embodiments, $R_4$ cannot be isopropyl in any of the compounds and methods described herein. In other embodiments, $R_4$ is isopropyl in any of the compounds and methods described herein.

EXAMPLES

Commercially available compounds were obtained from Sigma-Aldrich and were used without purification unless stated. $^1$H NMR, $^{13}$C NMR, and $^1$H-$^1$H COSY spectra were recorded at 500 MHz on a Bruker spectrometer and chemical shifts are given in δ-values [ppm] referenced to the residual solvent peak chloroform ($CDCl_3$) at 7.24 and 77.00, respectively. The LC-MS data were obtained from an Agilent

Example 1

Synthesis of (I-1)

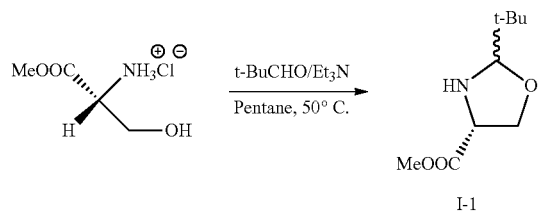

To a suspension of D-serine methylester hydrochloride (25 g, 160.67 mmol) in pentane (800 mL) at room temperature were added t-butyl aldehyde (20.73 g, 241 mmol) and Et$_3$N (17.85 g, 176.74 mmol). The reaction mixture was refluxed for 15 hrs at 50° C. using Dean-Stark apparatus. The resulting reaction mixture was cooled to room temperature, filtered through celite, and the celite cake was washed with pentane (2×40 mL). The combined filtrate was concentrated under reduced pressured and dried under high vacuum to afford product, I-1 (24.5 g, 131 mmol, 81.5% yield) as clear oil, which can be used without further purification. The compound I-1 was characterized by $^1$H-NMR (CDCl$_3$, 500 MHz). See FIG. 2.

Example 2

Synthesis of the Ester Precursor of Compound (II-1)

Method A

To a solution of t-butylacetoacetate (30 g, 0.19 mol) in dry THF (800 mL) at 0° C. was added t-BuOK (23.41 g, 95% w/w, 0.21 mol) and the solution was stirred for about 15 minutes. Allylbromide (18.39 g, 0.152 mol) was added and the solution was stirred at 0° C. for additional 15 min. The reaction mixture was then allowed to warm to room temperature and stirred for about 5 hours under an atmosphere of N$_2$. The above reaction mixture was then cooled to 0° C., quenched with H$_2$O (300 mL), and extracted with EtOAc (3×200 mL). The combined organic phase was dried over Na$_2$SO$_4$ and concentrated under reduced pressure. The crude product was purified by silica gel flash chromatography (5 cm ID×45 cm) using a solvent gradient of 100% hexanes (1.5 L) to 1.5% EtOAc/hexanes (3 L) to 2.5% EtOAc/hexanes (1 L) to 4% EtOAc/hexanes (700 mL) to afford pure product (14.5 g, 0.073 mol, 38.5% yield). Alternatively, The crude product was purified by fractional distillation (130° C. oil bath, 90-95° C. bp) under high vacuum (12 mm Hg) to afford product, the ester precursor of the compound (II-1) (66% yield).

Method B

To a solution of t-BuOK (50 g, 95% w/w, 0.42 mol) in dry THF (1.5 L) at 0° C. was added t-butylacetoacetate (65 g, 0.41 mol) and the solution was stirred for about 15 minutes under an atmosphere of N$_2$. Allylbromide (47 g, 0.39 mol) was added slowly and the solution was stirred at 0° C. for about 20 hours. The reaction mixture was allowed to warm to room temperature and stirred for additional 15 hours. The reaction mixture was then quenched with H$_2$O (1 L) at 0° C. and extracted with EtOAc (3×0.5 mL). The organic phase was dried over MgSO$_4$ and concentrated under reduced pressure. The crude product was purified by fractional distillation (130° C. oil bath, 90-95° C. bp) under high vacuum (12 mm Hg) to afford the product, the ester precursor of the compound (II-1) (54 g, 0.27 mol, 66% yield). $^1$H-NMR (CDCl$_3$, 500 MHz) (δ): 5.68 (m, 1H), 5.03 (br dd, J=1, 17 Hz, 1H), 4.97 (br dd, J=1, 10 Hz, 1H), 3.35 (t, J=7.5 1H), 2.48 (br t, J=7.0, 2H), 2.16 (s, 3H), 1.39 (s, 9H). See FIG. 3.

Example 3

Synthesis of the Protected Ester Precursor of Compound (II-1)

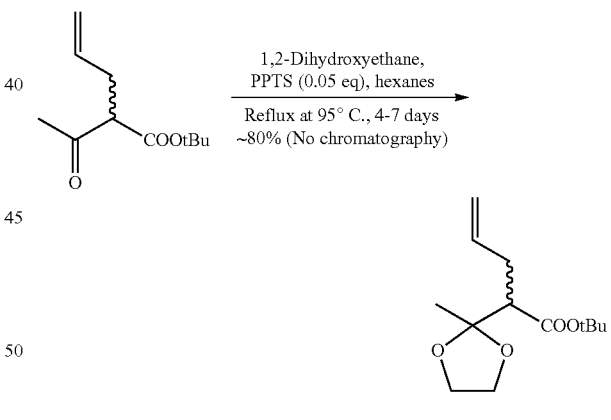

To a solution of the ester precursor (45 g, 0.23 mol) in hexanes (1.6 L) were added ethylene glycol (70.5 g, 1.15 mol) and PPTS (2.85 g, 0.011 mol). The reaction mixture was refluxed at 95° C. using Dean-Stark apparatus for 6 days (Note: 28.5 g, 0.46 mol of ethylene glycol was added to the reaction mixture every two days to maintain its concentration), then cooled to room temperature. The reaction mixture was then neutralized with 800 μL of Et$_3$N and diluted with H$_2$O (500 mL). The organic layer was separated, dried over Na$_2$SO$_4$ and concentrated under reduced pressure to afford product, the protected ester precursor of the compound (II-1) (44 g, 0.18 mmol, 80% yield), which can be used for the next step without purification. $^1$H-NMR (CDCl$_3$, 500 MHz) (δ): 5.72 (m, 1H), 5.06 (dd, J=1, 17 Hz, 1H), 4.97 (d, J=10 Hz, 1H), 3.94 (m, 4H), 2.60 (dd, J=3.6, 11.5 Hz, 1H), 2.43 (m, 1H), 2.29 (m, 1H), 1.42 (s, 9H), 1.38 (s, 3H). See FIG. 4.

Example 4

Synthesis of Compound (II-1)

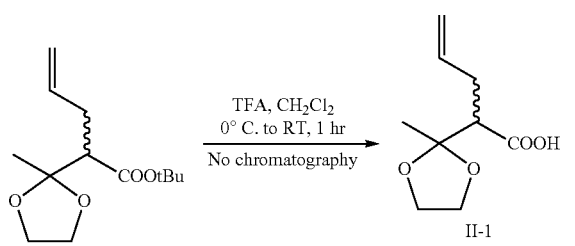

To a solution of the ester with protecting group moieties precursor (28 g, 0.115 mol) in $CH_2Cl_2$ (28 mL) at 0° C. was added trifluoroacetic acid (TFA neat, 56 mL, 0.727 mol) and the solution was stirred for about 5 min. The reaction mixture was then allowed to warm to room temperature and stirred for one hour. The reaction mixture was diluted with $CH_2Cl_2$ (400 mL) and extracted with ice cold water (3×300 mL). The organic layer was dried over $Na_2SO_4$, concentrated under reduced pressure and dried under high-vacuum for about one hour (to remove the residual TFA) to afford the product, compound II-1 (15.5 g, 0.083 mol, 72% yield) as light yellow oil, which can be used for the next step without purification. The compound II-1 was characterized by $^1$H-NMR ($CDCl_3$, 500 MHz): $^1$H-NMR ($CDCl_3$, 500 MHz) ($\delta$): 5.77 (m, 1H), 5.10 (br dd, J=1, 17 Hz, 1H), 5.02 (br d, J=10 Hz, 1H), 4.00 (m, 4H), 2.76 (dd, J=3.8, 11.0 Hz, 1H), 2.43 (m, 2H), 1.41 (s, 3H). See FIG. 5.

Example 5

Synthesis of Compound (III-1)

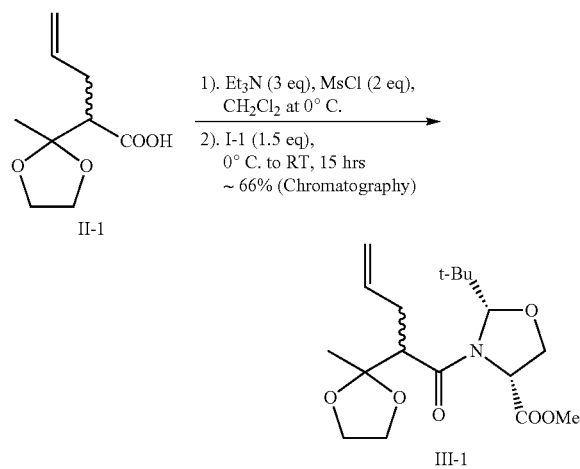

To a solution of compound II-1 (4.8 g, 25.81 mmol) in dry $CH_2Cl_2$ (200 mL) at 0° C. were added $Et_3N$ (7.82 g, 77.42 mmol) and methanesulfonyl chloride (5.89 g, 51.62 mmol) and the solution was stirred for about 10 min. Then compound I-1 (5.31 g, 28.4 mmol) was added, the reaction mixture was allowed to warm to room temperature slowly and stirred for about 15 hrs. Then the reaction mixture was quenched with $H_2O$ (200 mL) and extracted with $CH_2Cl_2$ (3×100 mL). The combined organic layer was dried over $Na_2SO_4$ and concentrated under reduced pressure to yield a mixture of two diastereomers (3:2). See FIG. 6b. The crude product was purified by silica flash chromatography (3 cm ID×30 cm) using a solvent gradient of 19:1 (500 mL) to 9:1 (500 mL) to 17:3 (500 mL) to 4:1 (1.5 L) to 3:1 (1 L) hexane/EtOAc to afford the product, compound III-1 (6 g, 16.9 mmol, 65.5% yield). The compound III-1 was characterized by $^1$H-NMR ($CDCl_3$, 500 MHz). See FIG. 6. MS (ESI) m/z 356 [M+H].

Example 6

Synthesis of Compound (IV-1)

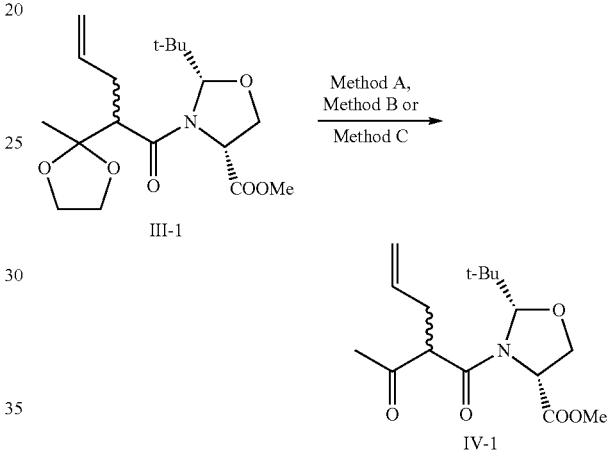

Method A: To a solution of compound III-1 (6 g, 16.9 mmol) in $CH_3CN$ (350 mL) were added sodium iodide (3.3 g, 21.97 mmol) and cerium (III) chloride heptahydrate (9.45 g, 25.35 mmol) and the reaction mixture was stirred at 60-65° C. for 4 hours (the reaction progress can be monitored by LC-MS). The above reaction mixture was then quenched with water (200 mL) and extracted with EtOAc (3×150 mL). The combined organic layer (cloudy) was concentrated under reduced pressure to remove all of the $CH_3CN$/EtOAc, leaving about 20 mL of $H_2O$ ($CH_3CN$ soluble part), which was further extracted with EtOAc (100 mL). The organic layer was dried over $Na_2SO_4$, and concentrated under reduced pressure to afford the product, IV-1 (4.4 g, 14.2 mmol, 83.5% yield) as a mixture of two diasteromers (3:2). See FIG. 7e. If desired, the product can be used for the next step without purification. The compound IV-1 was characterized by $^1$H-NMR ($CDCl_3$, 500 MHz) and NOESY ($CDCl_3$, 500 MHz). See FIGS. 7a and 7b. MS (ESI) m/z 312 [M+H]. A portion of the product was further purified by reverse phase HPLC using C-18 column (150 mm×21 mm), and an isocratic solvent system of 40% acetonitrile in $H_2O$ at a flowrate of 14.5 mL/min to afford individual diastereomers IV-1A and IV-1B as pure samples. The diastereomers IV-1A and IV-1B were characterized by $^1$H-NMR ($CDCl_3$, 500 MHz). See FIGS. 7c and 7d.

Compound IV-1A: $^1$H-NMR ($CDCl_3$, 500 MHz) ($\delta$): 5.73 (m, 1H), 5.34 (s, 1H), 5.12 (m, 1H), 5.05 (d, J=10.1 Hz, 1H), 4.64 (d, J=6.3 Hz, 1H), 4.53 (d, J=8.2 Hz, 1H), 3.90 (t, J=7.6 Hz, 1H), 3.80, (s, 3H), 3.67 (t, J=7.6 Hz, 1H), 2.60 (m, 2H), 2.27 (s, 3H), 0.91 (s, 9H); MS (ESI) m/z 312 [M+H]$^+$.

Compound IV-1B: $^1$H-NMR (CDCl$_3$, 500 MHz) (δ): 5.76 (m, 1H), 5.28 (s, 1H), 5.18 (br d, J=17.3 Hz 1H), 5.08 (d, J=10.1 Hz, 1H), 4.88 (m, 1H), 4.52 (d, J=8.2 Hz, 1H), 3.88 (m, 1H), 3.81, (m, 1H), 3.76 (s, 3H), 2.88 (m, 1H), 2.63 (m, 1H), 2.21 (s, 3H), 0.86 (s, 9H); MS (ESI) m/z 312 [M+H]$^+$.

Method B: A mixture of compound III-1 (175 mg, 0.493 mmol) and iodine (12.52 mg, 0.0493 mmol) in acetone (20 mL) was refluxed at 56° C. for one hour. The reaction mixture was then cooled to RT, the acetone was removed under reduced pressure, and the crude reaction product was dissolved in CH$_2$Cl$_2$ (20 mL). The CH$_2$Cl$_2$ solution was washed successively with 5% aqueous sodium thiosulfate (10 mL), H$_2$O (10 mL) and brine (10 mL). The resulting organic phase was dried over Na$_2$SO$_4$, concentrated under reduced pressure and purified by silica gel plug column (2.5 cm ID×6 cm) using a solvent gradient of 19:1 (50 mL) to 9:1 (100 mL) to 4:1 (100 mL) to 3:1 (100 mL) to 7:3 (100 mL) hexanes/EtOAc to afford the product, compound IV-1 (97 mg, 0.312 mmol, 63.3% yield).

Method C: A mixture of compound III-1 (500 mg, 1.40 mmol) and LiBF$_4$ (200 mg, 2.1 mmol) in CH$_3$CN (6 mL, wet with 2% H$_2$O) was stirred at 70° C. for 1.5 to 2 hrs (the reaction progress can be monitored by LC-MS). The above reaction mixture was then quickly cooled to 0° C., filtered through a short silica plug and concentrated under reduced pressure. The product was purified by silica gel column chromatography (1.25 cm ID×5 cm) using a solvent gradient of 19:1 (50 mL) to 9:1 (50 mL) to 4:1 (50 mL) hexanes/EtOAc to afford the purified product, compound IV-1 (260 mg, 0.84 mmol, 60% yield).

Example 7

Synthesis of Compound (V-1A)

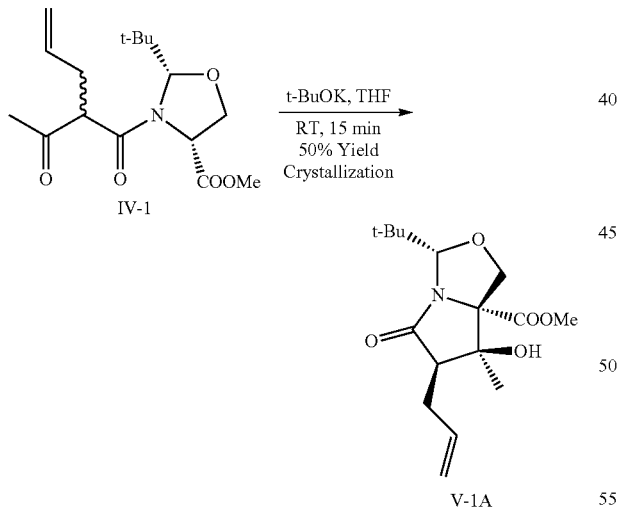

To a solution of compound IV-1 (26 g, 83.6 mmol) in dry THF (2.7 L) at RT was added t-BuOK (4.68 g, 41.8 mmol). The reaction mixture was stirred at RT for 15 min under an atmosphere of N$_2$ and then quenched with H$_2$O (900 mL) and extracted with EtOAc (3×400 mL). The combined organic phase was washed with saturated brine solution, dried over Na$_2$SO$_4$ and concentrated under reduced pressure. The reaction mixture was dissolved in 1:1 ether:hexanes (75 mL each) and transferred to a crystallization dish, where it was allowed to stand and crystallize. After an hour, the crystals (1$^{st}$ crop) were separated by decanting the mother liquor. The crystals were washed with ether (2×10 mL) and hexanes (2×10 mL). The combined mother liquor and washes was concentrated under reduced pressure and redissolved in 1:1 ether:hexanes (50 mL each) and the crystallization process was repeated the crystallization process as described above. The crystals (2$^{nd}$ crop) were separated by decanting the mother liquor. The crystals were washed with ether (2×10 mL) and hexanes (2×10 mL). The two crops of crystals were combined to obtain compound V-1A (13.5 g, 43.4 mmol, 51.9% yield by crystallization). The mother liquor was chromatographed on a silica gel flash column (30×4 cm) using solvent gradient of 19:1 (500 mL) to 9:1 (1 L) to 17:3 (500 mL) EtOAc/hexanes to yield the compound XXIX-1 (2.47 g), compound V-1A (3.05 g), compound V-1B (250 mg as a mixture) and compound V-1C (1.81 g). The two crops of crystals were combined to obtain a total yield of 63.6% of the compound V-1A. Compound V-1A was obtained as a colorless crystalline material. The structures of compounds V-1B, V-1C, and XXIX-1 are shown below.

Compound V-1A: $^1$H-NMR (CDCl$_3$, 500 MHz) (δ): 5.96 (m, 1H), 5.15 (br dd, J=1.5, 17.2 Hz, 1H), 5.05 (d, J=10.1 Hz, 1H), 4.93 (s, 1H), 4.50 (d, J=8.9 Hz, 1H), 4.26 (d, J=8.9 Hz, 1H), 3.77 (s, 3H), 3.10 (t, J=6.7 Hz, 1H), 2.56 (m, 1H), 2.31 (m, 1H), 1.96 (s, 1H), 1.30 (s, 3H), 0.87 (s, 9H). $^{13}$C-NMR (CDCl$_3$, 125 MHz) (δ): 177.9, 171.8, 136.7, 116.6, 96.7, 80.4, 79.2, 68.0, 53.3, 52.6, 36.5, 27.9, 25.0 (3×CH$_3$), 23.0. M.P. 113-114° C. (crystals obtained from 1:1; diethyl ether:hexanes). [α]$^{22}_D$ 8.4 (c 0.96, CH$_3$CN). MS (ESI) m/z 312 (M+H). See FIG. 8.

The compound V-1A was also characterized by $^{13}$C-NMR (CDCl$_3$, 125 MHz) and $^1$H-$^1$H COSY NMR (CDCl$_3$, 500 MHz). See FIGS. 9 and 10. The structure of compound V-1A was confirmed by x-ray crystallography, as shown in FIG. 11.

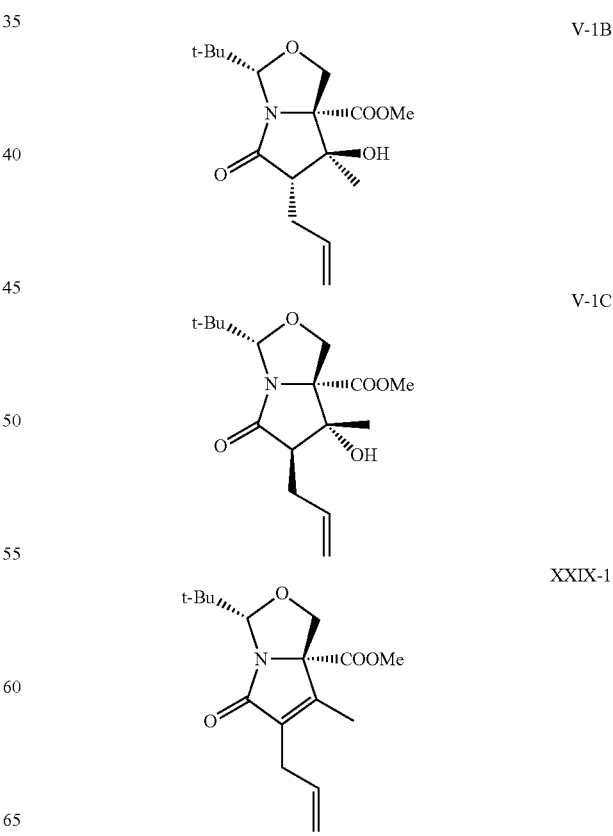

Compound V-1B: Compound V-1B was purified by reversed phase HPLC using the solvent gradient of 30% to 70% $CH_3CN/H_2O$ over 30 min, at a flow rate of 14.5 mL/min to yield pure compound. $^1$H-NMR ($CDCl_3$, 500 MHz) (δ): 5.88 (m, 1H), 5.09 (br dd, J=1.5, 17 Hz, 2H), 4.9 (s, 1H), 4.52 (d, J=9 Hz, 1H), 4.2 (d, J=9 Hz, 1H), 3.77 (s, 3H), 2.68 (m, 1H), 2.51 (t, J=7 Hz, 1H), 2.45 (m, 1H), 1.29 (s, 3H), 0.89 (s, 9H). See FIG. 25. MS (ESI) m/z 312 [M+H]$^+$. The structure was confirmed by x-ray crystallography, FIG. 26.

Compound V-1C: $^1$H-NMR ($CDCl_3$, 500 MHz) (δ): 5.93 (m, 1H), 5.16 (br dd, J=1, 17 Hz, 1H), 5.06 (br d, J=10 Hz, 1H), 4.88 (s, 1H), 4.58 (d, J=9.5 Hz, 1H), 3.96 (d, J=9.5 Hz, 1H), 3.79 (s, 3H), 3.43 (dd, J=6.3, 8.5 Hz, 1H), 2.53 (m, 1H), 2.17 (m, 1H), 1.27 (s, 3H), 0.86 (s, 9H). See FIG. 27. $^{13}$C-NMR ($CDCl_3$, 125 MHz) (δ): 175.8, 171.5, 135.8, 116.9, 96.2, 80.9, 78.3, 68.8, 53.3, 52.6, 36.5, 28.8, 25.0, 20.2. See FIG. 28. MS (ESI) m/z 312 [M+H]$^+$. The relative stereochemistry was determined by NOESY, FIG. 29.

Compound of XXIX-1: $^1$H-NMR ($CDCl_3$, 500 MHz) (δ): 5.81 (m, 1H), 5.04 (br dd, J=1.5, 7.5 Hz, 1H), 5.02 (s, 1H), 4.78 (d, J=8.5 Hz, 1H), 4.66 (s, 1H), 3.74 (s, 3H), 3.18 (d, J=8.5 Hz, 1H), 2.97 (t, J=6.5 Hz, 1H), 1.83 (s, 3H), 0.91 (s, 9H). See FIG. 30. $^{13}$C-NMR ($CDCl_3$, 125 MHz) (δ): 178.4, 170.0, 151.9, 133.4, 132.8, 116.1, 96.9, 78.0, 70.5, 52.9, 35.2, 27.6, 24.7, 12.1. See FIG. 31. MS (ESI) m/z 294 [M+H]$^+$.

Example 8

Synthesis of Compound (VI-1)

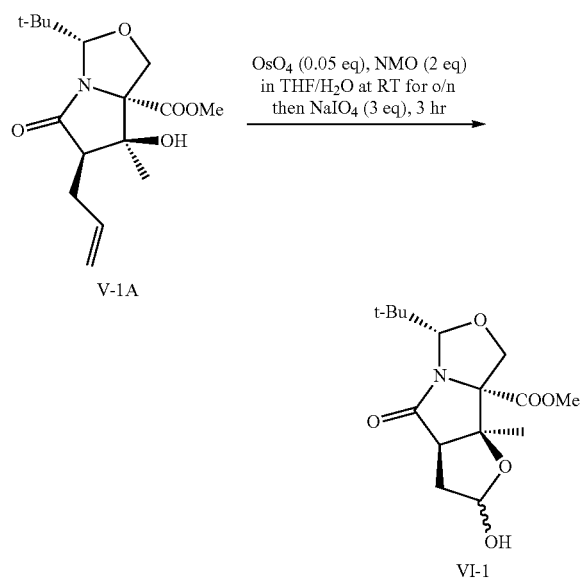

To a solution of compound V-1A (530 mg, 1.7 mmol) in $THF/H_2O$ (1:1, 12 mL) were added NMO (50% w/w aqueous solution, 750 μL, 3.4 mmol) and $OsO_4$ (2.5% wt. % in 2-methyl-2-propanol, 1.1 mL, 0.085 mmol). The resulting mixture was stirred at RT for 17 hours. Then, $NaIO_4$ (250 mg, 1.16 mmol) was added to the above reaction mixture and stirred for additional 3 hrs at 25° C. The reaction mixture was quenched with saturated $Na_2S_2O_3$ (10 mL) and saturated $NaHCO_3$ (10 mL) and extracted with $CH_2Cl_2$ (3×20 mL). The combined organic layer was dried over $Na_2SO_4$ and concentrated under reduced pressure. The crude product was purified by silica flash chromatography (1.25 cm ID×5 cm) using a solvent gradient of 19:1 (50 mL) to 9:1 (50 mL) to 4:1 (50 mL) hexanes/EtOAc to afford compound VI-1 (170 mg, 0.54 mmol, 94%) as a mixture of diastereomers. The compound VI-1 was characterized by $^1$H-NMR ($CDCl_3$, 500 MHz). See FIG. 12. MS (ESI) m/z 314 [M+H].

Example 9

Synthesis of Compound (VII-1)

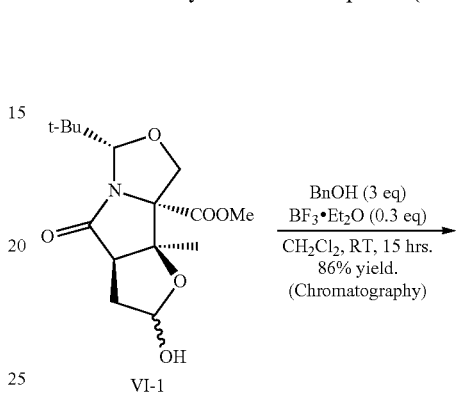

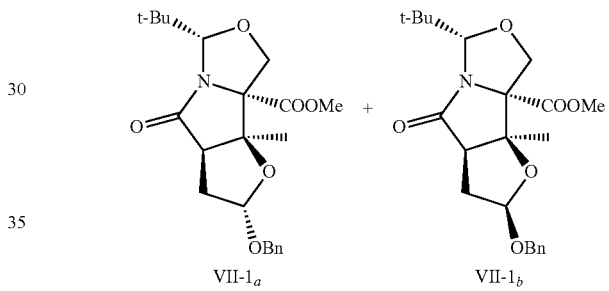

To a solution of compound VI-1 (170 mg, 0.54 mmol) in dry $CH_2Cl_2$ (3 mL) was added BnOH (170 μl, 1.64 mmol) followed by $BF_3 \cdot Et_2O$ (20 μl, 0.16 mmol). The reaction mixture was stirred at 25° C. for 15 hours. Then $Et_3N$ (100 μl, 0.7 mmol) was added to the above reaction mixture which was directly concentrated, followed by silica flash column (1.25 cm ID×5 cm) chromatography using a solvent gradient of 19:1 (50 mL) to 9:1 (50 mL) to 4:1 (50 mL) hexanes/EtOAc to afford compound VII-1$_a$ (83 mg, 0.21 mmol) and compound VII-1$_b$ (104 mg, 0.26 mmol). 86% total yield of compound VII-1$_a$ and compound VII-1$_b$.

Compound VII-1$_a$: $^1$H-NMR ($CDCl_3$, 500 MHz) (δ): 7.30 (m, 5H), 5.24 (dd, J=4.4, 6.3 Hz, 1H), 4.77 (s, 1H), 4.72 (d, J=12.0 Hz, 1H), 4.64 (d, J=8.5 Hz, 1H), 4.45 (d, J=11.7 Hz, 1H), 4.17 (d, J=8.5 Hz, 1H), 3.78 (s, 3H), 3.36 (d, J=8.5 Hz, 1H), 2.81 (ddd, J=1.0, 6.3, 14.2 Hz, 1H), 2.13 (m, 1H), 1.37 (s, 3H), 0.86 (s, 9H). See FIG. 13.

Compound VII-1$_b$: $^1$H-NMR ($CDCl_3$, 500 MHz) (δ): 7.27 (m, 5H), 5.19 (d, J=5.0 Hz, 1H), 4.65 (d, J=11.4 Hz, 1H), 4.65 (d, J=8.5 Hz, 1H), 4.60 (s, 1H), 4.45 (d, J=12.0 Hz, 1H), 4.21 (d, J=8.5 Hz, 1H), 3.76 (s, 3H), 3.17 (d, J=8.5 Hz, 1H), 2.60 (d, J=13.2 Hz, 1H), 2.13 (m, 1H), 1.23 (s, 3H), 0.82 (s, 9H). MS (ESI) m/z 404 [M+H]. See FIG. 14.

The structure of compound VII-1$_b$ was confirmed by crystal structure, as shown in FIG. 15.

Example 10

Synthesis of Compound (VIII-1$_b$)

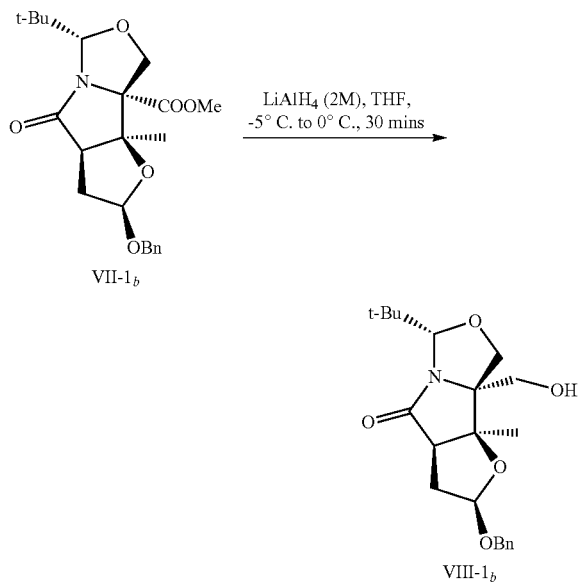

To a solution of compound VII-1$_b$ (40 mg, 0.1 mmol) in dry THF (2 mL) at −20° C. was added LiAlH$_4$ (2.0 M, 75 μl, 0.15 mmol). The reaction mixture was allowed to warm up to −5° C. in 10 min and stirred for an additional 20 min. The reaction mixture was then quenched with saturated aqueous potassium sodium tartrate (5 mL) and extracted with EtOAc (3×5 ml). The combined organic layer was dried with MgSO$_4$ and concentrated under reduced pressure to yield a crude product which was purified by silica flash chromatography (column 1.25 cm ID×10 cm) using a solvent gradient of 19:1 (50 mL) to 9:1 (100 mL) to 4:1 (200 mL) hexanes/EtOAc to afford the product, compound VIII-1$_b$ (19 mg, 0.051 mmol, 50% yield). The compound VIII-1$_b$ was characterized by $^1$H-NMR (CDCl$_3$, 500 MHz). See FIG. 16. MS (ESI) m/z 376 [M+H].

Example 11

Synthesis of Compound (VIII-1$_a$)

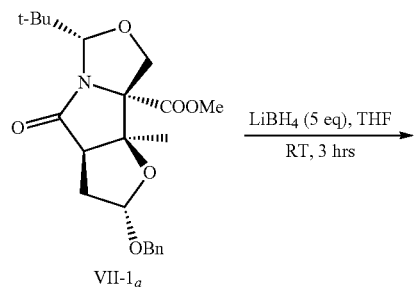

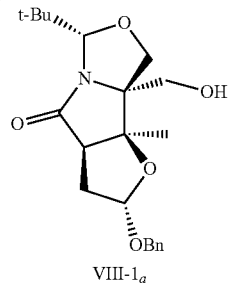

To a solution of compound VII-1$_a$ (90 mg, 0.22 mmol) in dry THF (5 mL) was added lithium borohydride (2M solution in THF, 558 uL, 1.1 mmol,) and stirred at RT. After 15 minutes of stirring, methanol (100 uL) was added to the reaction mixture at RT (room temperature was maintained by cooling the reaction mixture with water bath). After 3 hours of additional stirring, the reaction mixture was quenched with H$_2$O (20 mL) and extracted with ethyl acetate (2×20 mL). The combined organic layer was washed with brine (20 mL), dried over Na$_2$SO$_4$ and concentrated under reduced pressure to afford the product, compound VIII-1$_a$ as clear oil (75 mg, 0.2 mmol, 90.9% yield), which can be used in the next step without any column chromatography. The compound VIII-1$_a$ was characterized by $^1$H-NMR (CDCl$_3$, 500 MHz). See FIG. 17. MS (ESI) m/z 376 [M+H] and 398 [M+Na].

Example 12

Synthesis of Compound (IX-1$_b$)

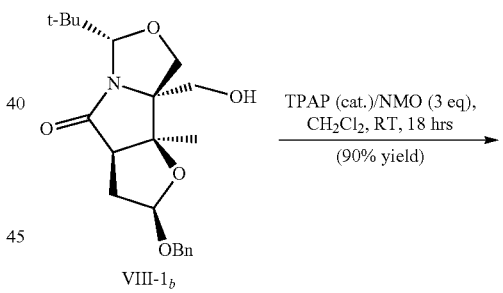

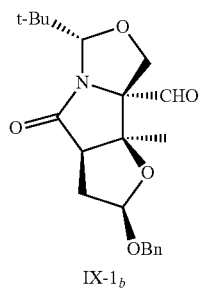

To a solution of VIII-1$_b$ (30 mg, 0.08 mmol) in dry CH$_2$Cl$_2$ (1 ml) were added NMO (28 mg, 0.24 mmol) and TPAP (3.0 mg, 0.008 mmol). The resulting mixture was stirred at RT for 18 hours. The reaction mixture was then concentrated and purified by silica flash chromatography (column 1.25 cm ID×10 cm) using a solvent gradient of 19:1 (50 mL) to 9:1 (100 mL) to 17:3 (200 mL) hexanes/EtOAc to afford the product, compound IX-1$_b$, as clear oil (27 mg, 0.072 mmol, 90% yield). The compound IX-1$_b$ was characterized by $^1$H-NMR (CDCl$_3$, 500 MHz). See FIG. 18. MS (ESI) m/z 374 [M+H].

Example 13

Synthesis of Compound (IX-1$_a$)

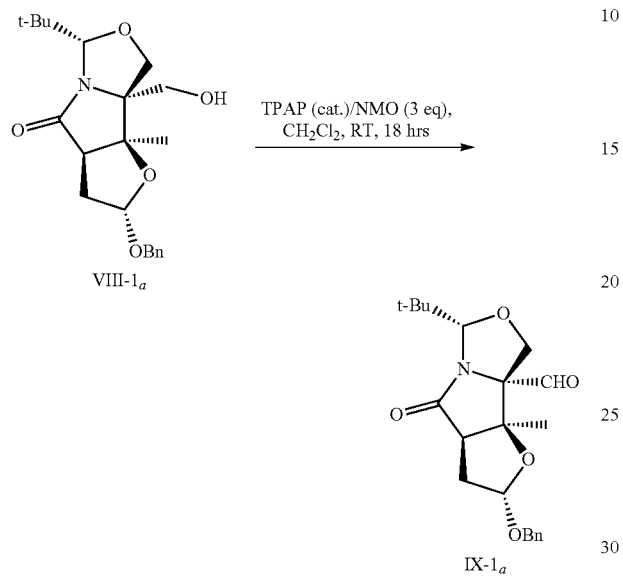

To a solution of alcohol, compound VIII-1$_a$ (40 mg, 0.107 mmol) in dry CH$_2$Cl$_2$ (3 ml) were added NMO (37.5 mg, 0.32 mmol) and TPAP (3.78 mg, 0.01 mmol). The reaction mixture was stirred at RT for 18 hours. The above reaction mixture was then concentrated and purified by silica flash chromatography (column 2.5 cm ID×6 cm) using a solvent gradient of 19:1 (50 mL) to 9:1 (100 mL) to 17:3 (200 mL) hexanes/EtOAc to afford the product, compound IX-1$_a$, as a white solid (34 mg, 0.091 mmol, 85.5% yield). The compound IX-1$_a$ was characterized by $^1$H-NMR (CDCl$_3$, 500 MHz). See FIG. 19. MS (ESI) m/z 374 [M+H] and 396 [M+Na].

Example 14

Synthesis of 9-Cyclohex-2-Enyl-9-Borabicyclo[3.3.1]Nonane

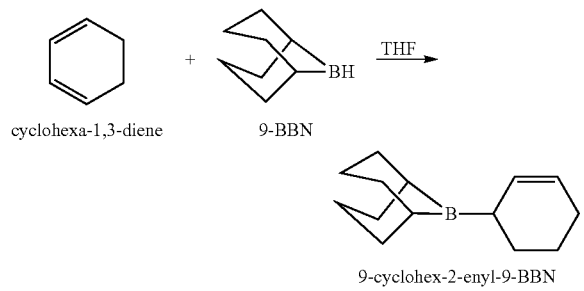

To a solution of 9-borabicyclo[3.3.1]nonane (9-BBN) in THF (0.5 M, 10.0 ml, 5.0 mmol) was added 1,3-cyclohexa- diene (97%) (490 µl, 5.0 mmol) and stirred for 24 hrs at RT to afford a solution of 9-cyclohex-2-enyl-9-BBN in THF (0.5 M) which was directly used to couple with compound of formula IX-1.

Example 15

Synthesis of Compound (X-1$_b$B)

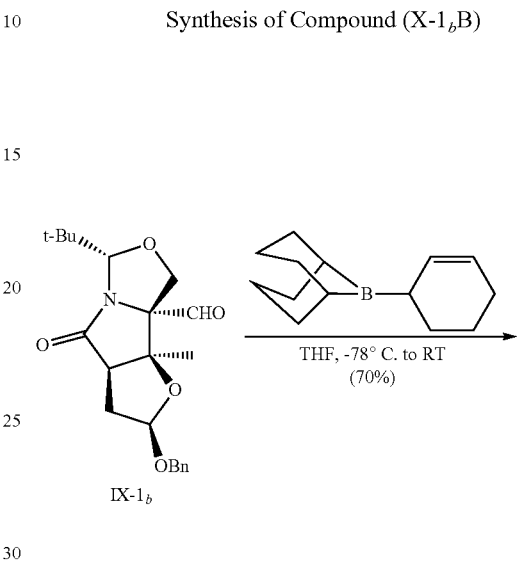

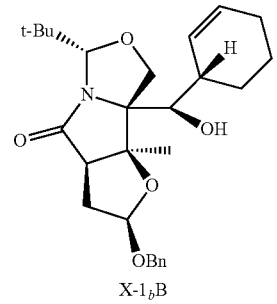

To a solution of compound IX-1$_b$ (20 mg, 0.053 mmol) in THF (0.5 ml) at −78° C. was added the 9-cyclohex-2-enyl-9-BBN solution (see Example 12) in THF (0.5 M, 320 µl, 0.16 mmol). The reaction mixture was allowed to warm to RT over 1.5 hr and stirred for additional 10 hrs at RT. Ethylamine (16 µl, 0.265 mmol) was then added to the above reaction mixture, and stirring continued for an additional 16 hrs at RT. The reaction mixture was then concentrated under reduced pressure and the resulting residue was purified by silica flash chromatography (column 1.25 cm ID×10 cm) using a solvent gradient of 19:1 (50 mL) to 9:1 (100 mL) to 17:3 (200 mL) hexanes/EtOAc to afford the product, compound X-1$_b$B, as a white solid (17.0 mg, 0.037 mmol, 70.4%) which was crystallized from hexanes/ethylether (1:1). The compound X-1$_b$B was characterized by $^1$H-NMR (CDCl$_3$, 500 MHz), and $^{13}$C-NMR (CDCl$_3$, 125 MHz). See FIGS. 20 and 21. The structure of compound X-1$_b$B was confirmed by X-ray crystal structure. See FIG. 22. MS (ESI) m/z 456 [M+H] and 478 [M+Na].

Example 16

Synthesis of Compound (X-1<sub>a</sub>B)

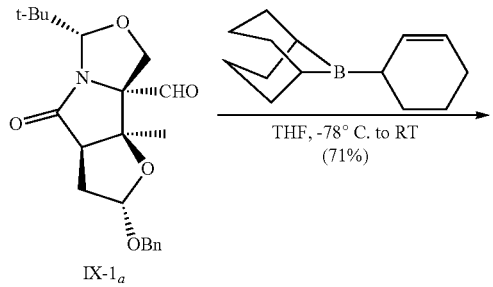

IX-1<sub>a</sub>

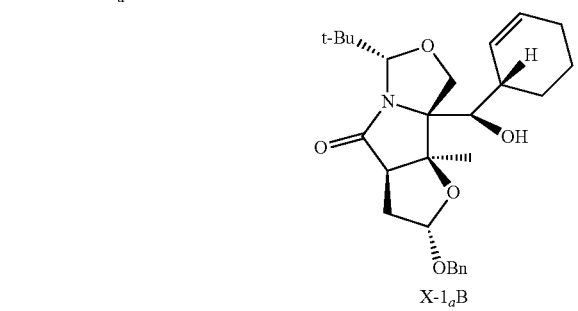

X-1<sub>a</sub>B

To a solution of aldehyde, compound IX-1<sub>a</sub>, (60 mg, 0.161 mmol) in THF (2.0 mL) at −78° C. was added the 9-cyclohex-2-enyl-9-BBN solution in THF (0.5 M, 0.96 mL, 0.48 mmol) and the reaction mixture was allowed to warm to RT over 1.5 hr and stirred for additional 10 hrs at RT. Ethylamine (50 μl, 0.81 mmol) was then added to the above reaction mixture, and stiffing continued for an additional 16 hrs at RT. The reaction mixture was then concentrated under reduced pressure and the resulting residue was purified by silica flash chromatography (column 1.25 cm ID×10 cm) using a solvent gradient of 19:1 (50 mL) to 9:1 (200 mL) of hexanes/EtOAc to afford a pure product, a compound X-1<sub>a</sub>B (52.0 mg, 0.114 mmol, 70.9%). The compound X-1<sub>a</sub>B was characterized by $^1$H-NMR (CDCl$_3$, 500 MHz), and $^{13}$C-NMR (CDCl$_3$, 125 MHz). See FIGS. 23 and 24. MS (ESI) m/z 456 [M+H] and 478 [M+Na].

Example 17

Synthesis of Compound (XXII-1)

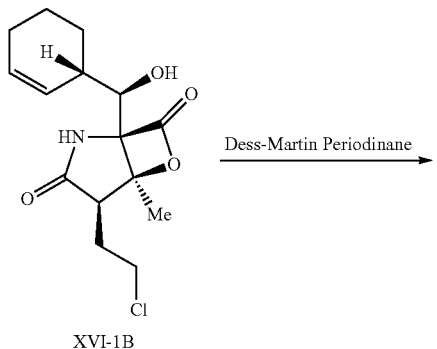

XVI-1B

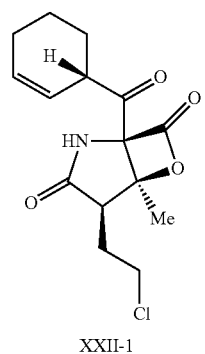

XXII-1

To a solution of compound XVI-1B (3.5 mg, 11.2 μmol) in CH$_2$Cl$_2$ (1 ml) in a scintillation vial (20 ml) were added Dess-Martin periodinane (23.7 mg; 56 μmol) and a magnetic stir bar. The reaction mixture was stirred at RT for about 16 hours. The progress of the reaction was monitored by analytical HPLC. The reaction mixture was then filtered through a membrane filter (0.2 μm) and purified by normal phase HPLC using a Phenomenex Luna 10u Silica column (25 cm×21.2 mm ID), ELSD detector, a solvent gradient of 25% to 80% EtOAc/hexanes over 19 min, 80 to 100% EtOAc/hexanes over 1 min, holding at 100% EtOAc for 5 min, at a flow rate of 14.5 ml/min to afford a pure compound of formula XXII-1. $^1$H NMR (DMSO-d$_6$, 500 MHz) δ 1.54 (s, 3H), 1.59 (m, 2H), 1.66-1.70 (m, 1H), 1.73-1.80 (m, 1H), 1.96 (m, 2H), 2.0-2.11 (m, 2H), 3.09 (t, 1H, J=7.0 Hz), 3.63 (brs, 1H), 3.83-3.88 (m, 1H), 3.89-3.93 (m, 1H), 5.50 (dd, 1H, J=2, 10 Hz), 5.92 (dd, 1H, J=2.5, 10 Hz), 9.70 (s, 1H, NH); MS (ESI), m/z 312 (M+H)$^+$ and 334 (M+Na)$^+$.

Example 18

Synthesis of Compound (XVI-1A) Via Chemical Reduction

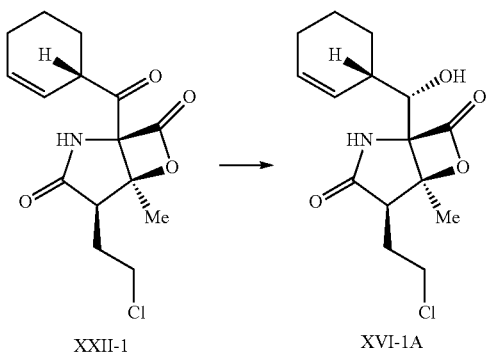

XXII-1    XVI-1A

The compound of formula XVI-1A was synthesized by reducing the keto group of the compound of formula XXII-1 with a common reducing agent(s) under various reaction conditions as shown in the Table 1.

TABLE 1[a]

| | Reaction Conditions | | | Product Ratio | | |
|---|---|---|---|---|---|---|
| NaBH$_4$ # eq | Solvent[b] | Temp in °C. | Time in min | (XVI-1A) | (XVI-1B) | |
| 1 | Monoglyme + 1% water | −78 | 14 | 5 | 95 | 0 |
| 1 | Monoglyme + 1% water | −10 | 14 | 30 | 50 | 20 |
| 1 | Monoglyme + 1% water | 0 | 14 | 33.3 | 33.3 | 33.3 |
| 2 | Monoglyme + 1% water | RT | 8 | 50 | 0 | 50 |
| 1 | Monoglyme + 1% water | RT | 8 | 45 | 10 | 45 |
| 0.5 | Monoglyme + 1% water | RT | 8 | 50 | 50 | 0 |
| 0.25 | Monoglyme + 1% water | RT | 8 | 50 | 50 | 0 |
| 1 | IPA + 1% water | RT | 10 | 50 | 0 | 50 |
| 0.5 | IPA + 1% water | RT | 12 | 60 | 10 | 30 |
| 0.25 | IPA + 1% water | RT | 8 | 50 | 40 | 10 |
| 0.25 | IPA + 5% water | RT | 8 | 10 | 0 | 10 |
| 0.5 | IPA | RT | 8 | 40 | 50 | 10 |
| 0.5 | IPA | 0 | 8 | 30 | 70 | 0 |
| 0.25 | IPA | RT | 8 | | No reaction | |
| 1 | THF + 1% water | RT | 10 | 50 | 0 | 50 |
| 0.5 | THF + 1% water | RT | 12 | 50 | 50 | 0 |
| 0.25 | THF + 1% water | RT | 8 | 30 | 70 | 0 |
| 1 + LiCl | Monoglyme + 1% water | −78 | 10 | 5 | 95 | 0 |
| 1 + LiCl | Monoglyme + 1% water | 0 | 10 | 27.2 | 36.4 | 36.4 |
| 1 + LiCl | Monoglyme + 1% water | 10 | 10 | 10 | 30 | 60 |
| 1 + CeCl$_3$ | Monoglyme + 1% water | −78 | 10 | 5 | 95 | 0 |
| 1 + CeCl$_3$ | Monoglyme + 1% water | 0 | 10 | 25 | 50 | 25 |
| 1 + CeCl$_3$ | Monoglyme + 1% water | 10 | 10 | 20 | 60 | 20 |

[a]Degradation or little to no product was observed using the following reagents. 1. NaBH$_4$ on 10%, Basic Al$_2$O$_3$, 2. K-Selectride, 3. KS-Selectride, 4. BTHF-(R)-CBS, 5. BTHF-(S)-CBS, 6. NaBH(OAc)$_3$, 7. (CH$_3$)$_4$NBH(OAc)$_3$, and 8. iPrMgCl;
[b]Methyl and ethyl ester derivatives were formed when MeOH and EtOH was used, respectively.

Example 19

Synthesis of Compound (XVI-1A) from Compound (XXII-1) Via Enzymatic Reduction

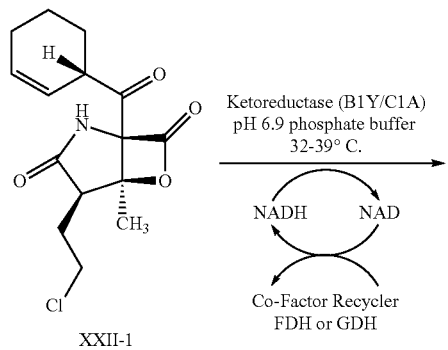

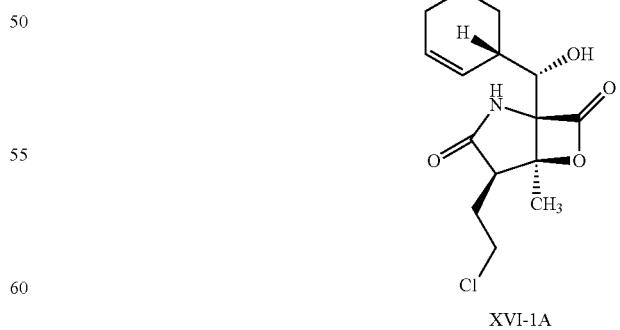

Method A: Compound XXII-1 was subjected to enzymatic reduction using ketoreductases KRED-EXP-C1A and KRED-EXP-B1Y (BioCatalytics, Pasadena Calif.). 20 mM of compound XXII-1 (62 mg, added as a DMSO solution, 0.4 mL), 60 mg of KRED-EXP-C1A or KRED-EXP-B1Y, 50 mM sodium formate 1 mM NAD+ and 30 mg of FDH-101 were dissolved in 10 mL of phosphate buffer (150 mM, pH 6.9). The reaction was stirred at 30° C. for 1 hour before it was extracted with EtOAc. The combined organic layers were evaporated to dryness using a speed-vacuum giving the product, compound XVI-1A, as a solid white powder. HPLC analysis (C18 reverse phase column (ACE C18, 5 m 150×4/6 nm)) and NMR showed only the formation of XVI-1A, as shown in Table 2. Both KRED-EXP-C1A and KRED-EXP-B1Y showed product formation. No detectable formation of the other diastereomeric alcohol, compound of formula XVI-1B was observed.

TABLE 2

| Ketoreductase | XXII-1 | XVI-1A | XVI-1B |
| --- | --- | --- | --- |
| KRED-EXP-C1A | 18%[1] | 82% | Not detected |
| KRED-EXP-B1Y | 21%[1] | 79% | Not detected |

[1]Includes a minor impurity similar to compound (XXII-1) in the calculated yield Reactions (10-100 mg scale) were performed on KRED-EXP-C1A and KRED-EXP-B1Y using glucose and glucose dehydrogenase (GDH) as a cofactor recycler at pH 6.9 (Method B is the optimized procedure). The products were extracted with EtOAc and analyzed by HPLC. The results are shown in Table 3.

TABLE 3

| XXII-1 (mg) | Ketoreductase # eq (w/w) | GDH #eq (w/w) | % Solvent in water | Time (h) | % Conversion[a,b] from XXII-1 to XVI-1A |
| --- | --- | --- | --- | --- | --- |
| 10 | C1A | 1 | 0.5 | ~20% DMSO | 1 | 70 |
| 10 | C1A | 1 | 0.1 | ~20% DMSO | 1 | 70 |
| 10 | C1A | 1 | 0.1 | ~20% DMSO | 2 | 85 |
| 10 | C1A | 1 | 0.1 | ~20% DMSO | 3 | 90 |
| 100 | C1A | 1 | 0.1 | ~20% DMSO | 1 | 70 |
| 100 | C1A | 1 | 0.1 | ~20% DMSO | 3 | 80[c] |
| 50 | C1A | 1 | 0.1 | ~20% DMSO | 4 | 90[c] |
| 10 | B1Y | 1 | 0.1 | ~20% DMSO | 1 | 90 |
| 10 | B1Y | 1 | 0.1 | 50% t-BuOAc | 1 | 40 |
|  |  |  |  |  | 20 | 50 |
| 10 | B1Y | 1 | 0.1 | 50% n-BuOAc | 1 | 0 |
|  |  |  |  |  | 24 | 20 |
| 10 | B1Y | 1 | 0.1 | 50% TBME | 1 | 5 |
|  |  |  |  |  | 24 | 80 |
| 10 | B1Y | 2 | 0.2 | ~20% DMSO | 0.67 | 95 |
| 10 | C1A | 2 | 0.2 | ~20% DMSO | 0.67 | 70 |
| 20 | B1Y | 2 | 0.2 | ~20% DMSO | 0.67 | 95[d] |
| 50 | B1Y | 2 | 0.2 | ~20% DMSO | 0.67 | 90[e] |

[a]At pH 6.9 using GDH, NAD, glucose
[b]Based on HPLC analysis of organic extract
[c]Recovered yield 40% after purification by flash column chromatography. Some decomposition product was detected in aqueous layer
[d]Recovered yield 90% after purification by flash column chromatography
[e]Recovered yield 85% after purification by crystallization As shown in Table 3, when KRED-EXP-C1A ketoreductase was used, the conversion from XXII-1 to XVI-1A was 70% complete after 1 h on 10 mg scale. Based on HPLC analysis of the organic extract, the conversion was 90% complete when the reaction time was increased to 3 h, but subsequent evaluation of the aqueous extract revealed that a portion of the product had decomposed, which is an expected hydrolysis product that forms in aqueous solution. The decomposition product has the structure shown below. Decomposition was minimized when biphasic solutions (50% aqueous t-BuOAc, n-BuOAc, TBME) were used, but the percent conversion was generally very low even with longer reaction times (20-24 h), except in 50% aqueous TBME. Of the two ketoreductase, KRED-EXP-B1Y ketoreductase was superior to KRED-EXP-C1A in the conversion of XXII-1 to XVI-1A. Doubling the concentrations of KRED-EXP-B1Y and GDH and decreasing the reaction time resulted in better yields and minimal decomposition of product (2-5%).

Decomposition Product:

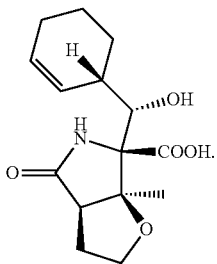

Method B: see Example 31.

Example 20

Synthesis of Compound (XXIII-1B) Via (X-1$_b$B)

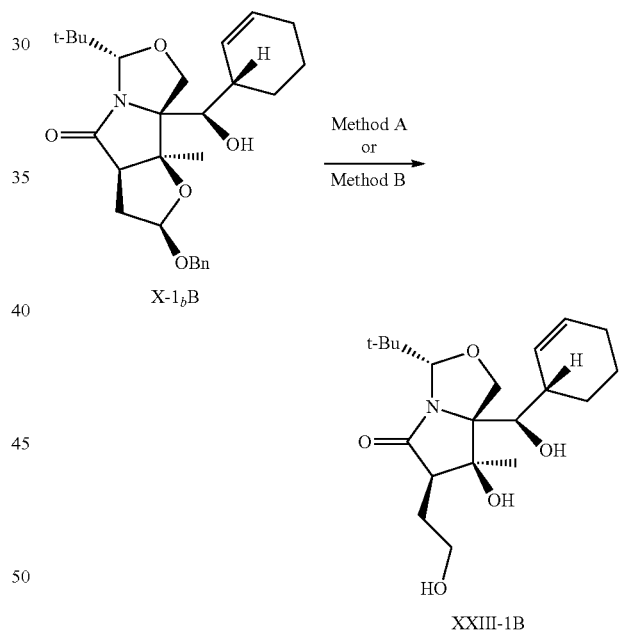

Method A: 1) HCl (0.5 M); 2) NaBH$_4$
Method B: 1) Na/NH$_3$ (liq.); 2) NaBH$_4$ Method A: To a solution of X-1$_b$B (400 mg, 0.88 mmol) in THF (20 mL) was added aqueous HCl (0.5 M, 2 mL). The reaction mixture was warmed to 60° C. and stirred for 10 hrs at this temperature. The above reaction mixture was diluted with H$_2$O (20 mL), then extracted with EtOAc (2×20 mL) and CH$_2$Cl$_2$ (3×20 mL). The combined organic phase was dried over MgSO$_4$ and concentrated under reduced pressure. The crude residue was re-dissolved in THF/H$_2$O ((2:1; 22.5 mL), then NaBH$_4$ (100 mg, 2.63 mmol) was added and stirred at 25° C. for 30 min. The reaction mixture was diluted with H$_2$O (20 mL) and extracted with EtOAc (2×20 mL) and CH$_2$Cl$_2$ (3×20 mL), and the organic phase was dried over MgSO$_4$ and concentrated under reduced pressure to afford XXIII-1B as crude white solid (260 mg, 81%) which can be used in the next step without purification. The compound XXIII-1B was characterized by $^1$H-NMR (CDCl$_3$, 500 MHz), and $^{13}$C-NMR (CDCl$_3$, 125 MHz). See FIGS. 32 and 33. MS (ESI) m/z 368.3 [M+H]$^+$.

Method B: Sodium metal (Na, 30 mg, 1.30 mmol) was dissolved in liquid ammonia (3 mL) at −78° C. and the resultant dark blue mixture was stirred for 5 min. A solution of X-1$_b$B (30 mg, 0.066 mmol) in dry THF (0.5 ml) was slowly added to the above reaction mixture and stirred at −78° C. for an additional 2 hrs. Solid ammonium chloride (NH$_4$Cl, 40 mg) was added slowly to the reaction mixture, which was then allowed to warm to RT (by removing the dry ice-acetone cold bath). Ammonia was evaporated during warm up. The white residue was washed with brine and extracted with EtOAc. The organic phase was concentrated to afford crude hemiacetal, which was directly used in the next reaction without purification.

To a solution of the above hemiacetal in THF:H$_2$O (2:1; 1.5 mL) was added NaBH$_4$ (8 mg, 0.20 mmol). The reaction mixture was stirred for 1 hr at RT and then diluted with brine and extracted with EtOAc. The organic phase was dried with MgSO$_4$, concentrated under reduced pressure and purified by silica flash chromatography (EtOAc in hexanes, 10% to 30%) to afford triol XXIII-1B as clear oil (18 mg, 0.049 mmol, 74.2% yield over two steps). The compound XXIII-1B was characterized by $^1$H-NMR (CDCl$_3$, 500 MHz), and $^{13}$C-NMR (CDCl$_3$, 125 MHz). See FIGS. 32 and 33. MS (ESI) m/z 368.3 [M+H]$^+$.

Example 21

Synthesis of Compound (XXIII-1B) Via (X-1$_a$B)

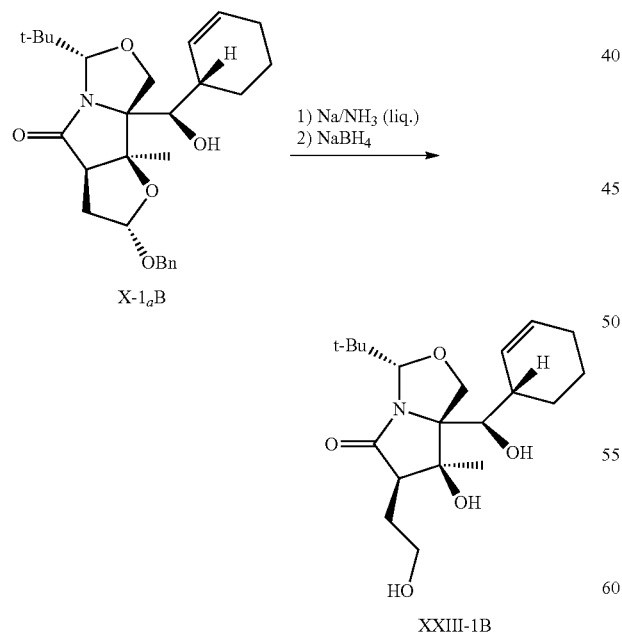

Sodium metal (Na, 20 mg, 0.88 mmol) was dissolved in liquid ammonia (3 ml) at −78° C. and the resultant dark blue mixture was stirred for 5 min. A solution of compound X-1$_a$B (20 mg, 0.044 mmol) in dry THF (0.5 ml) was slowly added to the above reaction mixture and stirred at −78° C. for additional 2 hrs. Solid ammonium chloride (NH$_4$Cl, 30 mg) was added slowly to the reaction mixture, which was then allowed to warm to RT (by removing the dry ice-acetone cold bath). Ammonia was evaporated during warm up. The white residue was washed with brine and extracted with EtOAc. The organic phase was concentrated under reduced pressure to afford crude hemiacetal which was directly used in the next reaction without purification.

To a solution of the above hemiacetal in THF:H$_2$O (2:1; 1.5 ml) was added NaBH$_4$ (5 mg, 0.13 mmol). The reaction mixture was stirred for 1 hr at RT and then diluted with brine and extracted with EtOAc. The organic phase was dried with MgSO$_4$, concentrated under reduced pressure and purified by silica flash chromatography (EtOAc in hexanes, 10% to 30%) to afford triol XXIII-1B as clear oil (11.3 mg, 0.031 mmol, 70% yield over two steps). The $^1$H-NMR (CDCl$_3$, 500 MHz) and $^{13}$C-NMR (CDCl$_3$, 125 MHz) spectra were the same as shown FIGS. 32 and 33, respectively. MS (ESI) m/z 368.3 [M+H].

Example 22

Synthesis of Compound (XXIV-1B) Via (XXIII-1B-Bz)

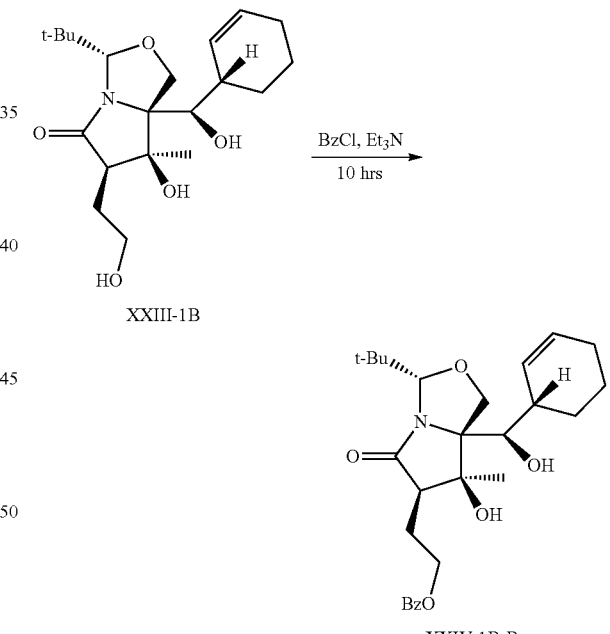

To a solution of XXIII-1B (120 mg, 0.33 mmol) in CH$_2$Cl$_2$ (5 mL) were added Et$_3$N (120 μl, 0.86 mmol) and benzoyl chloride (BzCl, 60 μl, 0.52 mmol). The reaction mixture was stirred at 25° C. for 10 hrs. Then the reaction mixture was directly concentrated under reduced pressure and the resulting product was purified by silica flash chromatography (EtOAc in hexanes, 10% to 30%) to afford XXIV-1B-Bz (136 mg, 0.29 mmol, 87%). The compound XXIV-1B-Bz was characterized by $^1$H-NMR (CDCl$_3$, 500 MHz). See FIG. 34. MS (ESI) m/z 472.3 [M+H]$^+$.

Example 23

Synthesis of Compound (XXV-1B-Bz) Via (XXIV-1B-Bz)

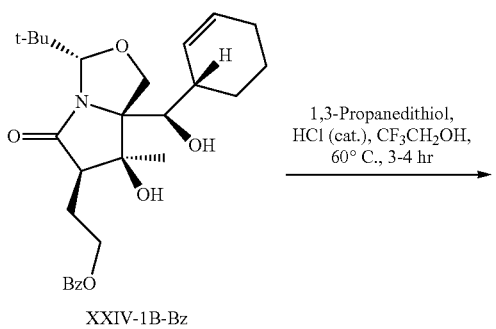

XXIV-1B-Bz 1,3-Propanedithiol, HCl (cat.), CF₃CH₂OH, 60° C., 3-4 hr

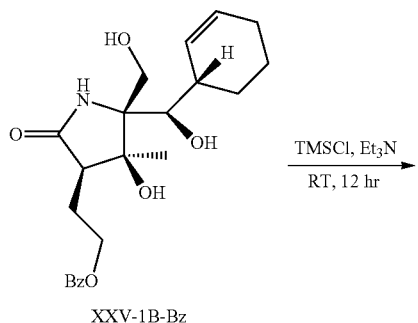

XXV-1B-Bz

To a solution of XXIV-1B-Bz (136 mg, 0.29 mmol) in CF₃CH₂OH (2 mL) were added 1,3-propanedithiol (200 μl, 2 mmol) and a catalytic amount of aqueous HCl (12N, 10 μL). The reaction mixture was stirred at 60° C. for 3-4 hr, concentrated under reduced pressure and the resulting crude product was then purified by silica flash chromatography (EtOAc in hexanes, 20% to 80%) to afford XXV-1B-Bz (110 mg, 0.27 mmol, 94%). The compound XXV-1B-Bz was characterized by ¹H-NMR (CDCl₃, 500 MHz), and ¹³C-NMR (CDCl₃, 125 MHz). See FIGS. 35 and 36. MS (ESI) m/z 404.3 [M+H]⁺.

Example 24

Synthesis of Compound (XXVp-1B-Bz-TMS) Via (XXV-1B-Bz)

XXV-1B-Bz

TMSCl, Et₃N
RT, 12 hr

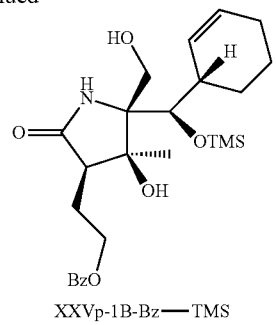

XXVp-1B-Bz—TMS

To a solution of XXV-1B-Bz (70 mg, 0.17 mmol) in CH₂Cl₂ (2 mL) were added Et₃N (480 μL, 3.47 mmol) and TMSCl (220 μL, 1.74 mmol) and the solution was stirred at 25° C. for 12 hrs. The reaction was quenched with saturated aqueous NaHCO₃ (5 mL) and extracted with CH₂Cl₂ (3×5 mL). The combined organic phase was dried over MgSO₄, concentrated under reduced pressure and then purified by silica flash chromatography (EtOAc in hexanes, 20% to 80%) to afford XXVp-1B-Bz-TMS (44 mg, 0.093 mmol, 53% yield). The compound XXVp-1B-Bz-TMS was characterized by ¹H-NMR (CDCl₃, 500 MHz), and ¹³C-NMR (CDCl₃, 125 MHz). See FIGS. 37 and 38. MS (ESI) m/z 476.3 [M+H]⁺.

Example 25

Synthesis of Compound (XXVI-1B-Bz) Via (XXVp-1B-Bz-TMS)

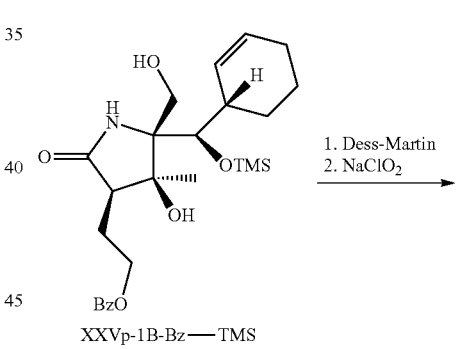

XXVp-1B-Bz—TMS

1. Dess-Martin
2. NaClO₂

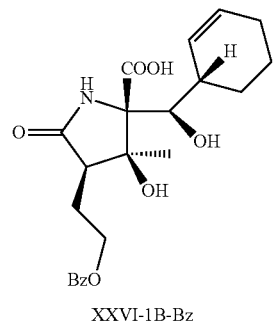

XXVI-1B-Bz

To a solution of XXVp-1B-Bz-TMS (120 mg, 0.25 mmol) in CH₂Cl₂ (5 mL) was added Dess-Martin periodinane (118 mg, 0.278 mmol) and the reaction mixture was stirred at 25° C. for 2 hrs. The reaction was quenched with saturated aqueous Na₂S₂O₃ (3 mL) and saturated aqueous NaHCO₃ (2 mL) and extracted with CH₂Cl₂ (2×5 mL). The combined organic phase was dried over MgSO₄ and concentrated under reduced pressure to afford the crude aldehyde as a white powder which was used for the next step without purification.

To a solution of the above freshly prepared aldehyde in t-BuOH/H$_2$O (2:1; 4.5 mL) was added NaH$_2$PO$_4$ (400 mg, 3.33 mmol) and the reaction mixture was cooled to 0° C. Then 2-methyl-2-butene (2M in THF, 3.70 mL, 7.57 mmol) and NaClO$_2$ (175 mg, 1.93 mmol) were added sequentially and stirred at 0° C. for 1.5 hrs. The reaction mixture was then diluted with brine (5 mL) and extracted with EtOAc (2×5 mL). The aqueous phase was acidified with HCl (0.5 M) to pH 3.0 and extracted with CH$_2$Cl$_2$ (3×5 mL). The combined organic phase was dried over MgSO$_4$ and concentrated under reduced pressure to yield a white solid residue which was purified by reversed phase HPLC using an ACE 5μ C18 column (150×21 mm ID) and a solvent gradient of 10% to 100% CH$_3$CN/H$_2$O/0.05% TFA over 22 min, holding at 100% CH$_3$CN/0.05% TFA for 3 min at a flow rate of 14.5 mL/min to afford the carboxylic acid XXVI-1B-Bz (66 mg, 0.16 mmol, 62.6% yield over two steps). The carboxylic acid XXVI-1B-Bz was characterized by $^1$H-NMR (CD$_3$OD, 500 MHz), and $^{13}$C-NMR (CD$_3$OD, 125 MHz). See FIGS. 39 and 40. MS (ESI) m/z 418.2 [M+H]$^+$.

Example 26

Synthesis of Compound (XV-1B) Via (XXVI-1B-Bz)

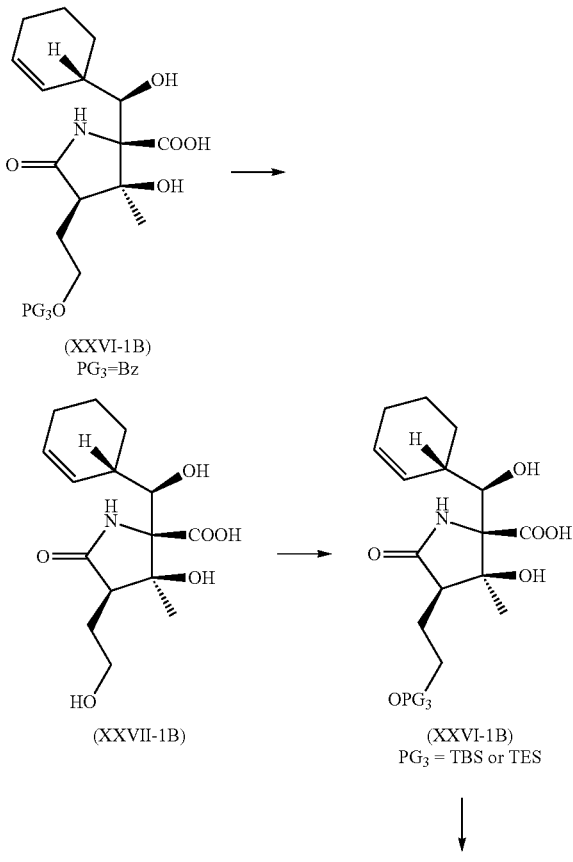

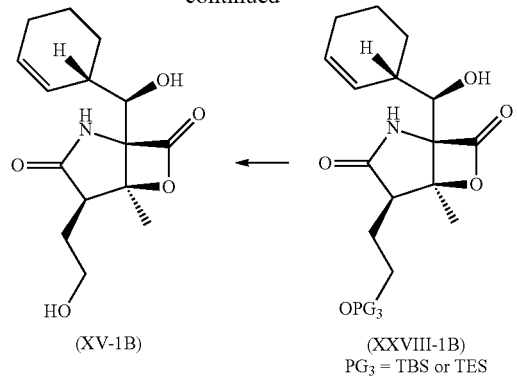

Method A: 1) K$_2$CO$_3$, MeOH; H$^+$; 2) TBSCl, imid.; 3) BOPCl; 4) HF.Pyr

To a solution of XXVI-1B-Bz (14 mg, 0.033 mmol) in MeOH (0.5 ml) was added K$_2$CO$_3$ (14 mg, 0.10 mmol) and the reaction mixture was stirred at 25° C. for 15 hrs. Then aqueous HCl (200 μl, 1.0 M) was added to this reaction mixture which was directly concentrated and dried under high vacuum to afford XXVII-1B in which the benzoyl group has been replaced by hydrogen as a white residue, which was directly used in the next step without further purification.

To a solution of the product obtained from the previous step in CH$_2$Cl$_2$ (0.50 ml) were added imidazole (7.0 mg, 0.10 mmol) and TBSCl (10 mg, 0.066 mmol) and the mixture was stirred at 25° C. for 10 hrs. Then the reaction mixture was directly concentrated under reduced pressure and dried well by high vacuum to afford XXVI-1B-TBS a white residue, which was directly used in the next step without further purification.

To a solution of XXVI-1B-TBS in CH$_3$CN (0.40 ml) were added pyridine (0.40 ml) and BOPCl (17 mg, 0.066 mmol) and the reaction mixture was stirred at 25° C. for 16 hrs. Then the reaction mixture was concentrated under reduced pressure and the products purified by silica gel chromatography using EtOAc/hexanes gradients (20% to 80%) to afford the XXVIII-1B-TBS (5.0 mg; $^1$H-NMR (CDCl$_3$, 500 MHz) See FIG. 41) and XV-1B (3.0 mg) as white solid.

To a solution of the above XXVIII-1B-TBS (5.0 mg) in THF (0.5 ml) were added pyridine (30 μl) and HF$^-$ pyridine (30 μl) and the reaction mixture was stirred at 25° C. for 2 hrs in a plastic tube. Then the reaction mixture was quenched with saturated aqueous NaHCO$_3$ (1 ml) and extracted with CH$_2$Cl$_2$ (3×1.0 ml). The organic phase was dried over MgSO$_4$, concentrated under reduced pressure and purified by silica gel flash chromatography using a EtOAc/hexanes gradient (20% to 80%) to afford XV-1B (4.0 mg, 0.013 mmol). Overall Yield=73%. The compound XV-1B was characterized by $^1$H-NMR (acetone-d$_6$, 500 MHz), and $^{13}$C-NMR (acetone-d$_6$, 125 MHz). See FIGS. 42 and 43. MS (ESI) m/z 296 [M+H]$^+$.

Method B: 1) K$_2$CO$_3$, MeOH; H$^+$; 2) TESCl, imid.; 3) BOPCl; 4) HF.Pyr 28%

To a solution of XXVI-1B-Bz (240 mg, 0.575 mmol) in MeOH (3.0 ml) was added K$_2$CO$_3$ (240 mg, 1.74 mmol) and the reaction mixture was stirred at 25° C. for 15 hrs. Then aqueous HCl (600 μl, 1.0 M) was added to this reaction mixture which was directly concentrated and dried under high vacuum to afford XXVII-1B as a white residue, which was directly used for the next step without further purification.

To a solution of the product obtained from the previous step in CH₂Cl₂ (5.0 ml) was added imidazole (195 mg, 2.87 mmol) and TESCl (0.39 ml, 2.30 mmol) and the reaction mixture was stirred at 25° C. for 18 hrs. Then the reaction mixture was directly concentrated under reduced pressure and dried well by high vacuum to afford XXVI-1B-TES as a white residue, which was directly used in the next step without further purification.

To a solution of XXVI-1B-TES in CH₃CN (3.0 ml) were added pyridine (3.0 ml) and BOPCl (290 mg, 1.15 mmol) and the reaction mixture was stirred at 25° C. for 18 hrs. Then the reaction mixture was filtered through a short silica-plug; the filtrate was concentrated under reduced pressure and dried by high vacuum to afford TES-β-lactone XXVIII-1B-TES as a white residue, which was directly used in the next step without further purification.

To a solution of the above TES-β-lactone residue (XXVIII-1B-TES) in THF (5.0 ml) were added pyridine (150 μl) and HF.pyridine (150 μl) and the reaction mixture was stirred at 25° C. for 5-6 hrs in a plastic tube. Then the reaction mixture was quenched with saturated aqueous NaHCO₃ (10 ml) and extracted with CH₂Cl₂ (3×10 ml). The organic phase was dried over MgSO₄, concentrated under reduced pressure and purified by silica flash chromatography (EtOAc in hexanes, 10% to 80%) to afford β-lactone XV-1B (47.0 mg, 0.16 mmol). Overall Yield=28%.

Example 27

Synthesis of Compound (XVI-1B) Via (XV-1B)

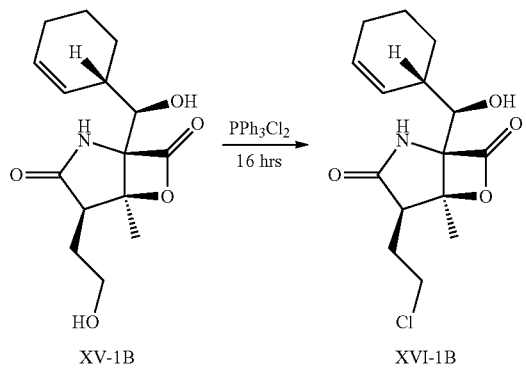

To a solution of XV-1B (35 mg, 0.118 mmol) obtained from Example 26 in CH₃CN (250 μl) were added pyridine (250 μl) and Ph₃PCl₂ (80 mg, 0.24 mmol) and the reaction mixture was stirred at RT for 18 hrs. Then the reaction mixture was concentrated under reduced pressure and purified by silica gel flash chromatography using a EtOAc/hexanes gradient (5% to 20%) to afford XVI-1B (21 mg, 57% yield). The compound XVI-1B was characterized by ¹H-NMR (CDCl₃, 500 MHz) and ¹³C-NMR (CDCl₃, 125 MHz). See FIGS. 44 and 45. MS (ESI) m/z 314 [M+H]⁺. MS (ESI) m/z 314 [M+H]⁺. HRMS (ESI) m/z 314.1151 [M+H]⁺ (calcd for C₁₅H₂₁ClNO₄, 314.1159, Δ=−2.4 ppm).

Example 28

Synthesis of Compound (XXII-1) Via (XVI-1B)

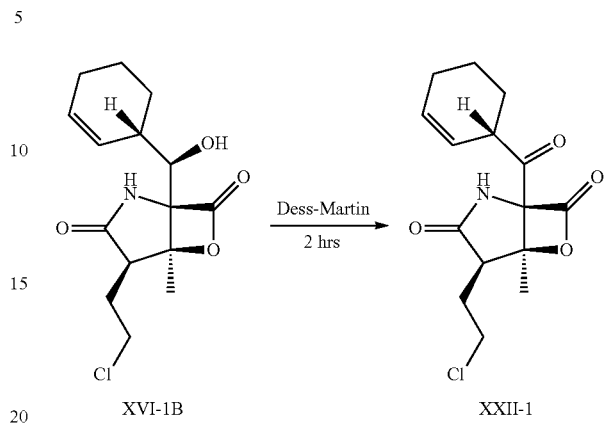

To a solution of compound XVI-1B (10 mg, 32 μmol) obtained from Example 27 in CH₂Cl₂ (4 mL) in a round bottom flask (25 mL) were added Dess-Martin periodinane (20.35 mg, 48 μmol) and a magnetic stir bar. The reaction mixture was stirred at RT for about 2 hours then quenched with saturated aqueous Na₂S₂O₃ (5 ml) and saturated aqueous NaHCO₃ (5 ml), and then extracted with CH₂Cl₂ (2×5 ml). The organic phase was dried over Na₂SO₄ and concentrated under reduced pressure. The resulting crude product was then purified by silica flash column (0.4 cm ID×3 cm) chromatography using a solvent gradient of 19:1 (5 mL) to 9:1 (5 mL) to 17:3 (5 mL) to 4:1 (10 mL) hexanes/EtOAc to afford XXII-1 (6 mg, 19.3 μmol, 60.3% yield). The compound XXII-1 was characterized by ¹H NMR (CDCl₃, 500 MHz). See FIG. 46. MS (ESI), m/z 312 [M+H]⁺ and 334 [M+Na]⁺.

Example 29

Synthesis of Compound (XVI-1A) Via (XXII-1) by Enzymatic Reduction

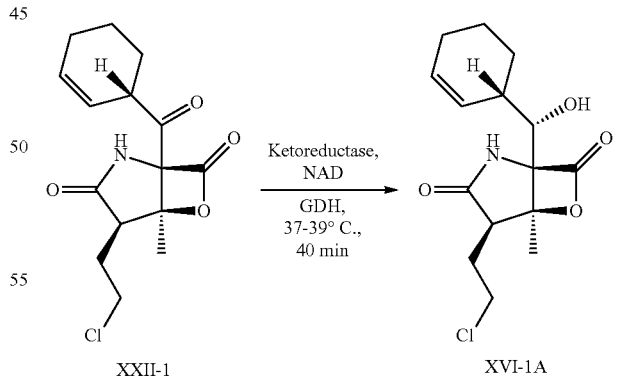

To a solution of XXII-1 (6 mg, 19.3 μmol) in DMSO (0.4 mL) obtained from Example 28 in a round bottom flask (25 mL), 600 μL of potassium phosphate buffer (150 mM, pH 6.9), 12 mg of ketoreductase KRED-EXP-B1Y, 1.2 mg of glucose dehydrogenase (GDH), 300 μL of glucose (50 mM) and 300 μL of NAD (1 mM) were added. The above reaction mixture was stirred at 37-39° C. for about 40 min and then extracted with EtOAc (2×10 mL); the combined organic phase was dried over Na$_2$SO$_4$ and concentrated under reduced pressure. This afforded about 5 mg of XVI-1A. (82.7% yield) as a crude product which was further purified by normal phase HPLC using a Phenomenex Luna 10μ Silica column (25 cm×21.2 mm ID) using a solvent gradient of 25% to 80% EtOAc/hexanes over 19 min, 80 to 100% EtOAc/hexanes over 1 min, holding at 100% EtOAc for 5 min, at a flow rate of 14.5 mL/min and monitoring the purification by evaporative light scattering detection (ELSD) to afford 2 mg of pure XVI-1A. [α]$_D$ –70° (c 0.05, CH$_3$CN). The compound XVI-1A was characterized by $^1$H-NMR (DMSO-d$_6$, 500 MHz) and $^{13}$C-NMR (DMSO-d$_6$, 125 MHz). See FIGS. 47 and 49. The $^1$H NMR spectra were in complete agreement with those of an authentic sample of XVI-1A (FIGS. 48 and 50 respectively). MS (ESI) m/z 314 [M+H]$^+$. HRESIMS m/z 314.1173 [M+H]$^+$ (calcd for C$_{15}$H$_{21}$ClNO$_4$, 314.1159, Δ=4.5 ppm).

Example 30

Synthesis of Compound (XXII-1) Via (XVI-1B) (Obtained as a Semisynthetic Derivative of a Fermentation Product of *Salinospora*)

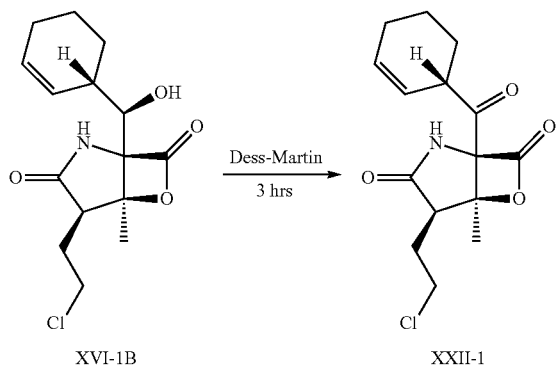

To a solution of XVI-1B (75 mg, 0.24 mmol) (obtained as a semi-synthetic derivative of XVI-1A, which was obtained by fermentation of *Salinospora tropica* as disclosed in U.S. Pat. No. 7,176,232, issued Feb. 13, 2007, which is hereby incorporated by reference in its entirety) in CH$_2$Cl$_2$ (35 mL) in a round bottom flask (150 mL) were added Dess-Martin periodinane (202.5 mg; 0.48 mmol) and a magnetic stir bar. The reaction mixture was stirred at RT for about 3 hours, over which the progress of the reaction was monitored by analytical HPLC. The reaction mixture was then quenched with saturated aqueous Na$_2$S$_2$O$_3$ (40 ml) and saturated aqueous NaHCO$_3$ (40 ml), and extracted with CH$_2$Cl$_2$ (2×40 ml). The organic phase was dried over Na$_2$SO$_4$ and concentrated by reduced pressure to afford XXII-1 (70 mg, 0.22 mmol, 94% yield). $^1$H NMR (DMSO-d$_6$, 500 MHz) δ 1.54 (s, 3H), 1.59 (m, 2H), 1.66-1.70 (m, 1H), 1.73-1.80 (m, 1H), 1.96 (m, 2H), 2.0-2.11 (m, 2H), 3.09 (t, 1H, J=7.0 Hz), 3.63 (brs, 1H), 3.83-3.88 (m, 1H), 3.89-3.93 (m, 1H), 5.50 (dd, 1H, J=2, 10 Hz), 5.92 (dd, 1H, J=2.5, 10 Hz), 9.70 (s, 1H, NH); MS (ESI), m/z 312 [M+H]$^+$ and 334 [M+Na]$^+$.

Example 31

Synthesis of Compound (XVI-1A) Via (XXII-1) by Enzymatic Reduction

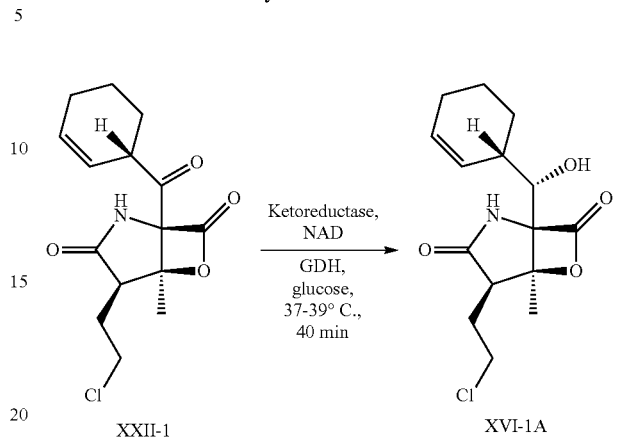

To a solution of XXII-1 (50 mg, 0.16 mmol) obtained from Example 30 in DMSO (1 mL) in a round bottom flask (25 mL), 5 mL of potassium phosphate buffer (150 mM, pH 6.9), 100 mg of ketoreductase KRED-EXP-B1Y, 10 mg of glucose dehydrogenase (GDH), 2.5 mL of glucose (50 mM) and 2.5 mL of NAD (1 mM) were added. The above reaction mixture was stirred at 37-39° C. for 40 min and then extracted with EtOAc (2×25 mL); the combined organic phase was dried over Na$_2$SO$_4$ and concentrated under reduced pressure to yield a crude product which was crystallized in 1:1 acetone: heptane (6 mL) in a 20 mL scintillation vial (by slow evaporation under nitrogen gas) to afford XVI-1A as white crystalline solid (42 mg, 0.13 mmol, 85% yield). The structure of XVI-1A was confirmed by comparison of its mp, specific rotation and $^1$H- and $^{13}$C-NMR spectra with those of an authentic sample.

Example 32

Synthesis of 2-Cyclohexenyl Zinc Chloride

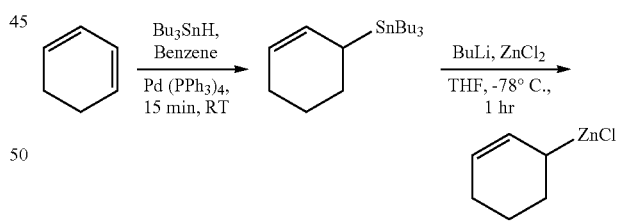

To a solution of 1,3-cyclohexadiene (0.96 g, 12 mmol, d=0.84, 1143 uL) and Pd(PPh$_3$)$_4$ (462.2 mg, 0.4 mmol) in benzene (10 mL) under nitrogen atmosphere, was added Bu$_3$SnH (1.16 g, 4 mmol, d=1.098, 1.06 mL) dropwise at room temperature and stirred for 15 minutes. After the solvent was removed on rotavap, the product was purified on silica flash chromatography (column 1.5 cm ID×20 cm) using a solvent gradient of 10:0 (100 mL) to 19:1 (100 mL) to 9:1 (100 mL) of hexanes/EtOAc to afford cyclohexenyltributyltin (3.5 g, 9.4 mmol, 78.6% yield) as a clear liquid. Cyclohexenyltributyltin was characterized by $^1$H-NMR (CDCl$_3$, 500 MHz). See FIG. 51.

To a solution of cyclohenexyltributyltin (0.92 g, 2.5 mmol) in THF (5 mL) at –78° C. under nitrogen was added nBuLi (1 mL, 2.5 M solution in hexane, 2.5 mmol). After an additional 30 min stifling, ZnCl₂ (340 mg, 2.5 mmol, dissolved in 2 ml of THF) was added and stirring was continued for 30 min at −78° C. to afford 2-cyclohexenyl zinc chloride.

Example 33

Synthesis of Compound X-1$_a$

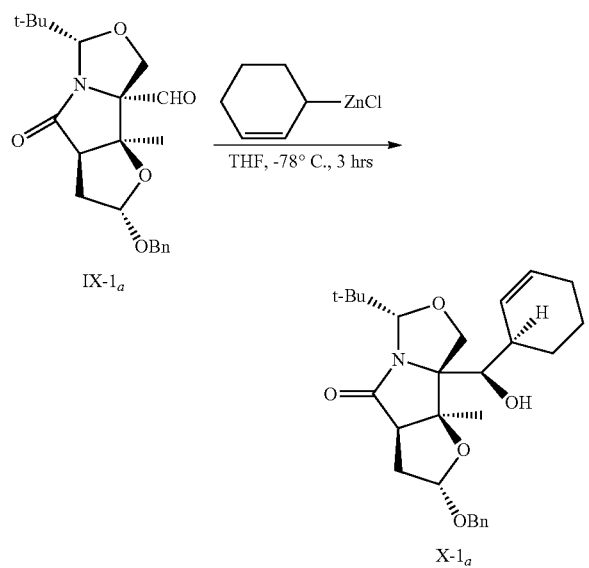

IX-1$_a$

X-1$_a$

To a solution of IX-1$_a$ (30 mg, 0.08 mmol) in 5 mL of THF at −78° C., 1 mL of cyclohexenyl zinc chloride (freshly prepared; Example 32) was added and stirred at −78° C. for about 3 hrs. The reaction was quenched with H₂O (15 mL) and extracted with EtOAc (2×15 mL). The combined organic phase was dried over anhydrous Na₂SO₄ and concentrated under reduced pressure to yield the crude product which was purified by silica flash chromatography (column 2.5 cm ID×6 cm) using a solvent gradient of 19:1 (50 mL) to 9:1 (50 mL) to 17:3 (50 mL) to 8:2 (50 mL) to 7:3 (50 mL) of hexanes/EtOAc to afford pure cyclohexene derivative X-1$_a$ (26 mg, 0.057 mmol, 71.4% yield). The compound X-1$_a$ was characterized by ¹H-NMR (CDCl₃, 500 MHz), and ¹³C-NMR (CDCl₃, 125 MHz). See FIGS. 52 and 53. MS (ESI) m/z 456.3 [MH]⁺ and 478.3 [M+Na]⁺.

Example 34

Synthesis of Compound X-1$_b$

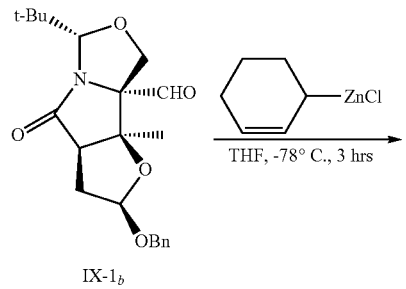

IX-1$_b$

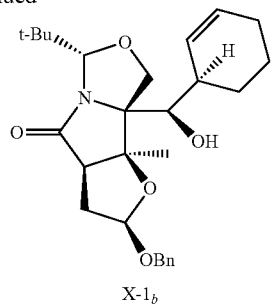

X-1$_b$

To a solution of IX-1$_b$ (35 mg, 0.094 mmol) in 5 mL of THF at −78° C., 1.2 mL of cyclohexenyl zinc chloride (freshly prepared; Example 32) was added and stirred at −78° C. for about 3 hrs. The reaction was quenched with H₂O (15 mL) and extracted with EtOAc (2×20 mL). The combined organic phase was dried over anhydrous Na₂SO₄ and concentrated under reduced pressure to yield a liquid residue. This residue was dissolved in 5 mL of hexanes and allowed to stand for an hour. A white solid was precipitated from the residue, which was separated by decanting the solvent. The solid material was further washed with hexanes (2×2 mL) and dried on high-vacuum to afford pure X-1$_b$ (32 mg, 0.066 mmol, 75% yield). The compound X-1$_b$ was characterized by ¹H-NMR (CDCl₃, 500 MHz), and ¹³C-NMR (CDCl₃, 125 MHz). See FIGS. 54 and 55. MS (ESI) m/z 456.3 [M+H]⁺ and 478.3 [M+Na]⁺. The stereochemistry was determined by X-ray crystallography (See FIG. 56).

Example 35

In Vitro Inhibition of 20S Proteasome Activity by Compound XVI-1A Obtained from Synthetic and Fermentation Sources The compound XVI-1A as obtained synthetically using a method described herein and by fermentation as described in U.S. Pat. No. 7,144,723, which is hereby incorporated by reference in its entirety. Both the synthetic and fermentation compounds XVI-1A were prepared as 20 mM stock solution in DMSO and stored in small aliquots at −80° C. Purified rabbit muscle 20S proteasome was obtained from Boston Biochem (Cambridge, Mass.). To enhance the chymotrypsin-like activity of the proteasome, the assay buffer (20 mM HEPES, pH7.3, 0.5 mM EDTA, and 0.05% Triton X100) was supplemented with SDS resulting in a final SDS concentration of 0.035%. The substrate used was suc-LLVY-AMC, a fluorogenic peptide substrate specifically cleaved by the chymotrypsin-like activity of the proteasome. Assays were performed at a proteasome concentration of 1 µg/ml in a final volume of 200 µl in 96-well Costar microtiter plates. Both the synthetic and fermentation compounds XVI-1A were tested as eight-point dose response curves with final concentrations ranging from 500 nM to 158 pM. After addition of test compounds to the rabbit 20S proteasomes, the samples were preincubated at 37° C. for five minutes in a temperature controlled Fluoroskan Ascent 96-well microplate reader (Thermo Electron, Waltham, Mass.). During this preincubation step, the substrate was diluted 25-fold in SDS-containing assay buffer. After the preincubation period, the reactions were initiated by the addition of 10 µl of the diluted substrate and the plates were returned to the plate reader. The final concentration of substrate in the reactions was 20 µM. Fluorescence of the cleaved peptide substrate was measured at $\lambda_{ex}$=390 nm and $\lambda_{em}$=460 nm. All data were collected every five minutes for 2 hour and plotted as the mean of duplicate data points. The $IC_{50}$ values (the drug concentration at which 50% of the maximal relative fluorescence is inhibited) were calculated by Prism (GraphPad Software) using a sigmoidal dose-response, variable slope model. To evaluate the activity of the compounds against the caspase-like activity of the 20S proteasome, reactions were performed as described above except that Z-LLE-AMC was used as the peptide substrate. Both the synthetic and fermentation compounds XVI-1A were tested at concentrations ranging from 5 μM to 1.6 nM. For the evaluation of these compounds against the trypsin-like activity of the 20S proteasome, the SDS was omitted from the assay buffer and Boc-LRR-AMC was used as the peptide substrate. The concentration of the test compounds used in these assays ranged from 500 nM to 158 pM.

Results ($IC_{50}$ values) shown in Table 4 and in FIGS. 57-59 illustrate that both synthetic and fermentation compounds XVI-1A have similar inhibitory activity against the chymotrypsin-like, trypsin-like and caspase-like activities of the 20S proteasome in vitro.

TABLE 4

IN VITRO INHIBITION OF PURIFIED RABBIT 20S PROTEASOMES BY THE SYNTHETIC AND FERMENTATION COMPOUNDS OF FORMULA XVI-1A

| Compound XVI-1A | $IC_{50}$ Values (nM) | | |
|---|---|---|---|
| | Chymotrypsin-like | Trypsin-like | Caspase-like |
| Fermentation | 2.6 | 35 | 387 |
| Synthetic | 3.2 | 37 | 467 |

Example 36

Effects on the Chymotrypsin-Like Activity of Proteasomes in RPMI 8226 Cells by Compounds XVI-1A Obtained from Synthetically and from Fermentation RPMI 8226 (ATCC, CCL-155), the human multiple myeloma cell line, was cultured in RPMI 1640 medium supplemented with 2 mM L-Glutamine, 1% Penicillin/Streptomycin, 10 mM HEPES and 10% Fetal Bovine Serum at 37° C., 5% $CO_2$ and 95% humidified air. To evaluate the inhibitory effects on the chymotrypsin-like activity of the 20S proteasome, test compounds prepared in DMSO were appropriately diluted in culture medium and added to $1\times10^6$/ml RMPI 8226 cells at final concentration of 1, 5 or 10 nM. DMSO was used as the vehicle control at a final concentration of 0.1%. Following 1 hr incubation of RMPI 8226 cells with the compounds, the cells were pelleted by centrifugation at 2,000 rpm for 10 sec at room temperature and washed 3× with ice-cold 1× Dubach's Phosphate-Buffered Saline (DPBS, Mediatech, Herndon, Va.). DPBS washed cells were lysed on ice for 15 min in lysis buffer (20 mM HEPES, 0.5 mM EDTA, 0.05% Triton X-100, pH 7.3) supplemented with protease inhibitor cocktail (Roche Diagnostics, Indianapolis, Ind.). Cell debris was pelleted by centrifugation at 14,000 rpm for 10 min, 4° C. and supernatants (=cell lysates) were transferred to a new tube. Protein concentration was determined by the BCA protein assay kit (Pierce Biotechnology, Rockford, Ill.). The chymotrypsin-like activity of the 20S proteasome in the RPMI 8226 cell lysates was measured by using the Suc-LLVY-AMC fluorogenic peptide substrate in the proteasome assay buffer (20 mM HEPES, 0.5 mM EDTA, pH 8.0) containing a final concentration of 0.035% SDS. The reactions were initiated by the addition of 10 μL of 0.4 mM Suc-LLVY-AMC (prepared by diluting a 10 mM solution of the peptide in DMSO 1:25 with assay buffer) to 190 μL of the cell lysates in 96-well Costar microtiter plate and incubated in the Thermo Lab Systems Fluoroskan plate reader at 37° C. Fluorescence of the cleaved peptide substrate was measured at $\lambda_{ex}$=390 nm and $\lambda_{em}$=460 nm. All data were collected every five minutes for 2 hour. The total protein used for each assay was 20 μg. The final concentration of Suc-LLVY-AMC and DMSO was 20 μM and 0.2%, respectively. After subtraction of the background (the values from wells containing buffer and substrate in the absence of cell lysate), the activity of test compound was expressed as % inhibition as normalized to the proteasome activity observed in the DMSO treated control cells.

Results in Table 5 show that exposure of RPMI 8226 cells to the fermentation or synthetic compounds XVI-1A resulted in a dose-dependent inhibition of the 20S proteasome chymotrypsin-like activity. In addition, a similar inhibition profile was observed when cells were exposed to compound XVI-1A obtained via fermentation or to compound XVI-1A obtained synthetically.

TABLE 5

INHIBITION OF THE CHYMOTRYPSIN-LIKE ACTIVITY OF PROTEASOME IN RPMI 8826 CELLS BY SYNTHETIC AND FERMENTATION COMPOUNDS XVI-1A

| | % inhibition of the 20S proteasome chymotrypsin-like activity in RPMI 8826 cells | |
|---|---|---|
| Concentration (nM) | Fermentation | Synthetic |
| 1 | 38 | 32 |
| 5 | 86 | 79 |
| 10 | 97 | 96 |

The examples described above are set forth solely to assist in the understanding of the embodiments. Thus, those skilled in the art will appreciate that the methods may provide derivatives of compounds.

One skilled in the art would readily appreciate that the present invention is well adapted to carry out the objects and obtain the ends and advantages mentioned, as well as those inherent therein. The methods and procedures described herein are presently representative of preferred embodiments and are exemplary and are not intended as limitations on the scope of the invention. Changes therein and other uses will occur to those skilled in the art which are encompassed within the spirit of the invention.

It will be readily apparent to one skilled in the art that varying substitutions and modifications can be made to the embodiments disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably can be practiced in the absence of any element or elements, limitation or limitations which is not specifically disclosed herein. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention. Thus, it should be understood that although the present invention has been specifically disclosed by preferred embodiments and optional features, modification and variation of the concepts herein disclosed can be resorted to by those skilled in the art, and that such modifications and variations are considered to be falling within the scope of the embodiments of the invention.

What is claimed is:

1. A compound of formula (X):

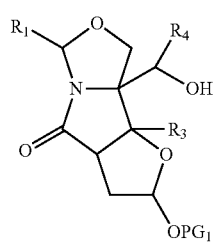

wherein:

$R_1$ is hydrogen or substituted or unsubstituted $C_{1-6}$ alkyl;

$R_3$ is selected from the group consisting of substituted or unsubstituted variants of the following: $C_{1-6}$ alkyl, $C_{3-6}$ cycloalkyl, $C_{2-6}$ alkenyl, $C_{3-6}$ cycloalkenyl, aryl, and arylalkyl;

$R_4$ can be selected from the group consisting of substituted or unsubstituted variants of the following: $C_1$-$C_{12}$ alkyl, $C_2$-$C_{12}$ alkenyl, $C_2$-$C_{12}$ alkynyl, $C_3$-$C_{12}$ cycloalkyl, $C_3$-$C_{12}$ cycloalkenyl, $C_3$-$C_{12}$ cycloalkynyl, $C_3$-$C_{12}$ heterocyclyl, aryl, heteroaryl, arylalkyl, heteroarylalkyl, (cycloalkyl)alkyl, (heterocyclyl)alkyl, acyl, acylalkyl, alkyloxycarbonyloxy, carbonylacyl, aminocarbonyl, azido, azidoalkyl, aminoalkyl, salt of an aminoalkyl, carboxyalkyl, salt of carboxyalkyl, alkylaminoalkyl, salt of an alkylaminoalkyl, dialkylaminoalkyl, salt of a dialkylaminoalkyl, phenyl, alkylthioalkyl, arylthioalkyl, carboxy, cyano, alkanesulfonylalkyl, alkanesulfinylalkyl, alkoxysulfinylalkyl, thiocyanoalkyl, boronic acidalkyl, boronic esteralkyl, guanidinoalkyl, salt of a guanidinoalkyl, sulfoalkyl, salt of a sulfoalkyl, alkoxysulfonylalkyl, sulfooxyalkyl, salt of a sulfooxyalkyl, alkoxysulfonyloxyalkyl, phosphonooxyalkyl, salt of a phosphonooxyalkyl, (alkylphosphooxy)alkyl, phosphorylalkyl, salt of a phosphorylalkyl, (alkylphosphoryl)alkyl, pyridinylalkyl, salt of a pyridinylalkyl, salt of a heteroarylalkyl and halogenated alkyl including polyhalogenated alkyl; and $PG_1$ is a protecting group moiety.

2. The compound claim 1, wherein $PG_1$ is selected from the group consisting of benzyl, a substituted benzyl, an alkylcarbonyl, an arylalkylcarbonyl, a substituted methyl ether, a substituted ethyl ether, a substituted benzyl ether, a tetrahydropyranyl ether, a silyl ether, an ester, and a carbonate.

3. The compound of claim 1, wherein $R_4$ is 2-cyclohexenyl.

4. The compound of claim 1, wherein $R_3$ is methyl.

5. The compound of claim 1, wherein $R_1$ is a substituted or unsubstituted $C_{1-6}$ alkyl.

6. The compound of claim 1, wherein the compound of formula (X) has the structure:

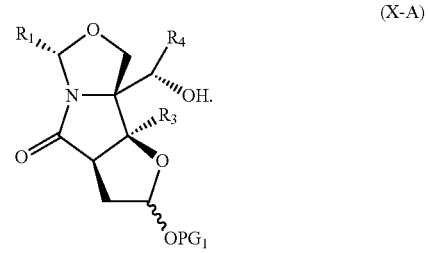

7. The compound of claim 1, wherein the compound of formula (X) has the structure:

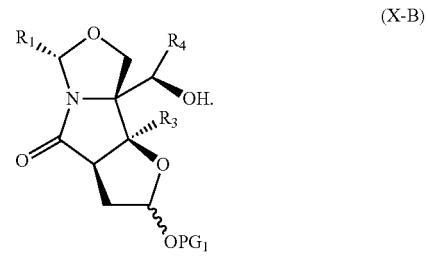

8. The compound of claim 1, wherein the compound of formula (X) has the structure:

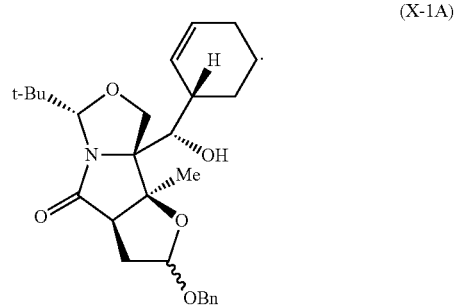

9. The compound of claim 1, wherein the compound of formula (X) has the structure:

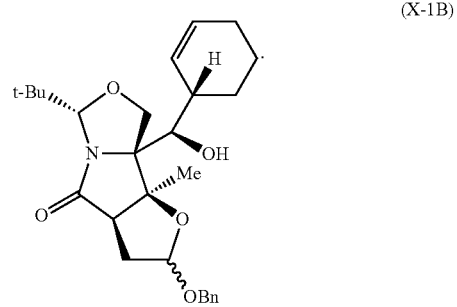

10. A method of forming a compound of formula (XV) from the compound of claim 1 comprising the steps of:
removing PG$_1$ on the acetal of the compound of formula (X), wherein PG$_1$ is a protecting group moiety, and reductively opening the hemiacetal using a reducing agent;
cleaving the hemiaminal ether group of a compound of formula (XXIV) or a compound of formula (XXIVp); and
forming a four membered lactone ring by performing a lactonization reaction using a compound selected from the group consisting of a compound of formula (XXVI), a compound of formula (XXVII), a compound of formula (XXVIp) and a compound of formula (XXVIIp), to form the compound of Formula (XV);
wherein the compound of formula (XV) has the following structure:

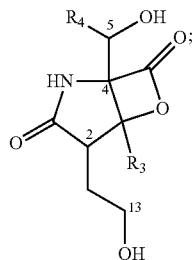

wherein the compound of formula (X) has the following structure:

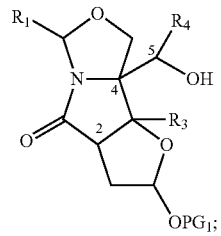

wherein the compound of Formula (XXIV) has the following structure:

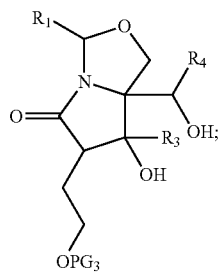

wherein the compound of Formula (XXIVp) has the following structure:

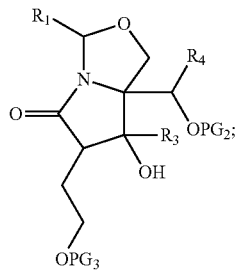

wherein the compound of Formula (XXVI) has the following structure:

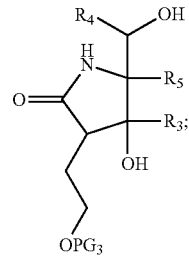

wherein the compound of Formula (XXVII) has the following structure:

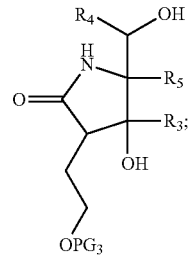

wherein the compound of Formula (XXVIp) has the following structure:

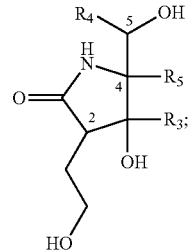

wherein the compound of Formula (XXVIIp) has the following structure:

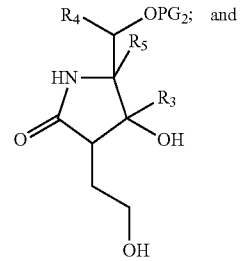

wherein:
R$_5$ is selected from the group consisting of —C(=O)OR$_6$, —C(=O)SR$_6$, —C(=O)NR$_6$R$_6$ and —C(=O)Z;
each R$_6$ is independently selected from the group consisting of hydrogen, halogen, a substituted or an unsubstituted C$_1$-C$_{24}$ alkyl, a substituted or an unsubstituted acyl, a substituted or an unsubstituted alkylacyl, a substituted or an unsubstituted arylacyl, a substituted or an unsubstituted aryl, a substituted or an unsubstituted arylalkyl, p-nitrophenyl, pentafluorophenyl, pentafluoroethyl, trifluoroethyl, trichloroethyl, and a substituted or an unsubstituted heteroaryl;
Z is a halogen; and
PG$_2$ and PG$_3$ are independently a protecting group moiety.

11. The method of claim 10, wherein the cleaving of the hemiaminal ether group is before the removal of PG$_1$ and reductively opening the hemiacetal, and before the formation of the four membered lactone ring.

12. The method of claim 10, wherein the cleaving of the hemiaminal ether group is after the removal of $PG_1$ and reductively opening the hemiacetal, but before the formation of the four membered ring.

13. The method of claim 10, further comprising substituting the C-13 primary hydroxy group of the compound of formula (XV) with a halogen, wherein the compound of formula (XV) has the following structure:

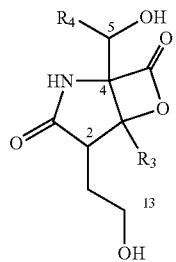

to form a compound of formula (XVI-A), wherein the compound of formula (XVI-A) has the following structure:

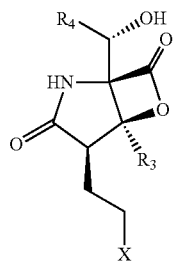

wherein X is a halogen.

14. The method of claim 10, further comprising substituting the C-13 primary hydroxy group of the compound of formula (XV) with a halogen, wherein the compound of formula (XV) has the following structure:

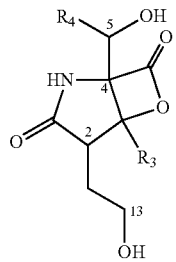

to form a compound of formula (XVI-B), wherein the compound of formula (XVI-B) has the following structure:

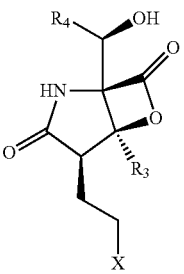

wherein X is a halogen.

15. The method of claim 14, further comprising the steps of:
(1) oxidizing the secondary hydroxy group of the compound of formula (XVI-B) using an oxidizing agent, wherein the compound of formula (XVI-B) has the following structure:

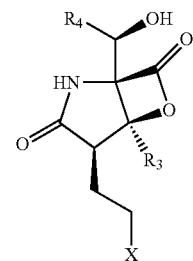

to form a compound of formula (XXII):

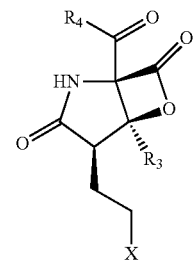

(2) reducing the keto group of the compound of formula (XXII) to form a compound of formula (XVI-A) using a reducing agent, wherein the compound of formula (XVI-A) has the following structure:

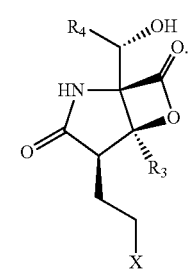

16. The method of claim 14, further comprising the step of:
(1) inverting the stereochemistry of the secondary hydroxy carbon center of the compound of formula (XVI-B), wherein the compound of formula (XVI-B) has the following structure:

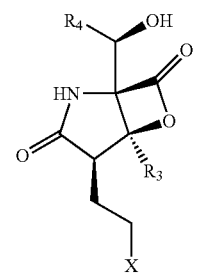

to form a compound of formula (XVI-A), wherein the compound of formula (XVI-A) has the following structure:

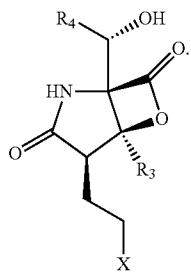

wherein the stereochemistry of the secondary hydroxy carbon center is inverted via a Mitsunobu transformation, or by oxidizing the C-5 secondary hydroxy group on the compound of formula (XVI-B) to a keto group with an oxidizing agent and then reducing the keto group to a hydroxy group with a reducing agent or via a selective enzyme transformation using a reducing enzyme.

17. A method of preparing the compound of claim 1 comprising adding $R_4$ to the compound of formula (IX) by reacting the compound of formula (IX) with an organometallic moiety containing at least one $R_4$ to form a compound of formula (X):

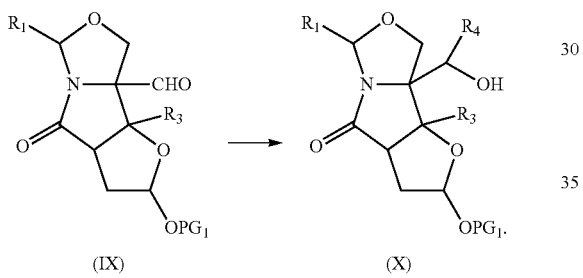

18. The method of claim 17, wherein the organometallic moiety is 9-cyclohex-2-enyl-9-borabicyclo[3.3.1]nonane.

19. The method of claim 17, wherein the compound of formula (IX) has the structure:

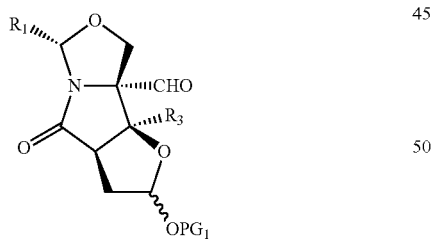

the compound of formula (X) has the structure:

(X-A)

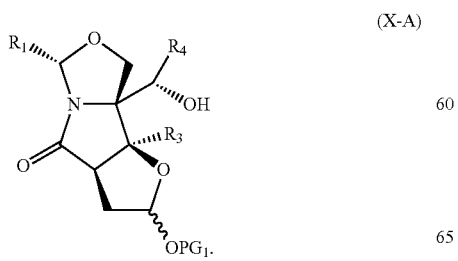

20. The method of claim 17, wherein the compound of formula (IX) has the structure:

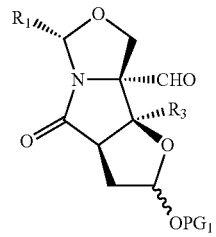

the compound of formula (X) has the structure:

(X-B)

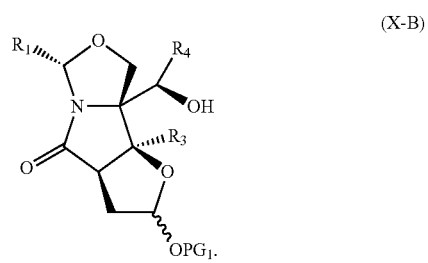

21. The method of claim 17, wherein the compound of formula (IX) has the structure:

(IX-1)

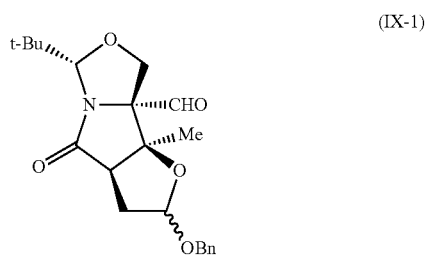

the compound of formula (X) has the structure:

(X-1A)

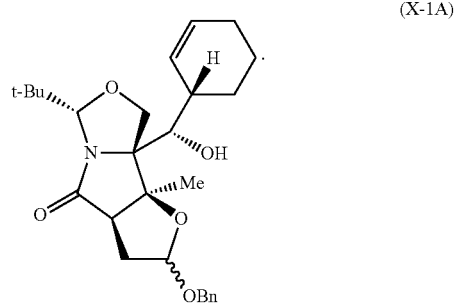

22. The method of claim 17, wherein the compound of formula (IX) has the structure:

(IX-1)

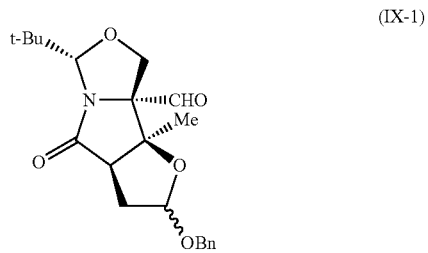

the compound of formula (X) has the structure:

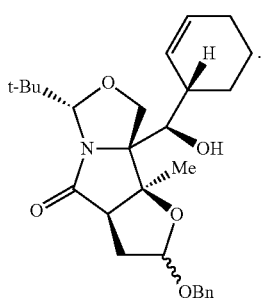
(X-1B)

23. A method of preparing a compound of formula (XXIII) comprising removing the protecting group moiety on the acetal on the compound of claim 1 and reductively opening the hemiacetal using a reducing agent to form a compound of formula (XXIII):

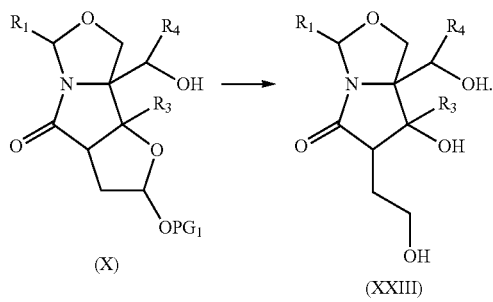

24. The method of claim 23, wherein the compound of formula (X) has the structure:

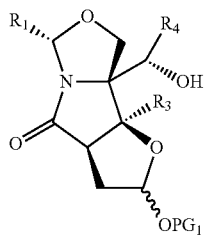
(X-A)

the compound of formula (XXIII) has the structure:

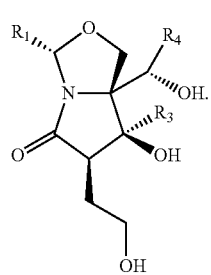
(XXIII-A)

25. The method of claim 23, wherein the compound of formula (X) has the structure:

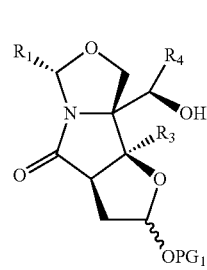
(X-B)

the compound of formula (XXIII) has the structure:

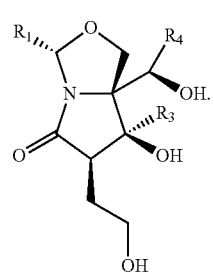
(XXIII-B)

26. The method of claim 23, wherein the compound of formula (X) has the structure:

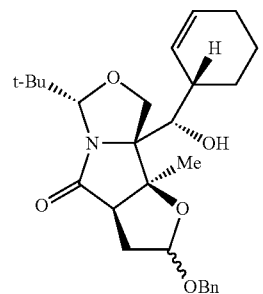
(X-1A)

the compound of formula (XXIII) has the structure:

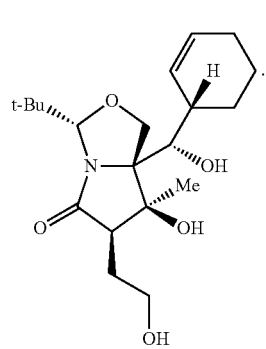
(XXIII-1A)

27. The method of claim 23, wherein the compound of formula (X) has the structure:

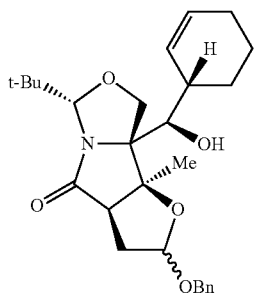
(X-1B)

the compound of formula (XXIII) has the structure:

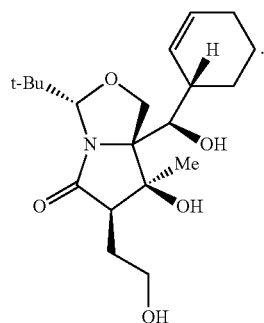
(XXIII-1B)

28. A method of preparing a compound of formula (Xp) comprising protecting the C-5 secondary hydroxy group of the compound of claim 1 with a suitable protecting group moiety to form a compound of formula (Xp):

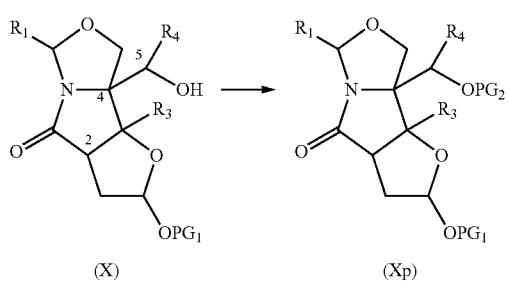

wherein: $PG_2$ is a protecting group moiety.

29. The method of claim 28, further comprising cleaving the hemiaminal ether of the compound of formula (Xp) with an acid to form a compound of formula (XIp):

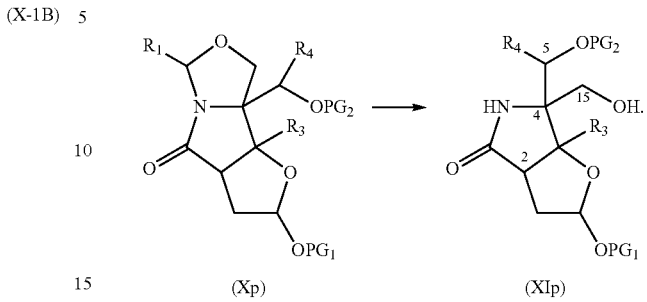

30. A method of preparing a compound of formula (XI) comprising cleaving the hemiaminal ether of the compound of claim 1 with an acid to form a compound of formula (XI):

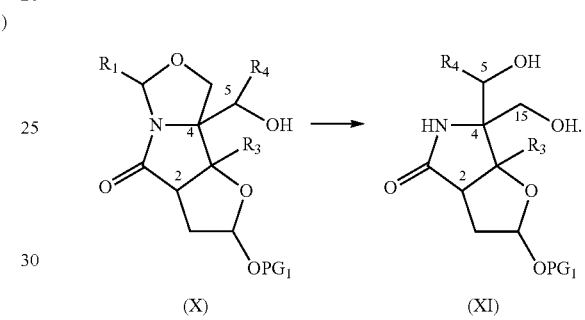

31. A method of preparing a compound of formula (XVII) comprising oxidizing the secondary alcohol group of the compound of claim 1 with an oxidizing agent to form a compound of formula (XVII):

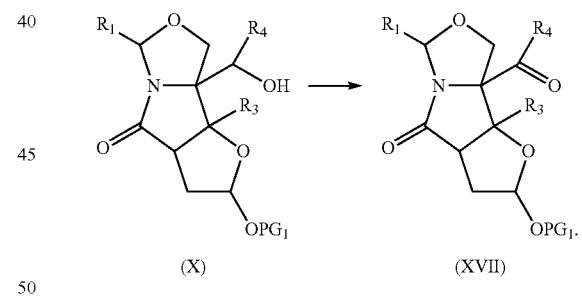

* * * * *

UNITED STATES PATENT AND TRADEMARK OFFICE
CERTIFICATE OF CORRECTION

PATENT NO.        : 8,067,616 B2
APPLICATION NO.   : 12/913624
DATED             : November 29, 2011
INVENTOR(S)       : Ling et al.

It is certified that error appears in the above-identified patent and that said Letters Patent is hereby corrected as shown below:

Column 10, line 53, Change ""(cycloalkyl)alkyl" to --"(cycloalkyl)alkyl"--.

Column 10, line 65, Change "arylalky" to --arylalkyl--.

Column 11, line 27, Change "dehydroganase" to --dehydrogenase--.

Column 11, line 38, Change "dicromate" to --dichromate--.

Column 26, lines 40-55, Change " 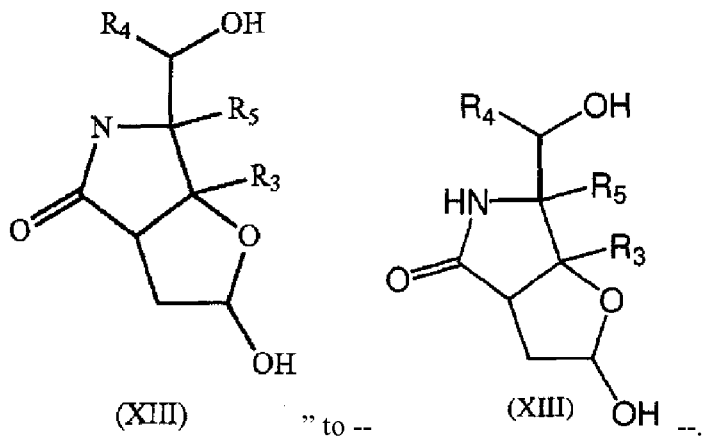 " to -- --.

Column 66, line 45, Change "(OTO," to --(OTf),--.

Column 87, lines 1-11, Change " 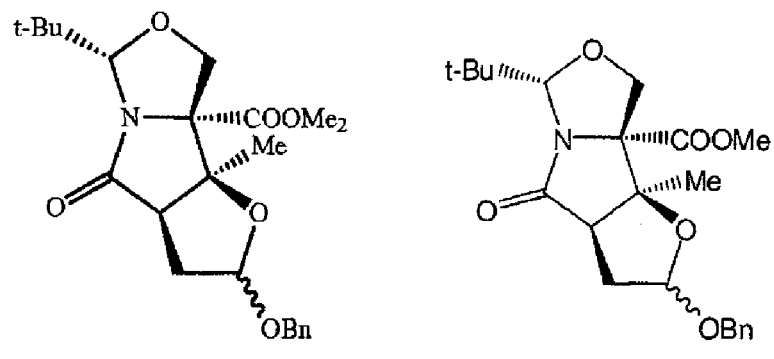 " to -- --.

Signed and Sealed this
Fourth Day of December, 2012

David J. Kappos
*Director of the United States Patent and Trademark Office*

CERTIFICATE OF CORRECTION (continued)
U.S. Pat. No. 8,067,616 B2

Column 113, line 4, Change "MeI-" to --MeI- --.

Column 116, line 52, Change "diasteromers" to --diastereomers--.

Column 125, line 36, Change "stiffing" to --stirring--.

Column 128, line (approx.) 45, Change "NaBH₄ on 10%," to --NaBH₄ on 10%--.

Column 136, line 46, Change "HF⁻ pyridine" to --HF·pyridine--.

Column 141, line 2, Change "stifling," to --stirring,--.

Column 145, line 58, In Claim 2, After "compound" insert --of--.

Column 148, lines 16-25, In Claim 10, Change " 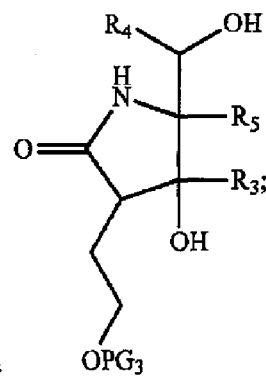 " to -- 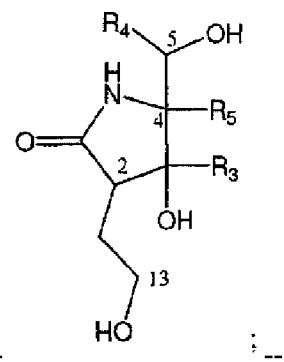 --.

Column 148, lines 28-38, In Claim 10, Change " 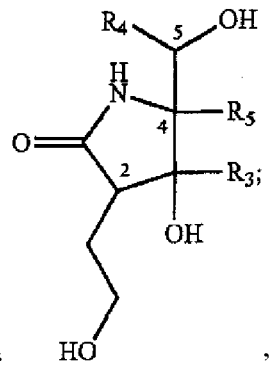 " to -- 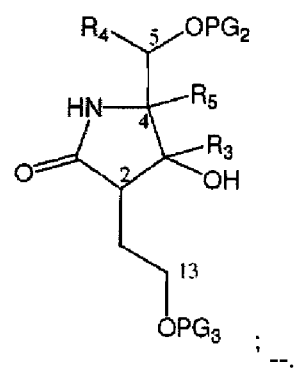 --.